(12) United States Patent
Hume et al.

(10) Patent No.: US 11,696,948 B2
(45) Date of Patent: Jul. 11, 2023

(54) VACCINES FORMED BY VIRUS AND ANTIGEN CONJUGATION

(71) Applicant: KBIO HOLDINGS LIMITED, London (GB)

(72) Inventors: Steven D. Hume, Owensboro, KY (US); Leigh Burden, Owensboro, KY (US); Joshua Morton, Evansville, IN (US); Greg Pogue, Austin, TX (US); Barry Bratcher, Owensboro, KY (US); Hugh A. Haydon, Louisville, KY (US); Carrie A. Simpson, Evansville, IN (US); Nick Partain, Owensboro, KY (US); Youngjun Oh, Owensboro, KY (US); John W. Shepherd, Owensboro, KY (US); Michael H. Pauly, Del Mar, CA (US)

(73) Assignee: KBIO HOLDINGS LIMITED, London (GB)

(*) Notice: Subject to any disclaimer, the term of this patent is extended or adjusted under 35 U.S.C. 154(b) by 24 days.

(21) Appl. No.: 16/919,943

(22) Filed: Jul. 2, 2020

(65) Prior Publication Data

US 2021/0000942 A1  Jan. 7, 2021

Related U.S. Application Data

(63) Continuation-in-part of application No. 16/709,063, filed on Dec. 10, 2019, which is a continuation-in-part of application No. 16/437,734, filed on Jun. 11, 2019.

(60) Provisional application No. 62/683,865, filed on Jun. 12, 2018, provisional application No. 63/013,284, filed on Apr. 21, 2020.

(51) Int. Cl.
| | |
|---|---|
| *A61K 39/215* | (2006.01) |
| *A61K 39/145* | (2006.01) |
| *A61K 39/12* | (2006.01) |
| *A61K 47/68* | (2017.01) |
| *C07K 16/46* | (2006.01) |
| *A61P 31/16* | (2006.01) |
| *A61P 31/14* | (2006.01) |
| *A61K 47/42* | (2017.01) |

(52) U.S. Cl.
CPC ............ *A61K 39/215* (2013.01); *A61K 39/12* (2013.01); *A61K 39/145* (2013.01); *A61K 47/42* (2013.01); *A61K 47/6811* (2017.08); *A61P 31/14* (2018.01); *A61P 31/16* (2018.01); *C07K 16/46* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,037,456 A | 3/2000 | Garger et al. | |
| 6,261,823 B1 | 7/2001 | Tang et al. | |
| 7,396,914 B2 | 7/2008 | Ambrosino et al. | |
| 7,629,443 B2 | 12/2009 | Jiang et al. | |
| 7,666,624 B2 | 2/2010 | Brennan | |
| 7,750,123 B2 | 7/2010 | Marasco et al. | |
| 7,901,921 B2 | 3/2011 | Coffey | |
| 7,939,318 B2 | 5/2011 | McCormick et al. | |
| 8,124,106 B2 | 2/2012 | Weggeman et al. | |
| 8,771,703 B2 | 7/2014 | Couture et al. | |
| 9,056,900 B2 | 6/2015 | Garry et al. | |
| 9,169,491 B2 | 10/2015 | Truan et al. | |
| 9,889,194 B2 | 2/2018 | Jiang et al. | |
| 10,052,370 B2 | 8/2018 | Savelyeva et al. | |
| 10,301,377 B2 | 5/2019 | Graham et al. | |
| 10,406,222 B2 | 9/2019 | Kyratsous et al. | |
| 10,590,394 B2 | 3/2020 | Steinmetz et al. | |
| 11,078,250 B2* | 8/2021 | Tan | A61K 38/22 |
| 11,213,482 B1* | 1/2022 | Gambotto | A61B 5/150984 |
| 2006/0188991 A1 | 8/2006 | McCormick et al. | |
| 2006/0288449 A1 | 12/2006 | Garger et al. | |
| 2007/0172846 A1 | 7/2007 | Zhang et al. | |
| 2009/0053261 A1 | 2/2009 | Lindbo et al. | |
| 2009/0117144 A1 | 5/2009 | Rasochova et al. | |
| 2010/0068175 A1 | 3/2010 | Gillies et al. | |
| 2010/0297174 A1 | 11/2010 | Garcia-Sastre et al. | |
| 2011/0086058 A1 | 4/2011 | Jiang et al. | |

(Continued)

FOREIGN PATENT DOCUMENTS

| | | |
|---|---|---|
| CN | 101268192 A | 9/2008 |
| CN | 101646772 A | 2/2010 |

(Continued)

OTHER PUBLICATIONS

He et al. (Biochemical and Biophysical Research Communications, 2004, p. 773-781).*

(Continued)

*Primary Examiner* — Agnieszka Boesen

(74) *Attorney, Agent, or Firm* — Wyatt, Tarrant & Combs, LLP; Max E. Bridges; Stephen C. Hall

(57) ABSTRACT

Disclosed herein are methods of forming compounds and exemplary compounds in the nature of a conjugated compound, which in some embodiments comprises an antigen and virus particle mixed in a conjugation reaction to form a conjugate mixture, such that the conditions and steps of forming these products allow for use of the conjugate mixture as a vaccine, including but not limited to use as a vaccine against various pathogens including for treatment of diseases caused by novel coronaviruses (including SARS-COV 2).

35 Claims, 72 Drawing Sheets

Specification includes a Sequence Listing.

(56) References Cited

U.S. PATENT DOCUMENTS

| | | | |
|---|---|---|---|
| 2011/0104753 A1 | 5/2011 | Couture et al. | |
| 2013/0280298 A1 | 10/2013 | Leclerc | |
| 2016/0296617 A1 | 10/2016 | Jiang et al. | |
| 2016/0362473 A1* | 12/2016 | Wang | C07K 14/745 |
| 2017/0002332 A1 | 1/2017 | Genethon et al. | |
| 2017/0258886 A1 | 9/2017 | Ivanov et al. | |
| 2018/0119110 A1 | 5/2018 | Schlegl et al. | |
| 2019/0374616 A1 | 12/2019 | Burden et al. | |
| 2020/0113999 A1 | 4/2020 | Burden et al. | |
| 2020/0368341 A1 | 11/2020 | Dutta et al. | |
| 2022/0087930 A1* | 3/2022 | Gambotto | A61K 39/39 |

FOREIGN PATENT DOCUMENTS

| | | |
|---|---|---|
| CN | 102271704 A | 12/2011 |
| CN | 102397559 A | 4/2012 |
| CN | 104845945 A | 8/2015 |
| EP | 1561758 B1 | 10/2005 |
| EP | 1926819 B1 | 1/2013 |
| WO | 03103605 A2 | 12/2003 |
| WO | 03103605 A3 | 12/2003 |
| WO | 2005056585 A2 | 6/2005 |
| WO | 2005056585 A3 | 6/2005 |
| WO | 2005091753 A2 | 10/2005 |
| WO | 2005091753 A3 | 10/2005 |
| WO | 2007038145 A2 | 4/2007 |
| WO | 2008073490 A1 | 6/2008 |
| WO | 2012128628 A1 | 9/2012 |
| WO | 2013010797 A1 | 1/2013 |
| WO | 2015105551 A1 | 7/2015 |
| WO | 2016156613 A1 | 10/2016 |
| WO | 2017011826 A1 | 1/2017 |

OTHER PUBLICATIONS

Mallajosyula et al. (Human Vaccines & Immunotherapeutics, 2014, p. 586-595).*

De Groot et al. (Journal of Virology, 2013, p. 7790-7792).*

The United States Patent and Trademark Office; The International Search Report and the Written Opinion of the International Searching Authority; dated Jun. 11, 2021; PCT/US2021/021087; pp. 1-15; United States Patent and Trademark Office; US.

Wen, Jianxin, Veterinary Immunology Laboratory Guide, China Agricultural University Press, Dec. 2016, pp. 29-30.

Akerblom, Anna and Peter Bergvall (2012). Constraints on Vaccine Production. BioProcess International, Industry Yearbook 2012-2013.

Altintoprak et al. "Bioengineered viral nanorings for the insertion into bio-hybrid systems," University of Stuttgart, Thesis, Apr. 12, 2016 (Apr. 12, 2016), pp. 113-140 of 199. Retrieved from the Internet:<https:f/d-nb.info/1161409939/34>t>n Aug. 12, 2019 (Aug. 12, 2019). entire document.

Arnaboldi, P. M., D'Arco, C., Peters, L. A., Seegers, J. F., Mayer, L., McCormick, A. A., Dattwyler, R. J. (2016) Intranasal delivery of a protein subunit vaccine using a Tobacco Mosaic Virus platform protects against pneumonic plague. Vaccine. 34(47):5768:5776. PMID: 27745954.

Banik, S., Mansour, A. A., Suresh, R. V., Wykoff-Clary, S., Malik, M., McCormick, A. A., Bakshi, C. S. (2015) Development of a Multivalent Subunit Vaccine against Tularemia Using Tobacco Mosaic Virus (TMV) Based Delivery System. PLoS One. 10(6):1-22. PMID: 26098553.

Bergmann, Katherin (Nov. 20, 2014), UV-C Irradiation: A New Viral Inactivation Method for Biopharmaceuticals. American Pharmaceutical Review. https:f/www.americanpharmaceuticalreview.com/Featured-Articles/169257-UV-Crradiation-A-New-Viral-Inactivation-Method-for-Biopharmaceuticals/.

Blom H, Akerblom A, Kon T, Shaker S, van der Pol L, Lundgren M. 2014. Efficient chromatographic reduction of ovalbumin for egg-based influenza virus purification. Vaccine 32:3721-3724.

Boon A, Finkelstein D, Zheng M, Liao G. H5N1 influenza virus pathogenesis in genetically diverse mice is mediated at the level of viral load. MBio [Internet]. 2011 ;2(5):1-10. Available from: http://mbio.asm.org/content/2/5/e00171-11. Short.

Bruckman, et al. Tobacco mosaic virus rods and spheres as supramolecular high-relaxivity MRI contrast agents. NIH Public Access Author Manuscript. National Institutes of Health, pp. 1-17. Also published as J Mater Chem B. 2013;1(10):1482-1490. doi:10.1039/C3TB00461A. https://pubmed.ncbi.nlm.nih.gov/23589767.

Chahal P. S. et al . . . Validation of a high-performance liquid chromatographic assay for the quantification of Reovirus particles type 3. J. Pharm. Biomed. Anal. 45, 417-421 (2007).

Chen Q, Lai H. Plant-derived virus-like particles as vaccines. Hum Vaccin Immunother. 2013;9(1):26-49. doi:10.4161/hv.22218 https://www.ncbi.nlm.nih.gov/pmc/articles/PMC3667944/.

Chu, et al.; Enhanced Stability of Inactivated Influenza Vaccine Encapsulated in Dissolving Microneedle Patches; Author Manuscript; HHS Public Access; Pharm Res.; Apr. 2016; pp. 868-878; 33(4); available in PMC Apr. 1, 2017; doi: 10.1007/s11095-015-1833-9.

Coenen, et al.; Stability of influenza sub-unit vaccine; Journal; Vaccine; 2006; pp. 525-531; 24; www.elsevier.com/locate/vaccine; www.sciencedirect.com; copyright 2005 Elsevier Ltd; available online Aug. 15, 2005.

Dai, et al.; Advances and challenges in enveloped virus-like particle (VLP)-based vaccines; Journal/Minireview; Journal of Immunological Sciences; 2018; pp. 36-41; 2(2); China.

De Boer et al. "Acid-Activated Structural Reorganization of the Rift Valley Fever Virus GC Fusion Protein," Journal of Virology, Oct. 3, 2012 (Oct. 3, 2012), vol. 86, No. 24, pp. 13642-13652. entire document.

Dorokhov YL, Sheveleva M, Frolova OY, Komarova T V., Zvereva AS, Ivanov PA, et al. Superexpression of tuberculosis antigens in plant leaves. Tuberculosis. 2007:87(3):2l8-24.

Fernandes P, Peixoto C, Santiago VM, Kremer EJ, Coroadinha AS, Alves PM. 2012. Bioprocess development for canine adenovirus type 2 vectors. Gene Ther 20:353-360.

Gasanova, Genetically Modified TMV Particles May Serve as Carrier for Chemical Conjugation of Influenza Antigens to Produce Multivalent Nanovaccines; Jun. 10, 2017; https://event.scribe.com/2017/sivb/ajaxcalls/PresentationInfo.asp?efp=SkpOQ0JVWEczODE5&PresentationID=285003&rnd=0.1628216.

GE Healthcare Life Sciences, Purification of influenza A/H1 N1 using CAPTO Core 700; Mar. 2012; Application note 29-0003-34 AA: pp. 1-6: www.gelifesciences.com/captocore: Sweden.

James et al., Sci Rep. 2016; 6: 36826. https://vww.ncbi.nlm.nih.gov/pmc/articles/PMC5101806/.

Kemnade, J.O., Seethammagari, M., Collinson-Pautz, M., Kaur, H., Spencer, D. M., McCormick, A. A. (2014) Tobacco mosaic virus efficiently targets DC uptake, activation and antigen-specific T cell responses in vivo. Vaccine 32 (33)4228-4233. PMID: 24923637.

Klimyuk V, Pogue G, Herz S, Butler J, Haydon H. Production of recombinant antigens and antibodies in Nicotiana benthamiana using 'magnifection' technology: GMP-compliant facilities for small- and large-scale manufacturing. Curr Top Microbiol Immunol. 2014;375:127-154. doi:10.1007/82_2012_212 https://pubmed.ncbi.nim.nih.gov/22527176/.

Kumru, et al.; Vaccine instability in the cold chain: Mechanisms, analysis and formulation strategies; Journal; Biologicals; 2014; pp. 237-259; 42; www.elsevier.com/locate/biologicais.

Kwon, et al.; Oral delivery of bioencapsulated exendin-4 expressed in chloroplasts lowers blood glucose level in mice and stimulates insulin secretion in beta-TC6 cells; Journal; Plant Biotechnology Journal; 2013; pp. 77-86; 11; doi: 10.1111/pbi.12008.

Mallajosyula et al. "Single-Dose Monomeric HA Subunit Vaccine Generates Full Protection From Influenza Challenge," Human Vaccines & Immunotherapeutics, Dec. 30, 2013 (Dec. 30, 2013), vol. 10, Iss. 3, pp. 586-595. entire document.

Mallajosyula, I. K., Hiatt, E., Hume, S. Johnson, A., Jeevan, T., Chikwamba, R, Webby, R J., Pogue, G. P., Bratcher, B., Haydon, H., McCormick, A. A. (2014) Single dose monomeric HA subunit vaccine generates full protection from influenza challenge. Hum. Vaccin. Immunother. 10:58695. PMID: 24378714.

(56) References Cited

OTHER PUBLICATIONS

Mallajosyula, J. K., Jeevan, T., Chikwamba, R., Webby, R. J., McCormick, A. A. (2016) A Single Dose TMV-HA Vaccine Protects Mice from H5N1 Influenza Challenge. Int. J. Vaccine. Res. 1(2):6. DOI: 10.15226/2473-2176/1/2/00106.

Mansour AA, Banik S, Suresh R V., Kaur H, Malik M, McCormick AA, et al. An improved tobacco mosaic virus (TMV)-conjugated multiantigen subunit vaccine against respiratory tularemia. Front Microbiol. 2018;9(JUN).

Manuel-Cabrera, et al.; Immune response to a potyvirus with exposed amino groups available for chemical conjugation; Virology Journal; 2012; pp. 9:75; http://www.virologyj.com.content/9/1/75.

McCormick AA, Corbo TA, Wykoff-Clary S, Nguyen L V., Smith ML, Palmer KE, et al. TMV-peptide fusion vaccines induce cell-mediated immune responses and tumor protection in two murine models. Vaccine. 2006;24(40-41):6414-23.

McCormick AA, Corbo TA, Wykoff-Clary S, Palmer KE, Pogue GP. Chemical conjugate TMV-Peptide bivalent fusion vaccines improve cellular immunity and tumor protection. Bioconjug Chem. 2006;17(5):1330-8.

McCormick AA, Shakeel A, Yi C, Kaur H, Mansour AM, Bakshi CS. Intranasal administration of a two-dose adjuvanted multiantigen TMV-subunit conjugate vaccine fully protects mice against Francisella tularensis LVS challenge, PLoS One. 2018;13(4).

Nestola, Piergiuseppe (2015). Improving Downstream Processing for Viral Vectors and Viral Vaccines. Dissertation Presented to Obtain the Ph.D degree in Chemical Engineering from the University of Lisbon.

Nikitin NA, Zenin VA, Trifonova EA, Ryabchevskaya EM, Kondakova OA, Fedorov AN, et al. Assessment of structurally modified plant virus as a novel adjuvant in toxicity studies. Regul Toxicol Pharmacol. 2018;97:127-33.

Nuzzaci, et al.; In vitro stability of Cucumber mosaic virus nanoparticles carrying a Hepatitis C virus-derived epitope under simulated gastrointestinal conditions and in vivo efficacy of an edible vaccine; Journal; Journal of Virological Methods; 2010; pp. 211-221; 165; www.elsevier.com/locate/jviromet.

Ortega, JT, et al, Role of changes in SARS-CoV-2 spike protein in the interaction with the human ACE-2 receptor: An in silico analysis. EXCLI J. 2020;19:410-417. Published Mar. 18, 2020. Doi:10.17179/excli2020-1167.

Palmer KE, Benko A, Doucette SA, Cameron TI, Foster T, Hanley KM, et al. Protection of rabbits against cutaneous papillomavirus infection using recombinant tobacco mosaic virus containing L2 capsid epitopes. Vaccine. 2006;24(26):5516-25.

Pogue, G. P., Lindbo, J. A., Garger, S. J., Fitzmaurice, W. P. 2002. Making an ally from an enemy: plant virology and the new agriculture. Ann. Rev. Phytopathol. 40:45 74.

Rohovie, et al.; Virus-like particles: Next-generation nanoparticles for targeted therapeutic delivery; Journal Review; AICHE Bioengineering & Translational Medicine; 2017; pp. 43-57; 2; wileyonlinelibrary.com/journal/btm2; DOI 10.1002/btm2.10049.

Rybicki, E.; Plant-based vaccines against viruses; Virology Journal; 2014; pp. 1-20; 11:205; http://www.virologyj.com/content/11/1/205.

Segura M. M., Kamen A. A. & Garnier A. Overview of current scalable methods for purification of viral vectors. Methods Mol. Biol. 737, 89-116 (2011).

Smith ML, Lindbo JA, Dillard-Telm S, Brosio PM, Iasnik AB, McCormick M, et al. Modified Tobacco mosaic virus particles as scaffolds for display of protein antigens for vaccine applications. Virology. 2006;348(2):475-88.

Smith, M. L., Corbo, T., Bemales, J., Lindbo, J. A., Pogue, G. P., Palmer, K. E., McCormick, A. A. 2007. Assembly of trans encapsidated recombinant viral vectors engineered from Tobacco mosaic virus and Semliki Forest virus and thei1 Valuation as immunogens. Virology 358:321-33.

Soema, et al.; Current and next generation influenza vaccines: Formulation and production strategies; Journal; European Journal of Pharmaceutics and Biopharmaceutics; 2015; pp. 251-263; 94; www.elsevier.com/locate/ejpb.

Stegmann et al. "Effects of Low pH on Influenza Virus," The Journal of Biological Chemistry, Dec. 25, 1987 Dec. 25, 1987), vol. 262, No. 36, pp. 17744-17749. entire document.

Steinmetz, Nicole, et al; Protein cages and virus-like particles: from fundamental insight to biomimetic therapeutics; The Royal Society of Chemistry 2020; Apr. 22, 2020, Biomater. Sci., 2020, *, 2771-2777.

Transfiguracion J., Bernier A., Arcand N., Chahal P. & Kamen A. Validation of a high-performance liquid chromatographic assay for the quantification of adenovirus type 5 particles. J. Chromatogr. B Biomed. Sci. Appl. 761, 187-194 (2001).

Tseng et al., Vaccine. Mar. 22, 2017. pii: S0264-410X(17)30322-5.

United States Patent and Trademark Office; The International Search Report and the Written Opinion of the International Searching Authority; Sep. 3, 2019; PCT/US2019/036559; pp. 1-10; United States Patent and Trademark Office; US.

World Health Organization (2014), Guidelines on viral inactivation and removal procedures intended to assure the viral safety of human blood plasma products. WHO Technical Report, Series No. 924. https://www.who.int/bloodproducts/publications/WHO_TRS_924_A4.pdf.

Wrapp, et. al. Cryo-EM structure of the 2019-nCoV spike in the prefusion conformation. Science. Mar. 13, 2020;367 (6483):1260-1263. doi:10.1126/science.abb2507.

United States Patent and Trademark Office; Notification of Transmittal of the International Search Report and the Written Opinion of the International Searching Authority, or the Declaration for PCT/US20/63902; dated May 7, 2021; pp. 1-15; United States Patent and Trademark Office Searching Authority; US.

Lindbo, John A., TRBO: A High-Efficiency Tobacco Mosaic Virus RNA-Based Overexpression Vector, Journal, Dec. 2007, pp. 1232-1240, vol. 145, Plant Physiology http://www.plantphysiol.org/content/plantphysiol/145/4/1232.full.pdf, www.plantphysiol.org, 2007 American Society of Plant Biologists.

Callow, K. A., et al. (1990). The time course of the immune response to experimental coronavirus infection of man. Epidemiology and Infection, 105(2), 435-446. https://doi.org/10.1017/S0950268800048019.

Du, L., et al. (2009). Recombinant receptor-binding domain of SARS-CoV spike protein expressed in mammalian, insect and *E. coli* cells elicits potent neutralizing antibody and protective immunity. Virology, 393(1), 144-150. https://doi.org/10.1016/j.virol.2009.07.018.

Du, L., et al. (2007). Receptor-binding domain of SARS-CoV spike protein induces long-term protective immunity in an animal model. Vaccine, 25(15), 2832-2838. https://doi.org/10.1016/j.vaccine.2006.10.031.

Gao, A. Q., et al. (Apr. 19, 2020). Title : Rapid development of an inactivated vaccine for SARS-CoV-2 Affiliation : Abstract : BioRxiv, Preprint, https://doi.org/10.1101/2020.04.17.046375.

Guyre, P. M., et al. (1997). Increased potency of Fc-receptor-targeted antigens. Cancer Immunology Immunotherapy, 45(3-4), 146-148. https://doi.org/10.1007/s002620050418.

Huang, A. T., et al. (Apr. 17, 2020). A systematic review of antibody mediated immunity to coronaviruses: antibody kinetics, correlates of protection, and association of antibody responses with severity of disease. MedRxiv, 2020.04.14.20065771. https://doi.org/10.1101/2020.04.14.20065771.

Liu, L., et al. (2019). Anti-spike IgG causes severe acute lung injury by skewing macrophage responses during acute SARS-CoV infection. JCI Insight, 4(4), 1-19. https://doi.org/10.1172/jci.insight.123158.

Loureiro, S., et al. (2011). Adjuvant-Free Immunization with Hemagglutinin-Fc Fusion Proteins as an Approach to Influenza Vaccines. Journal of Virology, 85(6), 3010-3014. https://doi.org/10.1128/jvi.01241-10.

Marshall, E., et al. (2004). Caution Urged on SARS Vaccines. In Science (vol. 303, Issue 5660, pp. 944-946). https://doi.org/10.1126/science.303.5660.944.

(56) References Cited

OTHER PUBLICATIONS

Ni, L., et al. (Mar. 20, 2020). Characterization of anti-viral immunity in recovered individuals infected by SARS-CoV-2. MedRxiv, 2020.03.17.20036640. https://doi.org/10.1101/2020.03.17.20036640.

Pleass, R. J. (2009). Fc-receptors and immunity to malaria: From models to vaccines. In Parasite Immunology (vol. 31, Issue 9, pp. 529-538). https://doi.org/10.1111/j.1365-3024.2009.01101.x.

Tseng, C. Te, et al. (2012). Immunization with SARS coronavirus vaccines leads to pulmonary immunopathology on challenge with the SARS virus. PLoS One, 7(4), e35421. https://doi.org/10.1371/journal.pone.0035421.

Wu, F., et al. (2020). Neutralizing antibody responses to SARS-CoV-2 in a COVID-19 recovered 1 patient cohort and their implications. MedRxiv, Preprint. http://europepmc.org/article/PPR/PPR139479 (Apr. 5, 2020).

Pillet, Stephane, et al. (2019). Immunogenicity and safety of a quadrivalent plant-derived virus like particle influenza vaccine candidate—Two randomized Phase II clinical trials in 18 to 49 and 50 years old adults. PLoS One, 14(6). https://doi.org/10.1371/journal.pone.0216533.

Pillet, S., et al. (2015). Plant-derived H7 VLP vaccine elicits protective immune response against H7N9 influenza virus in mice and ferrets. Vaccine, 33(46), 6282-6289. https://doi.org/10.1016/j.vaccine.2015.09.065.

Doonan, Essential Guides for Isolation/Purification of Enzymes and Proteins; Appendix 1; 2000; pp. 4547-4552; Academic Press.

Datar, et al., 18 Cell and Cell Debris Removal: Centrifugation and Crossflow Filtration; Biotechnology Second Edition, 1993, pp. 468-485; Edited by H.-J. Rehm and G. Reed; Part 1.

Datar, et al., 18 Cell and Cell Debris Removal: Centrifugation and Crossflow Filtration; Biotechnology Second Edition, 1993, pp. 486-503; Edited by H.-J. Rehm and G. Reed; Part 2.

United States Patent and Trademark Office; Invitation to Pay Additional Fees and, Where Applicable, Protest Fee; from the International Searching Authority; dated Feb. 17, 2021; PCT/US20/63902; pp. 1-24; United States Patent and Trademark Office; US.

Wu M, Shi J, Fan D, Zhou Q, Wang F, Niu Z, et al. Biobehavior in normal and tumor-bearing mice of tobacco mosaic virus. Biomacromolecuies. 2013;14(11):4032-7.

Xiong, et al. (Posh A. (eds) 2D PAGE: Sample Preparation and Fractionation. Methods in Molecular Biology, vol. 424. Humana Press (2008)).

Yang et al. "Harnessing an RNA-Mediated Chaperone for the Assembly of influenza Hemagglutinin in an immunologically Relevant Conformation," The FASEB Journal, Apr. 26, 2018 (Apr. 26, 2018), vol. 32, No. 5, pp. 2658-2675. entire document.

Yin et al. Tobacco Mosaic Virus as a New Carrier for Tumor Associated Carbohydrate Antigens. NIH Public Access Author Manuscript. National Institutes of Health, pp. 1-20. Also Published in Bioconjug Chem. Aug. 15, 2012; 23(8): 1694-1703. doi:10.1021/bc300244a. https://www.ncbi.nlm.nih.gov/pmc/articles/PMC3426870/.

Zhang, et al., Mixed-mode chromatography in pharmaceutical and biopharmaceutical applications, Journal of Pharmaceutical and Biomedical Analysis, 2016, 128:73-88.

Zhao D. et al . . . Enterovirus71 virus-like particles produced from insect cells and purified by multistep chromatography elicit strong humoral immune responses in mice. J. Appl. Microbiol. 119, 1196-1205 (2015).

Andersen, K.G., Rambaut, A., Lipkin, W.I. et al. The proximal origin of SARS-CoV-2. Nat Med 26, 450-452 (Mar. 17, 2020). https://doi.org/10.1038/s41591-020-0820-9.

Chan et al, Simulation of the clinical and pathological manifestations of Coronavirus disease 2019 (COVID-19) in golden Syrian hamster model: implications for disease pathogenesis and transmissibility, Clin. Infect. Diseases, (Mar. 26, 2020).

Du, L. et al, Receptor-binding domain of SARS-CoV spike protein induces long term protective immunity in an animal model, Vaccine. 2007.

Du, L. et al, The spike protein of SARS-CoV—a target for vaccines and therapeutic development, Nat. Rev. Microbiol. 2009; 7: 226-36.

Guyre, P.M., et al, Increased potency of Fc receptor-targeted antigens, Cancer Immunol, Immunother. 1997; 45: 146-148.

He, Y et al., Receptor-binding domain of SARS-CoV spike protein induces highly potent neutralizing antibodies: implication for developing subunit vaccine. Biochemical and Biophysical Research Communications 324 (2004) 773-781.

Jaune, M. et al, SARS CoV subunit vaccine: Antibody mediated neutralization and enhancement, Hong Kong Med. J. 2012.

Kam, Y.M., Antibodies against trimeric S. glycoprotein protect hamsters against SARS-CoV challenge despite their capacity to mediate Fc gamma R11-dependent entry into B cells in vitro, Vaccine. 2007.

Lan, J. et al. Structure of the SARS-CoV-2 spike receptor-binding domain bound to the ACE2 receptor. Nature https://doi.org/10.1038/s41586-020-2180-5 (Mar. 30, 2020).

Perlman, S. et al, Immunopathogenesis of coronavirus infections: Implications for SARS, Nature. 2005.

Tai, W., et al Characterization of the receptor-binding domain (RBD) of 2019 novel coronavirus: implication for development of RBD protein as a viral attachment inhibitor and vaccine. Nature Cellular & Molecular Immunology https://doi.org/10.1038/s41423-020-0400-4 (Mar. 19, 2020).

Tse, LV, et al, (Apr. 24, 2020) The Current and Future State of Vaccines, Antivirals and Gene Therapies Against Emerging Coronaviruses. Front. Microbiol. 11:658. doi: 10.3389/fmicb.2020.00658.

Lobner E, Traxlmayr MW, Obinger C, Hasenhindl C. Engineered IgG1-Fc—one fragment to bind them all. Immunol Rev. 2016;270(1):113-131. doi:10.1111/imr.12385, https://www.ncbi.nlm.nih.gov/pmc/articles/PMC4755133/.

Lu, et al (2014) Production and stabilization of the trimeric influenza hemagglutinin stem domain for potentially broadly protective influenza vaccines, PNAS, Jan. 7, 2014, vol. 111, No. 1, pp. 125-130; www.pnas.org/cgi/doi/10.1073/pnas.1308701110.

Chou, T et al. Epitope mapping and biological function analysis of antibodies produced by immunization of mice with an inactivated Chinese isolate of severe acute respiratory syndrome-associated coronavirus (SARS-CoV), Virology. Mar. 30, 2005;334(1):134-43. doi: 10.1016/j.virol.2005.01.035.PMID: 15749129.

He, Y et al. Identification and characterization of novel neutralizing epitopes in the receptor-binding domain of SARS-CoV spike protein: revealing the critical antigenic determinants in inactivated SARS-CoV vaccine. Vaccine. Jun. 29, 2006;24(26):5498-508. doi: 10.1016/j.vaccine.2006.04.054. Epub May 11, 2006.PMID: 16725238.

He, Y, et al. Cross-neutralization of human and palm civet severe acute respiratory syndrome coronaviruses by antibodies targeting the receptor-binding domain of spike protein. J Immunol. May 15, 2006:176(10):6085-92. doi: 10.4049/jimmunol.176.10.6085,. PMID: 16670317.

He, Y, et al. Vaccine design for severe acute respiratory syndrome coronavirus, Viral Immunol. 2005;18(2):327-32. doi: 10.1089/vim.2005.16.327.PMID: 16035944 Review.

Jiang, S, et al. SARS vaccine development. Emerg Infect Dis. Jul. 2005;11(7):1016-20. doi: 10.3201/1107.050219. PMID: 16022774 Review.

Kontermann, R. Strategies for extended serum half-life of protein therapeutics. Curr Opin Biotechnol (2011) 22(6):868-76. doi:10.1016/j.copbio.2011.06.012.

Mekhaiel, D, et al. Polymeric human Fc-fusion proteins with modified effector functions. Sci Rep (2011) 1:124. doi:10.1038/srep00124.

Roopenian, D, et al. FcRn: the neonatal Fc receptor comes of age. Nat Rev Immunol(2007) 7(9):715-25. doi:10.1038./nri2155.

Author Not Found—Research on Immunization and Prevention of Major Livestock and Poultry Diseases, pp. 167-168, China Agricultural Science and Technology Press, Dec. 1996 (English Translation).

* cited by examiner

Figure 64

Figure 68(A)
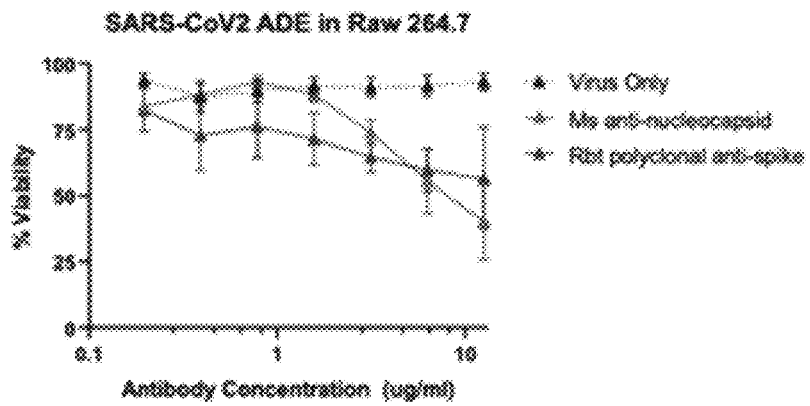
Figure 68(B)
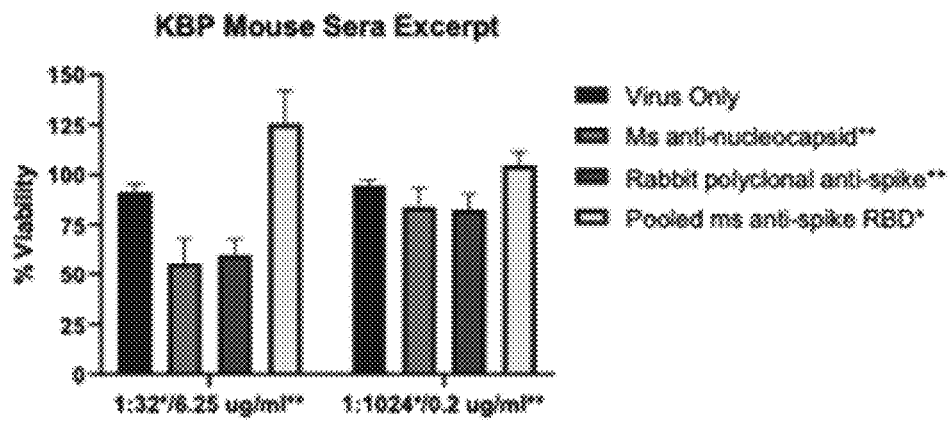
Figure 68(C)
Serum dilution
| One-way ANOVA with Tukey's P Values | | | | |
|---|---|---|---|---|
| | Virus Only | Ms Anti-Nucleocapsid | Rabbit Polyclonal Anti-Spike | Ms Anti-Spike RBD |
| Ms Anti-Nucleocapsid | 0.0348 | | NS | p<0.0001 |
| Rabbit Polyclonal anti-spike | 0.015 | NS | | p<0.0001 |
| Ms Anti-Spike RBD | NS | p<0.0001 | p<0.0001 | |

Figure 71

SEQUENCE LISTING

<160> NUMBER OF SEQ ID NOS: 8

<210> SEQ ID NO 1
<211> LENGTH: 26
<212> TYPE: PRT
<213> ORGANISM: Artificial Sequence
<220> FEATURE:
<223> OTHER INFORMATION: Designed peptide; signal peptide for Nicotiana
      benthamiana

<400> SEQUENCE: 1

Met Gly Lys Met Ala Ser Leu Phe Ala Thr Phe Leu Val Val Leu Val
1               5                   10                  15

Ser Leu Ser Leu Ala Ser Glu Ser Ser Ala
            20                  25

<210> SEQ ID NO 2
<211> LENGTH: 302
<212> TYPE: PRT
<213> ORGANISM: Artificial Sequence
<220> FEATURE:
<223> OTHER INFORMATION: SARS-2 virus Spike amino acids numbered 331-632

<400> SEQUENCE: 2

Asn Ile Thr Asn Leu Cys Pro Phe Gly Glu Val Phe Asn Ala Thr Arg
1               5                   10                  15

Phe Ala Ser Val Tyr Ala Trp Asn Ar

```
Asn Thr Ser Asn Gln Val Ala Val Leu Tyr Gln Asp Val Asn Cys Thr
        275                 280                 285

Glu Val Pro Val Ala Ile His Ala Asp Gln Leu Thr Pro Thr
    290                 295                 300

<210> SEQ ID NO 3
<211> LENGTH: 16
<212> TYPE: PRT
<213> ORGANISM: Artificial Sequence
<220> FEATURE:
<223> OTHER INFORMATION: Homo sapien; Fc Hinge

<400> SEQUENCE: 3

Val Glu Pro Lys Ser Cys Asp Lys Thr His Thr Cys Pro Pro Cys Pro
1               5                   10                  15

<210> SEQ ID NO 4
<211> LENGTH: 216
<212> TYPE: PRT
<213> ORGANISM: Artificial Sequence
<220> FEATURE:
<223> OTHER INFORMATION: Homo sapien; IgG1 171 allotype Fc

<400> SEQUENCE: 4

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 5
<211> LENGTH: 12
<212> TYPE: PRT
<213> ORGANISM: Artificial Sequence
<220> FEATURE:
<223> OTHER INFORMATION: SARS-2 virus Spike amino acids numbered 319-330
```

<400> SEQUENCE: 5

Arg Val Gln Pro Thr Glu Ser Ile Val Arg Phe Pro
1               5                  10

<210> SEQ ID NO 6
<211> LENGTH: 261
<212> TYPE: PRT
<213> ORGANISM: Artificial Sequence
<220> FEATURE:
<223> OTHER INFORMATION: SARS-2 virus Spike amino acids numbered 331-591

<400> SEQUENCE: 6

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Lys Ser Thr Asn Leu Val Lys Asn Lys Cys
        195                 200                 205

Val Asn Phe Asn Phe Asn Gly Leu Thr Gly Thr Gly Val Leu Thr Glu
    210                 215                 220

Ser Asn Lys Lys Phe Leu Pro Phe Gln Gln Phe Gly Arg Asp Ile Ala
225                 230                 235                 240

Asp Thr Thr Asp Ala Val Arg Asp Pro Gln Thr Leu Glu Ile Leu Asp
                245                 250                 255

Ile Thr Pro Cys Ser
            260

<210> SEQ ID NO 7
<211> LENGTH: 7
<212> TYPE: PRT
<213> ORGANISM: Artificial Sequence
<220> FEATURE:
<223> OTHER INFORMATION: Tobacco etch virus NIA cleavage sequence

<400> SEQUENCE: 7

Glu Asn Leu Tyr Phe Gln Gly
1               5

<210> SEQ ID NO 8
<211> LENGTH: 273
<212> TYPE: PRT
<213> ORGANISM: Artificial Sequence
<220> FEATURE:
<223> OTHER INFORMATION: SARS-2 virus Spike amino acids numbered 319-591

<400> SEQUENCE: 8

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe Asn
    210                 215                 220

Phe Asn Gly Leu Thr Gly Thr Gly Val Leu Thr Glu Ser Asn Lys Lys
225                 230                 235                 240

Phe Leu Pro Phe Gln Gln Phe Gly Arg Asp Ile Ala Asp Thr Thr Asp
                245                 250                 255

Ala Val Arg Asp Pro Gln Thr Leu Glu Ile Leu Asp Ile Thr Pro Cys
            260                 265                 270

Ser
```

VACCINES FORMED BY VIRUS AND ANTIGEN CONJUGATION

CROSS-REFERENCE TO RELATED APPLICATIONS

This patent application is a continuation-in-part application under 35 U.S.C. § 120, for which common subject matter, if any, is entitled to the benefit of the filing date of U.S. Nonprovisional patent application Ser. No. 16/709,063, filed on Dec. 10, 2019, which is a continuation-in-part application that claims the benefit of and priority to U.S. Nonprovisional patent application Ser. No. 16/437,734, filed on Jun. 11, 2019, which is a utility application that claims the benefit of and priority under 35 U.S.C. § 119(e) to U.S. Provisional Patent Application No. 62/683,865, with a filing date of Jun. 12, 2018, and further under 35 U.S.C. § 119(e) priority is claimed with U.S. Provisional Patent Application No. 63/013,284, filed on Apr. 21, 2020. The teachings and entire disclosure of all aforementioned applications are fully incorporated herein by reference.

REFERENCE TO A SEQUENCE LISTING

This application contains a Sequence Listing in compliance with 37 C.F.R. § 1.52(e) that is hereby incorporated by reference in its entirety. The sequence listing text file submitted via EFS contains the file "KBP_SequenceListings.txt" as a computer readable form, that was created on Aug. 4, 2020, and is 10,824 bytes in size.

FIELD OF INVENTION

The embodiments described herein include use of a multi-set process for producing highly purified, recombinant viruses as antigen carriers, and still further various embodiments relate to vaccine production using a purified virus and a purified antigen, including vaccines intended for prevention of novel coronaviruses, such as SARS-CoV2 (referred to herein as Covid-19 or SARS-2.) Disease.

BACKGROUND

Viruses have a nucleic acid molecule in a protein coat and replicate only inside the living cells of other organisms. Often thought of as harmful, a wide range of viruses are capable of infecting all types of life forms such as humans, livestock, and plants. Yet on the positive side, there is growing interest to use viruses for a range of therapeutic purposes, including without limitation vaccine creation, gene therapy, and cancer treatments, to name a few. However, to study viruses, understand their structure, and adapt viruses for molecular tools and for disease therapy vectors and carriers, viruses first must be purified to remove any cell debris, macro-molecular fibers, organelles, lipids, and other impurities that would interfere with the intended function of the virus.

Once purified, viruses are suitable for a number of uses. One that is relevant to the current disclosure is the traditional notion of using the virus (considered a pathogen in this context) for study and development of genetic strategies against viruses. But discussed at further length in the present disclosure is the use of purified viruses as antigen carriers to prepare a vaccine. Antigens are molecules that, when appropriately delivered to an organism, are capable of producing an immune response in that organism, by stimulating the production of antibodies through binding with an antibody within the organism that matches the molecular structure of the antigen. Recombinant antigens are produced from recombinant DNA, which through known techniques is cloned into vectors which are then introduced into specific host cells, such as bacteria, mammalian cells, yeast cells, and plant cells, to name some. The recombinant antigen is then expressed using the host cell's translational apparatus. After expression, the recombinant antigen can be harvested and attached to a virus via covalent bonds, through a process known as conjugation. Following conjugation of the antigen to the virus, the virus can serve as a carrier to deliver the antigen to an organism and activate the immune system response. In this way, a virus-antigen conjugate can provide a therapeutic use. Proper virus-antigen conjugation is needed for the antigen to activate an immune response that produces antibodies in the host cells of a source organism. Purification of both the virus and antigen fosters this proper conjugation.

Current methods to purify viruses generally are limited for use in small biochemical quantities, e.g., on the order of nanograms to milligrams, and have not been proven in industrial quantities, which are on the order of grams to kilograms. For example, a previously used method known as "Crude Infected Cell Lysate" utilizes crude cell lysates or cell culture media from virus-infected cells. Infected mammalian cells are lysed by freeze-thaw or through other known methods, the debris is removed by low-speed centrifugation, and supernatants are then used for experimentation. The intact infected organisms are ruptured or ground physically, and the resulting extract is clarified using centrifugation or filtration to produce crude virus preparations. However, this method suffers from high contamination with many non-virus factors that impact the ability to conduct experimentation and manipulate the virus.

A second example of prior purification steps is high-speed ultracentrifugation, by which viruses are pelleted, or further purified through pelleting, via a low-density sucrose solution, or suspended in between sucrose solutions of various densities. Limitations of this method include production of purified viruses in only small quantities due to the limited size and scalability of high velocity separations, and poor virus purity due to additional host proteins often co-purifying with virus samples.

A third method previously used to enhance virus purity is density gradient ultracentrifugation. In this method, gradients of cesium chloride, sucrose, iodixanol or other solutions are used for separation of assembled virus particles or for removal of particles lacking genetic content. Limitations of this method include the time required to purify the virus (often 2-3 days), the limited number of samples, the amount of samples that can be analyzed at a time (generally 6 per rotor), and the small quantity of virus that can be purified (generally micrograms to milligrams of final product).

Organic extraction and poly-ethylene glycol precipitation also have been used to purify viruses, including viruses from plants, such as by removing lipids and chloroplasts. Again, however, these known methods suffer from poor purity, with products typically still attached to host proteins, nucleic acids, lipids, and sugars which result in significant aggregation of resulting virus products. These limitations reduce the utility of the final product for compliance with the Current Good Manufacturing Practice (cGMP) regulations enforced by the US Food and Drug Administration (FDA).

Current cGMP regulations promulgated by FDA contain minimum requirements for the methods, facilities, and controls used in manufacturing, processing, and packing of a drug product. These regulations are aimed at safety of a product and ensuring that it has the ingredients and strength it claims to have. Accordingly, for viruses to be utilized in vaccine creation, gene therapy, cancer treatments, and other clinical settings, the final viral product must comply with the cGMP regulations. If a final viral product does not comply with the cGMP regulations, like the product from the polyethylene glycol precipitation method, its utility for use in the clinical setting either does not exist or is greatly diminished.

Scalability refers to a process that consistently and reproducibly produces the same product even as the quantity of product increases, e.g., going from laboratory scale (<0.1 square meters) to at least systems>20 square meters. The methods previously used as identified above all suffer from a lack of consistency, low scalability (i.e., creates product only in biochemical quantities), and a lack of compliance with the cGMP regulations.

In terms of large-scale production, plant-based production has garnered attention, although prominent limitations exist with their use. Plant-based production systems are capable of producing industrial scale yields at much less cost than animal cell production systems such as Chinese Hamster Ovary (CHO). However, certain conventional purification methods, which have been appropriate at some scale for non-plant viruses, will not work for plant-made viruses and antigens. These limitations arise because of myriad differences in purifying plant viruses, as opposed to the purification of viruses from animal cell cultures. While animal cells produce primary protein and nucleic acid impurities, plants are also sources of significant and additional impurities not found in animal cells. Some of these include lipid composition of chloroplast membranes and vacuolar membranes, simple and complex carbohydrate impurities, and nanoparticulate organellar impurities. Indeed, crude plant extracts will often foul the equipment used in processing and purifying the viral and antigen matter obtained from plants, for example due to accumulation of impurities on the separation membranes of the equipment or media beds leading. Such fouling inevitably leads to pressure flow failure, poor filtration and ultimately poor yield of product. Another problem is these impurities have a tendency to aggregate and become capable of co-purifying within any protein, virus, or other "product" desired from a plant. Accordingly, current methods for purifying viruses will not adequately remove all or even a sufficient amount of impurities, including but not limited to impurities found in plant extracts and have not been shown to adequately produce purified viruses.

Few advances have been seen for virus and antigen purification platforms consistently capable of producing highly purified viruses on the commercial scale, i.e. grams to kilograms and higher, and in a manner that complies with the cGMP regulations. Such improvements would allow for the clinical development for using tools in vaccine creation, gene therapy, and for cancer treatments. Along with other features and advantages outlined herein, the platforms described herein according to multiple embodiments and alternatives meet this and other needs.

To date, seven coronaviruses (CoVs) have been identified as being capable of human infection, including severe acute respiratory syndrome coronavirus (SARS-CoV), Middle East respiratory syndrome coronavirus (MERS-CoV), and the newly identified CoV (SARS-CoV2, 2019-nCoV, or Covid-19), When in the human population, these three viruses pose significant public health risks and exhibit high fatality rates: SARS-CoV: 10%, MERS-CoV: 34.4% and SARS-CoV2: 6.1%. Currently, Covid-19 has spread to more than 188 countries, infected more than 10 million people, and has been attributed to more than 500,000 deaths worldwide. These numbers are growing exponentially and the outbreak has created a world-wide health and economic crisis. The emergence of Covid-19, and its effects on human health and the economy, demand an urgent response, particularly a vaccine for prevention of Covid-19 Disease. In spite of a global effort to find a vaccine to control or slow infections, no antiviral therapeutics are currently approved to target human coronavirus. Instead, the primary treatment remains supportive and palliative care.

The development of effective SARS-CoV and MERS-CoV vaccines has also been met with limited success. Many traditional vaccine strategies have been utilized including inactivated virus, recombinant attenuated viruses, other live viral vectors, subunit vaccines or individual viral proteins expressed from DNA plasmids or RNA delivery systems. Traditional SARS vaccines have primarily focused on the Spike (5) protein due to its functionality in human receptor binding, membrane fusion, and viral entry. Furthermore, the S protein is the major antigen of coronaviruses and is the binding site of protective neutralizing antibodies that block virus receptor binding and initiation of infection. Although inactivated SARS-CoV preparations utilizing full-length S proteins induced neutralizing antibodies in immunized animals, these conventional vaccines were not as effective in humans and have been found to raise significant safety concerns (e.g. by actually enhancing viral infection in many systems). Likewise, while many different SARS and MFRS vaccines have been developed and tested, all have shown protection from infection through virus neutralization without accompanying immunopathology associated with full-length or trimerized S protein vaccines.

It will be appreciated that different viral vectors are known as carriers for a range of antigens, providing effective therapeutic delivery to a host organism, e.g., a mammal, such as a human. Such viral vectors tend to vary, however, in terms of an immune responses elicited by the vector separate from the particular antigen being delivered. For example, some viral vectors, such as the ERVEBO® Ebola Zaire Vaccine, are live viruses, which stimulate a response by the host's immune system. The response from the viral vector itself, however, in many cases will blunt the intended immune response to an antigen delivered by the viral vector, for example by showing immune dominance of the one antigen thereby preventing a response during later administration of the same or similar vaccine. Advantageously, it has been found that antigens of the present disclosure can be conjugated with a TMV NtK vector without the latter stimulating the host's immune response, without showing immune dominance of one antigen, and without affecting later dose administration for subsequent vaccines using the same viral vector. Also, avoiding such an immune response, caused by the viral vector itself, provides further advantages for bivalent, trivalent, and quadrivalent vaccines because the response for each antigen can be assessed without having to account for effects of the viral vector, both in the current administration of the vaccine as well as future administrations.

Accordingly, there is a significant, urgent, and global need for an effective and scalable vaccine strategy for the prevention of Covid-19 Disease which both elicits high levels of neutralizing antibodies and induces long lasting, potent neutralizing antibody titers for long periods after immunization. Along with other features and advantages outlined herein, the platforms described herein according to multiple embodiments and alternatives meet this and other needs. In doing so, a vaccine in accordance with present embodiments has exhibited strong immune responses in pre-clinical studies, has the ability to conjugate to multiple CoV antigens at once (i.e. a multivalent vaccine) which is a significant advantage over conventional monovalent vaccines, elicits high levels of neutralizing antibodies, and likely induces long lasting, potent neutralizing antibody titers for long periods after immunization.

SUMMARY OF EMBODIMENTS

In some embodiments according to the present disclosure, a virus purification method is directed to a multi-set process that comprises harvesting from a source organism virus material containing at least one virus; removing cellular debris from the at least one virus thereby clarifying the structure of the at least one virus; concentrating the separated and clarified virus which in some embodiments is performed with a filtration device comprising a membrane with pores of a size not to exceed a predetermined limit as selected by a user; and processing the concentrated virus by subjecting it to a series of separation procedures and collecting the virus after each separation procedure, wherein at least one separation procedure includes ion-exchange chromatography to separate host cell contaminants from the virus, and at least one separation procedure includes a multi-modal chromatography to separate residual impurities from the virus on the basis of at least size differences between the virus and the impurities, and chemical interaction occurring between the impurities and one or more chromatography ligands. In some embodiments, a plant is the source organism undergoing recombinant expression of a virus, with *Nicotiana benthamiana* and *Leinna minor* as non-limiting examples. When the source organism is a plant, harvesting may include seed production and plant germination with inducement of transient gene expression to from a desired protein, as discussed below. Alternatively, the source organism undergoing recombinant expression of a virus is a non-plant host such as, without limitation, bacterial, alga yeast, insect, or mammalian organisms.

Additionally, various aspects of multiple embodiments described herein are directed to producing or purifying, or both, an antigen which can be conjugated with a virus particle. In the present embodiments and alternatives, a virus particle includes without limitation, one of, some of, or all of viruses and/or fragments thereof, such as rod-shaped viruses, icosahedral viruses, enveloped viruses, and fragments of one or more of the foregoing. In some embodiments, a plant is the source organism undergoing recombinant expression of antigen; alternatively, the source organism undergoing recombinant expression of antigen is a non-plant host such as, without limitation, bacterial, algal, yeast, insect, or mammalian organisms.

Advantageously, a multi-set process practiced according to various embodiments described herein produces highly purified viruses or recombinant antigens, or both, on a commercial scale. Various steps are employed to improve the upstream purification processes, such as enriching plant viruses. Some embodiments utilize size exclusion chromatography, as well as other features, to produce purified recombinant viruses and recombinant antigens. Accordingly, various embodiments described herein provide one or more viruses and one or more antigens suitable for the preparation of one or more vaccines of conjugated virus and antigen.

With regard to viruses, through the practice of some embodiments of an inventive virus purification platform described herein, purification of rod-shaped plant viruses (such as tobacco mosaic virus, i.e., "TMV") and icosahedral plant viruses (such as red clover mosaic virus) has been achieved. According to multiple embodiments herein, purification of TMV and red clover mosaic virus was achieved, representing two structurally diverse viruses in terms of size and structure. For example, a smaller icosahedral virus like red clover mosaic virus has T=3 symmetry, dimensions of approximately 31-34 nm, and approximately 180 capsid proteins. Conversely, TMV is approximately 18 nm in diameter, 300 nm in length and contains 2160 capsid proteins. In view of this diversity, the inventive process has worked based on two structurally different viruses to allow virus passage into the permeate while retaining unwanted cellular debris. In use, operational parameters can be controlled so all types of viruses both pass into the permeate, while chlorophyll/cellular debris are retained, and the tangential flow (TFF) system continues to operate efficiently without unduly or untimely becoming fouled. Additional TFF steps are designed to retain virus while allowing smaller proteins to pass into the permeate, and dual chromatography steps are controlled to exclude viruses both large and small, while capturing host cell proteins, host cell DNA, endotoxin, and plant polyphenolics.

Based upon the successful purification of red clover mosaic virus and TMV, it is expected that the virus purification platform according to multiple embodiments and alternatives can successfully purify a wide array of virus particles including: viruses comprising a range of genetic materials (e.g. double- and single-stranded DNA viruses, and RNA viruses), geometries (e.g. rod-shaped, flexious rods, and icosahedral), and families (Caulimoviridae, Geminiviridae, Bromoviridae, Closteroviridae, Comoviridae, Potyviridae, Sequiviridae, Tombusviridae).

Non-limiting viruses upon which the embodiments described herein are expected to succeed include those of the genuses Badnavirus (e.g. commelina yellow mottle virus); Caulimovirus (e.g. cauliflower mosaic virus); SbCMV-like viruses (e.g. Soybean chlorotic mottle virus); CsVMV-like viruses (e.g. Cassava vein mosaicvirus); RTBV-like viruses rice tungro bacilliformvirus); petunia vein clearing-like viruses (e.g. petunia vein clearing virus); Mastrevirus (Subgroup I Geminivirus) (e.g. maize streak virus) and Curtovirus (Subgroup II Geminivirus) (e.g. beet curly top virus) and Begomovirus (Subgroup III Geminivirus) (e.g. bean golden mosaic virus); Alfamovirus (e.g. alfalfa mosaic virus); Ilarvirus (e.g. tobacco streak virus); Bromovirus (e.g. brome mosaic virus); Cucumovirus (e.g. cucumber mosaic virus); Closterovirus (e.g. beet yellows virus); Crinivirus (e.g. Lettuce infectious yellows virus); Comovirus (e.g. cowpea mosaic virus); Fabavirus (e.g. broad bean wilt virus 1); Nepovirus (e.g. tobacco ringspot virus); Potyvirus (e.g. potato virus Y); Rymovirus (e.g. ryegrass mosaic virus); Bymovirus (e.g. barley yellow mosaic virus); Sequivirus (e.g. parsnip yellow fleck virus); Waikavirus (e.g. rice tungro spherical virus); Carmovirus (e.g. carnation mottle virus); Dianthovirus (e.g. carnation ringspot virus); Machlomovirus (e.g. maize chlorotic mottle virus); Necrovirus (e.g. tobacco necrosis virus); Tombusvirus (e.g. tomato bushy stunt virus); Capillovirus (e.g. apple stem grooving virus); Carlavirus (e.g. carnation latent virus); Enamovirus (e.g. pea enation mosaic virus); Furovirus (e.g. soil-borne wheat mosaic virus); Hordeivirus (e.g. barley stripe mosaic virus); Idaeovirus (e.g. raspberry bushy dwarf virus); Luteovirus (e.g. barley yellow dwarf virus); Marafivirus (e.g. maize rayado fino virus); Potexvirus (e.g. potato virus X and clover mosaic viruses); Sobemovirus Southern bean mosaic virus); Tenuivirus (e.g. rice stripe virus); Tobamovirus (e.g. tobacco mosaic virus); Tobravirus (e.g. tobacco rattle virus); Trichovirus (e.g. apple chlorotic leaf spot virus); Tymovirus (e.g. turnip yellow mosaic virus; and Umbravirus (e.g. carrot mottle virus).

The successful virus purification has been accomplished on the commercial scale, and in a manner that complies with the cGMP regulations. In some embodiments, the source organism is a plant, but while some variations of present embodiments include production of plant-based viruses, the embodiments described herein are not limited to the manufacture or the purification of viruses in plants. In some embodiments, a virus purification platform begins by growing plants in a controlled growth room, infecting the plants with virus replication, recovering the viruses by rupturing the cells with a disintegrator and removing the plant fiber from the liquid via a screw press.

In some embodiments, involving both plant-based and non-plant viruses, purification steps include concentrating the clarified extract using tangential flow system, wherein the cassette pore size, transmembrane pressure, and load of clarified extract per square meter of membrane surface area are controlled. Transmembrane pressure (IMP) is the pressure differential between the upstream and downstream sides of the separation membrane and is calculated based on the following formula; ((feed pressure+retentate pressure)/2)–permeate pressure. To ensure passage of the viruses through the ceramic to create a clarified extract, in some embodiments the feed pressure, the retentate pressure, and the permeate pressure are each controlled to obtain an appropriate TMP. The clarified extract is concentrated further with an ion-exchange column volume and washed with ion-exchange chromatography equilibration buffer. In some embodiments, a Capto Q ion-exchange column is equilibrated and the feed is loaded and collected in the flow-through fraction. The column is then washed to baseline and the host cell contaminants are stripped from the column with high salt.

In some embodiments associated with plant-based viruses, an extraction buffer is added before removing chlorophyll and other large cellular debris such as macromolecular fibers, organelles, lipids, etc. using tangential flow ceramic filtration. In some embodiments, ceramic filtration promotes the retention of chlorophyll from plant hosts, cell debris, and other impurities while optimizing for virus passage. Whether for plant-based or non-plant viruses, this approach—wherein the desirable matter (virus or antigen) passes through as permeate and impurities are retained as retentate—promotes the scalability of the process. Additionally, parameters such as transmembrane pressure, ceramic pore size, and biomass loaded per square meter are all controlled to ensure passage of the virus through the ceramic to create a clarified extract. Ceramic TFF systems are highly scalable and parameters such as TMP, cross flow velocity, pore size, and surface area can be scaled readily to accept larger amounts of biomass. Additional ceramic modules are easily added to the system. Feed, retentate, and permeate pressure can also be controlled to maintain efficient cross flow velocity allowing little to no fouling of system. In some embodiments, cross velocity and pressure differential are set and controlled to produce a TMP of approximately 10-20 psi allowing for efficient passage of virus at smaller and larger scales. Ceramic TFF systems are amenable to using highly efficient cleaning chemicals such as nitric acid, bleach, and sodium hydroxide allowing for cleaning studies to be performed addressing GMP and/or cGMP requirements.

Whether for plant-based or non-plant viruses, a purification method according to multiple embodiments and alternatives, and otherwise consistent with the development of scalable and high-throughput methods for purifying viruses, utilizes at least one separation procedure using multi-modal chromatography to separate residual impurities from a virus on the basis of at least size differences between the virus and the impurities, and chemical interaction occurring between the impurities and one or more chromatography ligands. For example, conducting the at least one separation procedure with Capto® Core 700 chromatography resin (GE Healthcare Bio-Sciences) is included within the scope of embodiments. The Capto® Core 700 'beads' comprises octylamine ligands designed to have both hydrophobic and positively charged properties that trap molecules under a certain size, e.g. 700 kilodaltons (kDA). Because certain viruses are fairly large (e.g. greater than 700 kDA), and the bead exteriors are inactive, Capto® Core 700 permits purification of viruses by size exclusion, wherein the desirable matter (virus or antigen) passes through as permeate and impurities are retained as retentate.

In some embodiments, again for plant-based and non-plant viruses alike, prior to the multi-modal chromatography column, equilibration is performed with five column volumes of equilibration buffer. In some embodiments, the combined flow-through and wash fractions from Capto Q ion-exchange chromatography are loaded onto the multi-modal chromatography column and the virus is collected in the void volume of the column. The column is washed to baseline and stripped with high conductivity sodium hydroxide. Aspects of some embodiments provide for controlling the loading ratio, column bed height, residence time, and chromatography buffers during this step.

The purified virus is sterile filtered, for example with diafiltration, and stored.

With regard to antigens, through the practice of some embodiments of an inventive antigen purification platform described herein, the recombinant antigens H5 recombinant influenza hemagglutinin (rHA), H7 rHA, domain III of West Nile virus (WNV rDIII), and lassa fever virus recombinant protein 1/2 (LFV rGP1/2), H1N1 (Influenza A/Michigan), H1N1 (Influenza A/Brisbane), H3N2 (Influenza A/Singapore), H3N2 (Influenza A/Kansas), B/Colorado, B/Phuket, RBD-Fc 121 (receptor binding domain (RBD, S1 domain) of the SARS-2 spike glycoprotein fused to a human IgG1 Fc domain (herein "RBD-Fc 121" refers an amino acid sequence of the SARS-2 spike protein as explained in further detail below)), and RBD-Fc 139 (herein "RBD-Fc 139" refers to a different amino acid sequence of the SARS-2 spike protein, as explained below) have been produced and purified. Antigens for various embodiments herein can be from many sources, and may be produced using traditional recombinant protein manufacturing strategies, including bacterial, yeast, insect, mammalian or plant-based expression approaches.

In some embodiments, an antigen manufacturing platform begins by growing plants in a controlled growth room, infecting the plants for recombinant antigen replication, then antigen recovery using a disintegrator followed by removal of fiber from the aqueous liquid via a screw press. An extraction buffer is added to assist in removal of chlorophyll (in the plant context) and large cellular debris by filtration. Whether for plant-based or non-plant antigen, feed pressure, filtrate pore size, clarifying agent, and biomass loaded per square meter of membrane surface are controlled to facilitate passage of the antigens through the filter. A description (though non-limiting) of various in-process controls suitable for achieving large scale virus and antigen purification is expressed in further detail in the Examples section.

In some embodiments, both plant-based and non-plant antigens alike, clarified extract is next concentrated with a tangential flow system. During this optional step, factors including cassette pore size, transmembrane pressure, and load of clarified extract per square meter of membrane surface are controlled. In some embodiments, the optional step is skipped entirely. Following this, clarified extract is next concentrated and washed with an ion-exchange chromatography equilibration buffer. One way for this step to be undertaken is by loading feed onto an equilibrated Capto Q ion-exchange column, followed by washing with equilibration buffer and eluting/stripping with salt. Antigen fractions are then collected in the elution and prepared for cobalt immobilized metal affinity chromatography (IMAC). The IMAC is equilibrated, the feed is loaded, then washed with equilibration buffer and eluted. The elution fraction is diluted and checked for pH, then loaded onto a multi-modal ceramic hydroxyapatite (CHT) chromatography column. The CHT resin is equilibrated with equilibration buffer and the antigens are eluted. Loading ratio, column bed height, residence time, and chromatography buffers are among factors being controlled. Lastly, the antigen is concentrated and diafiltered with a saline buffer. The recombinant antigen is sterile filtered and then stored.

Still further, in accordance with various embodiments disclosed herein, the following monovalent formulations have been successfully conjugated: H7 rHA to TMV, H1N1 (Influenza A/Michigan) to TMV, H3N2 (Influenza A/Singapore) to TMV, B/Colorado to TMV, B/Phuket to TMV, RBD-Fc 121 (SARS-2) to TMV, and RBD-Fc 139 (SARS-2) to TMV. In accordance with the various embodiments herein, the bivalent formulation of TMV to two Influenza B viruses (B/Colorado and B/Phuket) has also been successfully conjugated, as well as the quadrivalent conjugation of TMV to H1N1 (Influenza A/Michigan), H3N2 (Influenza A/Singapore), B/Phuket, and B/Colorado. A "quadrivalent" influenza vaccine is designed to protect against four different influenza viruses: two influenza A viruses and two influenza B viruses. For many years, trivalent vaccines were commonly used, but now quadrivalent vaccines are the most common because they may beneficially provide broader protection against circulating influenza viruses by adding another B virus. Herein, the term "multivalent" vaccine refers to more than one antigen conjugated to a virus. In some embodiments, the protein consists of any type of therapeutic agent capable of being conjugated to a virus to create a vaccine, and then delivered to a source organism to produce an immune response according to multiple embodiments and alternatives. Accordingly, the disclosures herein provide compositions comprising an array of virus-protein conjugates, including virus-antigen conjugates. In some embodiments, the virus selected is TMV, or any of a number of viruses identified and/or indicated by the teachings herein. Additionally, in some embodiments the protein can be an antigen, such as but not limited to influenza hemagglutinin antigen (HA), including without limitation ones listed in this paragraph including as soluble forms of HA proteins found on a surface of an influenza virus that mediates virus infection. In some embodiments, the HA exhibits at least about 50% trimer formation. HAs are clinically important because they tend to be recognized by certain antibodies an organism produces, providing the main thrust of protection against various influenza infections. Because HA antigenicity and, therefore, HA immunogenicity are tied to conformation, it is known that HA trimerization is advantageous over the monomeric form in terms of triggering immune responses.

In some embodiments, conjugation begins by concentrating and diafiltering purified antigen and virus into a slightly acidic buffer. The antigen and virus are then combined based upon molarity and mixed. A freshly prepared water-soluble carbodiimide, such as 1-ethyl-3-(3-dimethylaminopropyl) carbodiimide (also known as EDC) is added to the mixture while mixing based upon molarity. A chemical reagent for converting carboxyl groups to amine reactive N-hydroxysulfosuccinimide esters, such as ThermoFisher's Sulfo-NHS, is then added based upon molarity. The reaction is continued until a predetermining stop time. The reaction is then quenched, with one exemplary involving the addition of an amine group (e.g., liquid containing free amines) and any chemical linker(s) used in facilitating the reaction (e.g., EDC, Sulfo-NHS) is removed through a multi-modal chromatography step or diafiltration, with the mixture then being diluted to target concentration. In some embodiments, the conjugated and purified virus particles that are decorated with proteins and antigens may be used for vaccines and/or diagnostic tools. These particles may be used as diagnostic tools because of their ability to track antigens in the host organism.

In some embodiments, the purified virus—antigen fusion may be derived from genetic fusion, in addition to the various embodiments disclosed herein. The antigen and virus structural proteins (located in the coat) form a single continuous open reading frame. In some embodiments, the reading frame produces an antigen-coat protein in a plant such that the coat protein self assembles into virus particles. Next, the plant materials are harvested and the virus particles are purified according to the embodiments disclosed herein. The virus particles decorated with the fusion-coat proteins may then be used as a vaccine and/or a diagnostic tool according to the various embodiments disclosed.

Some viruses as icosahedral viruses as a non-limiting example) swell under certain pH conditions and in some embodiments this "swelling" may be used for conjugation. According to multiple embodiments and alternatives, the purified virus may be conjugated to a therapeutic agent by subjecting the virus structure to acidic pH conditions that cause the virus to "swell." By treating the virus structure with neutral pH conditions, the virus structure relaxes and creates pores between pentamer or other structural subunits of the virus. Next, a therapeutic agent (such as a chemotherapeutic agent), is added to the buffer and allowed to diffuse into the relaxed virus particle. By changing the pH again, the virus particles tighten and remove the pore structures packing the pentamer or structural submits together such that chemical diffusion in or out of the virus particle is prevented. Next, the plant materials are harvested, the virus particles are purified, and the virus particles containing a therapeutic agent are used for drug delivery, according to the embodiments disclosed herein.

Accordingly, multiple embodiments and alternatives encompass production of one or more highly purified viruses. Still further, multiple embodiments and alternatives encompass production or purification or both of a recombinant antigen. Still further, multiple embodiments and alternatives encompass conjugation of purified antigens and viruses for use as vaccines. Indeed, in pre-clinical studies, TMV-platform vaccines produced in accordance with the embodiments described herein stimulated efficacious immune responses against a number of pathogens, comprising both viral and antibacterial systems. Further, vaccines produced on the inventive TMV-platform demonstrate the ability to conjugate to multiple coronavirus (CoV) antigens at once (i.e. a multivalent vaccine) to stimulate efficacious immune responses. This provides a significant advantage over conventional monovalent vaccines, including through the application of these vaccines against Covid-19 Disease and influenza (as non-limiting examples). The purification of viruses may be practiced by itself in accordance with the present embodiments. Likewise, the production or purification of recombinant antigens may be practiced alone in accordance with the present embodiments. Optionally, as well, different aspects of these multiple embodiments can be combined, in which combining embodiments would include, among other ways of practicing these embodiments, starting with one or more source organisms, from which are produced one or more viruses and one or more antigens, then purifying such viruses and antigens, then forming vaccines which are conjugates between at least one antigen and at least one virus.

BRIEF DESCRIPTION OF THE FIGURES

The drawings and embodiments described herein are illustrative of multiple alternative structures, aspects, and features of the multiple embodiments and alternatives disclosed herein, and they are not to be understood as limiting the scope of any of these embodiments and alternatives. It will be further understood that the drawing figures described and provided herein are not to scale, and that the embodiments are not limited to the precise arrangements, depictions, and instrumentalities shown.

FIG. 63(A) illustrates the Th1 response (IgG2a and IgG2c) associated with the analysis, FIG. 63(B) illustrates the Th2 response (IgG1) associated with the analysis, and FIG. 63(C) is a stack plot comparison of relative IgG2 versus IgG1 antibody response by an ELISA analysis.

FIG. 64 is a graph illustrating the cell viability after incubation with SARS2 virus with murine sera, according to multiple embodiments and alternatives.

FIG. 68(A) is a graph showing results on the viability of macrophages exposed to nucleocapsid and spike proteins of SARS-2 with non-inventive antibodies added, as an indicator of antibody enhancement of disease. FIG. 68(B) is a graph of mouse sera containing antibodies, which were generated from TMV:RBD-Fc vaccines according to multiple embodiments and alternatives, following exposure to nucleocapsid and spike proteins of SARS-CoV2. FIG. 68(C) shows statistical differences applicable to the graphs in FIGS. 68(A-B).

FIG. 71 illustrates the receptor binding domain of the spike protein sequence alignment of SARS-2 and other related coronaviruses.

MULTIPLE EMBODIMENTS AND ALTERNATIVES

A multi-set process according to multiple embodiments and alternatives herein improves upstream purification processes, further enriching plant viruses, and facilitates the conjugation of virus and antigen to form a vaccine. Steps for producing and purifying a virus in accordance with multiple embodiments and alternatives are listed and discussed in connection with Table 1 and FIG. 1. Likewise, steps for producing and purifying an antigen are listed and discussed in connection with Table 2. Although the various platforms have a specific embodiment described for them below, the scope of the embodiments contained herein are not limited to any one specific embodiment.

Virus Production and Purification

Figure 1:
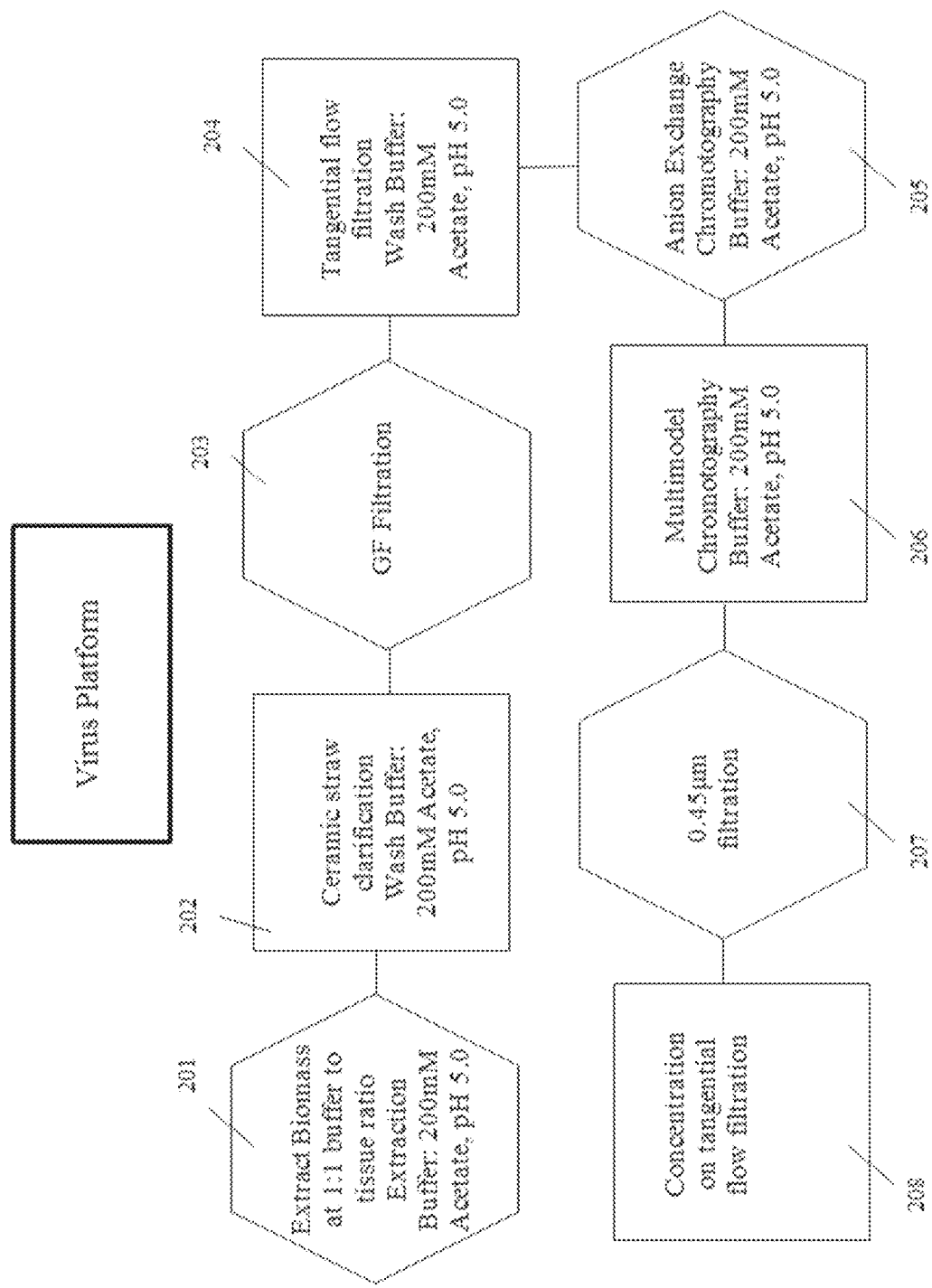
FIG. 1 is a flow chart showing the steps in a certain virus purification platform within the scope of the present disclosure, according to multiple embodiments and alternatives.

Table 1 and FIG. 1 illustrate the steps of the virus purification platform according to multiple embodiments and alternatives.

TABLE 1

Production and Purification of Virus

| Operative Steps | Unit Operations | In-Process Controls | In-Process Analytics |
|---|---|---|---|
| 1 | Plant Growth (25 DPS) Nb | Irrigation, Light Cycle, Fertilizer, Media, Humidity, Temperature | Plant Height, structure and leaf quality |
| 2 | Infection with virus | Inoculum Concentration, Rate of Application | N/A |
| 3 | Viral Replication (7 DPI) Plant Growth | Irrigation, Light Cycle, Humidity, Temperature | N/A |
| 4 | Harvest of Aerial Tissue | Visual Inspection of Plants | N/A |
| 5 | Disintegration of Plant Cells (Extraction) | Blade Type and RPM, Screen Sizes, Buffer:Tissue Ratio | pH, Conductivity, SDSPage, Endotoxin, Nicotine |
| 6 | Clarification of Plant Extract | Ceramic Size, TMP, kg/m$^2$ | pH, Conductivity, SDSPage, Endotoxin, Nicotine |
| 7 | Concentration of Clarified Plant Extract | Pore Size, TMP, Pore Material, kg/m$^2$ | pH, Conductivity, SDSPage, Endotoxin, Nicotine |
| 8 | Ion-Exchange Chromatography | kg/L, Bed Height, Residence Time | pH, Conductivity, SDSPage, Endotoxin, Nicotine |
| 9 | Multi-Modal Chromatography | kg/L, Bed Height, Residence Time | pH, Conductivity, SDSPage, Endotoxin, Nicotine |
| 10 | Concentration of Purified Virus | Pore Size, TMP, Pore Material, kg/m$^2$ | UV260, TEM, DLS, SDSPage, Endotoxin, Nicotine, Amino Acid |

This purification platform is designed for commercial scalability and compliance with the cGMP regulations and utilizes one buffer throughout the entire purification process. According to multiple embodiments and alternatives, the steps of the virus purification platform are given in connection with plant expression. However, steps after the aerial tissue harvesting and cell rupture as described below also would apply to non-plant viruses (except where context is clearly related to plants, e.g., reference to oval of plant fiber).

In accordance with multiple embodiments and alternatives described herein, virus expression is accomplished through methods that are appropriate for a particular host. In some embodiments, virus-based delivery of genes to a plant host is accomplished with a modified TMV expression vector that causes tobacco plants to recombinantly form the virus. One such available alternative is the GENEWARE® platform described in U.S. Pat. No. 7,939,318, "Flexible vaccine assembly and vaccine delivery platform." This transient plant-based expression platform described in this patent employs the plant virus TMV to harness plant protein production machinery, which expresses a variety of viruses in a short amount of harvest time post inoculation (e.g., less than 21 days). Tobacco plants inoculated with the virus genes express the particular virus in infected cells, and the viruses are extracted at harvest. Inoculation occurs by, as examples to be selected by a user of the methods herein described, hand inoculation of a surface of a leaf, mechanical inoculation of a plant bed, a high-pressure spray of a leaf, or vacuum infiltration.

Besides *Nicotiana benthamiana*, other plant and non-plant hosts are contemplated by this disclosure, including those mentioned in the Summary. Besides the GENEWARE® platform, other strategies can be employed to deliver genes to plant (*Lemna gibba* or *Lemna minor* as non-limiting examples) and non-plant organisms (algae as a non-limiting example). These other strategies include Agro-infiltration, which introduces the viral gene via an *Agrobacterium* bacterial vector to many cells throughout the transfected plant. Another is electroporation to open pores in the cell membranes of the host to introduce the genes that recombinantly produce the viruses and antigens such as but not limited to those described in Examples 1 and 3 below. Another is TMV RNA-based overexpression (TRBO) vector, which utilizes a 35S promotor-driven TMV replicon that lacks the TMV coat protein gene sequence, as described in John Lingo, "TRBO: A High-Efficiency Tobacco Mosaic Virus RNA-Based Overexpression Vector," Plant Physiol. Vol. 145, 2007.

In some embodiments, growth of *Nicotiana benthamiana* wild type plants occurs in a controlled growth room. Plant growth is controlled via irrigation, light, and fertilized cycles. Plants are grown in a soilless media and temperature is controlled throughout the process.

After an appropriate number of days post sow (DPS), for example 23-25 DPS, the plants are infected with the virus replication. After infection, the plants are irrigated with water only and controlled via light cycle and temperature for a certain number of days post infection (DPI) depending on the type of virus.

Plants are inspected for height, infection symptoms, and the aerial tissue is harvested.

Virus recovery/cell rupture involves a disintegrator configured with an optimized blade/screen size followed by removal of residual cellulosic plant fiber from aqueous liquid (such as through a screw press, as one example).

An appropriate extraction buffer (e.g., 200 mM Sodium Acetate, pH 5.0; step 201 of FIG. 1 as a non-limiting example) is added to the resulting extract at a 1:1 buffer:tissue ratio. Removal of chlorophyll and large cellular debris at pilot scale involves the use of tangential flow (TFF) ceramic filtration (1.4 micron/5.0 micron). Transmembrane pressure, ceramic pore size and biomass loaded per square meter of membrane surface are all controlled to ensure passage of the virus through the ceramic. In some embodiments, the feed pressure, retentate pressure, and permeate pressure are set and controlled to produce a resulting transmembrane pressure in a range of about 1.5-2 Bar TMP.

Ceramic permeate is further clarified via the use of glass fiber depth filtration (step 203 of FIG. 1 as a non-limiting example).

Clarified extract is concentrated with a TFF system (available from Sartorius AG). Cassette pore size (100-300 kDa), an appropriate IMP as described herein, and load of clarified extract per square meter of membrane surface area are controlled.

The clarified extract is concentrated to NMT 2× the ion-exchange column volume and washed 7× with ion-exchange chromatography equilibration buffer (200 mM Sodium Acetate, pH 5.0, step 204 of FIG. 1 provides a non-limiting example). The Capto Q ion-exchange column is equilibrated for five column volumes with 200 mM Sodium Acetate, pH 5.0 (step 205 of FIG. 1 provides a non-limiting example), and the feed is loaded and collected in the flow-through fraction. The column is washed to baseline and host cell contaminants are stripped from the column with high salt.

The flow through and wash fractions are collected, combined and prepared for multi-modal Capto® Core 700 chromatography. The multi-modal chromatography column is equilibrated with five column volumes of equilibration buffer (200 mM Sodium Acetate, pH 5.0; step 206 of FIG. 1 provides a non-limiting example).

The combined flow-through and wash fractions from Capto Q ion-exchange chromatography are loaded onto the column and the virus collected in the void volume of the column. The column is washed to baseline and stripped with high conductivity sodium hydroxide. Loading ratio, column bed height, residence time and chromatography buffers are all controlled. Formulation and concentration of virus (step 208, FIG. 2) takes place in some embodiments with a TFF System (such as the Sartorius AG system). Pore size (30-300 kDa), an appropriate TMP as described herein, load per square meter of membrane surface area and pore material are all controlled. Virus is concentrated to an appropriate concentration, such as 10 mg/ml, and in some embodiments is diafiltered with an appropriate buffer, such as Sodium Phosphate. Formulated virus is sterilized and stored appropriately. In some embodiments, sterilization is provided via a PES filter.

All examples provided herein are meant as illustrative of various aspects of multiple embodiments and alternatives of any or all of virus production, virus purification, antigen production, antigen purification, and virus-antigen conjugation. These examples are non-limiting and merely characteristic of multiple alternative embodiments herein.

Example 1—Purification of Icosahedral Red Clover Mosaic Virus

Figure 2:
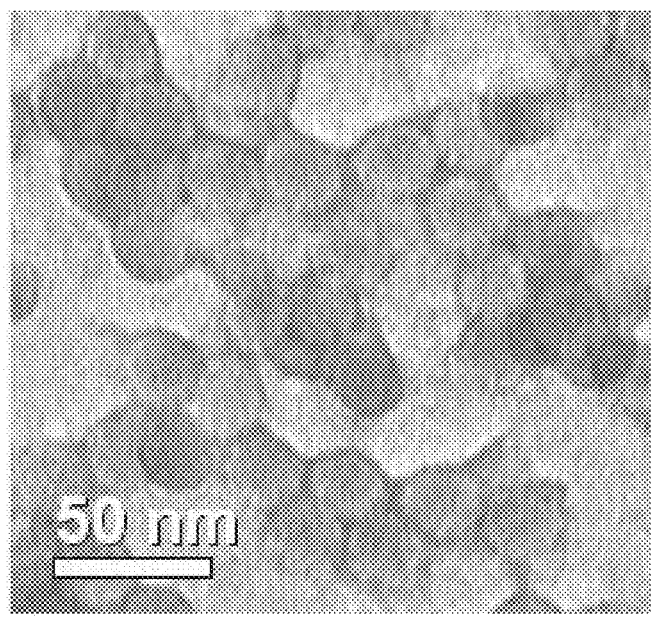
FIG. 2 is purified icosahedral red clover mosaic virus, according to multiple embodiments and alternatives.
Figure 3:
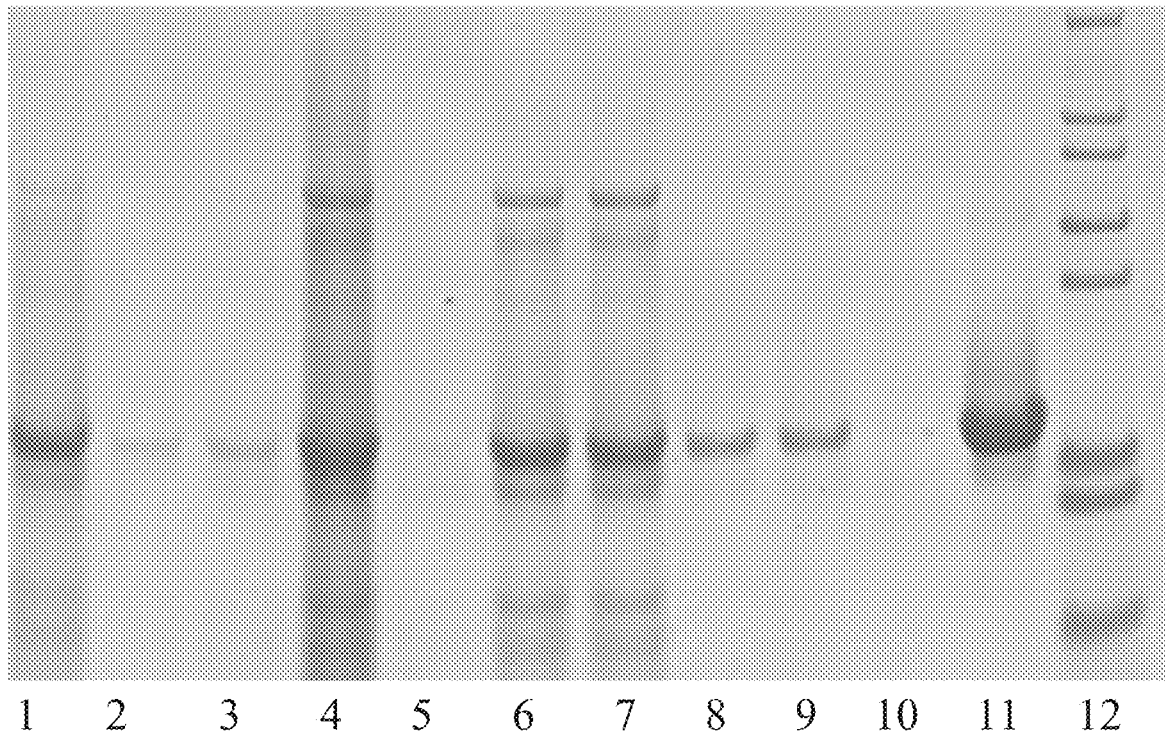
FIG. 3 is a western blot analysis of the purification of the icosahedral red clover mosaic virus, according to multiple embodiments and alternatives.
Figure 4:
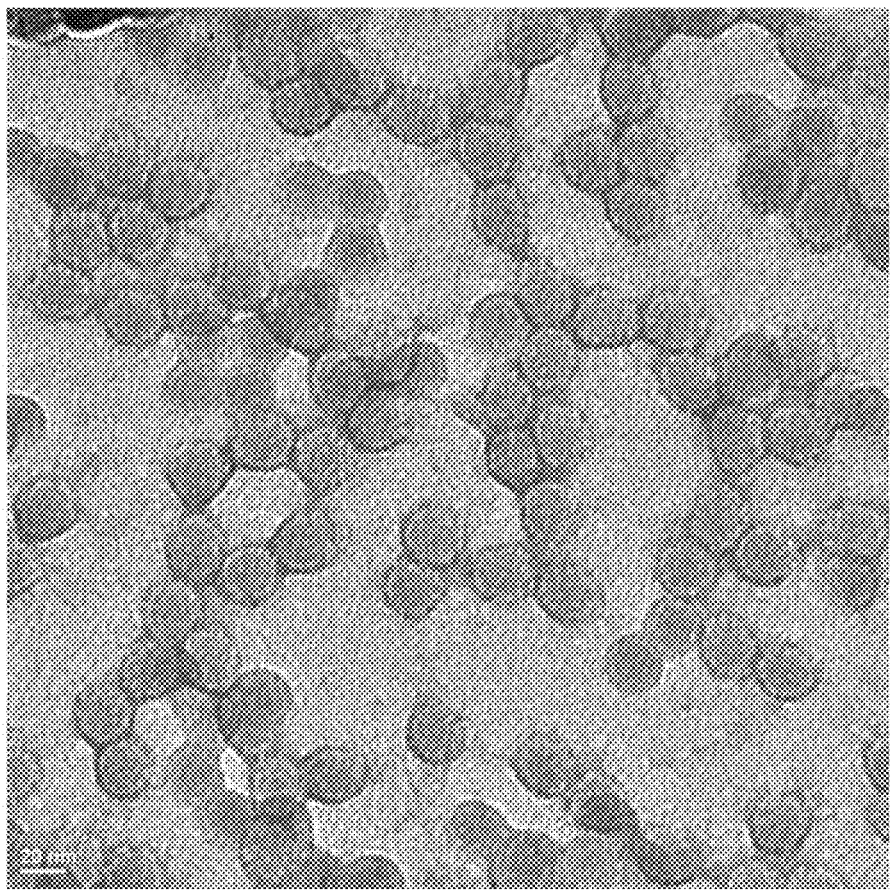
FIG. 4 is purified icosahedral red clover mosaic virus, according to multiple embodiments and alternatives.
Figure 5:
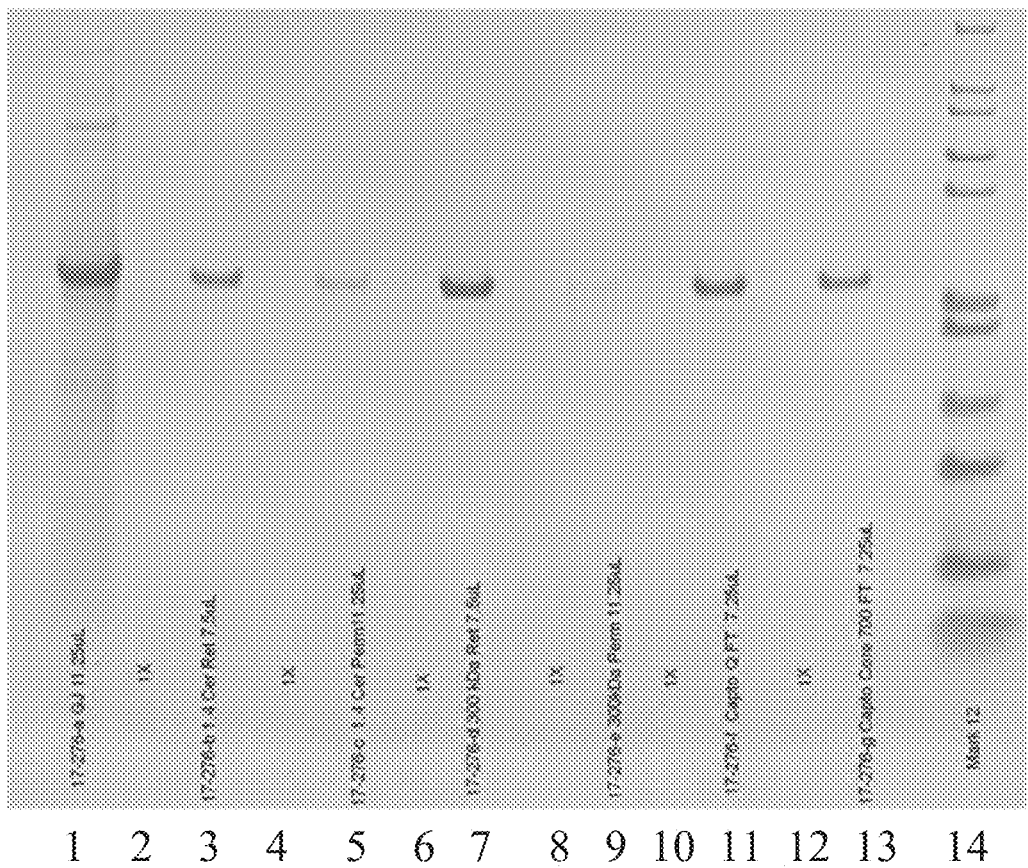
FIG. 5 is a western blot analysis of the purification of the icosahedral red clover mosaic virus, according to multiple embodiments and alternatives.

The Western Blot, provided in FIG. 3 as a known technique for detecting various proteins in a mixture, shows successful purification of the icosahedral red clover mosaic virus illustrated in FIG. 2. Similarly, the Western Blot in FIG. 5 shows successful purification of the icosahedral red clover mosaic virus illustrated in FIG. 4. Both viruses were purified according to the embodiments described herein. In accordance with the known detection technique, target proteins were extracted from the tissue. Then proteins of the sample were separated using gel electrophoreses based on their isoelectric point, molecular weight, electrical charge, or various combinations of these factors. Samples were then loaded into various lanes in the gel, with a lane reserved for a "ladder" containing a mixture of known proteins with defined molecular weights. For example, in FIG. 3, lane 12 serves as the ladder. A voltage was then applied to the gel, causing the various proteins to migrate through the gel at different speeds based on the aforementioned factors. The separation of the different proteins into visible bands within each lane occurred as provided in FIGS. 3 and 5, respectively. With the Western Blot, a purer product is characterized by a clear and visible band, and such is characterized in these figures.

FIGS. 3 and 5 illustrate the virus purification platform successfully purifying the icosahedral red clover mosaic virus. Each lane of the western blot shows the purity of the virus after the conclusion of a different step in the virus purification platform. In FIG. 3, the lanes include: lane 1—green juice, lane 2—TFF Ceramic Clarification Retentate, lane 3—TFF Ceramic Clarification Permeate, lane 4 TFF Cassette Retentate, lane 5—TFF Cassette Permeate, lane 6—ion Exchange, lane 7—Ion Exchange, lane 8—multimodal, lane 9—multimodal, lane 10—30TFF Permeate, lane 11—30K Retentate, lane 12—marker. In FIG. 5, the lanes of the western blot include the following: lane 1—Green Juice, lane 3—TFF Ceramic Clarification Retentate, lane 5—TFF Ceramic Clarification Permeate, lane 7—TFF Cassette Retentate, lane 9—TFF Cassette Permeate, lane 11—ion Exchange, lane 13—Multimodal, and Lane 14—Marker.

Once the final step has occurred in the virus purification platform, the resulting viral product is highly purified, as shown by the visible band in lane 11 of FIG. 3 and lane 13 of FIG. 5.

Example 2—Purification of Rod-Shaped TMV

Figure 6:
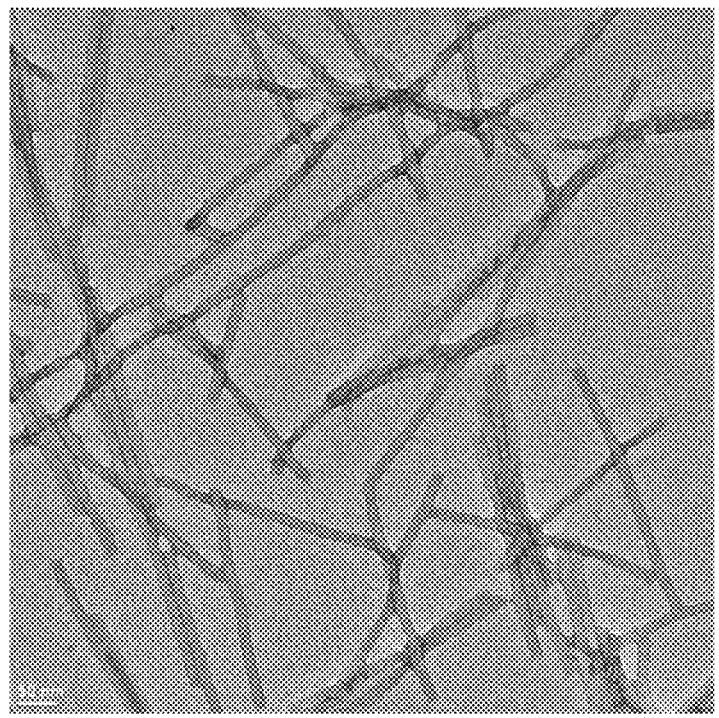
FIG. 6 is purified rod-shaped tobacco mosaic virus, according to multiple embodiments and alternatives.
Figure 7:
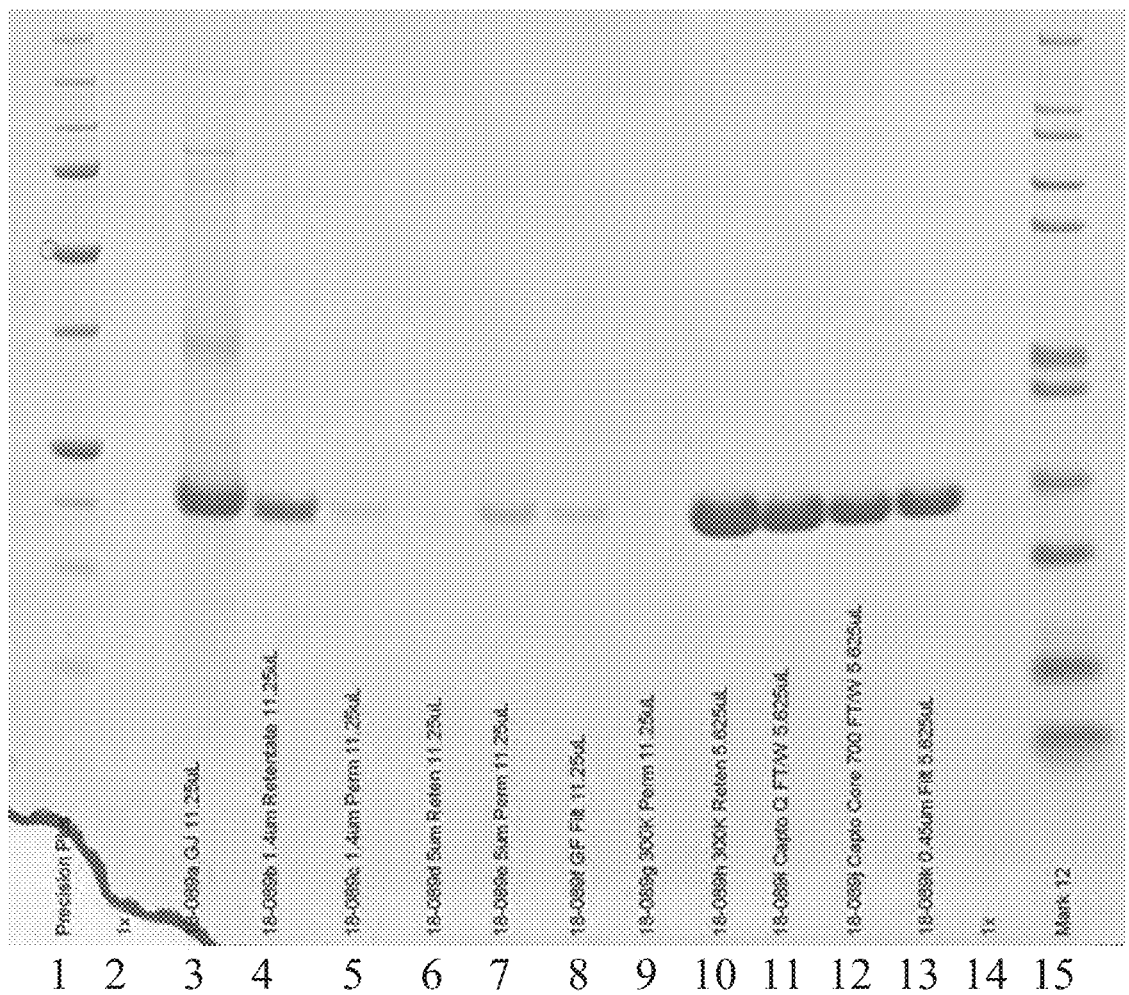
FIG. 7 is a western blot analysis of the purification of the rod-shaped tobacco mosaic virus, according to multiple embodiments and alternatives.

FIG. 6 shows a purified rod-shaped TMV, and FIG. 7 illustrates a virus purification platform used in achieving this purified TMV, within the scope of multiple embodiments and alternatives disclosed herein. Similar to FIGS. 3 and 5, FIG. 7 illustrates the purity of the virus product after the conclusion of the various steps of the current virus purification platform. After the final purification step, the resulting product is highly purified virus product consistent with a clear and visible band in lane 13 of FIG. 7.

Accordingly, an inventive virus purification platform has successfully purified every virus on which the inventors have applied these methods, including both an icosahedral virus and a rod-shaped virus, and this platform is expected to be reproducible and consistently purify on a commercial scale virtually any type (if not all types) of virus.

Production and Purification of Recombinant Antigen

Figure 8:
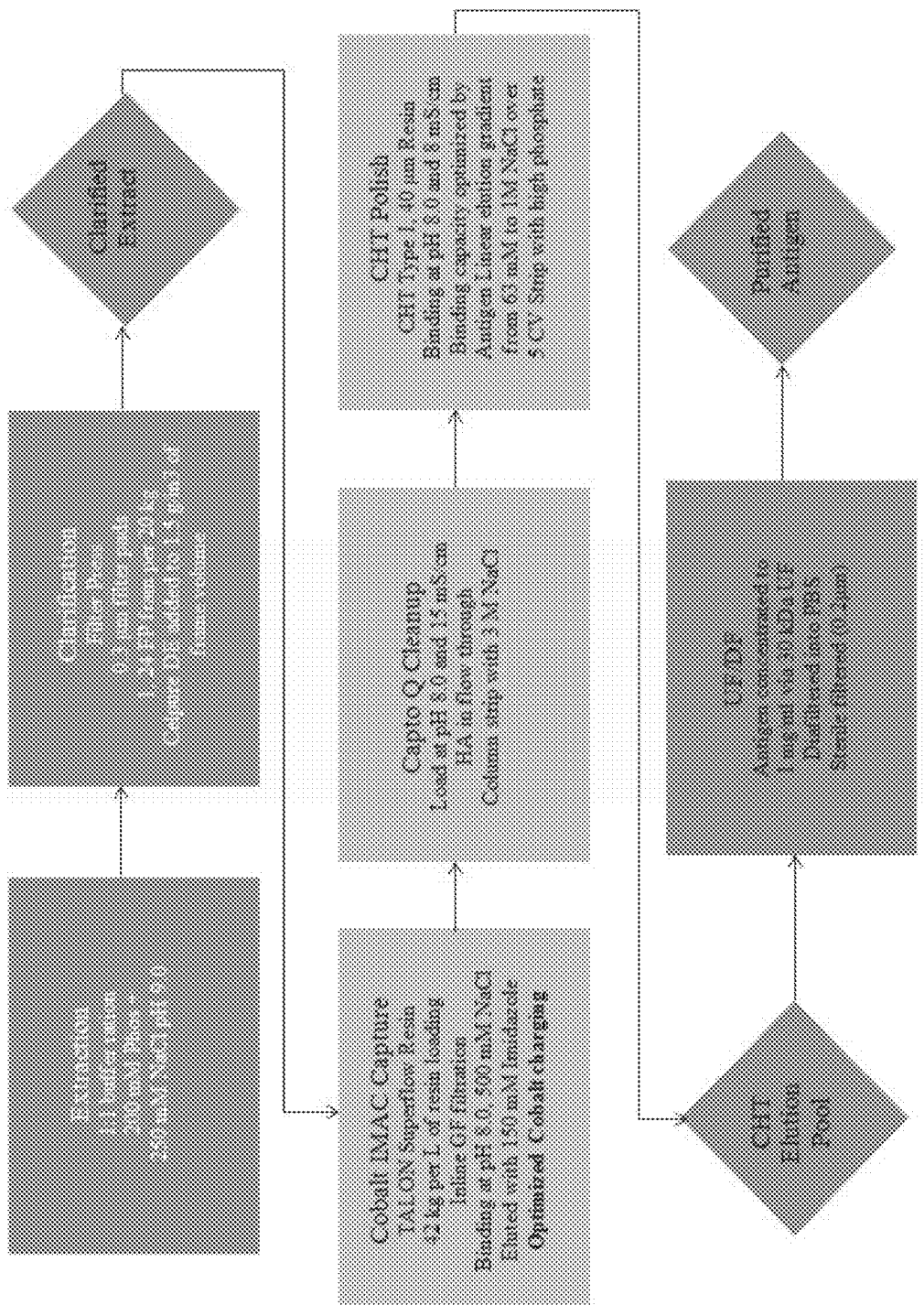
FIG. 8 is a flow chart showing the steps of an antigen manufacturing platform, according to multiple embodiments and alternatives.

Table 2 and FIG. 8 illustrate the steps of the antigen purification platform according to multiple embodiments and alternatives.

TABLE 2

Production and Purification of Recombinant Antigen

| Operative Steps | Unit Operations | In-Process Controls | In-Process Analytics |
|---|---|---|---|
| 1 | Plant Growth (25 UPS) Nb | Irrigation, Light Cycle, Fertilizer, Media, Humidity, Temperature | Plant height, structure and leaf quality |
| 2 | GENEWARE Infection with Target Antigen | Inoculum Concentration, Rate of Application | |
| 3 | Replication (7-14 DPI) Plant Growth | Irrigation, Light Cycle, Humidity, Temperature | |
| 4 | Harvest of Aerial Tissue | Visual Inspection of Plants | |
| 5 | Disintegration of Plant Cells (Extraction) | Blade Type and RPM, Screen Sizes, Buffer:Tissue Ratio | pH, Conductivity, SDSPage, Endotoxin, Nicotine |
| 6 | Clarification of Plant Extract | Filter Press Pore Size, Feed Pressure, kg/m2 | pH, Conductivity, SDSPage, Endotoxin, Nicotine |
| 7 | Concentration of Clarified Plant Extract | Pore Size, TMP, Pore Material, kg/m$^2$ | pH, Conductivity, SDSPage, Endotoxin, Nicotine |
| 8 | Capto Q Chromatography | kg/L, Bed Height, Residence Time | pH, Conductivity, SDSPage, Endotoxin, Nicotine |
| 9 | ColMAC or ConA | kg/L, Bed Height, Residence Time | pH, Conductivity, SDSPage, Endotoxin, Nicotine |
| 10 | Ceramic Hydroxyapatite | kg/L, Bed Height, Residence Time | pH, Conductivity, SDSPage, Endotoxin, Nicotine |

TABLE 2-continued

Production and Purification of Recombinant Antigen

| Operative Steps | Unit Operations | In-Process Controls | In-Process Analytics |
|---|---|---|---|
| 11 | Concentration/Formulation of Purified Antigen | Pore Size, TMP, Pore Material, kg/m$^2$ | UV260, TEM, DLS, SDSPage, Endotoxin, Nicotine, Amino Acid |

This purification platform is designed for commercial scalability and compliance with the cGMP regulations and utilizes one buffer throughout the entire purification process. According to multiple embodiments and alternatives, the steps of the antigen purification platform are as follows:

Growth of *Nicotiana benthamiana* wild type plants in a controlled growth room. Plant growth is controlled via irrigation, light and fertilizer cycles. Plants are grown in a soilless media and temperature is controlled throughout the process. After an appropriate number of DPS, for example 23 to 25, plants are infected for protein replication of a selected antigen. Once tagged, the protein is sufficient for retention in the ER of the transgenic plant cell. After infection plants are irrigated with water only and controlled via light cycle and temperature for an appropriate number of days post infection, such as 7-14 days depending on the type of antigen. Plants are inspected for height and infection symptoms, and the aerial tissue is harvested.

Recovery of antigen produced by the plants involves a disintegrator configured with an optimized blade/screen size followed by removal of residual cellulosic plant fiber from aqueous liquid (such as through a screw press, as one example).

A suitable extraction buffer is added to the resulting extract at an appropriate ratio, such as a 1:1 buffer:tissue ratio or a 2:1 buffer:tissue ratio. In some embodiments, the extraction buffer may be 50-100 mM Sodium Phosphate+2 mM EDTA+250 mM NaCl+0.1% Tween80, pH 8.5. Removal of chlorophyll and large cellular debris involves the use of filtration. Celpure300 is added at a ratio of 33 g/L and mixed for 15 minutes. Feed pressure (<30 PSI), filtrate pore size (0.3 microns), clarifying agent (Celpure300) and biomass loaded per square meter of membrane surface are all controlled to ensure passage of the antigens.

Clarified extract is concentrated with a TFF system (such as the Sartorius AG system). In some embodiments, the cassette pore size (for e.g., 30 kDa), an appropriate TMP as described herein, and load of clarified extract per square meter of membrane surface area are controlled.

The clarified extract is concentrated and washed 7× with an appropriate ion-exchange chromatography equilibration buffer (such as 50 mM Sodium Phosphate 75 mM NaCl, pH 6.5), The Capto Q ion-exchange column is equilibrated for five column volumes with 50 mM Sodium Phosphate+75 mM NaCl, pH 6.5, the feed is loaded, washed with equilibration buffer, and the column eluted/stripped with high salt.

Antigen fractions are collected in the elution for preparation for Cobalt IMAC chromatography. IMAC is equilibrated for five column volumes with 50 mM Sodium Phosphate+500 mM Sodium Chloride, pH 8.0, feed is loaded, washed with equilibration buffer and eluted using imidazole.

The elution fraction is diluted to conductivity, pH is checked and loaded onto a multi-modal ceramic hydroxyapatite (CHT) chromatography column. The CHT resin is equilibrated with five column volumes of equilibration buffer (5 mM Sodium Phosphate, pH 6.5). Antigens are eluted using a gradient of phosphate and NaCl. Loading ratio, column bed height, residence time and chromatography buffers are all controlled. Formulation and concentration of the antigens takes place using a TFF system (such as the Sartorius AG system). Pore size (in kDa), TMP, load per square meter of membrane surface area and pore material are all controlled, as further discussed herein.

Antigen is next concentrated to a suitable concentration, such as 3 mg/ml, and diafiltered with a suitable buffer (for example, phosphate buffered saline, pH 7.4). Formulated antigen is sterilized and stored appropriately. In some embodiments, sterilization is provided via a PES filter.

Figure 9:
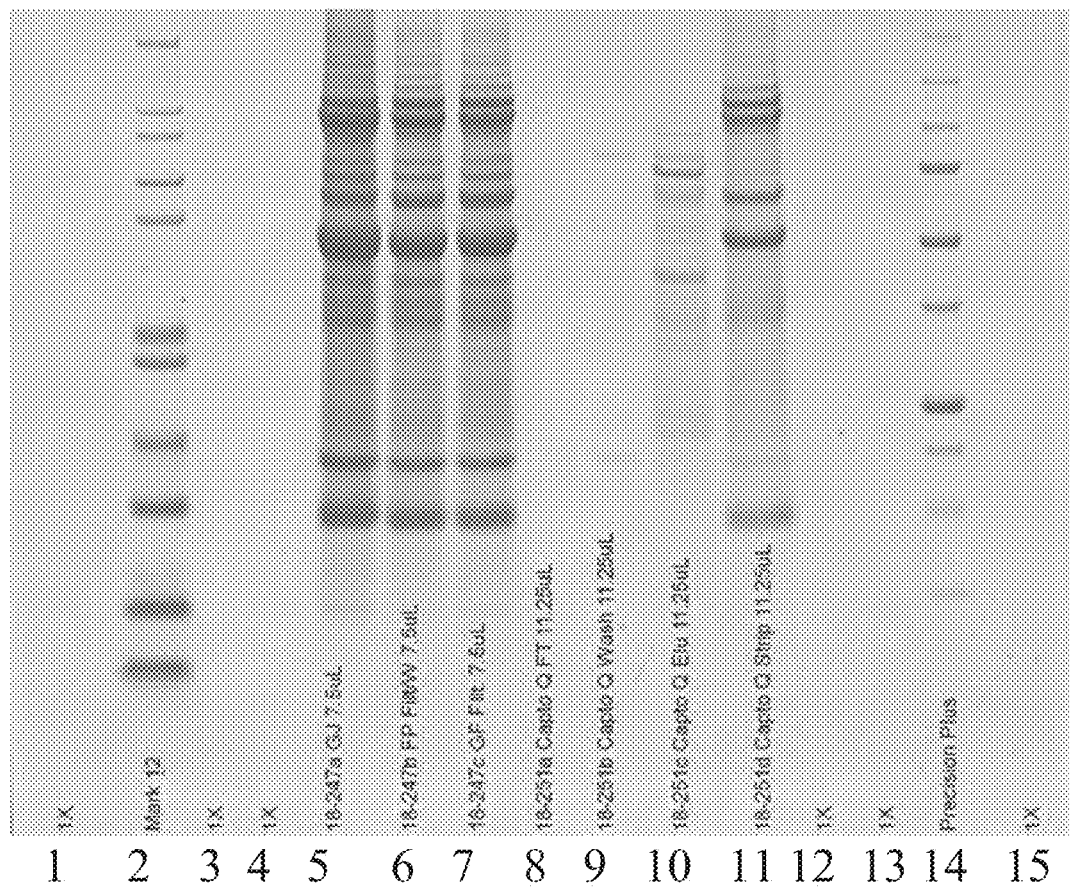
FIG. 9 is a western blot analysis of some of the steps of an antigen manufacturing platform, according to multiple embodiments and alternatives.
Figure 10:
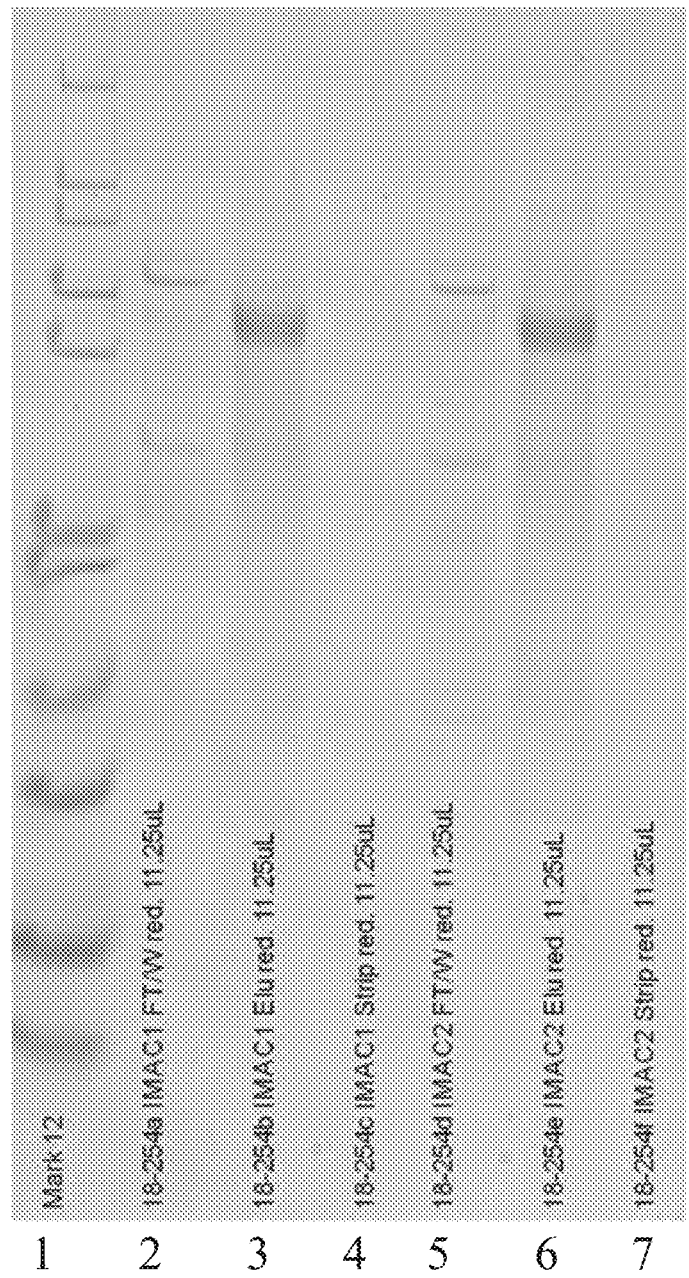
FIG. 10 is a western blot analysis of some of the steps of an antigen manufacturing platform, according to multiple embodiments and alternatives.
Figure 11:
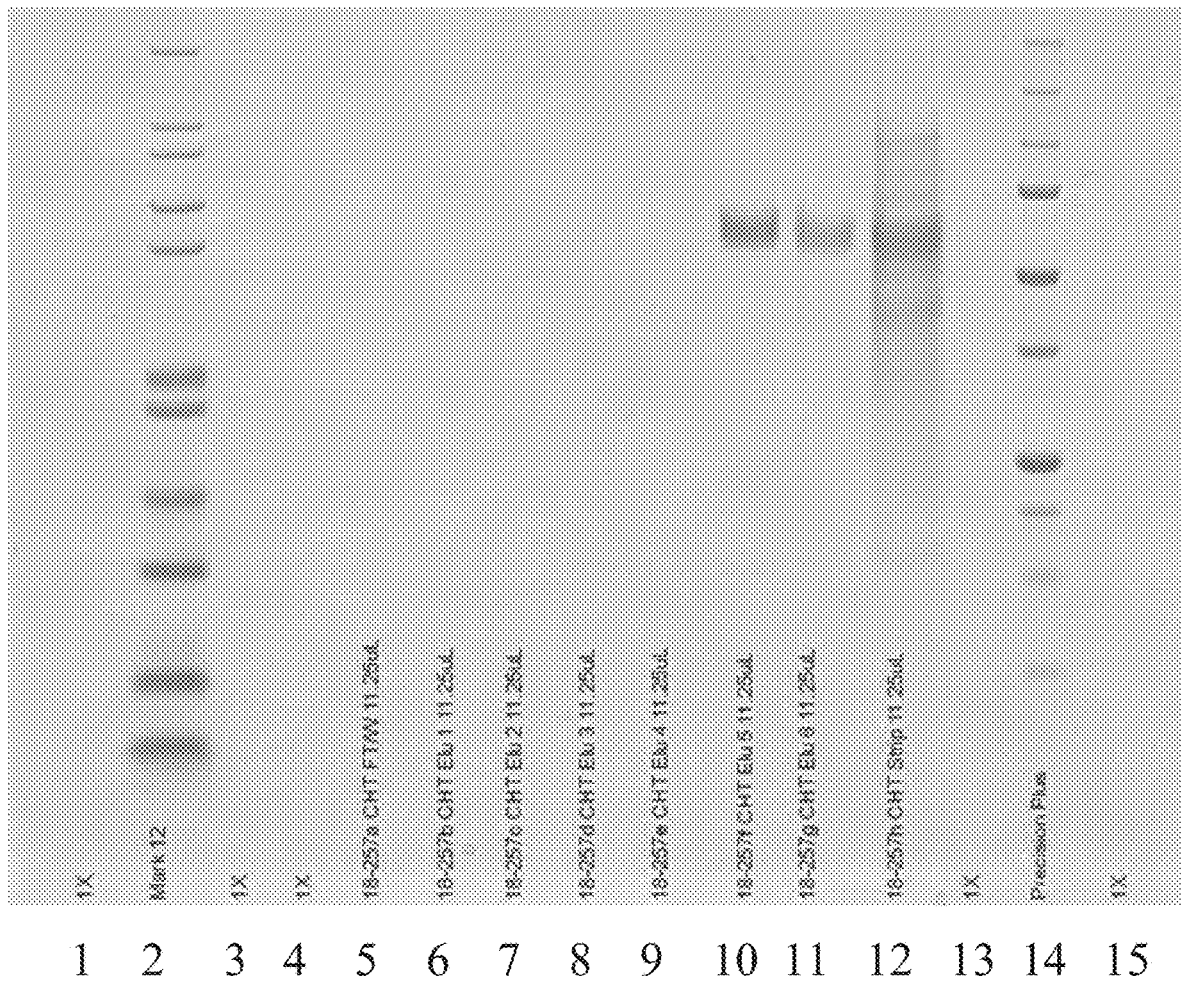
FIG. 11 is a western blot analysis of some of the steps of an antigen manufacturing platform, according to multiple embodiments and alternatives.

FIGS. 9, 10, and 11 illustrate the various steps of the antigen purification platform according to multiple embodiments and alternatives. FIG. 9 shows the purity of the antigen product after the Capto Q chromatography step has concluded, FIG. 10 shows the purity of the antigen product after the affinity chromatography step, and FIG. 11 shows the purity after the CHT chromatography column.

Examples 3, 4, 5, and 6—H5 rHA, H7 rhA, WNV rDIII, and LFV rGP1/2

Figure 12:
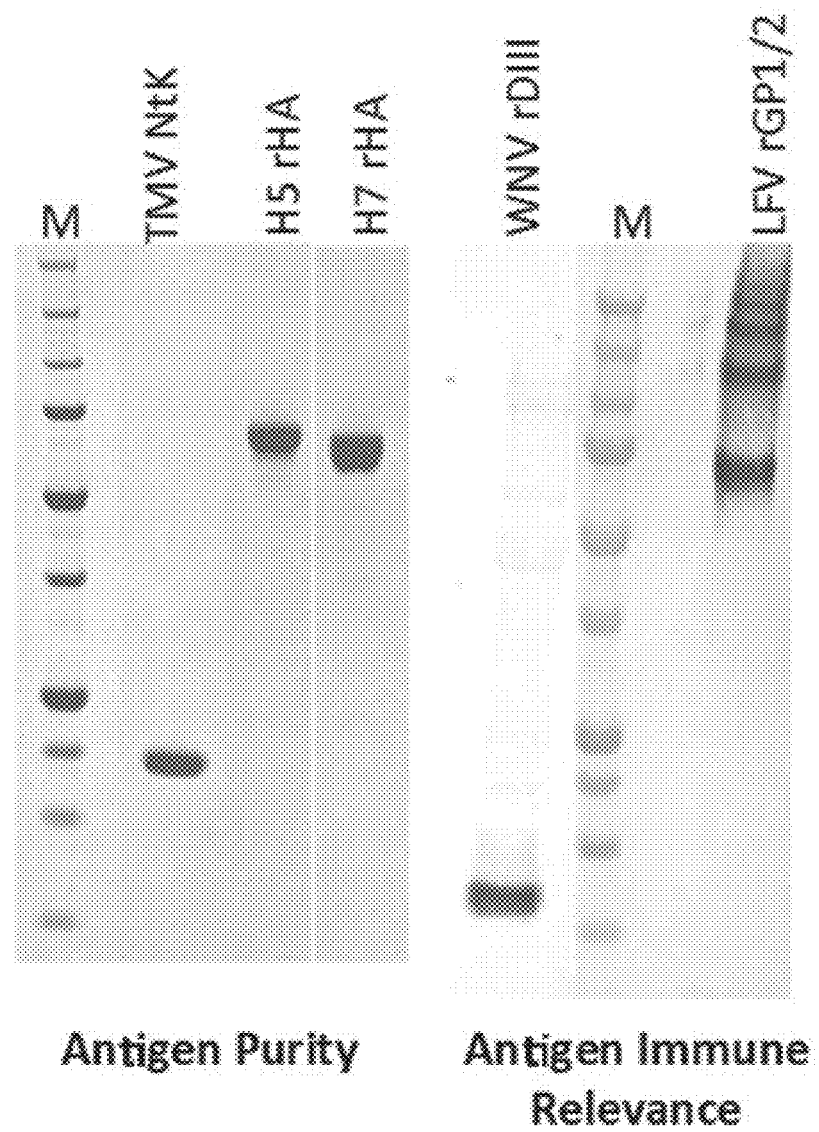
FIG. 12 is a western blot analysis of the purification of various antigens through the antigen manufacturing platform, according to multiple embodiments and alternatives.

As shown in FIG. 12, the antigen purification platform according to multiple embodiments and alternatives has successfully purified H5 rHA, H7 rhA, WNV rDIII, and LFV rGP1/2, FIG. 12 contains two images taken from the conclusion of the antigen purification platform: the image on the left contains a SDS Page gel indicating purity for the viral vector TMV NtK (where NtK is an abbreviation for N-terminal lysine) and influenza antigens, and the image on the right contains a western blot indicating the immunoreactivity for West Nile and Lassa Fever antigens. As shown by the clear and visible bands in FIG. 12, each antigen product is highly pure. Therefore, the antigen purification platform according to multiple embodiments and alternatives consistently purified each type of antigen on a commercial scale it was used with in a manner that is also compliant with cGMP regulations. In the same manner, this platform is expected to be reproducible to purify virtually any type (if not all types) of antigen.

Production of Recombinant Antigen—Virus Conjugates

Table 3 illustrates the steps of the conjugation of recombinant antigen according to multiple embodiments and alternatives.

TABLE 3

Production and Purification of Recombinant Antigen

| Operative Steps | Unit Operations | In-Process Controls | In-Process Analytics |
|---|---|---|---|
| 1 | Concentration/Diafiltration of Antigen | Pore Size, TMP, Pore Material, kg/m$^2$ | UV280 or BCA, SDSPage, pH, Conductivity |
| 2 | Concentration/Diafiltration of TMV 1295.10 | Pore Size, TMP, Pore Material, kg/m$^2$ | UV260, SDSPage, pH, Conductivity |
| 3 | Formulation of EDC Concentrate | Mixing, Weight Check | |
| 4 | Formulation of Sulfo-NHS Concentrate | Mixing, Weight Check | |
| 5 | Combine Antigen and TMV 1295.10 | Molar Ratio, Mixing, Volume | pH, Conductivity, SDSPage |
| 6 | Addition of EDC | EDC Molarity, Mixing, Volume | pH, Conductivity, SDSPage |
| 7 | Addition of Sulfo-NHS | Sulfo-NHS Molarity, Mixing Volume | pH, Conductivity, SDSPage |
| 8 | Conjugation Reaction | Time, Temperature, Mixing | |
| 9 | Reaction Quenching | Time, Temperature, Mixing, Molarity of Amine Group | |
| 10 | Diafiltration to Remove Reactants | Pore Size, TMP, Pore Material, kg/m$^2$ | pH, Conductivity, SDSPage, Reactants (EDC/NHS) |
| 11 | Concentration/Formulation of Purified Vaccine (Drug Substance) | Pore Size, TMP, Pore Material, kg/m$^2$ | Certificate of Analysis |

In an embodiment, the steps of a conjugation platform are as follows:

Purified antigen and virus are separately concentrated and diafiltered into a slightly acidic buffer, such as a 2-(N-morpholino) ethanesulfonic acid (MES) buffer containing NaCl.

A water soluble carbodiimide, such as 1-ethyl-3-(3-dimethylaminopropyl) carbodiimide (known as EDC) is formulated in purified water to a molarity of 0.5 M.

A chemical reagent for converting carboxyl groups to amine reactive N-hydroxysulfosuccinimide esters, such as ThermaoFisher's Sulfo-NHS, is formulated in purified water to a molarity of 0.1 M.

Antigen and virus are combined based upon weight or molarity and mixed to homogeneity (e.g. 1:1 mg:mg addition).

The freshly prepared water soluble carbodiimide (such as EDC) is added to the mixture while mixing based upon molarity.

A chemical reagent for converting carboxyl groups to amine reactive esters (such as Sulfo-NHS) is added based upon molarity within one minute of EDC addition. The conjugation reaction begins and is continued until a predetermined mixing stop time, such as four hours, and the room temperature is controlled.

The reaction is quenched by adding free amines, and the chemical linker (for example EDC and Sulfo-NHS) is removed through a multi-modal chromatography step, such as Capto® Core 700, or diafiltration into a phosphate buffered saline. According to multiple embodiments and alternatives, the residual impurities are removed from the results of the conjugation reaction, sometimes referred to herein as a conjugate mixture, based on sized differences between impurities as the retentate, and the conjugate mixture as the permeate.

The conjugate mixture is diluted to target concentration. At this point, the virus-antigen conjugate is prepared for use as a purified vaccine/drug substance. A suitable delivery mechanism of the vaccine would include a liquid vial or lyophilized material to be reconstituted with physiologic buffering for project injection. Injection could be intramuscular or sub-cutaneous. Other delivery methods are contemplated, including without limitation intra-nasal.

Example 7—Conjugation of H7 rHA to TMV

Figure 13:
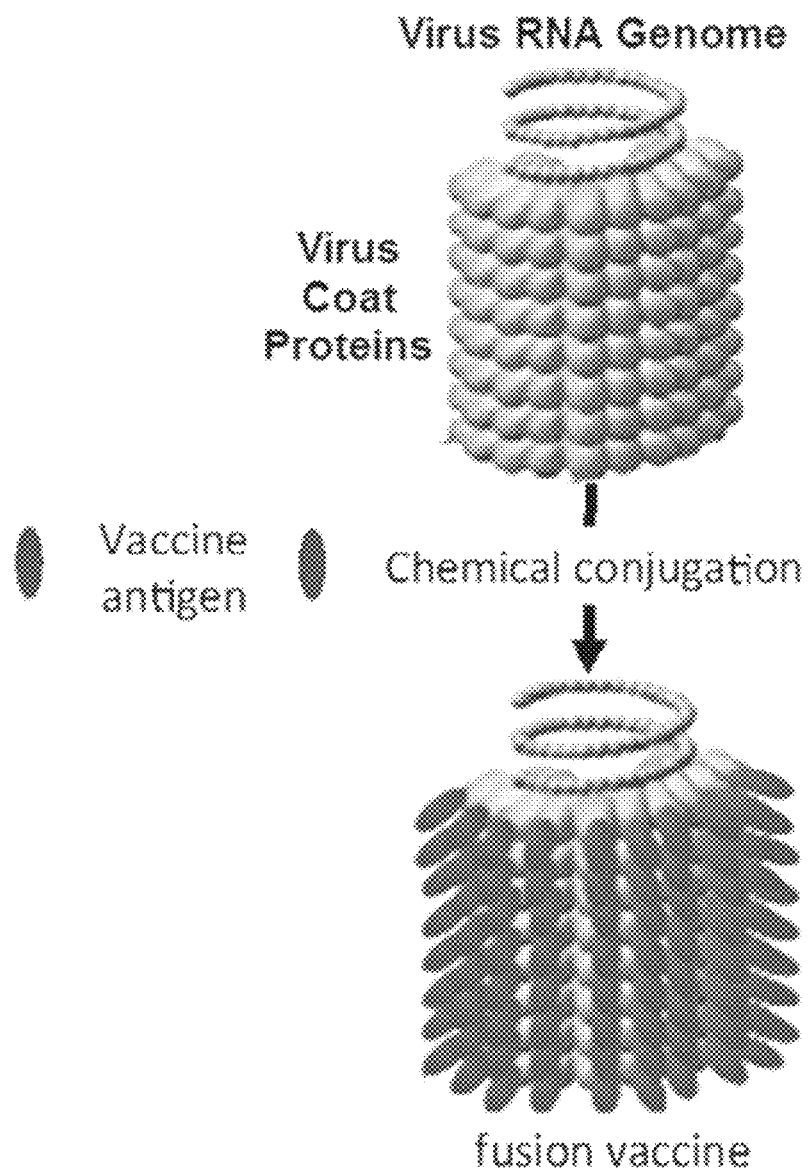
FIG. 13 is an illustration of the conjugation of recombinant antigen to a virus, according to multiple embodiments and alternatives.

FIG. 13 provides an illustration of the conjugation of a recombinant antigen (denoted by the "vaccine antigen") to a virus, with lighter- and darker-shaded ovals representing the extent of conjugation for the vaccine antigen depicted in the example. The lighter shade represents free virus, while the darker shade represents antigen conjugated to the protein coat of the virus. Also, as indicated in FIG. 13, some viruses contain coat positioned proteins around the RNA genome. For example, the viral vector TMV NtK includes N-terminal lysines that serve as connector points to the coat proteins. In some embodiments, portions of the virus associated with N-terminal lysine residues are modified to enhance presentment for binding of recombinant antigen providing amine-targeted conjugation of the protein, for example antigen to virus. In connection with the discussion of radial measurement herein, the viral radius greatly increases following conjugation of the recombinant antigens to the viral coat proteins. In some embodiments, modification is performed when enveloped viruses are changed to allow enhanced presentment of their residues.

Figure 14:
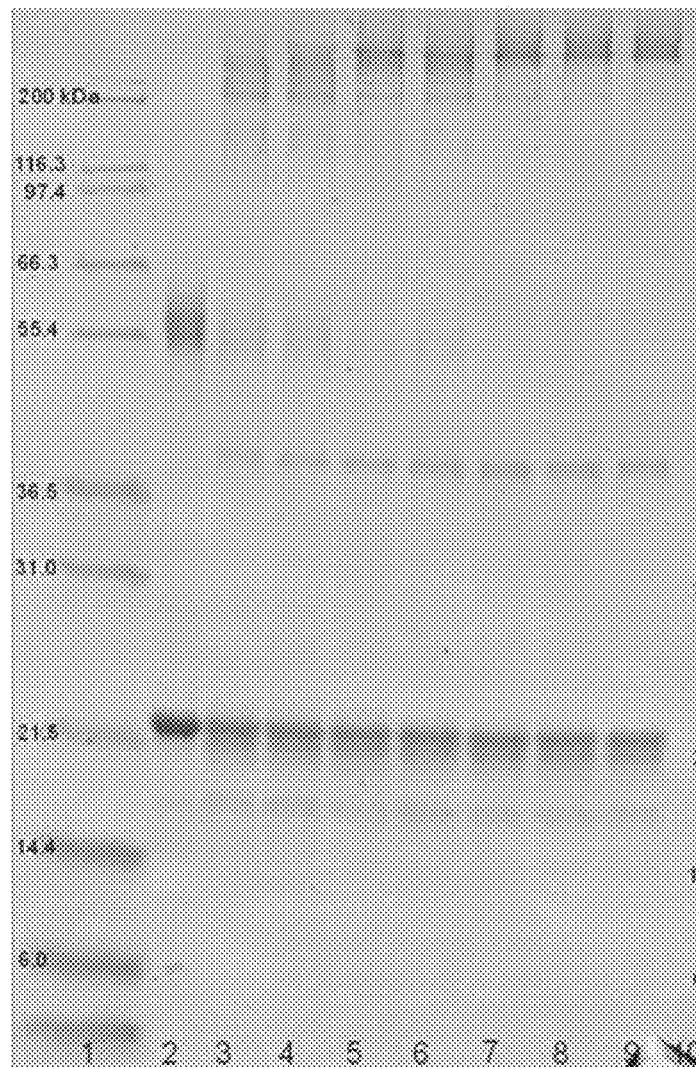
FIG. 14 is a SDS-PAGE analysis of the conjugation of an antigen to a virus, according to multiple embodiments and alternatives.
Figure 15:
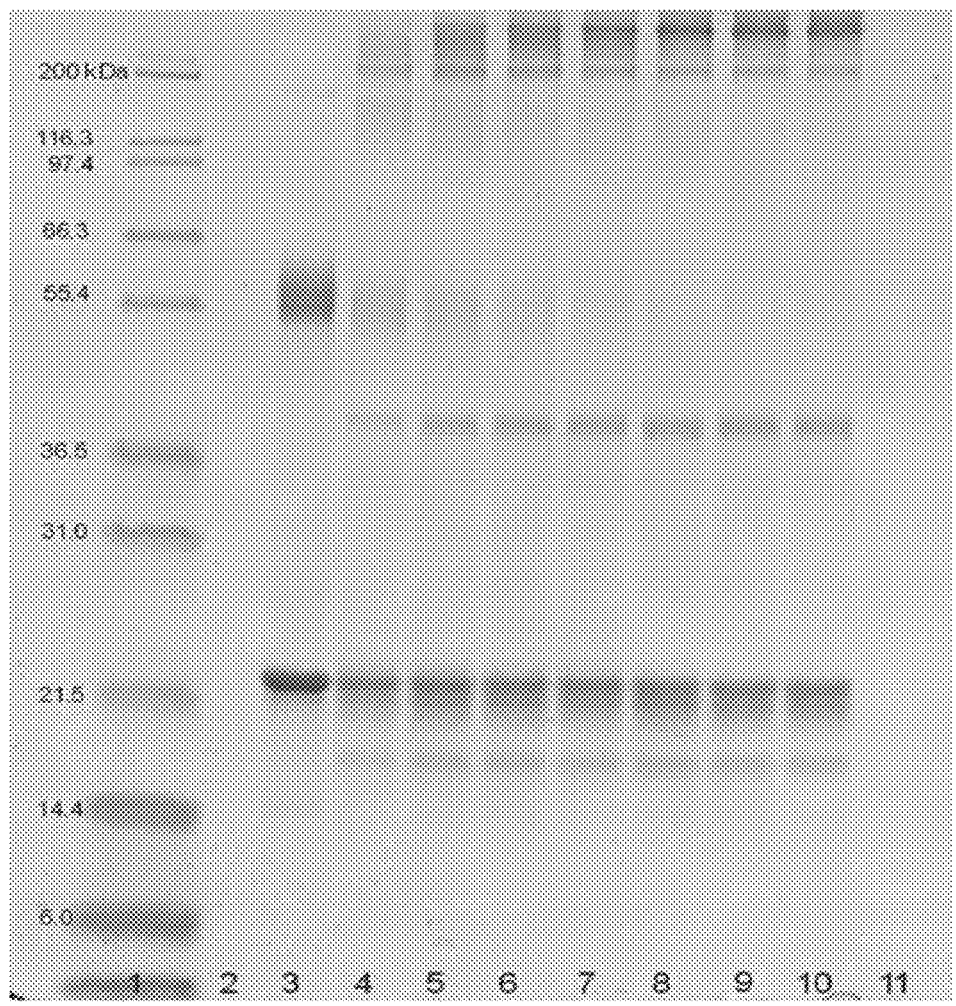
FIG. 15 is a SDS-PAGE analysis of the conjugation of an antigen to a virus, according to multiple embodiments and alternatives.
Figure 16:
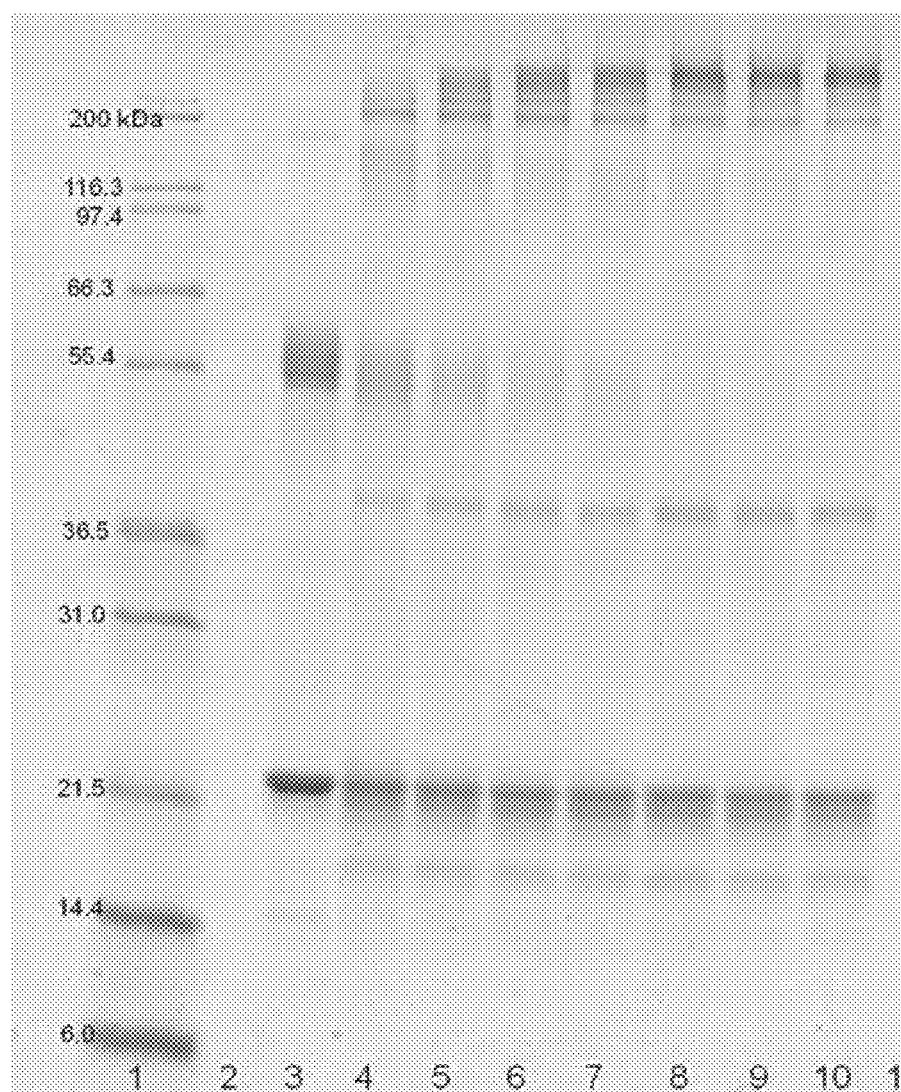
FIG. 16 is a SDS-PAGE analysis of the conjugation of an antigen to a virus, according to multiple embodiments and alternatives.

As shown in FIGS. 14-20, the conjugation platform of recombinant antigen to virus has successfully conjugated H7 rHA to TMV. FIGS. 14-16 show an analysis based on sodium dodecyl sulfate-polyacrylamide gel electrophoresis ("SDS-PAGE") of the conjugation between H7 rHA to TMV at pH 5.50. As illustrated in these figures, nearly all of the H7 rHA was conjugated to the TMV within 2 hours. The disappearance of the rHA protein band and simultaneous appearance of complexes staining above the 200KDa marker indicates the complex formation. The reactivity of the bands with HA-specific antibodies further establishes this conclusion.

Figure 17:
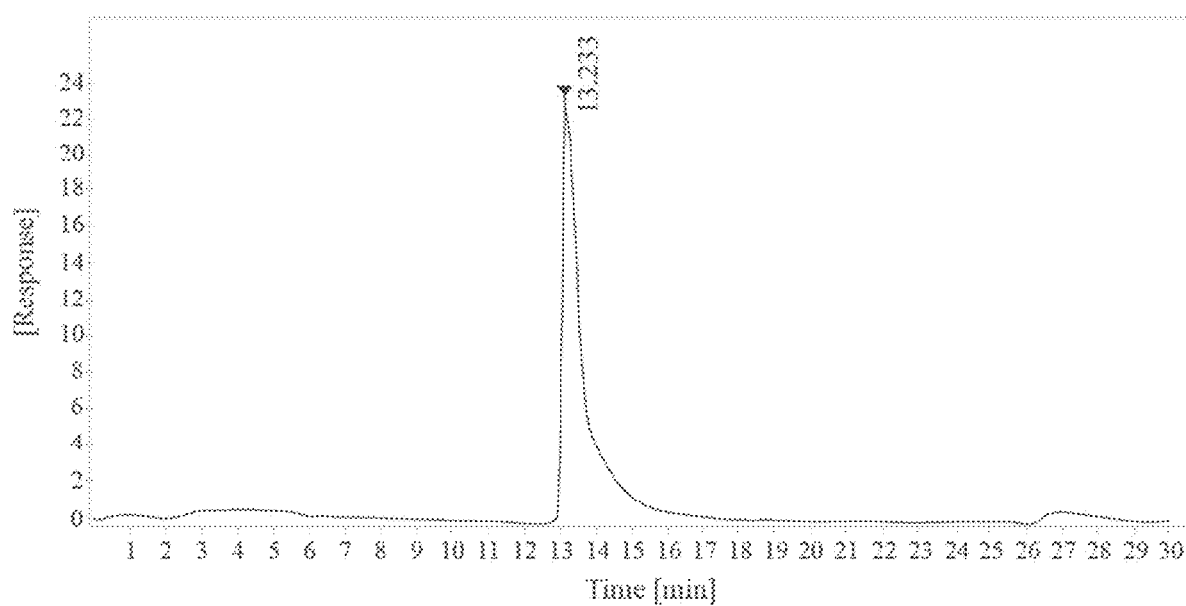
FIG. 17 is a report of size exclusion-high-performance liquid chromatography (SEC-HPLC) of a free TMV product, according to multiple embodiments and alternatives.

SEC-HPLC reports also indicated successful conjugation of H7 rHA to TMV in accordance with the current embodiments of the conjugation platform. FIG. 17 shows a SEC-HPLC report of free TMV product. In FIG. 17, the SEC-HPLC report of the free TMV product produced the signal data detailed in Table 4 below.

TABLE 4

SEC-HPLC Data of Free TMV

| RT [min] | Width [min] | Area | Height | Area % | Peak Symmetry |
|---|---|---|---|---|---|
| 13.233 | 0.77 | 1078.39 | 23.41 | 100 | 0.39 |

Figure 18:
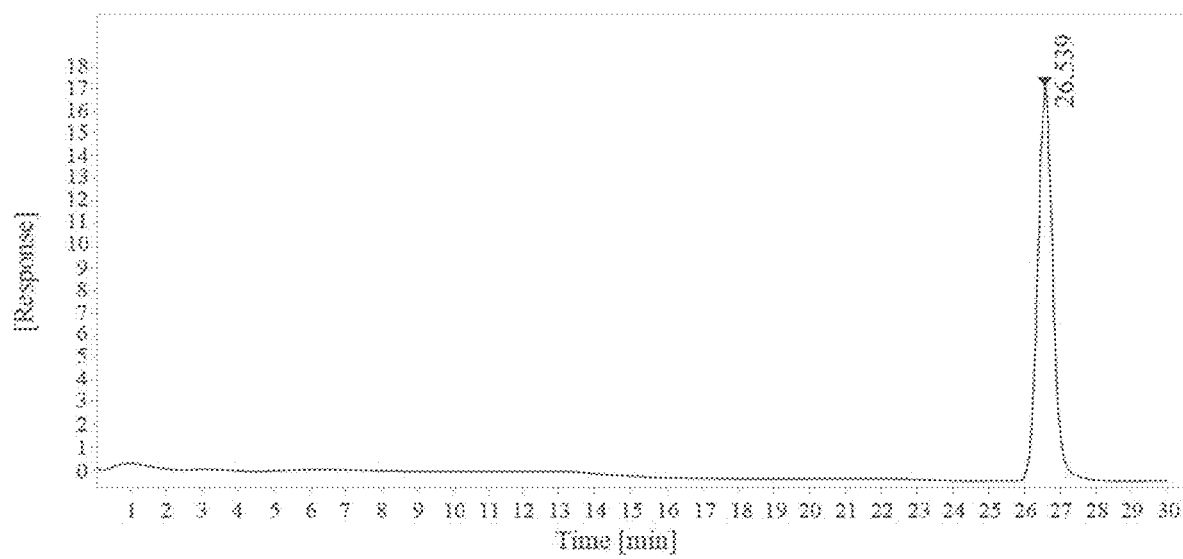
FIG. 18 is a report of SEC-HPLC of conjugation between a virus and an antigen for fifteen minutes, according to multiple embodiments and alternatives.

FIG. 18 shows a SEC-HPLC report after H7 rHA is conjugated to TMV for fifteen minutes according to current embodiments of the conjugation platform. In FIG. 18, the SEC-HPLC report after H7 rHA is conjugated to TMV for fifteen minutes produced the signal data detailed in Table 5.

TABLE 5

SEC-HPLC Data After H7 rHA is conjugated to TMV for 15 Minutes

| RT [min] | Width [min] | Area | Height | Area % | Peak Symmetry |
|---|---|---|---|---|---|
| 26.539 | 0.52 | 553.75 | 17.65 | 100 | 0.83 |

Figure 19:
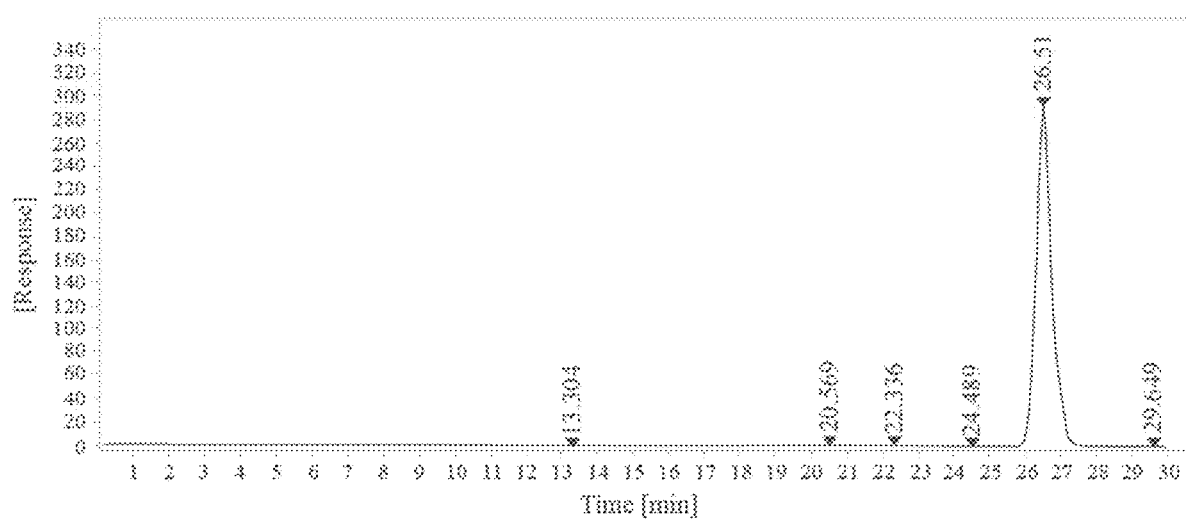
FIG. 19 is a report of SEC-HPLC of conjugation between a virus and an antigen two hours, according to multiple embodiments and alternatives.

FIG. 19 shows a SEC-HPLC report after H7 rHA is conjugated to TMV for two hours according to current embodiments of the conjugation platform. In FIG. 19, the SEC-HPLC report taken after H7 rHA is conjugated to TMV for two hours according to current embodiments of the conjugation platform produced the signal data detailed in Table 6 below,

TABLE 6

SEC-HPLC Data After H7 rHA is conjugated to TMV for 2 Hours

| RT [min] | Width [min] | Area | Height | Area % | Peak Symmetry |
|---|---|---|---|---|---|
| 13.304 | 0.73 | 37.30 | 0.86 | 0.36 | 0.43 |
| 20.569 | 1.83 | 167.16 | 1.52 | 1.59 | 0.00 |
| 22.336 | 1.17 | 62.55 | 0.89 | 0.59 | 0.64 |
| 24.489 | 2.05 | 73.35 | 0.60 | 0.70 | 1.34 |
| 26.510 | 0.54 | 10153.91 | 316.30 | 96.56 | 0.80 |
| 29.649 | 0.83 | 21.16 | 0.42 | 0.20 | 2.15 |

Figure 20:
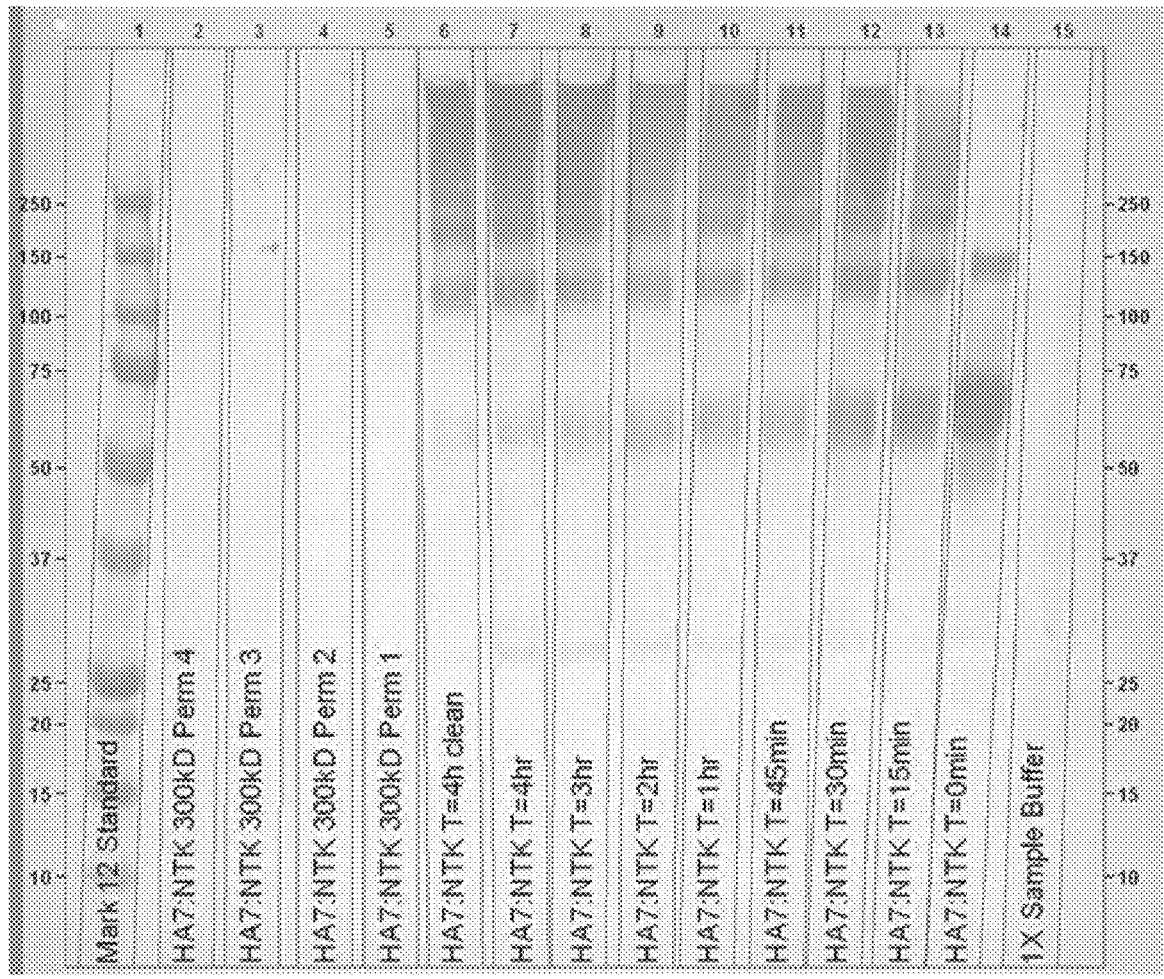
FIG. 20 is a western blot analysis of conjugation between a virus and an antigen, according to multiple embodiments and alternatives.

As illustrated in FIGS. 19 and 20, the SEC-HPLC reports indicated that all TMV rods were coated with some H7 rhA after conjugation for fifteen minutes, and more H7 rhA was added to the rods for up to two hours. After two hours, no additional conjugation was detected. According to multiple embodiments and alternatives, the SEC-HPLC reports indicate that the conjugation reaction achieves at least about 50% reduction in non-conjugated, native molecular weight, virus coat protein, and that approximately 3% free TMV remained after conjugation took place for four hours.

As illustrated in FIG. 20, western blot analysis of the conjugate product indicated successful conjugation of H7 rhA to TMV via covalent attachment. FIG. 20 shows a western blot analysis of the various steps of the conjugation platform according to current embodiments, wherein all samples were loaded at 10 µL. The various lanes illustrate different conjugation reaction times between the antigen and the virus. Lanes 14 and 13 show that all the TMV rods were coated with the antigen after fifteen minutes. After two hours, lanes 6-9 illustrate that no additional conjugation took place.

Example 8 Inactivation of TMV NtK

In order to avoid viral contamination of biopharmaceutical products, it is often necessary to inactivate (or sterilize) the virus to ensure the virus is no longer infectious. In addition, many regulatory agencies have enacted rules (such as the cGMP regulations) that require at least one effective inactivation step in the purification process of viral products. While UV-C radiation has been used in water treatment systems for many years, its use with biopharmaceutical products remains unexplored and there are limited studies regarding its ability to effectively inactivate viruses.

Accordingly, following virus production and purification but prior to conjugation with recombinant antigen, various UV-C conditions (i.e. energy density and wavelength) and various TMV concentrations were evaluated in order to effectively inactivate and sterilize TMV NtK. While many energy densities were tested, only the higher levels of energy densities successfully inactivated TMV NtK. In addition, it was determined that successful virus inactivation is concentration dependent because when the TMV solution was not diluted to an appropriate concentration, the UV-C irradiation did not effectively sterilize every virus in the sample. Therefore, the TMV solution must be appropriately diluted to permit the UV-C irradiation to interact with and effectively inactivate each virus.

Figure 21:
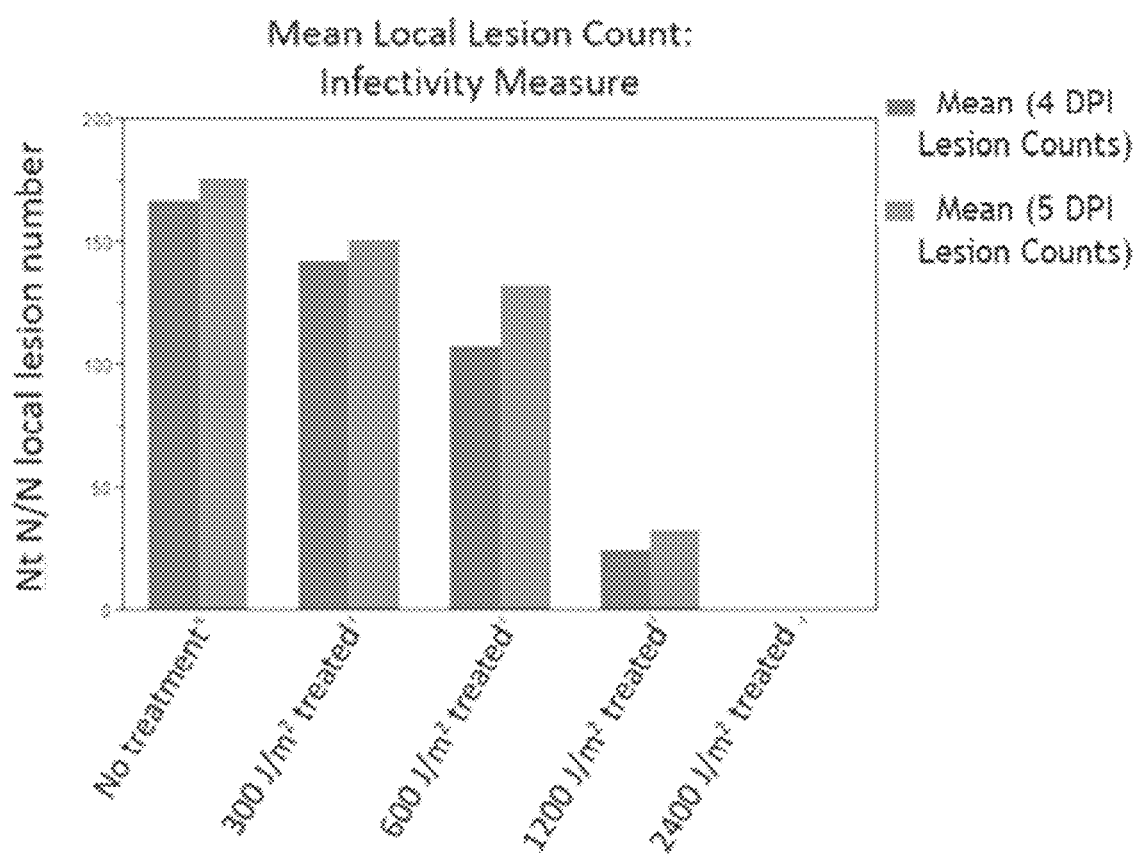
FIG. 21 is a graph illustrating the infectivity of viruses treated with various levels of UV irradiation, according to multiple embodiments and alternatives.
Figure 22:
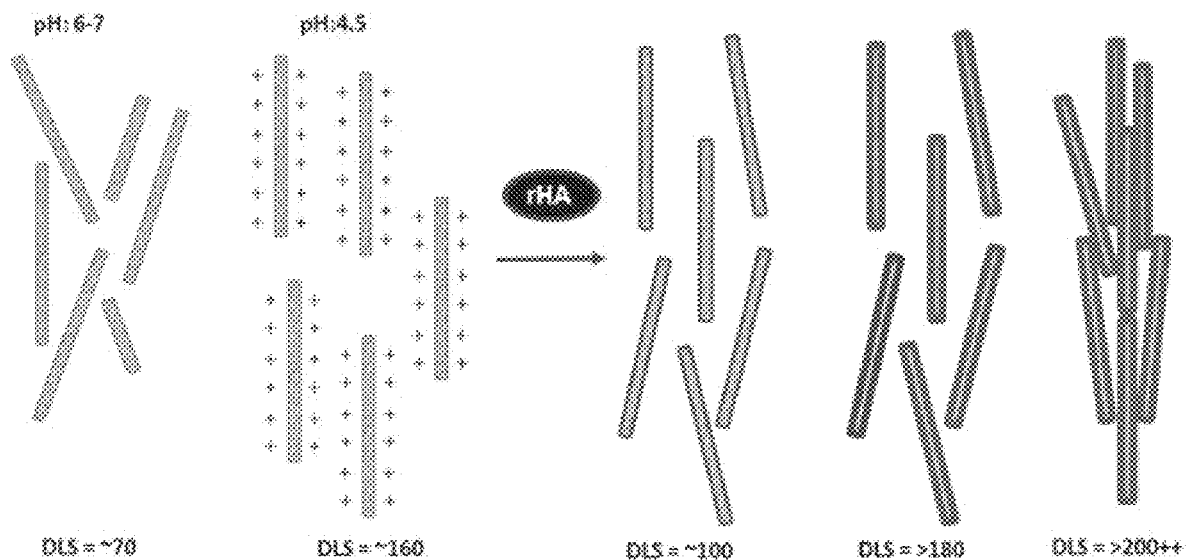
FIG. 22 is an illustration of some of the steps of the conjugation platform of recombinant antigen to a virus, according to multiple embodiments and alternatives.
Figure 23:
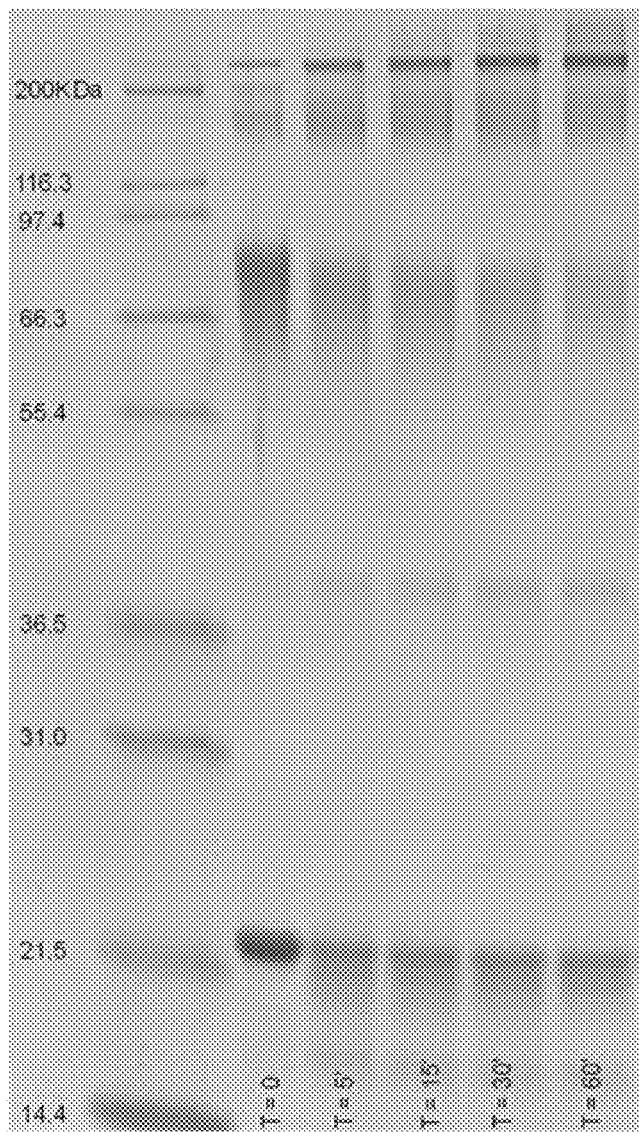
FIG. 23 is a SDS-PAGE analysis of the conjugation of an antigen to a virus, according to multiple embodiments and alternatives.
Figure 24:
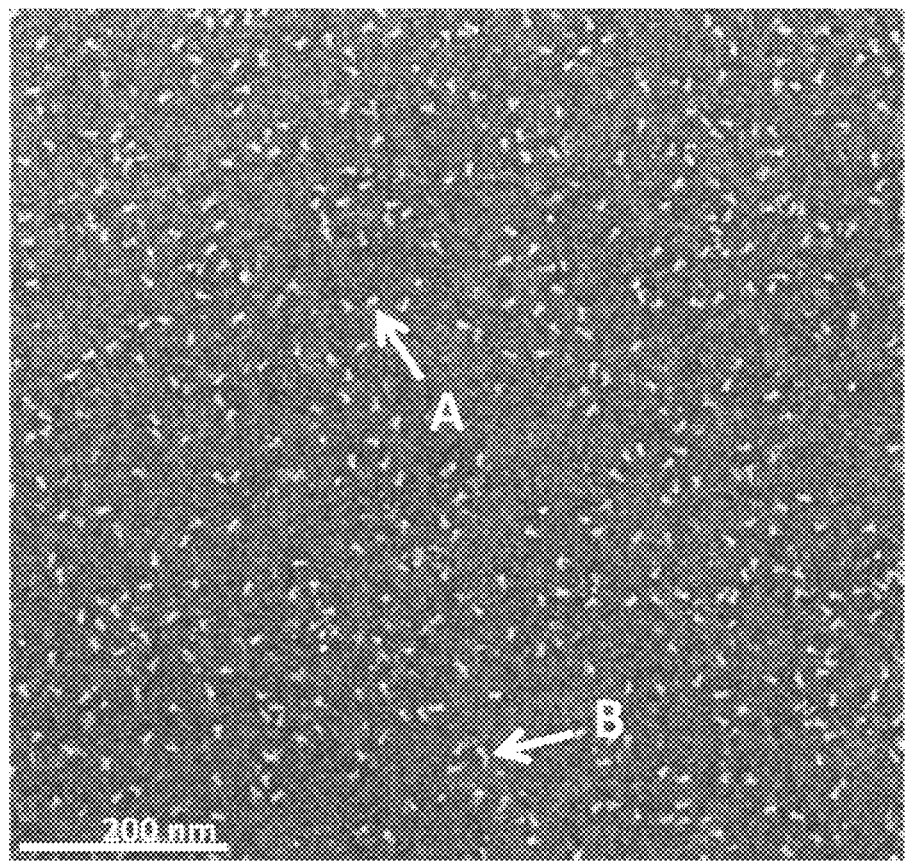
FIG. 24 is a negative stain transmission electron microscopy (TEM) image of recombinant antigen, according to multiple embodiments and alternatives.
Figure 25:
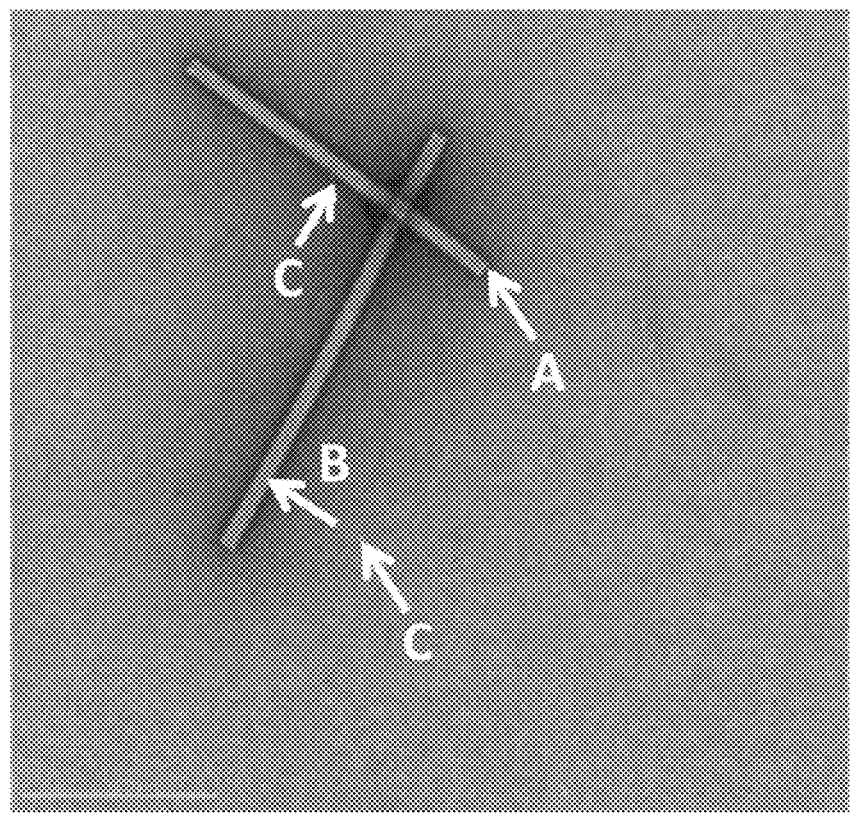
FIG. 25 is a negative stain TEM image of a virus, according to multiple embodiments and alternatives.
Figure 26:
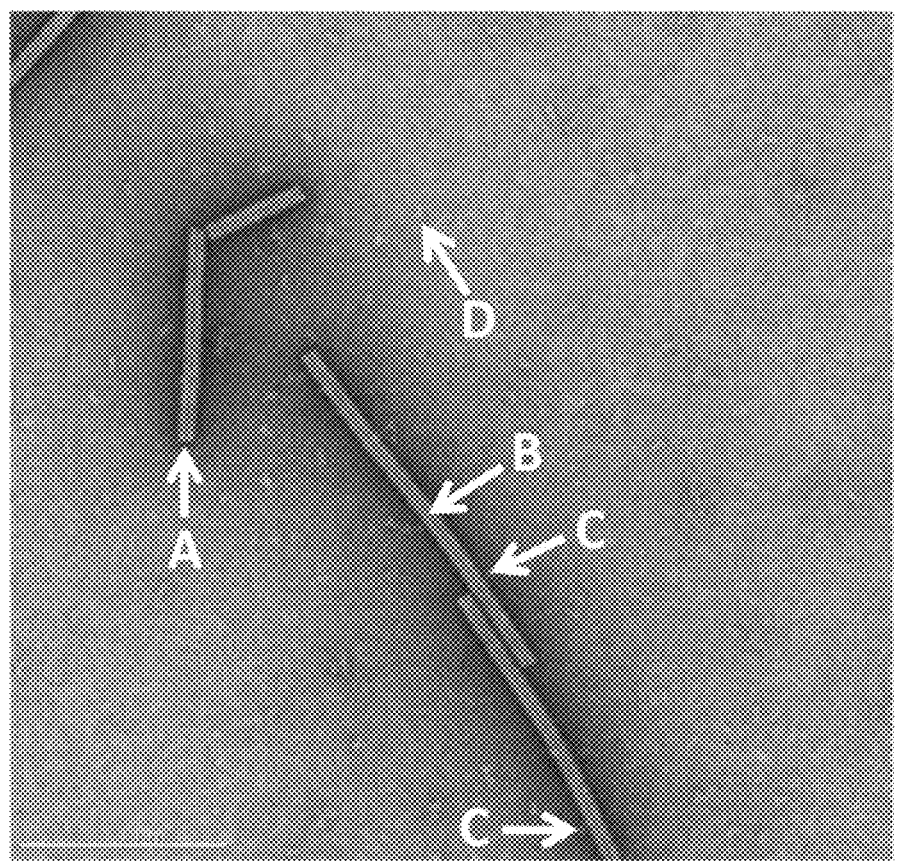
FIG. 26 is a negative stain TEM image of a recombinant antigen conjugated to another recombinant antigen with added virus, according to multiple embodiments and alternatives.
Figure 27:
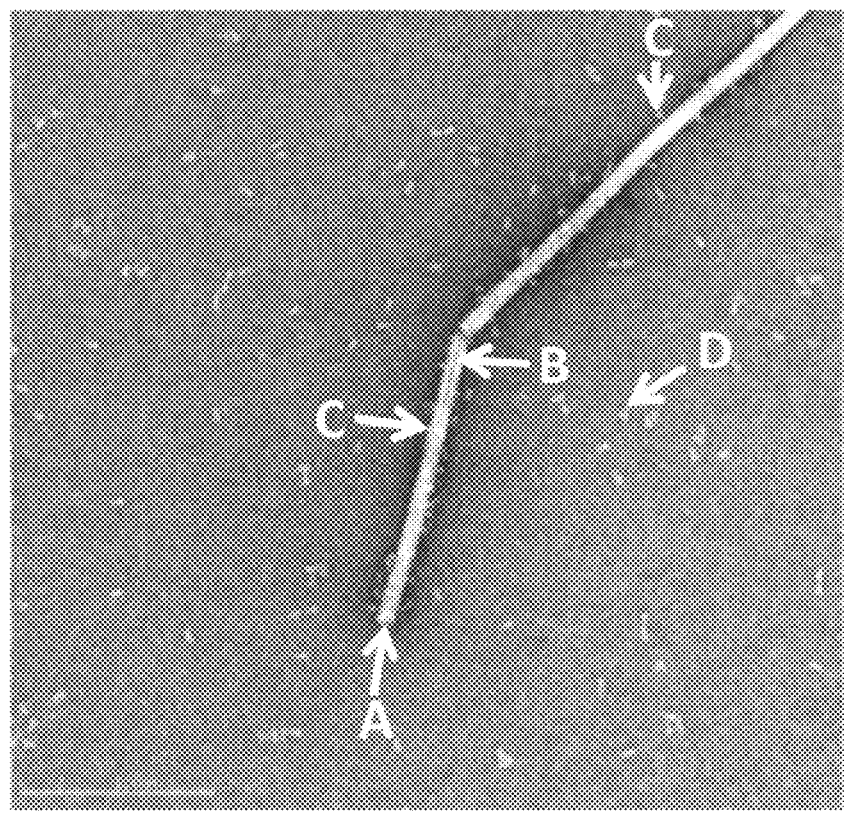
FIG. 27 is a negative stain TEM image of recombinant antigen conjugated to a virus at a virus to recombinant antigen ratio of 1:1, according to multiple embodiments and alternatives.
Figure 28:
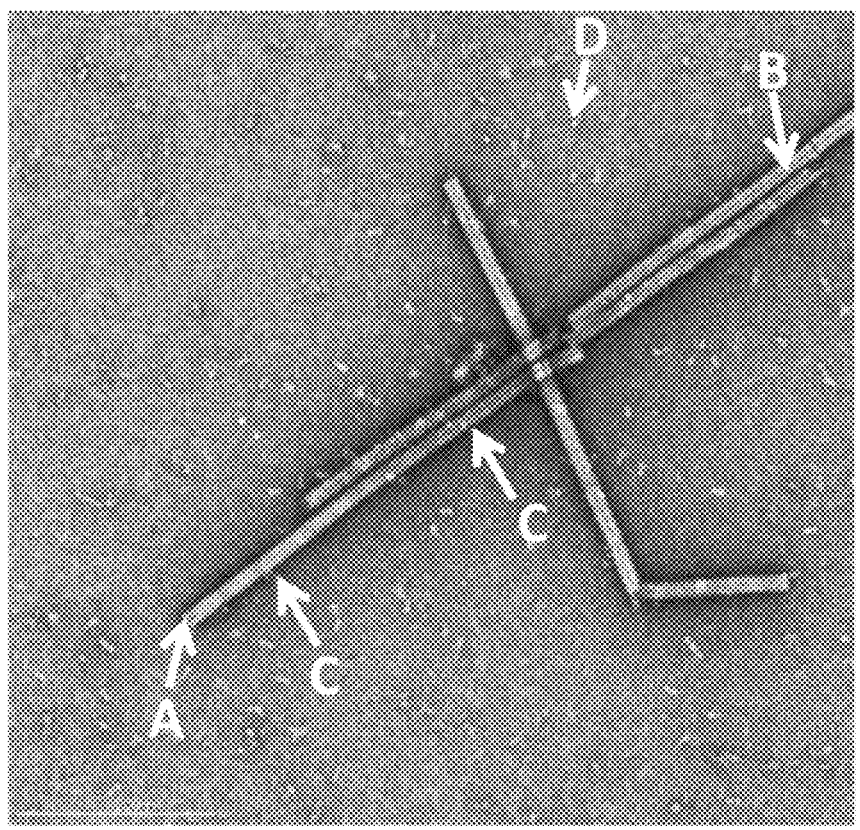
FIG. 28 is a negative stain TEM image of recombinant antigen conjugated to a virus at a virus to recombinant antigen ratio of 1:1, according to multiple embodiments and alternatives.
Figure 29:
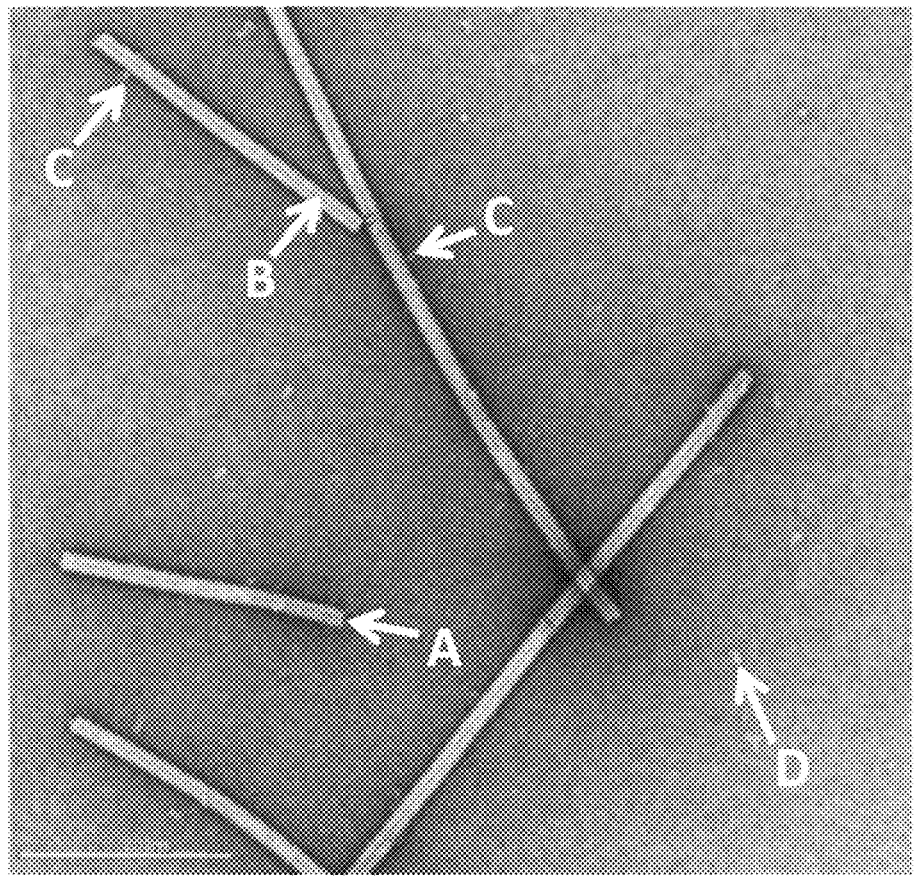
FIG. 29 is a negative stain TEM image of recombinant antigen conjugated to a virus at a virus to recombinant antigen ratio of 4:1, according to multiple embodiments and alternatives.

As shown in FIG. 21, various amounts of UV-C irradiation (with energy densities between 300 $J/m^2$ and 2400 $J/m^2$) were tested on *Nicotiana tabacum* plants to evaluate infectivity. As shown in FIG. 21, the lesions were reduced to zero after an UV-C energy dosage of 2400 $J/m^2$, therefore indicating successful inactivation of the virus. In addition, energy dosages at much higher levels were also tested, and it was determined that successful inactivation of TMV NtK also occurred at energy densities ranging between 4800 $J/m^2$ and 5142 $J/m^2$.

According to multiple embodiments and alternatives, the steps of the viral inactivation (following purification but before conjugation) are as follows:

Dilution of the TMV NtK solution to a concentration less than 50 micrograms/ml, as measured by A260 (which is a common method of quantifying nucleic acids by exposing a sample to UV light at a wavelength of 260 nm and measuring the amount of light that passes through the sample).

0.45 micron filtration of the TMV solution to remove bacteria and any other large species that might interfere with UV line of sight, and other purification steps according to present embodiments, occur immediately before inactivation with UV light.

Inactivating the TMV NtK by exposing the virus to light in the UV spectrum with an energy density between about 2400 $J/m^2$ and about 5142 $J/m^2$. In some embodiments, the energy density of the UV light is between about 4800 $J/m^2$ and about 5142 $J/m^2$. According to multiple embodiments and alternatives, the wavelength of the UV light is 254 nm.

Next, the inactivated TMV NtK is ready to be conjugated to the recombinant antigen.

These viral inactivation steps are designed for commercial scalability and compliance with the cGMP regulations Example 9—pH Dependency of Conjugation To evaluate whether incubating the virus at an acidic pH results in high quality conjugation, an experiment was performed using the same batches of virus, antigen, buffers, and esters, but changing only the formulation of the virus. In reaction 1, TMV was formulated into 1× MES Conjugation Buffer at pH 5.50 at a concentration of 3.1 mg/ml, according to multiple embodiments and alternatives. In reaction 2, TMV was concentrated to 11.0 mg/ml in phosphate buffer and added directly as 15% of the conjugation reaction volume. After these steps, the conjugation process was monitoring by SEC wherein an ordered decrease in free TMV from zero minutes (indicated by T=0) would indicate successful conjugation.

As shown in Tables 7 and 8, reaction 1 exhibited successful conjugation (due to the ordered decrease in free TMV from zero minutes) while reaction 2 was unsuccessful as shown by the percent remaining free TMV.

TABLE 7

Reaction 1, Successful Conjugation-TMV Formulated in Acidic pH

| Sample | Reaction 1, (TMV Formulated in MES at 3.1 mg/mL) | Free TMV Peak Area by SEC | Remaining % Free TMV |
|---|---|---|---|
| Free MK | 284.8 nm | 11104 | N/A |
| T = 0 | 154.9 nm | 9732 | 100% |
| T = 5 | 139.8 nm | 3909 | 40% |
| T = 15' | 142.8 nm | 1815 | 19% |
| T = 30' | 149.4 nm | 1039 | 11% |
| T = 45' | 155.6 nm | 769 | 8% |
| T = 60' | 153.2 nm | 777 | 8% |

TABLE 8

Reaction 2, Unsuccessful Conjugation-TMV Formulated in Phosphate Buffer

| Sample | Reaction 2 (TMV at 11.0 mg/mL in Phosphate Buffer) | Free TMV Peak Area by SEC | Remaining % Free TMV |
|---|---|---|---|
| Free NtK | 64.2 nm | 27590 | N/A |
| T = 0 | 67.5 nm | 14750 | 100% |
| T = 5 | 68.8 nm | 14916 | 101% |
| T = 15' | 66.9 nm | 13046 | 88% |
| T = 30' | 73.3 nm | 11705 | 79% |
| T = 45' | 75.8 nm | 8109 | 55% |
| T = 60' | 80.0 nm | 11020 | 75% |

Accordingly, as shown in Table 7, incubation of the virus in acidic pH results in a conjugation greater than 90%. If the acidic pH incubation step does not occur, then the percent conjugation remains less than 50% (as shown in Table 8).

Based on this experiment, a model for conjugation (shown in FIG. 22) was developed. According to multiple embodiments and alternatives, conjugation between purified virus and purified antigen (denoted by "rHA" in FIG. 22) is greatly enhanced by improving the chemical readiness of the virus to engage the antigen (referred to herein as "activating," "activation," or "activates") by exposing the virus to a conjugation environment. In some embodiments, virus activation occurs by formulating the virus in an acidic pH prior to the conjugation reaction such that positive charge aggregates on the virus surface. In some embodiments, the activating step involves exposing the virus to a pH of about 5.5 or less for a period of time sufficient for activation. In some embodiments, such period of exposure to the conjugation environment is between about 18 and 72 hours. According to multiple embodiments and alternatives, processing the purified virus in an acidic pH activates the virus by charging the coat protein lysine. As a result of this activation step in the conjugation environment, positive charges aggregate on the virus surface (as shown in FIG. 22) via the clustering of the amine groups and the virus is ready for conjugation with the carboxyl end of the recombinant antigen.

The virus activation steps, according to multiple embodiments and alternatives, are in contrast with traditional approaches in which the pH when storing viruses generally is maintained at or near neutral pH. As shown in FIG. 22, the traditional approach does not aggregate positive charge on the virus surface, and as a result the percent conjugation remains below 50% (see Table 8). Furthermore, the conventional approach utilizes phosphate buffers which promote solubility at the expense of having favorable surface charge.

During the investigation of successful conjugations involving TMV, it was observed that successful conjugations generally occurred when the Dynamic Light Scattering (DLS)-measured radius of the virus increased during the activation step by at least a factor of 2.75 (see Table 9A, compared to Table 9B). In general, successful TMV conjugations (such as discussed with Table 9C) were characterized by an increase in DLS radius from about 70 nm to about 195 nm or higher, as shown in these tables.

Based on the successful conjugation which utilized virus activation, a platform was developed for conjugating purified antigen to purified virus. According to multiple embodiments and alternatives, the steps for preparing the purified antigen for conjugation are as follows:

To ensure pH control of the conjugation reaction, the purified antigen is formulated into a reaction buffer immediately prior to reaction initiation.

Prior to conjugation, purified antigens are stored in phosphate buffered saline at neutral to slightly basic pH.

The antigen pH target typically is pH 5.50 to 6.50, depending upon the nature of the molecule.

To facilitate conjugation to the virus, the storage buffer is replaced with a MES/NaCl buffer at acidic pH using ultrafiltration. The protein concentration is also increased to greater than 3 mg/mL.

The conjugation reaction is then initiated within four hours of antigen preparation completion to prevent destabilizing the protein structure.

According to multiple embodiments and alternatives, the steps for preparing the purified virus for conjugation are as follows:

After storage at neutral pH, the virus is activated at acidic pH prior to conjugation. For successful reactions, the virus is formulated from phosphate buffer at pH 7.4 into acetate buffer at pH 5.50 for a minimum of about 18 hours to a maximum of about 72 hours prior to the conjugation reaction start. In some embodiments, the virus is formulated from phosphate buffer at pH 7.4 into acetate buffer at pH 4.50 for a minimum of about 18 hours to a maximum of 72 hours prior to the conjugation reaction start. It was observed that storage of the virus for greater than 72 hours at acidic pH creates self-association between the viruses which causes virus insolubility and inhibits the efficiency of the conjugation.

Tables 9A and 9B further demonstrate the activation step in terms of increasing the radius of the virus (in this case, TMV) as measured by DLS, Specifically, Table 9A provides data for DLS radius increase of TMV after being activated, and before a successful conjugation occurred, with the antigens listed in the right-hand column. The "Factor by which radius increased" divides the TMV radius after activation by the typical TMV radius at neutral pH, which is about 70 nm, Conversely, Table 9B provides data for DLS radius increase of TMV after an activation step was started, in advance of unsuccessful attempts at conjugation, with the antigens listed in the right-hand column. In Tables 9A and 9B, the left column represents the standard radius of TMV rods at neutral pH and under general storage conditions, i.e., before any activation occurs.

TABLE 9A

Free TMV radii as measured by DLS (Prior to successful conjugation)

| TMV radius at neutral pH | TMV radius after activation (nm) (DLS results) | Factor by which radius increased | Antigen |
|---|---|---|---|
| 70 nm | 195.2 | 2.789 | SG |
| 70 nm | 207.2 | 2.960 | SG |
| 70 nm | 249.1 | 3.559 | SG |
| 70 nm | 249.1 | 3.559 | SG |
| 70 nm | 228.6 | 3.266 | SG |
| 70 nm | 234.1 | 3.344 | SG |
| 70 nm | 234.1 | 3.344 | SG |
| 70 nm | 441.3 | 6.304 | SG |
| 70 nm | 284.8 | 4.069 | SG |
| 70 nm | 517.6 | 7.394 | SG |
| 70 nm | 574.0 | 8.200 | SG |
| 70 nm | 448.2 | 6.403 | SG |
| 70 nm | 209.7 | 2.966 | PH |
| 70 nm | 220.4 | 3.149 | PH |
| 70 nm | 495.6 | 7.080 | PH |
| 70 nm | 517.6 | 7.394 | PH |
| 70 nm | 266.8 | 3.811 | CO |
| 70 nm | 495.6 | 7.080 | CO |
| 70 nm | 517.6 | 7.394 | CO |
| 70 nm | 295.4 | 4.220 | MI |
| 70 nm | 517.6 | 7.394 | MI |
| 70 nm | 574.0 | 8.200 | MI |
| | Average (nm): 413.5 | Average Factor for Increase: 5.176 | |

TABLE 9B

Free TMV radii as measured by DLS (Prior to unsuccessful conjugation)

| TMV radius at neutral pH (standard) | TMV radius after activation (nm) (DLS results) | Factor by which radius increased | Antigen |
|---|---|---|---|
| 70 nm | 95.4 | 1.363 | SG |
| 70 nm | 105.4 | 1.506 | SG |
| 70 nm | 156.0 | 2.229 | SG |
| 70 nm | 176.5 | 2.521 | PH |
| | Average (nm) 133.3 | Average Factor for Increase: 1.905 | |

Following these preparation steps, the antigen and virus reactants were mixed to form a conjugate mixture and the conjugation progress was monitored using DLS and SDS-PAGE methods. Table 9C illustrates the average molecular radius of the conjugation reaction over time using DLS after the virus was activated using acidic pH. As shown in Table 9C, molecular radius is one indicator of successful coating of the viral rods with antigen molecules.

TABLE 9C

TMV NtK SEC and DLS History

| Soluble NTK SEC Peak Area | DLS Radius (nm) |
|---|---|
| 10750 | 496 |
| 9651 | 518 |
| 7106 | 574 |
| 5538 | 660 |

In turn, FIG. 23 shows an analysis based on the SDS-PAGE of the conjugation between the activated TMV NtK and purified antigen according to multiple embodiments and alternatives. As shown in FIG. 23, the ordered reduction in both free TMV NtK and free antigen over time, coupled with the appearance of protein bands of >200 kDA, indicates successful conjugation.

Example 10—TEM Imaging of Different Ratios of Purified Virus to Purified Antigen for Conjugation The desired conjugation reaction between purified virus and purified antigen is represented by the following formula:

Virus+Antigen→Virus-Antigen (Formula 1)

However, it is well known that antigens are prone to self-conjugation and the desired reaction may not be obtained, as shown by the following formula:

Virus+Antigen→Virus-Antigen+Antigen-Antigen (Formula 2)

Self-conjugation of the purified antigen is a problem for the successful development of vaccines because the antigen-antigen conjugates are not removed during the size chromatography step and the result is a minimized or reduced immune response.

To address this self-conjugation problem, various experiments were performed to determine how to consume the unreacted antigens and antigen conjugates. First, the antigens were capped by exposing them to reagents that inhibited self-conjugation. While it was anticipated that this traditional approach would be successful, this approach failed because the reaction occurred too quickly.

Next, the virus to antigen ratios were adjusted to determine suitable conjugation ratios. As shown in Tables 10 and 11 and FIGS. 24-30, seven different samples were analyzed by negative stain transmission electron microscopy (TEM) imaging. Samples 1-3 were control groups and samples 4-7 contained different hemagglutinin (HA) to TMV ratios (at the mixing step of the conjugation platform, as shown at operative step 5 of Table 3).

TABLE 10

TEM Imaging Samples-Control Groups

| Sample | Description | Lot | Apprx. Volume (μl) | Temp. Stored | Concentration |
|---|---|---|---|---|---|
| 1 | HA Alone | 19UL-SG-001 | 100 | 4° C. | 1.01 mg/ml free HA |
| 2 | TMV NtK Alone | 18HA-NTK-001 | 100 | 4° C. | 0.54 mg/ml free TMV NtK |
| 3 | HA:HA Conjugates with added TMV NtK | 19UL-SG-004 | 100 | 4° C. | 2.335 mg/ml |

TABLE 11

TEM Imaging Samples-Conjugates

Figure 30:
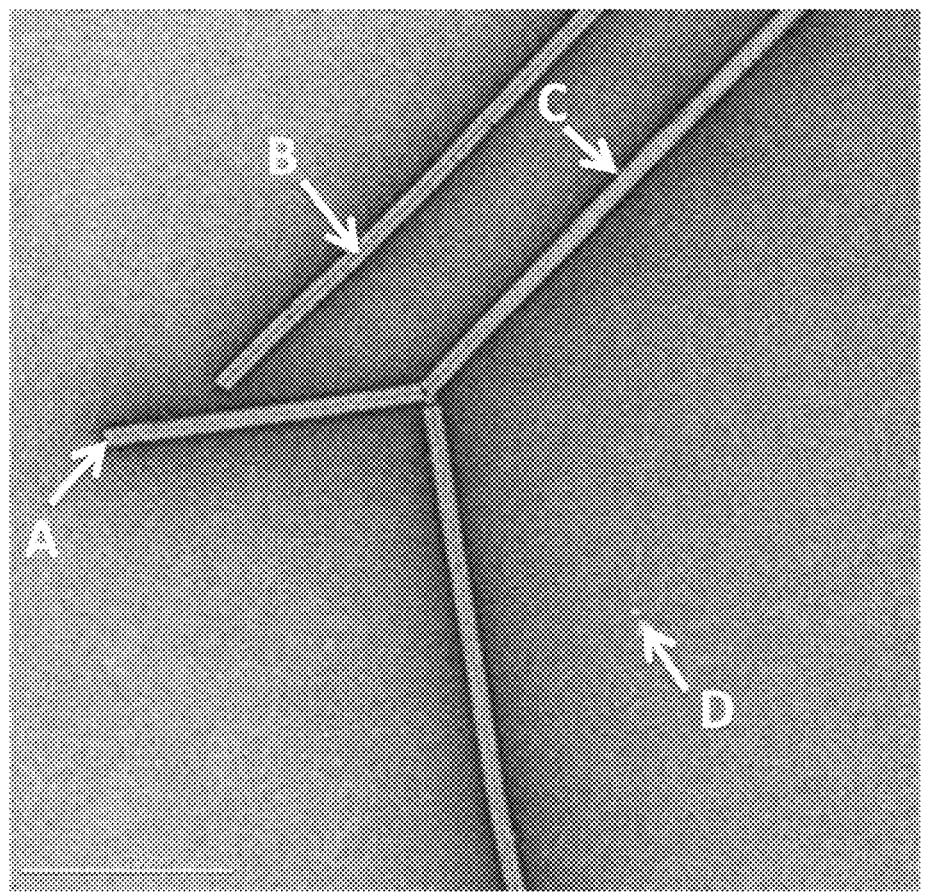
FIG. 30 is a negative stain TEM image of recombinant antigen conjugated to a virus at a virus to recombinant antigen ratio of 16:1, according to multiple embodiments and alternatives.

| Sample | Ratio | Lot | Approx. Volume (μl) | Temp. Stored | Concentration |
|---|---|---|---|---|---|
| 4 | TMV:HA = 1:1 | 18KBP-VP-SG-002 | 100 | 4° C. | 5.2 mg/ml |
| 5 | TMV:HA = 1:1 | 19UL-SG-001 | 100 | 4° C. | 1.688 mg/ml |
| 6 | TMV:HA = 4:1 | 19UL-SG-002 | 100 | 4° C. | 1.387 mg/ml |
| 7 | TMV:HA = 16:1 | 19UL-SG-003 | 100 | 4° C. | 3.479 mg/ml |

In the various designations listed herein, "KBP-VP" describes a TMV Antigen Presentation and is provided for reference purposes only. FIG. 24 is a TEM image of sample 1 (free HA, lot 19UL-SG-001) at a magnification of 52,000× and a scale bar of 200 nm. In FIG. 24, this sample contained small globular arrows (indicated by arrow A) and elongated particles (indicated by arrow B) that ranged from ~5 nm to ~9 nm in size. The appearance of these particles shows a regular structure consistent with ordered aggregation of HA in keeping with native trimer conformation. In addition, the particles were well dispersed with minimal instances of clumping.

FIG. 25 is a TEM image of sample 2 (TMV NtK alone, lot 18HA-NTK-001) at a magnification of 52,000× and a scale bar of 200 nm. In FIG. 25, rod-shaped particles (arrow A) were observed in sizes ranging from ~125 nm to ~700 nm in length and ~18 nm to ~20.5 nm in width. These dimensions are consistent with the size and shape of TMV particles. In addition, a central ~4 nm channel was observed in the rods (arrow B), which is a known characteristic of TMV. Multiple rods were frequently aligned parallel to their long axis and the surface of the rods were generally smooth. On a few occasions, small ~8 nm to ~10 nm globular particles (arrow C) were observed both associated with the surface of the rods and not associated with the rod-shaped particles in the background. These globular particles (arrow C) did not resemble individual HA trimers.

FIG. 26 is a TEM image of sample 3 (HA:HA Self-Conjugates with added. TMV NtK, lot 19UL-SG-004) at a magnification of 52,000× and a scale bar of 200 nm. In FIG. 26, rod-shaped particles were observed that ranged from ~25 nm to ~885 nm in length to ~18 μm to ~20.5 μm in width (arrow A) and a central ~4 nm inner channel (arrow B). The rods were either not decorated at all or sparsely decorated with small, proteinaceous particles of various sizes and shapes arrow C). Some of the small, proteinaceous particles were also seen in the background, not associated with the rods (arrow D). FIG. 26 illustrates larger clumps of HA particles, but the TMV looks identical to the unconjugated TMV (shown in FIG. 25) as expected.

FIG. 27 is a TEM image of sample 4 (TMV:HA in a 1:1 ratio, lot 18 KBP-VP-SG-002) at a magnification of 52,000× and a scale bar of 200 nm. In FIG. 27, rod-shaped particles were observed that ranged in size from ~50 nm to more than ~1000 nm in length and ~18 μm to ~20.5 nm in width (arrow A) with a ~4 nm central inner channel (arrow B). The particle rods were similar in size and shape to the conjugated. TMV observed in FIG. 28, with the exception that the majority of the rods were heavily decorated with small proteinaceous densities on their surface (arrow C). Some of the small, proteinaceous particles were also seen in the background, not associated with the rods (arrow D). The sample 5 shown in FIG. 27 looks superior to the other TEM images which is most likely due to the difference in virus treatment prior to conjugation. For this batch, the virus was formulated at pH 5.50, then the pH was reduced to 4.50 for 15 minutes, and brought back up to pH 5.50 at the start of the conjugation reaction. For the batches shown in FIGS. 28-30, the virus was formulated directly into pH 4.50 and held overnight before the conjugation.

FIG. 28 is a TEM image of sample 5 (TMV:HA in a 1:1 ratio, lot 19UL-SG-001) at a magnification of 52,000× and a scale bar of 200 nm. In FIG. 28, many rod-shaped particles were visible that ranged from ~65 nm to ~720 nm in length and ~18 nm to ~20.5 nm in width (arrow A) with a ~4 nm central inner channel (arrow B). The particle rods were similar in size and shape to the free TMV NtK (sample 2) observed in FIG. 25. However, in contrast to the unconjugated virus shown in FIG. 25, the particle rods observed in FIG. 28 were moderately decorated with proteinaceous densities (arrow C). These densities were irregular in shape and size, and appeared to be randomly associated with the surface of the rods with no obvious pattern. Some of the small, proteinaceous particles were also seen in the background, not associated with the rods (arrow D).

FIG. 29 is a TEM image of sample 6 (TMV:HA in a 4:1 ratio, lot 19UL-SG-002) at a magnification of 52,000× and a scale bar of 200 nm. In FIG. 29, rod-shaped particles were observed that ranged from ~25 nm to more than ~1000 nm in length, and ~18 nm to ~20.5 nm in width (arrow A) with a ~4 nm central inner channel (arrow B). The particle rods observed in FIG. 29 were similar in dimension to the previously conjugated samples, but the level of surface decoration of the small proteinaceous densities (arrow C) ranged from moderate to sparse. Some of the small, proteinaceous particles were also seen in the background, not associated with the rods (arrow D).

FIG. 30 is a TEM image of sample 7 (TMV:HA in a 16:1 ratio, lot 19UL-SG-003) at a magnification of 52,000× and a scale bar of 200 nm. In FIG. 30, rod-shaped particles were observed that ranged in size from ~30 nm to more than ~1000 nm in length and ~18 nm to ~20.5 nm in width (arrow A) with a ~4 nm central inner channel (arrow B). The particle rods observed in FIG. 30 were similar in overall morphology to the previous conjugated samples. However, the rods were only sparsely decorated with protein (arrow C) or not decorated at all. Only a few small, proteinaceous particles were seen in the background, not associated with the rods (arrow D).

FIGS. 24-30 illustrate that the 1:1 ratio exhibited full rod decoration, the 4:1 ratio exhibited moderate decoration, and the 16:1 ratio exhibited sparse decoration. Stated differently, the 1:1 ratio generated virus rods with heavy antigen decoration (i.e. more density) of HA antigen, while the 16:1 ratio generated viral rods with less antigen decoration (i.e. less density) of HA antigen on each rod. As a byproduct of the conjugation reaction, HA-HA self-conjugates were observed, principally in the 1:1 ratio reactions. Furthermore, compared with the 1:1 reactions, there appeared to be less free HA or HA-HA conjugates in the 4:1 reaction and even less with the 16:1 reaction in TEM images as well as SDS-PAGE reaction analyses (data not shown). In other words, there was higher conjugation efficiency of HA to solely TMV rods overall at the 16:1 ratio, but less density of HA per rod than the 1:1 reaction.

Example 11—Sedimentation Velocity Analysis of Different Conjugation Conditions Sedimentation velocity ("SV"), as measured in an analytical ultracentrifuge ("AUC"), is an ideal method for obtaining information about protein heterogeneity and the state of association of aggregation. Specifically, aggregates or different oligomers can be detected on the basis of different sedimentation coefficients. This method also detects aggregates or other minor components at a level below 1% by weight. Furthermore, SV provides high quality quantitation of the relative amounts of species and provides accurate sedimentation coefficients for any aggregates.

In order to measure the amount of self-conjugated and unreacted HA, as well as the amount of HA occupancy on TMV NtK with different conjugation conditions, the total signal associated with the sedimentation of free antigen, free virus, and various TMV:HA ratios were measured using SV-AUC. The following samples and descriptions are provided in Table 12:

TABLE 12

Samples and Descriptions for SV-AUC

| Sample | Description | Lot | Concentration |
|---|---|---|---|
| 1 | HA Alone | 19S-G-001 | 1.01 mg/ml |
| 2 | TMV Ntk Alone | 18HA-NTK-001 | 0.54 mg/ml |
| 3 | TMV:HA = 1:1 | 19UL-SG-004 | 1.0 mg/ml |
| 4 | TMV:HA = 1:1 | 18 KBP-VP-SG-002 | 1.0 mg/ml |
| 5 | TMV:HA = 1:1 | 19UL-SG-001 | 0.8 mg/ml |
| 6 | TMV:HA = 4:1 | 19UL-SG-002 | 1.0 mg/ml |
| 7 | TMV:HA = 16:1 | 19UL-SG-003 | 1.0 mg/ml |

These stocks were shipped cold (not frozen) and subsequently stored at 2-8° C. until analyzed. 1×PBS from Corning was used for sample dilution and as a reference blank. Sample 1 was diluted 1:1, and samples 2-7 were diluted 1:3 with 1×PBS to create the sedimentation velocity samples. These dilutions were carried out to bring the total absorbance of the sample within the linear range of the absorbance detection system.

Methods—The diluted samples were loaded into cells with 2-channel charcoal-epon centerpieces with 12 mm optical pathlength. 1×PBS was loaded into the reference channel of each cell. The loaded cells were placed into an analytical rotor, loaded into an analytical ultracentrifuge, and brought to 20° C. The rotor was then brought to 3000 rpm and the samples were scanned (at 280 nm) to confirm proper cell loading. For samples 2-7, the rotor was brought to the final run speed of 9,000 rpm. Scans were recorded at this rotor speed as fast as possible (every 3 min) for 11 hours (250 total scans for each sample). For sample 1 (the free HA), the rotor was brought to 35,000 rpm and scans were recorded every 4 min for 5.3 hours. The data was then analyzed using the c(s) method described in Schuck, P. (2000), "Size-distribution analysis of macromolecules by sedimentation velocity ultracentrifugation and Lamm equation modeling," *Biophys. J.* 78, 1606-1619. Using this method, raw scans were directly fitted to derive the distribution of sedimentation coefficients, while modeling the influence of diffusion on the data to enhance the resolution.

Results and Discussion—The high-resolution sedimentation coefficient distributions for samples 1-7 are shown in FIGS. 31-37. In these figures, the vertical axis provides the concentration and the horizontal axis provides the separation on the basis of sedimentation coefficient. Each distribution has been normalized by setting the total area under the curve to 1.0 (100%) to ensure the area under each peak provides the fraction of that species. Since samples 2-7 contain material sedimenting over a broad range of sedimentation coefficients, the data analysis has been pushed to cover species sedimenting as fast as 2000 Svedburg units (S), and therefore the horizontal axis is on a log scale. To compensate for the effect that log scaling could distort the visible area of the peaks, the vertical axis has been multiplied by e sedimentation coefficient, which correctly scales the relative peak areas. The data for sample 1 (free HA) is presented traditionally using a linear sedimentation coefficient scale.

FIG. 31 is normalized sedimentation coefficient distribution for sample 1 (HA alone, lot 195-G-001). Since free antigen is much smaller in size than virus, this sample was analyzed at a much faster rotor speed (35,000 rpm) than samples 2-7 (9,000 RPM) in order to adequately characterize the size distribution. As shown in FIG. 31, sample 1 is somewhat homogeneous, providing 73.7% main peak at 8.967 S. This was the expected result for the HA antigen-only sample. This sedimentation coefficient together with the width of the main boundary imply this main peak species has a molar mass of ~222 kDa, which may indicate the main peak corresponds to roughly a HA trimer of the expected ~70 kDa monomer. It is not physically possible for this sedimentation coefficient to correspond to monomer; instead, the main peak corresponds to an oligomeric state larger than monomer. As noted in Table 13 below, SEC HPLC data at HA3 Singapore release, >90% of HA was identified in trimer status, with 3 of the 4 samples analyzed having greater than 50% trimerization.

TABLE 13

Extent of trimerization

| Antigen | Pre-Clinical Lot | HA lot number | SEC Trimer % | SEC Monomer % |
|---|---|---|---|---|
| B/Colorado | 18 KBP-VP CO-001 | 18HA-CO-003 | 55.05% | 44.95% |
| A/Michigan | 18 KBP-VP-MH-002 | 18HA-MH-007 | 11.93% | 88.07% |

TABLE 13-continued

Extent of trimerization

| Antigen | Pre-Clinical Lot | HA lot number | SEC Trimer % | SEC Monomer % |
|---|---|---|---|---|
| B/Phuket | 18 KBP-VP-PH-002 | 18HA-PH-003 | 84.51% | 15.49% |
| A/Singapore | 18 KBP-VP-SG-002 | 18HA-SG-003 | 94.52% | 3.90% |

Figure 31:
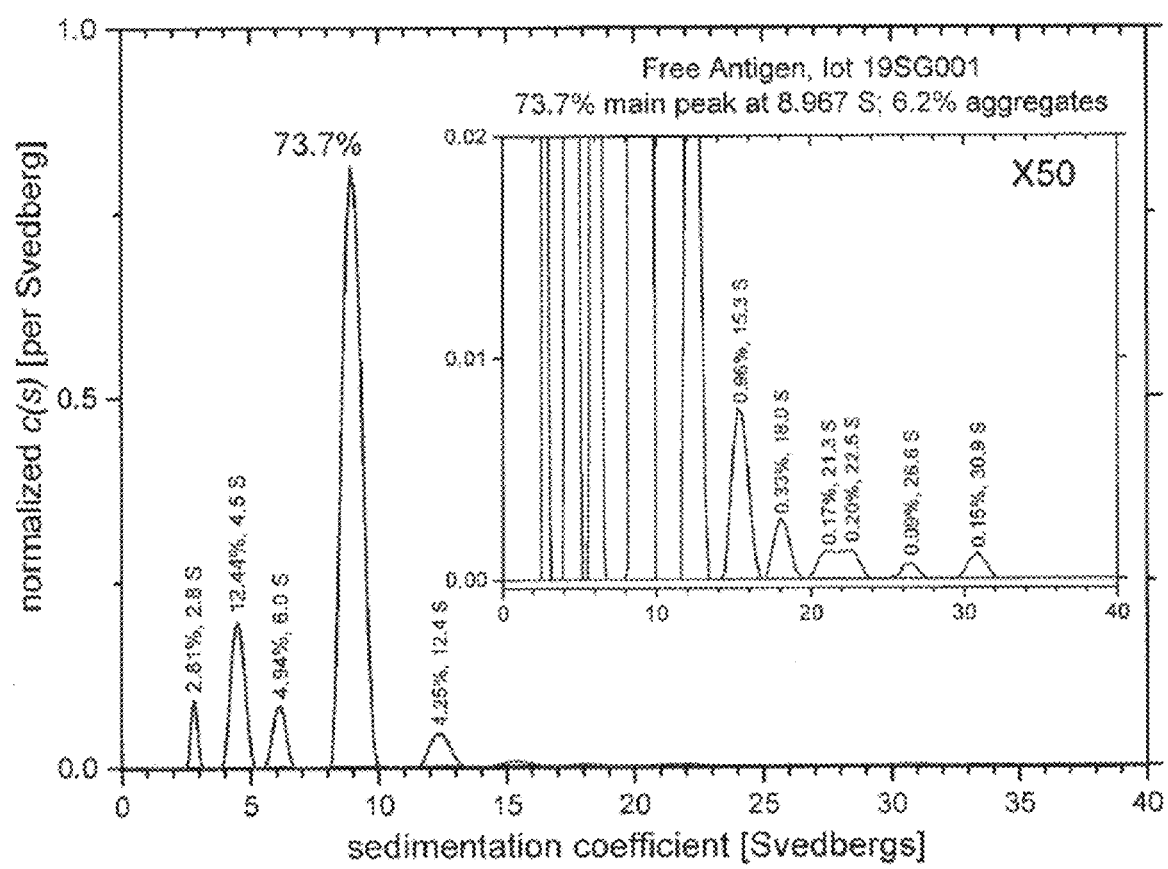
FIG. 31 is a normalized sedimentation coefficient distribution of an antigen, according to multiple embodiments and alternatives.

As also shown in FIG. 31, seven minor peaks sedimenting faster than the main peak were detected, which together represent 6.2% of the total sedimenting absorbance. Presumably those two peaks represent product aggregates rather than high molecular weight impurities. The principal aggregate species at 12.4 S (4.25%) is sedimenting 1.4 times faster than the monomer, a ratio that falls within the range of 1.4 to 1.5 usually observed for dimers. While that ratio suggests that this species is a dimer of the main peak material (possibly a hexamer of the ~70 kDa monomer), its sedimentation coefficient could also suggest that it is a highly extended or partially-unfolded trimer of the main peak material (possibly a nonamer of the ~70 kDa monomer).

In FIG. 31, the next peak at 15.3 S (0.96%) is sedimenting 1.7× faster than monomer which suggests a trimer of the main peak material. No absorbance was detected for any sedimentation coefficients larger than 30.9 S. Also, three minor peaks sedimenting more slowly than the main peak were also detected at 2.8 S (2.81%), 4.5 S (12.44%), and 6.0 S (4.94%). Of these minor peaks, the peak at 4.5 S most likely corresponds to antigen monomer.

Figure 32:
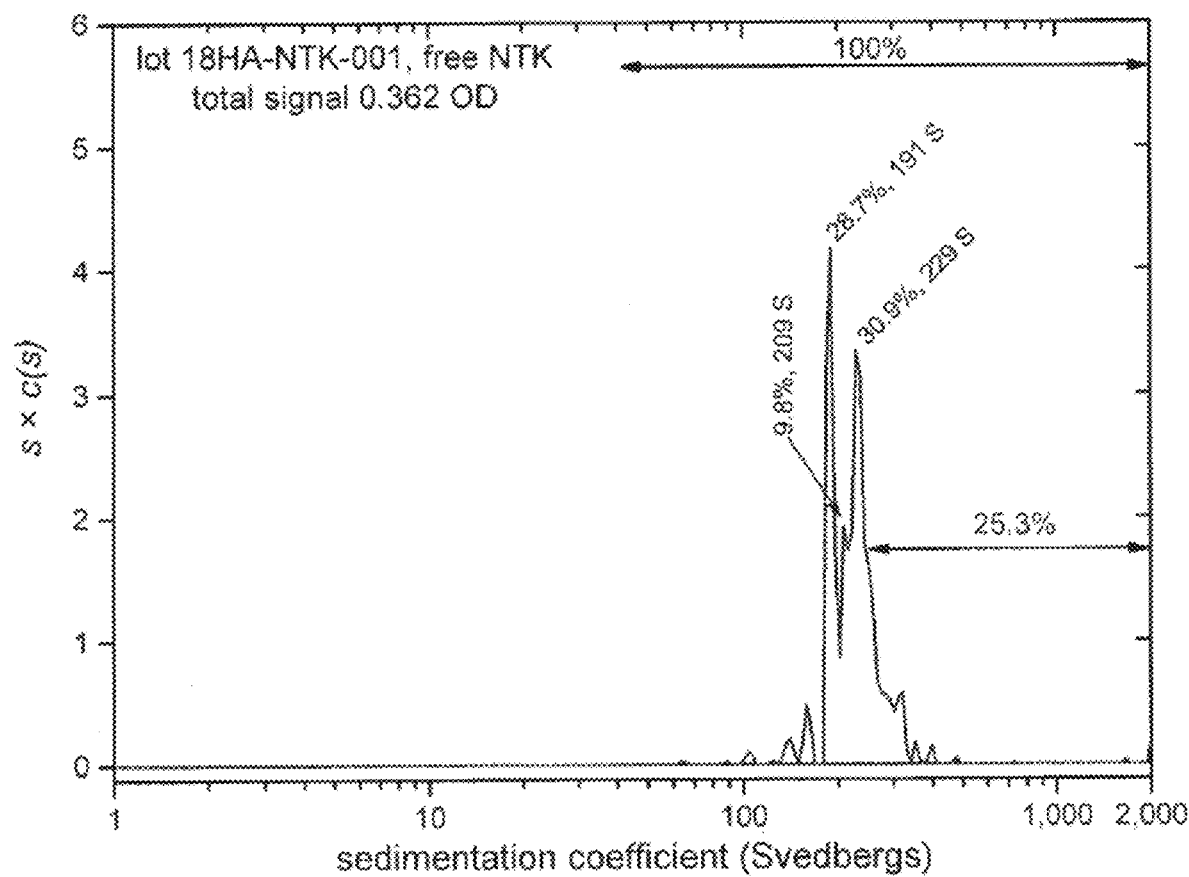
FIG. 32 is a normalized sedimentation coefficient distribution of a virus, according to multiple embodiments and alternatives.

FIG. 32 is the normalized sedimentation coefficient distribution for sample 2 (free TMV NtK, lot 18HA-NTK-001). As shown in FIG. 32, no sedimenting material was detected below ~60 S. This sample appeared quite heterogeneous, with the most abundant peak sedimenting at 229 S (30.9%). The second most abundant peak was detected at 191 S (28.7%). It is not clear which peak corresponds to fully assembled virus. In addition, 25.3% of the total signal was observed sedimenting from 229 S to 2,000 S, the largest sedimentation coefficient allowed in this Example 11. It is unclear what the partially-resolved peaks from ~60 S to 2000 S represent.

FIGS. 33-37 show the normalized sedimentation coefficient distribution for virus-antigen conjugates. Each of these figures shows a significant absorbance of about 0.15 OD that did not sediment. This was established by increasing the rotor speed to 35,000 RPM after the completion of each run, in order to pelletize all remaining material. This material was not observed in either the free antigen or the free TMV NtK samples. However, since this material did not sediment, it did not affect the results of the measured size distributions.

Figure 33:
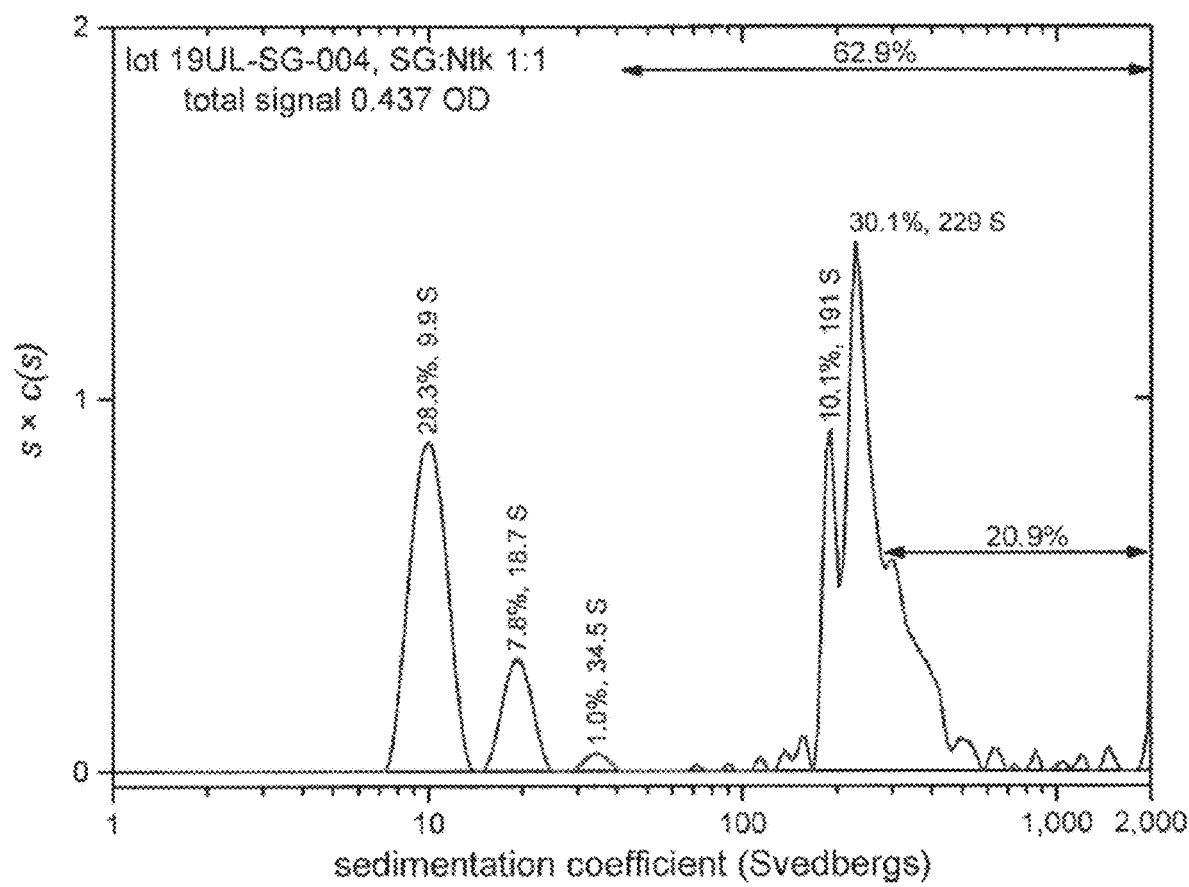
FIG. 33 is a normalized sedimentation coefficient distribution of recombinant antigen conjugated to a virus at a virus to recombinant antigen ratio of 1:1, according to multiple embodiments and alternatives.

FIG. 33 is the normalized sedimentation coefficient distribution for sample 3 (TMV to HA at 1:1 Ratio, lot 19UL-SG-004). As illustrated in FIG. 33, the results in the sedimentation coefficient range from about 40 S to 2000 S, and are similar to those observed for free virus (shown in FIG. 33). Three peaks were also observed in the sedimentation coefficient range of 1-40 S: 9.9 S (28.3), 18.7 S (7.8%), and 34.5 S (1.0%). The peak observed at 9.9 S may correspond to the main peak observed in the free HA sample (shown in FIG. 32). The variety of smaller peaks may reflect HA-HA self-conjugation events.

Figure 34:
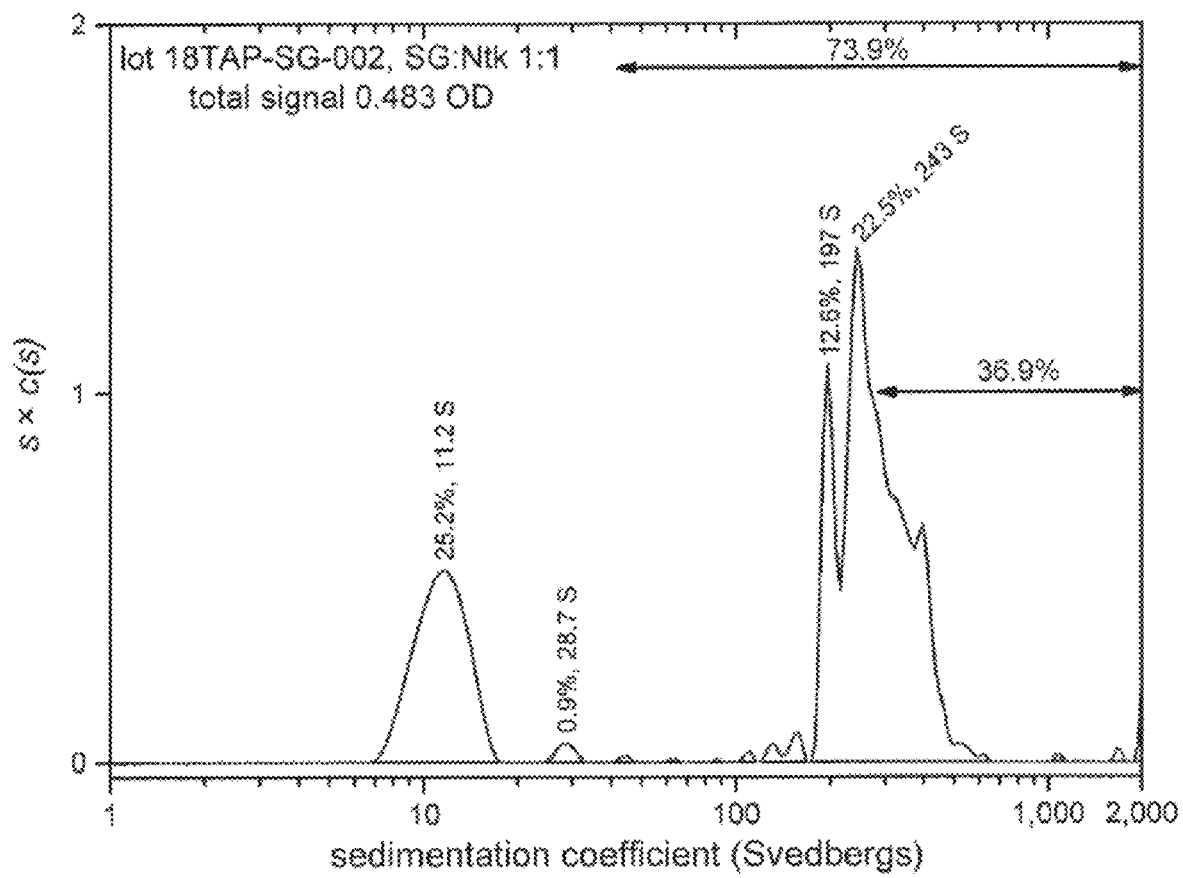
FIG. 34 is a normalized sedimentation coefficient distribution of recombinant antigen conjugated to a virus at a virus to recombinant antigen ratio of 1:1, according to multiple embodiments and alternatives.
Figure 35:
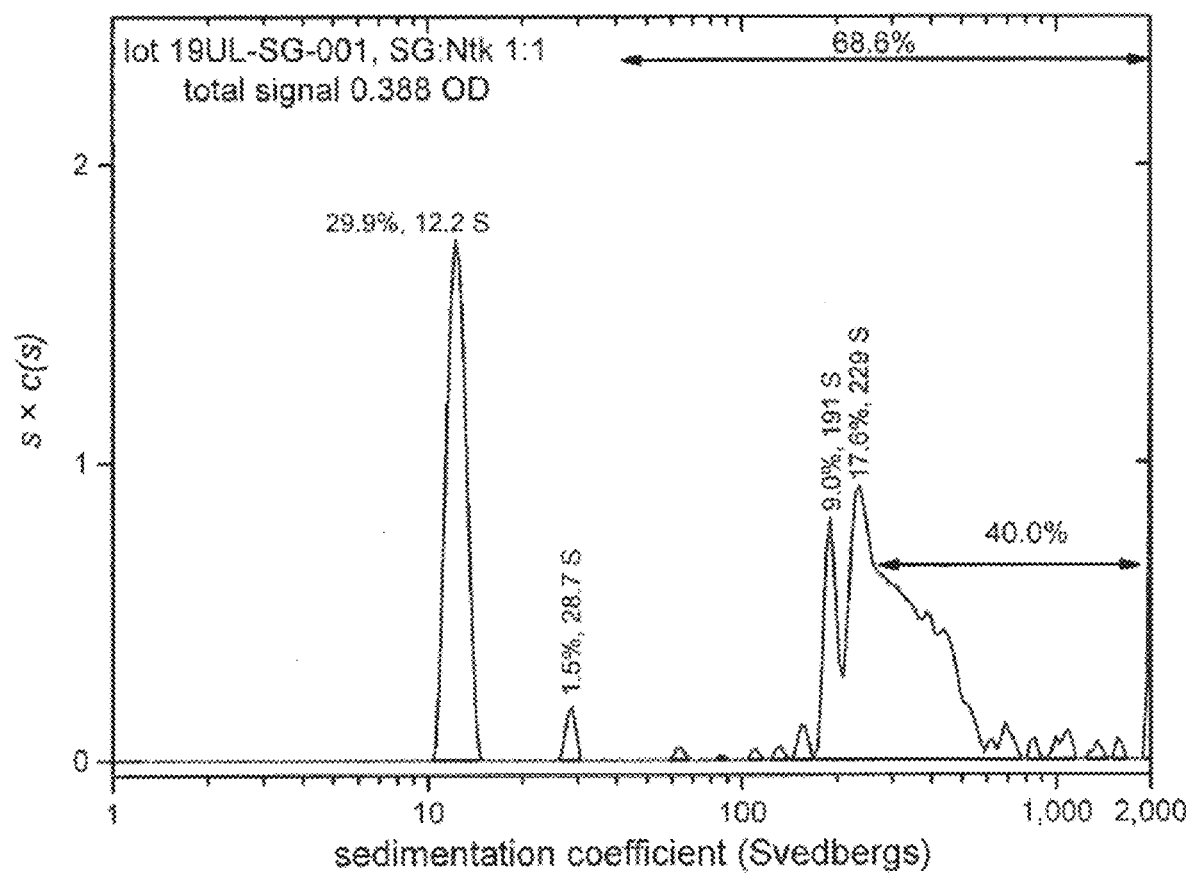
FIG. 35 is a normalized sedimentation coefficient distribution of recombinant antigen conjugated to a virus at a virus to recombinant antigen ratio of 1:1, according to multiple embodiments and alternatives.

FIG. 34 is the normalized sedimentation coefficient distribution for sample 4 (TMV to HA at 1:1 Ratio, lot 18 KBP-VP-SG-002) and FIG. 35 is the normalized sedimentation coefficient distribution for sample 5 (TMV to HA at 1:1 Ratio, lot 19UL-SG-001). The results shown in FIGS. 34 and 35 are similar to those discussed for sample 3 (and shown in FIG. 33). However, some notable differences were observed, First, it is difficult to comment on differences observed for the free antigen sample (from 1-40 S) because of poor resolution at this rotor speed. Nevertheless, FIGS. 34 and 35 show more total signal present from 40 S-2,000 S (which is indicative of virus associated material) than sample 3.

Figure 36:
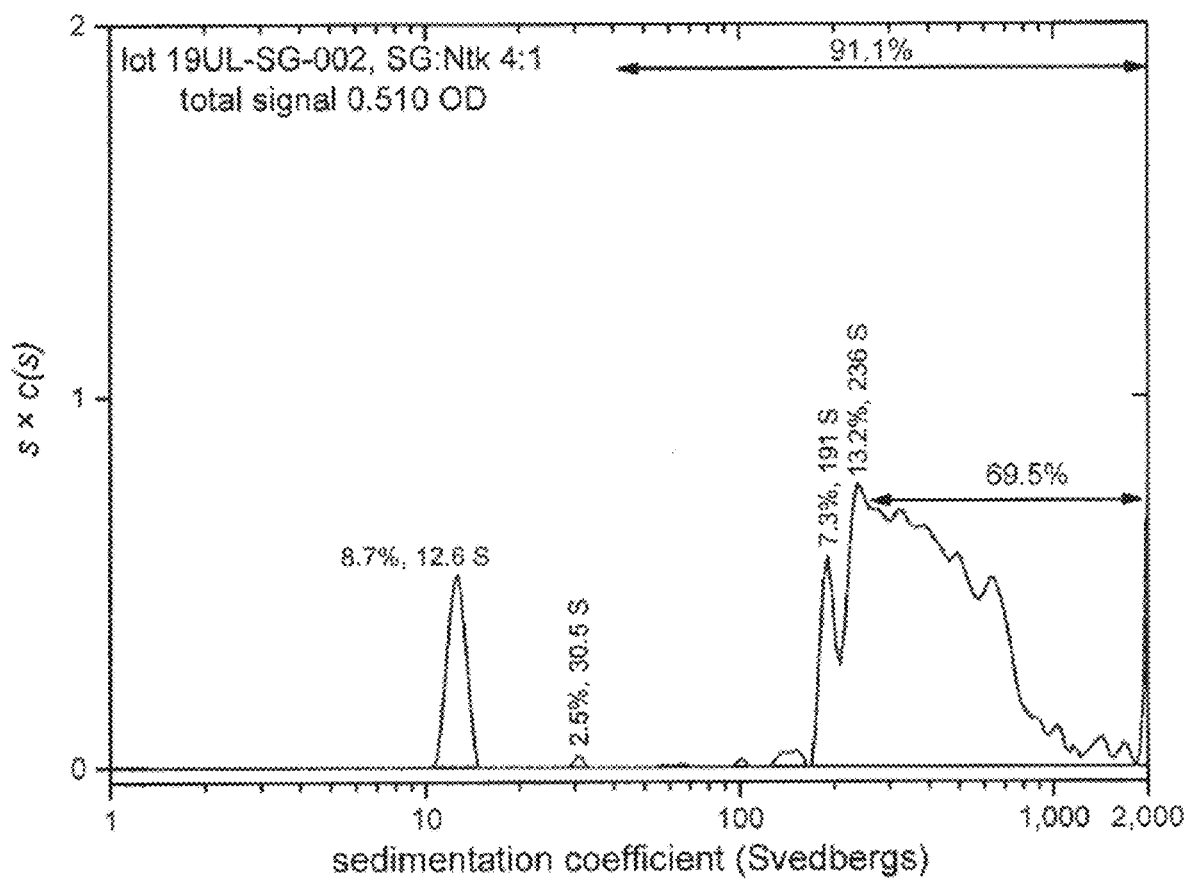
FIG. 36 is a normalized sedimentation coefficient distribution of recombinant antigen conjugated to a virus at a virus to recombinant antigen ratio of 4:1, according to multiple embodiments and alternatives.
Figure 37:
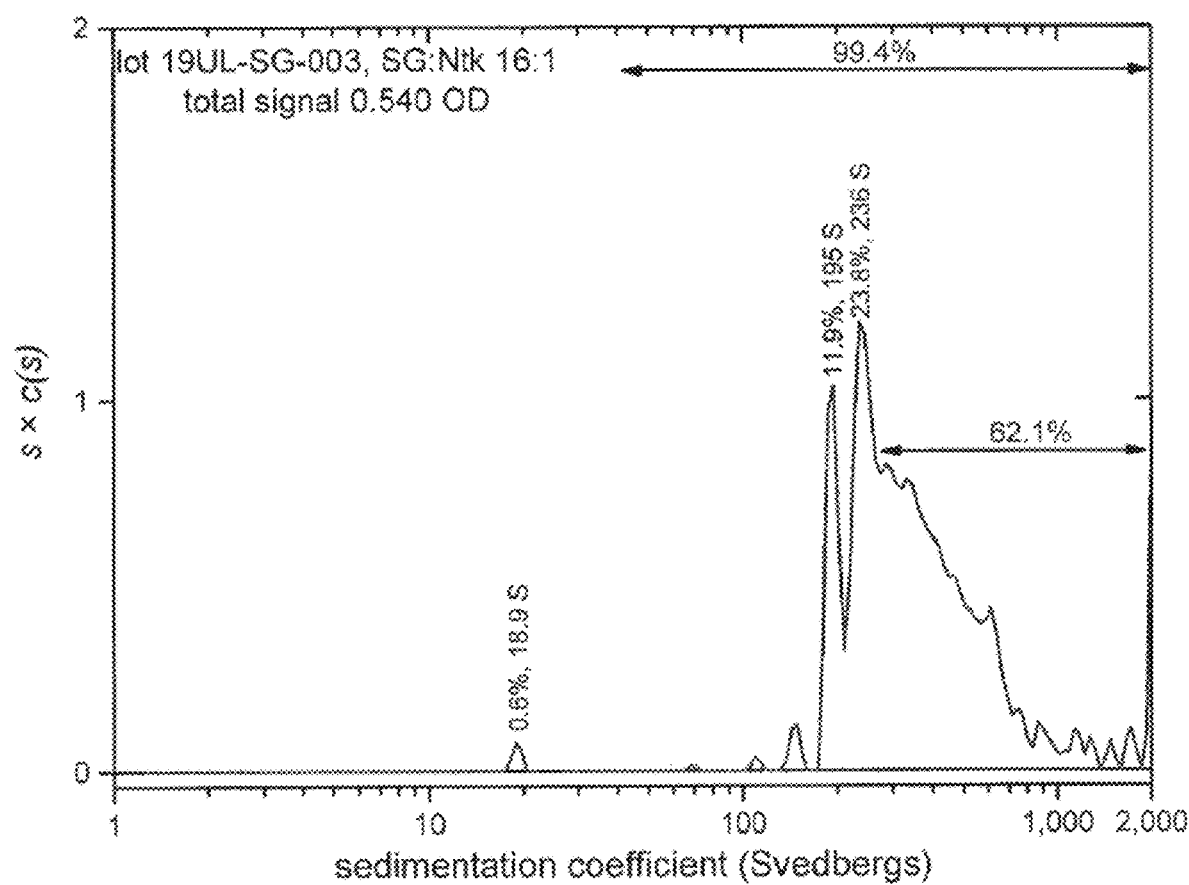
FIG. 37 is a normalized sedimentation coefficient distribution of recombinant antigen conjugated to a virus at a virus to recombinant antigen ratio of 16:1, according to multiple embodiments and alternatives.
Figure 38:
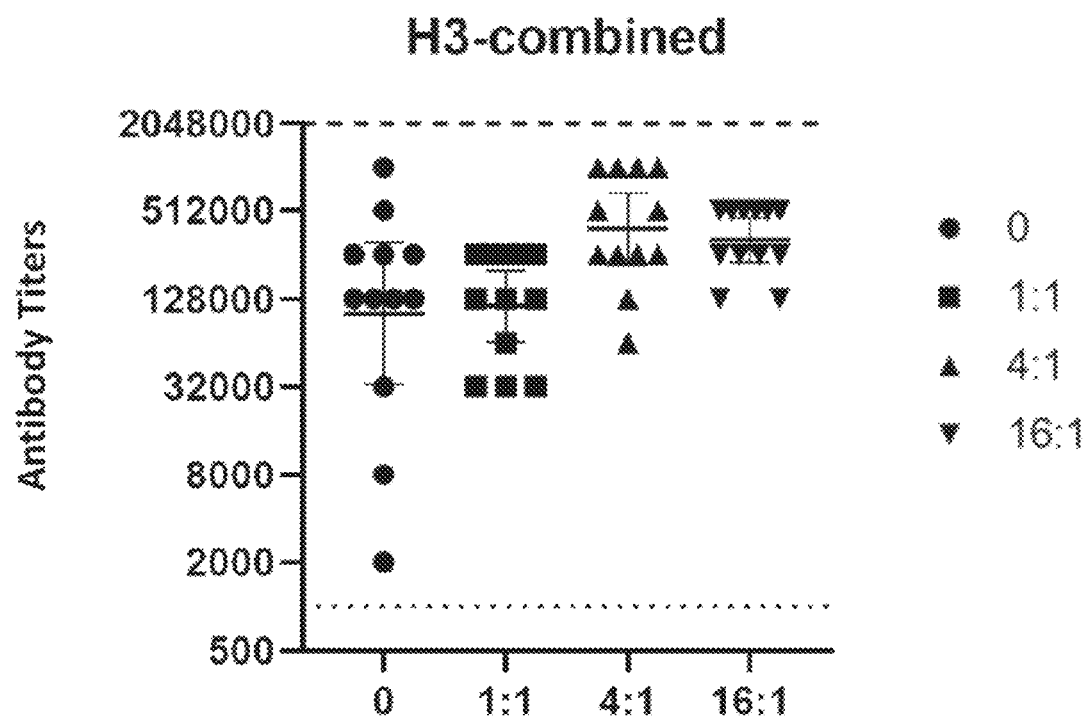
FIG. 38 is a scatterplot of antigen-relevant titers in a source organism following administration of virus-antigen products at various virus to recombinant ratios, according to multiple embodiments and alternatives.
Figure 39:
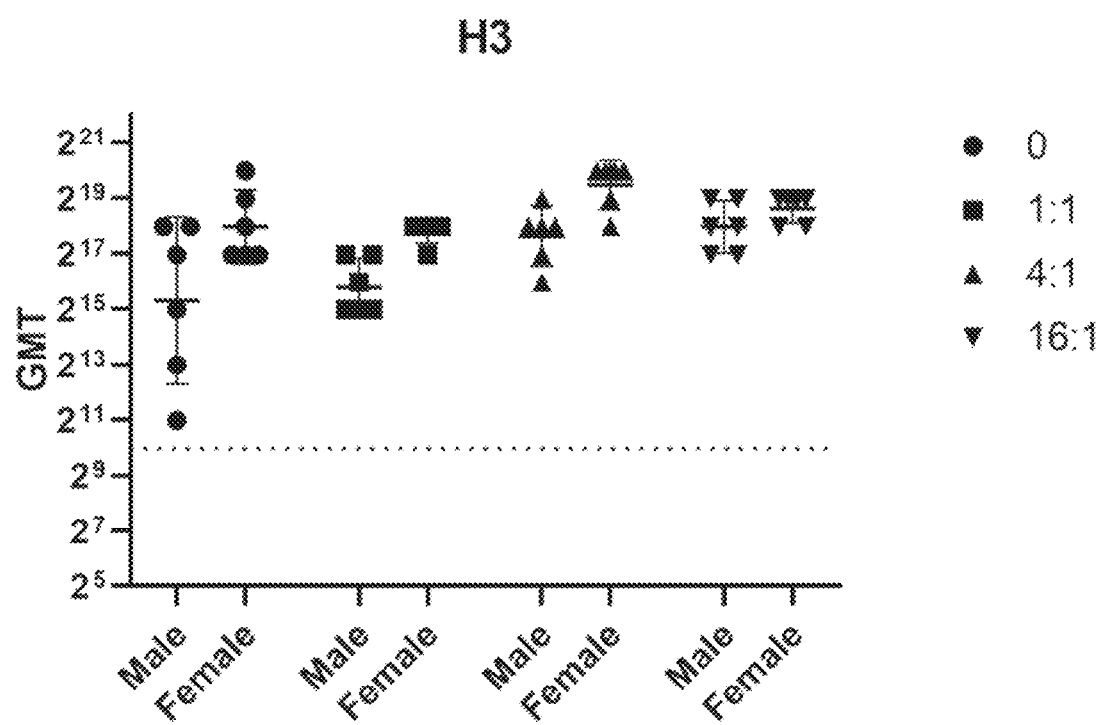
FIG. 39 is a geometric mean testing illustrating the antigen-relevant titers in a source organism following administration of virus-antigen products at various virus to recombinant ratios, according to multiple embodiments and alternatives.

FIG. 36 is the normalized sedimentation coefficient distribution for sample 6 (TMV to HA at a 4:1 ratio, lot 19UL-SG-002), and FIG. 37 is the normalized sedimentation coefficient for sample 7 (TMV to HA at a 16:1 ratio, lot 19UL-SG-003). FIG. 36 shows 91.1% total virus-associated material (i.e. virus-antigen conjugates) and FIG. 37 shows 99.4% virus-associated material (i.e. virus-antigen conjugates).

The results for the virus-antigen normalized sedimentation coefficient distribution, as shown in FIGS. 33-37, are set forth in Table 14. As previously noted, the fraction between 1-40 S indicates the percent HA monomer/trimer, and the fraction between 40-2000 S indicates the percent TMV NtK-HA conjugate, according to multiple embodiments and alternatives.

TABLE 14

SV-AUC Results of the Different Virus-Antigen Conjugates

| Sample | Lot | Ratio | Fraction Between 1-40 S (%) (HA monomer/trimer) | Fraction Between 40-2000 S (%) (TMV NtK-HA Conjugate) |
|---|---|---|---|---|
| 3 | 19UL-SG-004 | 1:1 | 37.1 | 62.9 |
| 4 | 18 KBP-VP SG-002 | 1:1 | 26.1 | 73.9 |
| 5 | 19UL-SG-001 | 1:1 | 31.4 | 68.6 |
| 6 | 19UL-SG-002 | 4:1 | 11.2 | 91.1 |
| 7 | 19UL-SG-003 | 16:1 | 0.6 | 99.4 |

The results in Table 14 indicate that a 1:1 ratio has more self-conjugation of HA and HA products, as compared to the 4:1 and 16:1 ratios. In addition, increasing the TMV:HA ratio results in virtually complete engagement of HA products in TMV-conjugation events (approaching almost 100% conjugation in sample 7).

According to multiple embodiments and alternatives, decreasing the amount of HA in a conjugation reaction, by increasing the TMV NtK to HA ratio from 1:1 to 16:1, results in: (1) reducing the aggregation of HA antigen on each TMV rod, as observed by Example 10 and FIGS. 24-30; (2) decreasing the amount of self-conjugation and unreacted HA events to nearly zero, as shown by FIGS. 31-37 and Table 14; and (3) increasing the association of HA (as a percentage) to TMV compared with self-conjugation and unreacted HA events, as shown by FIGS. 31-37 and Table 14.

Example 12—Immune Response in Mice

To determine immune response following administration of the inventive virus-antigen conjugates, mice were administered the conjugates as vaccines via intramuscular injection. Each vaccine was a TMV:HA conjugate produced at a 1:1 (TMV:HA) ratio as described herein, administered to most of the animals on Day 0 and 14 of the study (control animals were administered buffer alone, TMV alone, or HA alone). Those administered vaccine received either 15, 7.5, or 3.75 mcg (micrograms) of antigen, as shown below in Table 15. One cohort had samples drawn on Day 7, another at Days 14 and 21, and a third at Days 28, 42, and 90, with the samples then subjected to hemagglutination inhibition (HAI) assay.

Based on the assay, no measurable response from any animal for any vaccine occurred at Days 7 or 14. However, initial responses were seen in some animals on Day 21. Specifically, 10/27 animals showed low level responses (only 1 of them >80 HAI titers) for H1N1 vaccine (Influenza A/Michigan/45/2015 (H1N1pdm09)). Also, 22/27 showed low level responses (only 2 of them >80) for H3N2 vaccine (Influenza A/Singapore/INFIMH-16-0019/2016). On Day 28, the number of animals within this cohort responding measurably to H1N1 vaccine was 8/29 with a single animal at 80 HAI titers and all others less. For H3N2 vaccine, the number responding measurably was 14/29, also with a single animal at 80 HAI titers and all others less.

The most pronounced results were observed from blood samples taken at Day 42 and Day 90, which are presented in Table 15, below. In this table, a standard error of the mean (SEM) is provided with the average and the fraction of animals responding (Fr.Resp.). It will be noted that in each cohort, some of the mice received vaccines for Influenza B viruses (B/Colorado/06/2017 (V) and B/Phuket/3073/2013 (Y), respectively). No response was detected in these animals on any of the days, as expected because B-type influenza viruses and corresponding HA immunogens are known to not generate HAI titers in mice with the efficiency and effectiveness as A-type HA immunogens.

TABLE 15

Immune response based on dose and time post-vaccination

| | Day 42 Average HAI Titers | | | | Day 90 Average HAI Titers | | | |
|---|---|---|---|---|---|---|---|---|
| Immunogen | H1N1 | Fr. Resp | H3N2 | Fr. Resp | H1N1 | Fr. Resp | H3N2 | Fr. Resp |
| 1. Vehicle alone | 0 | 0 | 0 | 0 | 0 | 0 | 0 | 0 |
| 2.TMV alone: 15 mcg | 0 | 0 | 0 | 0 | 0 | 0 | 0 | 0 |
| 3.HA Quad 15 mcg | 0 | 0 | 0 | 0 | 0 | 0 | 0 | 0 |
| 4.HA Quad 7.5 mcg | 0 | 0 | 0 | 0 | 0 | 0 | 0 | 0 |
| 5.HA Quad 3.75 mcg | 0 | 0 | 0 | 0 | 0 | 0 | 0 | 0 |
| 6.V-HA Quad 15 mcg | 20 ± 5.477 | 7/10 | 27 ± 7.218 | 8/10 | 274 ± 66.336 | 10/10 | 136 ± 33.442 | 10/10 |
| 7.V-HA Quad 7.5 mcg | 26 ± 4.733 | 9/10 | 22 ± 9.466 | 6/10 | 174 ± 40.797 | 9/10 | 84 ± 45.77 | 6/10 |
| 8.V-HA Quad 3.75 mcg | 19 ± 4.566 | 7/9 | 17 ± 4.969 | 6/9 | 224 ± 62.993 | 8/9 | 40 ± 10.423 | 7/9 |

Separate from the previously described immune response study, and to further evaluate the inventive system in terms of suitable virus to antigen ratios, the humoral immune response in mice was evaluated following vaccination at various TMV:HA conjugate ratios (i.e., 1:1, 4:1, 16:1) of both Influenza A Antigen and Influenza B Antigen along with controls as noted below. In this manner, various conjugation ratios and their effect on immune response were studied. The mice receiving vaccination were administered 15 meg HA via injection on Day 0 and Day 14 of the study, in a subcutaneous region dorsally. The serum antibody responses to the vaccination were then analyzed for HA-specific activity. Tables 15 (H3 influenza virus used as capture protein) and 16 (recombinant H3 protein used as capture protein) show the groupings of mice (12 mice per grouping), and the agents that were administered, with the right-hand column in each table presenting ELISA antibody (Ab) titers results.

TABLE 16

TMV:HA ratio study-A-type influenza HA.

| Grouping | Vaccine | Conjugation ratio (TMV:Antigen) | Average ELISA Ab Titer |
|---|---|---|---|
| 1. | Phosphate-buffered saline | n/a | 0 |
| 2. | TMV-H3 | H3 HA:HA | 0 |
| 3. | TMV-H3 | 1:1 | 0 |
| 4. | TMV-H3 | 4:1 | 120 |
| 5. | TMV-H3 | 16:1 | 200 |

FIG. 38 is a scatterplot associated with Table 16, which provides graphical analysis of H3:HA Ab titers following administration of vaccine at ratios of 0, 1:1, 4:1, and 16:1 (TMV:HA). FIG. 39 also illustrates graphically the results of geometric mean testing of antigen-relevant Ab titers, using recombinant H3 antigen (Table 17) as coating or capture H3 virus as capture protein (Table 17) that binds with anti Influenza A H3 Antigen antibody. In terms of density (surface area of TMV occupied by HA), the trend for the three ratios progresses from 1:1 (most dense)>4:1>16:1 (least dense), as demonstrated by TEM and AUC analyses. In these figures representing ELBA results obtained with H3 antigen, the highest immune response was observed with the least dense conjugate. That is, the trend for immune response was 16:1>4:1>1:1 and went in reverse of the trend for density. Thus, surprisingly it was found at these ratios for TMV:HA, lesser density of conjugation tended to provide better immune response. Possible explanations for this surprising finding that antigenicity does not correlate with maximum HA conjugation events include: (1) more uniform antigen with less to no-unreacted or self-conjugated protein when the density is comparatively lower; (2) there could be more efficient processing of conjugated antigen and more preserved/uniform antigen conformation; and (3) the TMV rods (by way of example) may stimulate more antigen presenting cells to migrate to the injection site and stimulate processing of attached antigen, or some combination of these factors. Note, however, that just the presence of TMV particles does not replace the need for conjugation (see, e.g., Tables 14 and 15).

In addition to Influenza A H3 Antigen, Influenza B Antigen also was studied (B-Phuket HA) using the binding propensity of recombinant Influenza B Phuket Antigen and its corresponding antibody. Table 17, below, presents the results of this part of the study that was there is not as clear of a showing of 16:1>4:1>1:1 based on the results of average ELISA Ab titers.

TABLE 17

TMV:HA ratio study-B-type influenza HA.

| Grouping | Vaccine | Conjugation ratio (TMV:Antigen) | Average ELISA Ab Titer |
|---|---|---|---|
| 1. | Phosphate-buffered saline | n/a | 0 |
| 2. | TMV-B | B Phuket HA:HA | 283± |
| 3. | TMV-B | 1:1 | 211± |
| 4 | TMV-B | 4:1 | 56± |
| 5. | TMV-B | 16:1 | 329± |

Even so, the 16:1 ratio demonstrated the highest average antibody titer. Thus, is reasonable to predict the same relationship between density and immune response applies to the study of the Influenza B Antigen (B-Phuket HA). That is, as with the results of H3 antigen, immune response will be higher for less dense forms of the conjugates. Additionally, there is reason to believe the conjugation reaction for the 4:1 ratio did not proceed as the reactions for the other ratios because of possible abnormalities during conjugation, and the fact that neither electron microscopy nor ultracentrifugation analysis were performed on this sample. In any case, the data here show immune response at all three ratios. The fact that immune response was achieved at multiple ratios underscores the robustness of the system for not being tied to any one particular ratio. This flexibility as seen with the particular TMV-conjugated vaccines probably gives further indication that the system will work well both when other antigens are conjugated to TMV besides the H3 and H1 antigens included in these studies, as well as when other virus carriers besides TMV are used for the carrier.

In terms of clinical utility, a product conjugated in accordance with any of multiple embodiments and alternatives described herein may be utilized as a vaccine by delivering the purified antigen via a purified virus, such as but not limited to the virus-antigen conjugates described in Examples 7, 9, 10, 11, and 12. Still further, embodiments of the present disclosure include any vaccine products packaged in any number of forms (e.g., vial) with appropriate buffers and additives, being manufactured from any virus-protein conjugate compositions, the conjugation of which is provided for herein. In this respect, embodiments include those wherein such vaccine products are amenable to delivery in the form of unit doses provided to a subject, such as but not limited to administration by syringe or spray through routes that include, but are not limited to, subcutaneous, intramuscular, intradermal administration, and nasal, as well as administration orally by mouth and/or topically, to the extent clinically indicated. By way of non-limiting example, and without detracting from the breadth and scope of the embodiments herein, the size of TMV (typically 18 nm×300 nm) and its rod-like shape promotes antigen uptake by antigen presenting cells (APCs), and thus serves to enhance immunity promoted by T cells (such as Th1 and Th2), including cellular responses, and to provide adjuvant activity to surface conjugated subunit proteins. This activity is also stimulated through viral RNA/URI interaction. As a result, the combined effect of vaccine uptake directly stimulates activation of the APCs. Humoral immunity is typically balanced between IgG1 and IgG2 subclasses through subcutaneous and intranasal delivery. Upon mucosal vaccine delivery, responses also include substantial systemic and mucosal IgA. Cellular immunity is also very robust, inducing antigen-specific secretion, similar to a live virus infection response. Whole antigen fusions allow for native cytotoxic T lymphocyte (CU) epitope processing, without concern for human leukocyte antigen (HLA) variance.

The broad (humoral and cellular) and augmented (amplitude and effectiveness) immune responses associated with the multi-set purification platform according to current embodiments are in sharp contrast to subunit proteins tested without TMV conjugation, which induce little or no cellular or humoral immunity. The impact of these immune responses is that vaccines created via the multi-set platform, according to current embodiments, promotes highly protective responses as single dose vaccines and offers speed and safety not offered by other conventional vaccine platforms. Indeed, the conjugation platform is shown to work on a wide array of viruses and proteins (including antigens), combined within a broad range of ratios and successfully administered at various doses, which again are indicative of the robustness of the system. Additional advantages of the multi-set platform for producing vaccines in current embodiments include: a proactive antigen-stimulating approach for systemic immune protection against pathogen challenge, the platform is highly adaptable to produce antigenic domains from disease pathogens (including virus glycoproteins or non-secreted pathogen antigens), and the platform serves as an efficacious vaccine platform for both virus and bacterial pathogens.

In addition to advantages regarding vaccine applications, plant virus particles purified via the multi-set platform according to current embodiments can be formulated for various drug delivery purposes. These different purposes may include: 1) immune therapy—through the conjugation of therapeutic antibodies to the surface of virus particles and their delivery to enhance cytotoxic effect; 2) gene therapy—through loading specific nucleic acids for introduction into particular cell types for genetic modification, and 3) drug delivery—through loading chemotherapeutic agents into virus particles for targeted tumor delivery.

As a brief example of the many advantages of the methods discussed herein, the multi-set platform according to multiple embodiments could be utilized as a drug delivery tool by first causing the purified virus to swell by exposing it to a pH shift as discussed above. Subsequently, the virus in this condition would be incubated with a solution of concentrated chemotherapeutic agent, such as doxorubicin, and the pH is then reverted to neutral thereby causing the virus to return to its pre-swollen state and thereby entrapping the chemotherapeutic molecules. Next, the virus particle could be delivered to an organism by a delivery mechanism chosen from a group that includes, but is not necessarily limited to, injection for targeted treatment of tumors.

Accordingly, the above descriptions offer multiple embodiments and a number of alternative approaches for (i) the plant-based manufacture and purification of viruses; (ii) the plant-based manufacture and purification of antigens; and (iii) the formation of virus-antigen conjugates outside the plant that are therapeutically beneficial as vaccines and antigen carriers; and (iv) the delivery of therapeutic vaccines comprising a purified virus and purified antigen.

Example 13—Vaccine Stability Under Refrigerated and Room Temperature Conditions

Vaccines have dramatically improved human and animal health. For instance, in the 20th Century alone, vaccines have eradicated smallpox, eliminated polio in the Americas; and controlled a variety of diseases throughout the world. However, vaccines are highly unstable and very sensitive to changes in temperature. As discussed in Coenen et. al., *Stability of influenza sub-unit vaccine. Does a couple of days outside the refrigerator matter?* Vaccine 24 (2006), 525-531; influenza vaccines are generally unacceptable and inactive after five weeks at room temperature storage (i.e. ~25° C.). Of all the influenza vaccines discussed in the F. Coenen article, only one vaccine exhibited stability for 12 weeks at room temperature storage. This is a significant problem with other vaccine types too. Accordingly, all current vaccines must generally be refrigerated during the entire supply chain from the moment of commercial production until administration, often referred to as the "cold chain."

While in a refrigerated environment, the majority of vaccines remain stable for the typical seventy-eight week goal of stability. However, the absolute requirement for cold chain is a global problem that has limited the availability of vaccines worldwide because it is often difficult to guarantee in developing countries and has led to widespread vaccine loss. Many efforts have been made to create room temperature stable vaccines, but as discussed in the literature, those efforts have been unsuccessful. In addition, the cold chain is very costly to maintain for manufacturers; as well as the doctors and organizations receiving, storing, and applying the vaccines to populations. Accordingly, there is a significant and global need for increasing the stability of vaccines and enhancing vaccine-antigen stability in order to reduce the dependency on the cold chain and to ensure vaccines retain their potency until administration. In addition, improving stability can prolong the vaccine shelf life, which would facilitate the stockpiling of vaccines in the preparation of a potential pandemic and prevent vaccine loss in unfavorable conditions. Along with other features and advantages outlined herein, the scope of present embodiments meet these and other needs. In doing so, the inventive purification and conjugation platform extends the stability of protein-virus conjugates under both refrigerated and room temperature conditions.

There are several methods for determining antigen quality and vaccine stability including: (1) protein concentration s measured by BCA Protein assay (which is based on the principle that proteins can reduce $Cu^{2+}$ to $Cu^{+1}$ in an alkaline solution which results in a purple color formation), (2) storage potency as measured by VaxArray® antibody array binding (which utilizes multiplexed sandwich immunoassays), (3) SDS-Page purity as measured in terms of a single migrating band, (4) pH as a measurement of the physical pollution properties, and when possible, (5) size exclusion chromatography to characterize the multimeric structure of the antigen. Moreover, a vaccine is considered unacceptable for use if it fails the BCA Protein assay, the VaxArray® test, or the SDS-Page analysis. In other words, if a vaccine fails any one of these three tests, the vaccine is unacceptable for use and inactive.

Accordingly, the five tests mentioned in the previous paragraph were conducted on the following influenza HA antigens produced and purified in accordance with multiple embodiments and alternatives: H1N1 (A/Michigan), H3N2 (A/Singapore), H1N1 (A/Brisbane), H3N2 (A/Kansas), B/Colorado, and B/Phuket. The following tables provide the stability data and storage potency as measured at release and various times after filling into vials and stored under refrigerated conditions (4° to 8° C.). As used herein, an initial concentration or integrity refers to the concentration or integrity of a compound, conjugate mixture, pharmaceutical product, vaccine, or the like at its release date, and the release date is determined based on 21 C.F.R. Part 11 and ICH Q1A Stability Testing of New Drug Substances and Products, Revision 2 (November 2003), with the full contents of both being incorporated by reference herein.

TABLE 18

Stability of Purified H1NI (A/Michigan) Under Refrigerated Conditions

| Test Parameters | Test Method | Units | Initial (CoA) | 1 month | 3 months | 4 months | 5 months | 6 months |
|---|---|---|---|---|---|---|---|---|
| Concentration | BCA | mg/mL | 1.081 | 1.057 | 1.068 | 1.066 | 1.060 | 0.921 |
| Purity | SDS PAGE | % | 97% | >99% | 92% | 88% | 81% | 76% |
| Purity | SEC | Peak 1% | 11.93% | 6.18% | 0.00% | 2.83% | 4.77% | 4.92% |
|  |  | Peak 2% | 88.07% | 93.82% | 100.00% | 97.17% | 95.23% | 95.71% |
| Physical/Chemical Properties | pH | NA | 7.4 | 7.4 | 7.4 | 7.2 | 7.3 | 7.3 |
| Storage Potency | VaxArray® | μg/mL | 93 | 164 | 987 | 1300 | 1085 | 1176 |

TABLE 19

Stability of Purified H3N2 (A/Singapore) Under Refrigerated Conditions

| Test Parameters | Test Method | Units | Initial (CoA) | 1 month | 3 months | 4 months | 5 months | 6 months |
|---|---|---|---|---|---|---|---|---|
| Concentration | BCA | mg/mL | 0.855 | 0.900 | 0.891 | 0.908 | 0.885 | 0.795 |
| Purity | SDS PAGE | % | >99% | >99% | >99% | >99% | >99% | >99% |
| Purity | SEC | Peak 1% | 94.52% | 97.95% | 100.00% | 100.00% | 100.00% | 100.00% |
|  |  | Peak 2% | 3.90% | 0.00% | 0.00% | 0.00% | 0.00% | 0.00% |

TABLE 19-continued

Stability of Purified H3N2 (A/Singapore) Under Refrigerated Conditions

| Test Parameters | Test Method | Units | Initial (CoA) | 1 month | 3 months | 4 months | 5 months | 6 months |
|---|---|---|---|---|---|---|---|---|
| Physical/Chemical Properties | pH | NA | 7.4 | 7.4 | 7.4 | 7.2 | 7.3 | 7.3 |
| Storage Potency | VaxArray ® | µg/mL | 746 | 671 | 1037 | 624 | 872 | 1089 |

TABLE 20

Stability of H1N1 (A/Brisbane) Under Refrigerated Conditions

| Test Parameters | Test Method | Units | Initial (CoA) | 1 month | 3 months |
|---|---|---|---|---|---|
| Concentration | BCA | mg/mL | 0.804 | 0.810 | 0.967 |
| Purity | SDS PAGE | % | >99% | 78% | 73% |
| Purity | SEC | Trimer % Monomer % | 20.85% Trimer 79.15% Monomer | 11.21% Trimer 88.79% Monomer | 100% single peak |
| Storage Potency | VaxArray ® | µg/mL | 1205 | 1064 | 768 |

TABLE 21

Stability of H3N2 (A/Kansas) Under Refrigerated Conditions

| Test Parameters | Test Method | Units | Initial (CoA) | 1 month | 3 months |
|---|---|---|---|---|---|
| Concentration | BCA | mg/mL | 0.9 | 0.923 | 1.211 |
| Purity | SDS PAGE | % | 95% | 93% | 90% |
| Purity | SEC | Trimer % Monomer % | 30.92% Trimer 69.08% Monomer | 5.20% Trimer 94.80% Monomer | 100% single peak |
| Storage Potency | VaxArray ® | µg/mL | 916 | 1061 | 1094 |

TABLE 22

Stability of B/Colorado Under Refrigerated Conditions

| Test Parameters | Test Method | Units | Initial (CoA) | 1 month | 3 months | 4 months | 5 months | 6 months |
|---|---|---|---|---|---|---|---|---|
| Concentration | BCA | mg/mL | 0.848 | 0.855 | 0.862 | 0.873 | 0.885 | 0.777 |
| Purity | SDS PAGE | % | 99% | 63% | 46% | 40% | 38% | 35% |
| Purity | SEC | Peak 1% Peak 2% | 55.05% 44.95% | 39.70% 49.86% | 38.87% 61.13% | 20.77% 79.23% | 20.88% 79.12% | 39.55% 60.45% |
| Physical/Chemical Properties | pH | NA | 7.3 | 7.5 | 7.4 | 7.3 | 7.3 | 7.4 |
| Storage Potency | Vax Array ® | µg/mL | 541 | 446 | 733 | 528 | 823 | 1082 |

TABLE 23

Stability of B/Phuket Under Refrigerated Conditions

| Test Parameters | Test Method | Units | Initial (CoA) | 1 month | 3 months | 4 months | 5 months | 6 months |
|---|---|---|---|---|---|---|---|---|
| Concentration | BCA | mg/mL | 0.957 | 0.895 | 0.912 | 0.951 | 0.818 | 0.819 |
| Purity | SDS PAGE | % | 96.1% | >99% | 97% | 97% | 93% | 91% |

TABLE 23-continued

Stability of B/Phuket Under Refrigerated Conditions

| Test Parameters | Test Method | Units | Initial (CoA) | 1 month | 3 months | 4 months | 5 months | 6 months |
|---|---|---|---|---|---|---|---|---|
| Purity | SEC | Peak 1% | 84.51% | 90.05% | 91.98% | 85.96% | 85.76% | 92.47% |
|  |  | Peak 2% | 15.49% | 9.95% | 8.02% | 14.04% | 14.24% | 7.53% |
| Physical/ Chemical Properties | pH | NA | 7.4 | 7.4 | 7.3 | 7.3 | 7.3 | 7.4 |
| Storage Potency | VaxArray ® | µg/mL | 910 | 945 | 888 | 952 | 812 | 924 |

Figure 40:
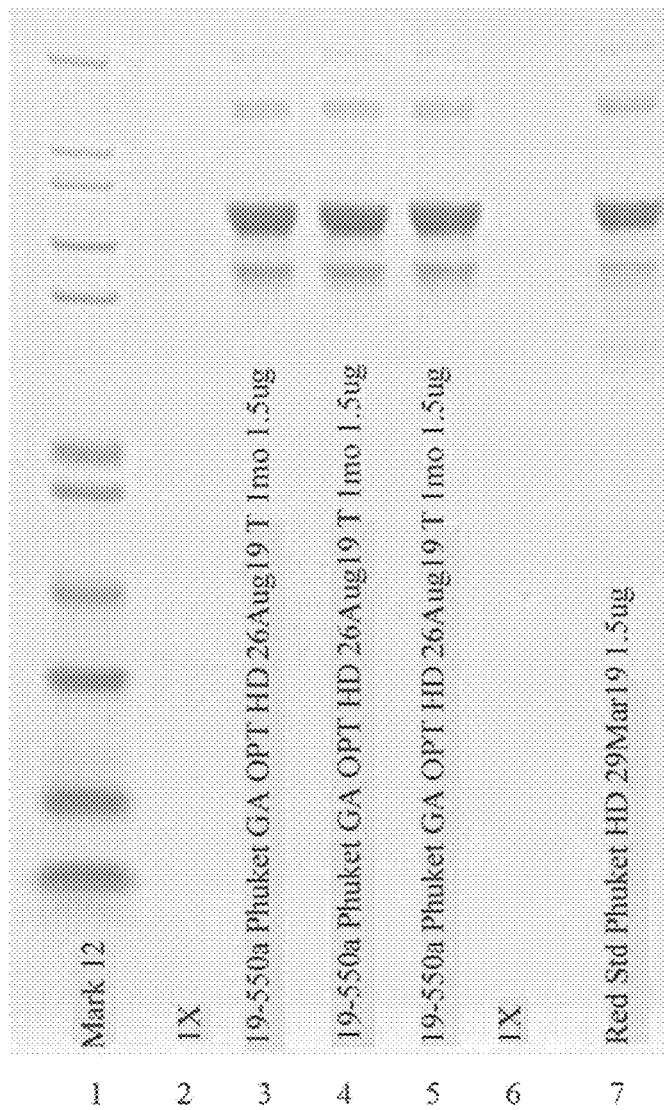
FIG. 40 is a SDS-PAGE analysis of a purified recombinant antigen, according to multiple embodiments and alternatives.

Tables 18-23 illustrate that the purified free antigens exhibit different patterns of stability. For instance, some antigens like H1N1 (A/Michigan) and H3N2 (A/Singapore) appeared stable after 6 months with no significant deviations in measurements (as is typically observed). However, the other antigens such as B/Colorado and H1N1 (A/Brisbane), and to a lesser extent H3N2 (A/Kansas) and B/Phuket, exhibited degradation, loss of trimer, or loss of other key properties under these conditions. For example, FIG. 40 is a SDS-PAGE analysis of purified. B/Phuket after 1 month under refrigerated conditions. In FIG. 40, the degradant bands of lower molecular weight below the intact band at ~60 kDA indicate that the purified B/Phuket antigen has degraded. As expected, the data in Tables 18-23 and FIG. 40 indicate that different proteins exhibit different stabilities under refrigerated conditions.

When the same purified antigens are conjugated to TMV, according to multiple embodiments and alternatives, the stability profile and storage potency changes. In some embodiments, the inventive method enhances a measure of stability of a conjugated compound comprising a protein and virus particle, and includes activating the virus particle and then mixing the virus particle and the antigen in a conjugation reaction to form a conjugate mixture, resulting in enhanced stability when the conjugated compound is placed in an unrefrigerated environment and after a time period of at least 42 days following a release date. An exemplary storage temperature is at least 20° C. The stability enhancement can be gauged by comparing the stability of the conjugate mixture to that of the antigen alone. A suitable measure is any one or more of antigen concentration, antigen integrity, or antigen potency. For example, when the measure of stability is antigen concentration, as measured by BCA or other appropriate methodology, a difference between concentration of the conjugated compound and concentration of the antigen alone of at least 10% is within the scope of present embodiments. Likewise, when the measure of stability is antigen integrity, as measured by SDS-PAGE, SEC-HPLC or other appropriate methodology, a difference between integrity of the conjugated compound and integrity of the antigen alone of at least 10% is within the scope of present embodiments. Likewise, when the measure of stability is antigen potency, as measured by antigen-antibody interaction based on ELISA results, or VaxArray®, surface plasmon resonance or other appropriate methodology, a difference between potency of the conjugated compound and potency of the antigen alone of at least 30% is within the scope of present embodiments.

Accordingly, the following tables provide the stability data of several monovalent formulations (at a TMV to antigen ratio of 1:1) at release and various times after filling into vials and stored under refrigerated conditions (2° to 8° C.):

TABLE 24

Stability of the H1N1 (A/Michigan) to TMV Conjugate Under Refrigerated Conditions

| Test Parameters | Test Method | Initial (CoA) | 1 month | 3 months | 6 months |
|---|---|---|---|---|---|
| Appearance | Appearance | Clear, Liquid | Clear, Liquid | Cloudy, Liquid | Cloudy, Liquid |
| Phys

TABLE 26

Stability of the B/Phuket to TMV Conjugate Under Refrigerated Conditions

| Test Parameters | Test Method | Initial (CoA) | 1 month | 3 months | 6 months |
|---|---|---|---|---|---|
| Appearance | Appearance | Cloudy, Liquid | Cloudy, Liquid | Cloudy, Liquid | Cloudy, Liquid |
| Physical/Chemical Properties | pH | 7.6 | 7.5 | 7.4 | 7.5 |
| Protein Concentration | BCA | 0.874 | 1.010 | 0.995 | 0.940 |
| Purity | SDS PAGE | >99.0 | 97.1 | 95.4 | 95.1 |
| Storage Potency | VaxArray ® | 333 | 393 | 442 | 477 |
| Average Size Radius | DLS | 1040.7 | 1094.1 | 1428.2 | 1284.9 |
| Polydispersity |  | 47.5 | 42.1 | 49.6 | 53.3 |

TABLE 27

Stability of the B/Colorado to TMV Conjugate Under Refrigerated Conditions

| Test Parameters | Test Method | Initial (CoA) | 1 month | 3 months | 6 months |
|---|---|---|---|---|---|
| Appearance | Appearance | Cloudy, Liquid | Cloudy, Liquid | Cloudy, Liquid | Cloudy, Liquid |
| Physical/Chemical Properties | pH | 7.6 | 7.5 | 7.5 | 7.5 |
| Protein Concentration | BCA | 0.961 | 1.020 | 1.077 | 0.959 |
| Purity | SDS PAGE | >99.0 | 96.0 | 96.0 | 94.9 |
| Storage Potency | VaxArray ® | 218 | 653 | 599 | 585 |
| Average Size Radius | DLS | 2377.8 | 1025.7 | 1337.6 | 1153.9 |
| Polydispersity |  | 49.5 | 55.6 | 53.3 | ≥57.1 |

In each of the conjugates described in Tables 24-27, the purity, pH, protein concentration, and storage potency is maintained through at least six months of storage under refrigerated conditions. Further, the polydiversity is also consistent over this timeframe. Polydiversity refers to the variability of particle size in a complex product, and generally the lower the polydiversity the better the product.

In addition to the monovalent formulations, the following quadrivalent conjugate produced according to multiple embodiments and alternatives at a 1:1 TMV to antigen ratio exhibits strong stability under both refrigerated (4° to 8° C.) and room temperature (22° to 28° C.) conditions:

TABLE 28

Stability of the Quadrivalent Conjugate Under Refrigerated Conditions

| Test Parameters | Test Method | Initial (CoA) | 1 month | 3 months | 6 months |
|---|---|---|---|---|---|
| Appearance | Appearance | Cloudy, Liquid | Cloudy, Liquid | Cloudy, Liquid | Cloudy, Liquid |
| Physical/Chemical Properties | pH | 7.5 | 7.5 | 7.4 | 7.5 |
| Protein Concentration | BCA | 0.799 | 0.911 | 0.983 | 0.953 |
| Identity | VaxArray ® | Antigen Binding Occurs | Antigen Binding Occurs | Antigen Binding Occurs | Antigen Binding Occurs |
| Storage Potency | VaxArray ® | A/Michigan: NtK = 123 µg/ml a/Singapore: NtK = 106 µg/ml B/Phuket: NtK = 117 µg/ml B/Colorado: NtK = 78 µg/ml | A/Michigan: NtK = 155 µg/ml a/Singapore: NtK = 110 µg/ml B/Phuket: NtK = 140 µg/ml B/Colorado: NtK = 179 µg/ml | A/Michigan: NtK = 103 µg/ml a/Singapore: NtK = 106 µg/ml B/Phuket: NtK = 114 µg/ml B/Colorado: NtK = 134 µg/ml | A/Michigan: NtK = 123 µg/ml a/Singapore: NtK = 101 µg/ml B/Phuket: NtK = 116 µg/ml B/Colorado: NtK = 134 µg/ml |

TABLE 29A

Stability of the Quadrivalent Conjugate Under Room Temperature Conditions

| Test Parameters | Test Method | Initial (CoA) | 2 weeks | 1 month | 2 months |
|---|---|---|---|---|---|
| Appearance | Appearance | Cloudy, Liquid | Cloudy, Liquid | Cloudy, Liquid | Cloudy, Liquid |
| Physical/Chemical Properties | pH | 7.5 | 7.5 | 7.5 | 7.4 |
| Protein Concentration | BCA | 0.799 | 0.959 | 0.909 | 1.098 |
| Identity | VaxArray ® | Antigen Binding Occurs | Antigen Binding Occurs | Antigen Binding Occurs | Antigen Binding Occurs |
| Storage Potency | VaxArray ® | A/Michigan: NtK = 123 µg/ml a/Singapore: NtK = 106 µg/ml B/Phuket: NtK = 117 µg/ml B/Colorado: NtK = 78 µg/ml | A/Michigan: NtK = 115 µg/ml a/Singapore: NtK = 108 µg/ml B/Phuket: NtK = 96 µg/ml B/Colorado: NtK = 62 µg/ml | A/Michigan: NtK = 126 µg/ml a/Singapore: NtK = 173 µg/ml B/Phuket: NtK = 84 µg/ml B/Colorado: NtK = 124 µg/ml | A/Michigan: NtK = 24 µg/ml a/Singapore: NtK = 29 µg/ml B/Phuket: NtK = 29 µg/ml B/Colorado: NtK = 26 µg/ml |

TABLE 29B

Stability of the Quadrivalent Conjugate Under Room Temperature Conditions

| Test Parameters | Test Method | Initial (CoA) | 3 months | 6 months |
|---|---|---|---|---|
| Appearance | Appearance | Cloudy, Liquid | Cloudy, Liquid | Cloudy, Liquid |
| Physical/Chemical Properties | pH | 7.5 | 7.4 | 7.5 |
| Protein Concentration | BCA | 0.799 | 0.980 | 0.920 |
| Identity | VaxArray ® | Antigen Binding Occurs | Antigen Binding Occurs | Antigen Binding Occurs |
| Storage Potency | VaxArray ® | A/Michigan: NtK = 123 µg/ml a/Singapore: NtK = 1.06 µg/ml B/Phuket: NtK = 117 µg/ml B/Colorado: NtK = 78 µg/ml | A/Michigan: NtK = 113 µg/ml a/Singapore: NtK = 115 µg/ml B/Phuket: NtK = 80 µg/ml B/Colorado: MK = 139 µg/ml | A/Michigan: NtK = 114 µg/ml a/Singapore: NtK = 80 µg/ml B/Phuket: NtK = 99 µg/ml B/Colorado: NtK = 120 µg/ml |

Tables 28, 29A and 29B illustrate that the quadrivalent conjugate remains consistent and stable in terms of protein concentration, storage potency, pH and appearance under both refrigerated and room temperature conditions for at least six months. Table 30 provides the percent change in the storage potency of the various antigens described in Tables 29A and 29B by comparing the initial potency to the storage potency at the particular time.

TABLE 30

Percent Change in Storage Potency from the Initial Potency via VaxArray ®

|  | 2 Weeks | 1 month | 2 months | 3 months | 6 months |
|---|---|---|---|---|---|
| A/Michigan | 93.50% | 102.44% | 19.51% | 91.87% | 92.68% |
| A/Singapore | 101.89% | 163.21% | 27.36% | 108.49% | 75.47% |
| B/Phuket | 82.05% | 71.80% | 24.79% | 68.00% | 84.62% |
| B/Colorado | 79.49% | 158.97% | 33.33% | 178.00% | 153.85% |

Accordingly, as shown in Table 30, when the conjugate was placed in the unrefrigerated environment, the storage potency at the end of 30 days was at least 70% of the initial potency of the conjugate mixture within the first day post-conjugation. At the end of 90 days, the storage potency of the conjugate mixture stored in the unrefrigerated environment was at least 68% of the initial potency, and the storage potency of the conjugate mixture was at least 75% at the end of at least 180 days.

The following tables illustrate the stabilizing effect of the embodiments described herein by comparing the release conditions of the purified recombinant antigen with the same protein conjugated to TMV according to multiple embodiments and alternatives. Furthermore, stability after six months under refrigerated conditions (4° to 8° C.) was compared between the purified antigen and the same antigen conjugated to TMV by analyzing the protein concentration, potency, SDS-page purity, and PH, as follows:

TABLE 31

Comparison Between the Stability of Purified B/Colorado Antigen and the B/Colorado to TMV Conjugate

| | Colorado Release Data | | Colorado 6 month Stability | |
|---|---|---|---|---|
| Assay | Free Antigen | Conjugated (1:1) | Free Antigen | Conjugated (1:1) |
| BCA (mg/mL) | 0.848 | 0.961 | 0.777 | 0.959 |
| VaxArray ® Potency (μg/mL) | 541 | 218 | 1082 | 585 |
| SDS PAGE Purity (%) | 99 | >99.0 | 35 | 94.9 |
| pH | 7.3 | 7.6 | 7.4 | 7.5 |

TABLE 32

Comparison Between the Stability of Purified B/Phuket Antigen and the B/Phuket to TMV Conjugate

| | Phuket Release Data | | Phuket 6 month Stability | |
|---|---|---|---|---|
| Assay | Free Antigen | Conjugated (1:1) | Free Antigen | Conjugated (1:1) |
| BCA (mg/mL) | 0.957 | 0.874 | 0.819 | 0.940 |
| VaxArray ® Potency (μg/mL) | 910 | 333 | 924 | 447 |
| SDS PAGE Purity (%) | 96.1 | >99.0 | 91.0 | 95.1 |
| pH | 7.4 | 7.6 | 7.4 | 7.5 |

TABLE 33

Comparison Between the Stability of Purified H3N2 (A/Singapore) Antigen and the H3N2 (A/Singapore) to TMV Conjugate

| | Singapore Release Data | | Singapore 6 month Stability | |
|---|---|---|---|---|
| Assay | Free Antigen | Conjugated (1:1) | Free Antigen | Conjugated (1:1) |
| BCA (mg/mL) | 0.855 | 0.828 | 0.795 | 0.957 |
| VaxArray ® Potency (μg/mL) | 746 | 363 | 1089 | 500 |
| SDS PAGE Purity (%) | >99 | >99.0 | >99 | 92.9 |
| pH | 7.4 | 7.6 | 7.3 | 7.5 |

TABLE 34

Comparison Between the Stability of Purified H1N1 (A/Michigan) Antigen and the H1N1 (A/Michigan) to TMV Conjugate

| | Michigan Release Data | | Michigan 6 month Stability | |
|---|---|---|---|---|
| Assay | Free Antigen | Conjugated (1:1) | Free Antigen | Conjugated (1:1) |
| BCA (mg/mL) | 1.081 | 0.898 | 0.921 | 0.994 |
| VaxArray ® Potency (μg/mL) | 93 | 325 | 1176 | 208 |
| SDS PAGE Purity (%) | 97 | >99.0 | 76 | 91.7 |
| pH | 7.4 | 7.6 | 7.3 | 7.5 |

Tables 31-34 illustrate the stability inducing properties of the purification and conjugation embodiments, most clearly for the B/Colorado, B/Phuket, and H1N1 (A/Michigan) antigens in terms of purity measures. For the H3N2 (A/Singapore) and 9/Colorado antigens, the stability of the conjugate is also shown in terms of antigen concentration. As shown in Tables 31-34, the purification and conjugation processes, according to multiple embodiments and alternatives, stabilized the antigen's physical properties, antigenic reactivity and other quantitative stability features.

Furthermore, Tables 29A, 29B, and 30 illustrate that the quadrivalent conjugate, produced according to multiple embodiments and alternatives, exhibits strong stability measures for at least six months, or twenty-four weeks, at room temperature storage (22° to 28° C.). Compared to conventional vaccines which exhibit an average stability of ~5 weeks at room temperature (as discussed in the F. Coenen article mentioned above), the vaccines according to multiple embodiments and alternatives exhibit stability for at least 5× greater than conventional influenza vaccines and several times longer than purified antigens. Accordingly, the formulation and conjugation processes according to multiple embodiments and alternatives stabilize extremely unstable antigens—such as B/Colorado—and extend the stability of other antigens—such as H3N2 (A/Singapore), H1N1 (A/Michigan), and B/Phuket—far beyond the stability limits of free-antigens and conventional vaccines.

Example 14(a) to 14(h)—Quadrivalent Influenza Vaccine Studies

In order to demonstrate the safety, efficacy and utility of the embodiments disclosed herein for immunogenicity and protection against seasonal virus challenge, several preclinical studies were conducted using a quadrivalent seasonal vaccine candidate (referred to for purposes of this example as "QIV vaccine"). The vaccine used in the studies was manufactured in accordance with multiple embodiments and alternatives disclosed herein. The subject QIV vaccine contained the following influenza HA antigens from the 2018/2019 North America seasonal influenza vaccine strains recommended by the World Health Organization, the Centers for Disease Control and Prevention, and the FDA's Vaccines and Related Biological Products Advisory Committee (VRBPAC), (A/Michigan/45/2015(H1N1)pdm09, A/Singapore/INFIMH-16-0019/2016 (H3N2), B/Phuket/3073/2013 (B Yamagata lineage), and B/Colorado/06/2017 (B Victoria lineage), conjugated to inactivated TMV NtK. In some embodiments, the four vaccine antigen conjugates, in a phosphate buffer solution with 0.01% thimerosal as a preservative (as a non-limiting example), are blended together to create a single injectable, quadrivalent vaccine formulation. As discussed in more detail below, these studies demonstrated that the embodiments disclosed herein augment the immunogenicity of recombinant hemagglutinin protein antigens. This was determined by various measures and analyses, including hemagglutination inhibition and neutralizing antibody titers. Likewise, the studies described in this example indicate the QIV seasonal vaccine is immunogenic, as it provided a level of protection in all mammalian disease models tested to date from challenge with viral strains homologous to the vaccine strain HA antigens. Except where otherwise noted, the content of the inactivated TMV NtK and HA intermediates incorporated into the conjugation reaction were equal (1:1) on a mg:mg basis (i.e. weight (wt)) for the studies. Subsequent studies with the QIV vaccine conjugated at an 8:1 TMV NtK:HA ratio (on a mg:mg basis) of the drug substance intermediates, as a non-limiting example, showed desirable humoral responses.

Table 35 provides an overview of the studies conducted on the QIV vaccine in accordance with the present example. "GLP" refers to Good Laboratory Practices, such as the CPMP Note for Guidance on Preclinical Pharmacological and Toxicological Testing of Vaccines (CPMP/SWP/465/95) and the World Health Organization Guidelines on Non-Clinical Evaluation of Vaccines (WHO Technical Report Series, No. 927), with the full contents of both being incorporated by reference herein. Additional discussion of various aspects of the studies follows the table.

TABLE 35

Overview of QIV Non-Clinical Studies for Example 14(a) to 14(h)

| Study Description | Summary |
|---|---|
| 14(a)-Evaluate Impact of Conjugation to TMV on Immunogenicity, and Evaluate Durability of Response Non-GLP, on mice | QIV vaccine induced a dose-dependent humoral immune response (HAI titers). There were no adverse effects or injection site reactions detected. |
| 14(b)-Evaluate Impact of Conjugation to TMV on Immunogenicity, and Evaluate Durability of Response Non-GLP, on mice | QIV vaccine induced a detectable humoral immune response based on HAI and virus neutralization assays, Titers were first detectable on Day 21 and were highest on Day 90 post vaccination. There were no adverse effects or injection site reactions detected. |
| 14(c)-Immunogenicity Challenge, Non-GLP, on ferrets | QIV vaccine induced a detectable humoral immune response based on HAI and virus neutralization assays against the four antigens. The log reduction in viral titers observed in the QIV vaccinated ferrets challenged with A/Michigan/45/2015 (H1N1) was superior when compared to Fluzone ® and placebo. Equivalent log reduction in viral titers was observed in the QIV vaccinated ferrets and Fluzone ® when compared to placebo in animals challenged with A/Singapore/INFIMH-16-0019/2016 (H3N2) virus. These data indicate that the QIV is immunogenic and provides a level of protection to influenza infection in ferrets. There were no adverse effects or injection site reactions detected. |
| 14(d)-Matrix immunogenicity to Evaluate Desirable Formulation Ratio, Non-GLP, on mice | Immunization of mice with monovalent vaccine conjugated to varying ratios (1:1 to 24:1 TMV NtK:antigen) of TMV NtK scaffold. Humoral immune responses indicated that a TMV NtK:HA ratio of 8:1 (mg:mg) was a desirable formulation ratio for QIV |
| 14(e)-Pharmacokinetic: Biodistribution Using 1:1 Ratio of Virus to Antigen, Non-GLP; on rabbits | Study employed a monovalent vaccine conjugated to inactivated or live TMV NtK carrier at a 1:1 ratio of TMV NtK:antigen. Distribution determined by quantitation of TMV NtK through a RT-qPCR methodology, Peak TMV NtK values were measured at injection site muscle 1 day post dosing and declined over the 7 day time course. Lymph nodes and spleen had relatively stable levels of TMV NtK vRNA genome copy numbers over the time course. Liver, heart, and testes had low levels near the limit of quantitation (LOQ) 1 day post-dosing that was below LOQ over the rest of the time-course. Vaccine values were below the LOQ in other tissues examined (blood, brain, lung, kidney and thymus). The biodistribution pattern of TMV NtK vRNA genome was consistent with both live and inactivated TMV NtK. No injection site reactions were detected. |
| 14(f) Pharmacokinetic: Biodistribution Using 8:1 Ratio of Virus to Antigen, Non-GLP, on rabbits | Study employed a vaccine conjugated to inactivated or live TMV NtK carrier at a 8:1 ratio of TMV NtK:HA antigen. RT-gPCR results consistently show that TMV vRNA copy number peaked on 1 day post-dosing in almost all organs except the injection site (muscle) which peaked at 3 days post-dosing and declined thereafter. Biodistribution data also demonstrate a significant decline of residual vaccine after 1 day post-dosing in all of the organs tested except injection site (near or below the LOQ). Two immune organs (spleen and lymph nodes) had relatively stable levels of TMV vRNA genome copy numbers over the time course. |

TABLE 35-continued

Overview of QIV Non-Clinical Studies for Example 14(a) to 14(h)

| Study Description | Summary |
|---|---|
| 14(g) Safety: Repeat dose toxicity, GLP on rabbits | Intramuscular administration of two doses of QIV (1:1 TMV NtK:Antigen ratio) at doses of 15 or 45 µg/HA once every four weeks was well tolerated No treatment-related or toxicologically significant clinical findings or inoculation site reactogenicity were observed. No treatment-related or toxicologically significant effects were observed for body weights, body weight changes, food consumption, body temperatures, ophthalmology, clinical chemistry, hematology, and organ weights. A robust immunogenic response was also seen in rabbits receiving the low and high dose of the vaccine which was detected in most animals on Study Days 42, 49, and 57. |
| 14(h) Safety: Repeat dose toxicity, GLP on rabbits | Intramuscular administration of two doses of QIV (45 µg/ HA + 1.44 mg TMV NtK) or TMV NtK (1.44 mg) carrier once every four weeks was well tolerated No treatment-related or toxicologically significant clinical findings or inoculation site reactogenicity were observed. No treatment-related or toxicologically significant effects were observed for body weights, body weight changes, food consumption, body temperatures, ophthalmology, clinical chemistry, hematology, and organ weights. A robust immunogenic response was also seen in rabbits receiving the QIV vaccine which was detected in most animals on Study Days 42, 49, and 57, |

As summarized in Table 36, an immunogenicity study in BALB/c mice, using monovalent and quadrivalent preparations respectively, was conducted to evaluate a desirable formulation ratio, and to monitor for injection site reactions and clinical signs of toxicity.

TABLE 36

Immunogenicity in BALB/c Mice-Example 14(a)

| Group | N | Antigen Dose (µg) | Vaccination (Study Days) | Blood Collection (Study Days) |
|---|---|---|---|---|
| 1 | 5 | 0[a] | 0, 14 | 0, 14, 28 |
| Monovalent [b] | | | | |
| 2 | 5 | 1.5 | 0, 14 | 0, 14, 28 |
| 3 | 5 | 30 | 0, 14 | 0, 14, 28 |
| Quadrivalent [c] | | | | |
| 4 | 5 | 1.5 | 0, 14 | 0, 14, 28 |
| 5 | 5 | 7.5 | 0, 14 | 0, 14, 28 |
| 6 | 5 | 15 | 0, 14 | 0, 14, 28 |
| 7 | 5 | 30 | 0, 14 | 0, 14, 28 |

[a] Phosphate buffered saline only
[b] Monovalent Vaccine: A/Singapore/INFIMH-16-0019/2016 (H3N2)
[c] QIV Vaccine: A/Michigan/45/2015 (H1N1), A/Singapore/INFIMH-016-0019/2016 (H3N2), B/Colorado/06/2017 and B/Phuket/3073/2013

The study was conducted in the spirit of GLP regulations. BALB/c mice (N=5/group) were immunized on Day 0 and Day 14 with the respective vaccine preparations. The animals were bled to prepare sera for HAI antibody titer analysis prior to dosing on Day 0 and Day 14, with a final bleed collected on Day 28.

Table 37 (below) provides the number of animals that generated detectable HAI titers, the titer range from positive animals, and the geometric mean titer (GMT). The GMT value was calculated using the following formula set forth in Armitage and Berry, Statistical Methods in Medical Research, $2^{nd}$ Edition (1987), pp. 31-33, the full contents of which are incorporated herein by reference:

$$GM = \{x_1 x_2 x_3 \ldots x_n\}^{1/n} \quad \text{(Formula 3)}$$

As shown in Table 37, prior to the first vaccination (Day 0), HAI titers for sera samples from all study groups were below the limit of detection (<10). On Day 14 (prior to the second vaccination), antibody titers were below detectable levels in all groups except for the following: ⅕ mice in Group 3 (30 µg dose of the monovalent vaccine) had an HAI titer of 10 to A/Singapore/INFIMH-16-0019/2016 (H3N2) and ⅖ mice in Group 7 (30 µg dose of the quadrivalent vaccine) produced a titer of 10 to A/Singapore/INFIMH-16-0019/2016 (H3N2). In Table 37, HAI antibody titers were the reciprocal of the highest dilution of sera that inhibited hemagglutination by 4 HA units of virus.

TABLE 37

Immunogenicity in BALB/c Mice Results - Example 14(a)

| | Antigen | Day 14 | | | | Day 28 | | | |
|---|---|---|---|---|---|---|---|---|---|
| Group | (µg) | H1N1[a] | H3N2[b] | B/Vict[c] | B/Yam[d] | H1N1 | H3N2 | B/Vic | B/Yam |
| 1 | None | 0/5 | 0/5 | 0/5 | 0/5 | 0/5 | 0/5 | 0/5 | 0/5 |
| Monovalent (H3N2) | | | | | | | | | |
| 2 | 1.5 | 0/5 | 0/5 | 0/5 | 0/5 | 0/5 | 1/5 (40; 40) | 0/5 | 0/5 |
| 3 | 30 | 0/5 | 1/5 (10; 10)[e] | 0/5 | 0/5 | 0/5 | 5/5 (10-160; 40) | 0/5 | 0/5 |

TABLE 37-continued

Immunogenicity in BALB/c Mice Results - Example 14(a)

| Group | Antigen (μg) | Day 14 | | | | Day 28 | | | |
|---|---|---|---|---|---|---|---|---|---|
| | | H1N1 [a] | H3N2 [b] | B/Vict [c] | B/Yam [d] | H1N1 | H3N2 | B/Vic | B/Yam |
| Quadrivalent KBP-VP-V001 | | | | | | | | | |
| 4 | 1.5 | 0/5 | 0/5 | 0/5 | 0/5 | 1/5 (20; 20) | 2/5 (20; 20) | 1/5 (20; 20) | 0/5 |
| 5 | 7.5 | 0/5 | 0/5 | 0/5 | 0/5 | 5/5 (10-320; 53) | 4/5 (20-40; 28) | 1/5 (40; 40) | 0/5 |
| 6 | 15 | 0/5 | 0/5 | 0/5 | 0/5 | 4/5 (20-160; 95) | 2/5 (20-40; 28) | 2/5 (10; 10) | 0/5 |
| 7 | 30 | 0/5 | 2/5 (10; 10) | 0/5 | 0/5 | 5/5 (160-640; 279) | 5/5 (20-80; 52) | 2/5 (40; 40) | 0/5 |

[a] A/Michigan/45/2015 (H1N1pdm09);
[b] A/Singapore/INFIMH-16-0019/2016 (H3N2);
[c] B/Colorado/06/2017 (Vic)
[d] B/Phuket/3073/2013 (Yam)
[e] Parenthetical data are the titer range and geometric mean titer (GMT).

On day 14, HAI titers were detected against the H3N2 virus in the high (30 dose only in the monovalent and QIV vaccine groups. On Day 28, there were dose-dependent increases in HAI titers against A/Michigan/45/2015 (H1N1) in the quadrivalent vaccine and A/Singapore/INFIMH-16-0019/2016 (H3N2) in both the monovalent and quadrivalent vaccines. HAI: titers were detectable at antigen doses as low as 1.5 μg in a few animals with the majority of animals generating antibody titers at 7.5 μg per HA antigen. No detectable titer was produced by the mice that had been vaccinated with the monovalent vaccine to the other three strains tested. While less pronounced, the QIV vaccine also induced HAI titers in a subset of mice against B/Colorado/06/2017. There were no detectable HAI titers generated against the Yamagata lineage B/Phuket/3073/2013 component.

In sum, based on HAI assay data, the monovalent formulation vaccine induced a detectable humoral immune response to the H3N2 virus. The QIV formulation induced a detectable humoral immune response against three of the four antigens. The induced immune response against influenza H1N1 and H3N2 antigens seen in mice vaccinated with the monovalent and QIV vaccine formulations was dose dependent. As shown in Table 37, the H1N1 GMT ranged from 20 to 279 (increasing with the increasing dose) and the H3N2 GMT ranged from 20 to 52. In addition, no adverse clinical signs or injection reactions were observed with the monovalent or QIV vaccinations.

As summarized in Table 38, an immunogenicity study in naïve mice (BALB/c mice) was conducted by assessing the immunogenicity of quadrivalent vaccines with and without TMV conjugation (1:1 ratio of TMV NtK:HA antigen), over time. The purpose of the study was to confirm the results from the prior study shown in Table 37, compare the immunogenicity of QIV to a vaccine wherein the same antigens are not conjugated to the TMV NtK carrier, and analyze the durability of the immune response over 90 days. The vaccines in the following table were conjugated at a 1:1 ratio of TMV NtK:HA antigen.

TABLE 38

QIV Vaccine Immunogenicity in BALB/c Mice - Example 14(b)

| Group | Treatment Group | N | Vaccine Dose Antigen (μg) | Vaccination (days) | Cohort Number | Cohort N | Blood collections (days) | Cohort Necropsy Day |
|---|---|---|---|---|---|---|---|---|
| 1 | Vehicle Control | 28 | None | 0, 14 | 1 | 9 | −1, 7 | 7 |
| | | | | | 2 | 9 | −1, 14, 21 | 21 |
| | | | | | 3 | 10 | −1, 28, 42, 90 | 90 |
| 2 | TMV NtK Control | 28 | 60 μg TMV NtK | 0, 14 | 1 | 9 | −1, 7 | 7 |
| | | | | | 2 | 9 | −1, 14, 21 | 21 |
| | | | | | 3 | 10 | −1, 28, 42, 90 | 90 |
| 3 | HA Antigen | 28 | 15 μg/HA 60 μg Total HA | 0, 14 | 1 | 9 | −1, 7 | 7 |
| | | | | | 2 | 9 | −1, 14, 21 | 21 |
| | | | | | 3 | 10 | −1, 28, 42, 90 | 90 |
| 4 | | 28 | 7.5 μg/HA 30 μg Total HA | 0, 14 | 1 | 9 | −1, 7 | 7 |
| | | | | | 2 | 9 | −1, 14, 21 | 21 |
| | | | | | 3 | 10 | −1, 28, 42, 90 | 90 |
| 5 | | 28 | 3.75 μg/HA 15 μg Total HA | 0, 14 | 1 | 9 | −1, 7 | 7 |
| | | | | | 2 | 9 | −1, 14, 21 | 21 |
| | | | | | 3 | 10 | −1, 28, 42, 90 | 90 |
| 6 | Quadrivalent Vaccine (referred to | 28 | 15 μg/HA 60 μg Total HA 60 μg TMV NtK | 0, 14 | 1 | 9 | −1, 7 | 7 |
| | | | | | 2 | 9 | −1, 14, 21 | 21 |
| | | | | | 3 | 10 | −1, 28, 42, 90 | 90 |

TABLE 38-continued

QIV Vaccine Immunogenicity in BALB/c Mice - Example 14(b)

Figure 41:
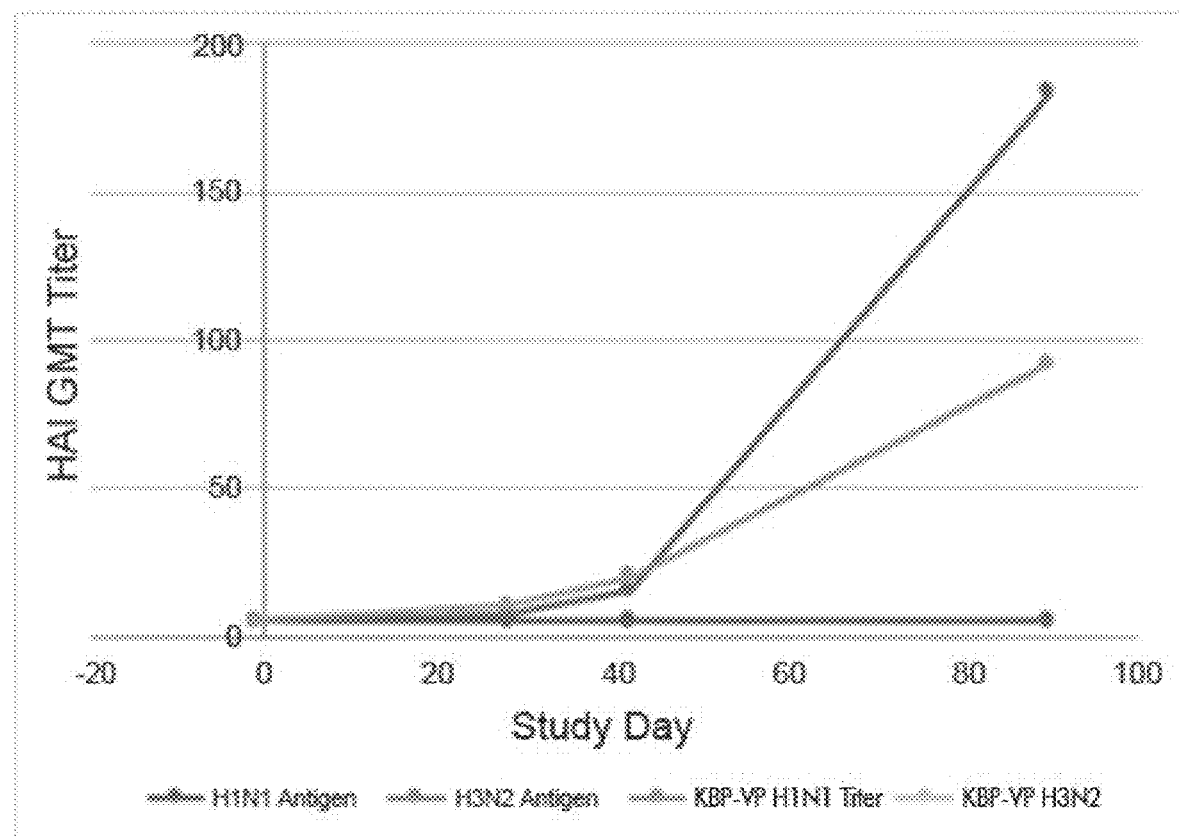
FIG. 41 is a graph of the immunogenicity of a quadrivalent vaccine in mice, according to multiple embodiments and alternatives.

| Group | Treatment Group | N | Vaccine Dose Antigen (µg) | Vaccination (days) | Cohort Number | Cohort N | Blood collections (days) | Cohort Necropsy Day |
|---|---|---|---|---|---|---|---|---|
| 7 | in FIG. 41 as "KBP-VP H1N1 and | 28 | 7.5 µg/HA 30 µg Total HA 30 µg TMV NtK | 0, 14 | 1 2 3 | 9 9 10 | −1, 7 −1, 14, 21 −1, 28, 42, 90 | 7 21 90 |
| 8 | KBP-VP H3N2") | 28 | 3.75 µg/HA 15 µg Total HA 15 µg TMV NtK | 0, 14 | 1 2 3 | 9 9 10 | −1, 7 −1, 14, 21 −1, 28, 42, 90 | 7 21 90 |

FIG. 41 shows the QIV vaccine induction of H1N1 and H3N2 hemagglutination inhibition (HAI) titers in the mice over time. The data includes the geometric mean titer (GMT) of BALB/c mice dosed with 15 µg per HA of QIV vaccine. The GMT value was calculated using the following formula:

$$GM = \{x_1 x_2 x_3 \ldots x_n\}^{1/n} \quad \text{(Formula 3)}$$

The mice with a titer value ≤10 were assigned a titer value of 5 for GMT calculation, in accordance with the previously mentioned Armitage and Berry.

As shown in FIG. 41, and Tables 39 and 40 below, HAI titers were only observed in animals receiving the QIV vaccine (referred to in FIG. 41 as "KBP-VP HIM" and KBP-VP H3N2") and only to the H1N1 and H3N3 antigens. There was no detectable immune response generated to the unconjugated antigens. Titers were below detectable levels until Day 21 against A/Michigan/45/2015 (H1N1) and A/Singapore/INFIMH-16-0019/2016 (H3N2). HAI titers remained detectable on Day 28 and Day 42 and were highest on Day 90. Moreover, the humoral response continued to increase for at least 90 days, a feature that conventional influenza vaccines are not known for. Since there was no detectable response with antigen alone, this test further supports the efficacy of conjugating the antigen to the TMV NtK carrier in producing an immune response.

TABLE 39

Percentage of Animals and HAI Geometric Mean Titers Generated Against Influenza A Antigens - Days 21 and 28

| | | Day 21 | | | | Day 28 | | | |
|---|---|---|---|---|---|---|---|---|---|
| | Anti- | H1N1 [a] | | H3N2 [b] | | H1N1 | | H3N2 | |
| Group | gen (µg) | % | GMT | % | GMT | % | GMT | % | GMT |
| 1 | None | 0 | 0 | 0 | 0 | 0 | 0 | 0 | 0 |
| 2 | TMV NtK | 0 | 0 | 0 | 0 | 0 | 0 | 0 | 0 |
| 3 [c] | 15 | 0 | 0 | 0 | 0 | 0 | 0 | 0 | 0 |
| 4 [c] | 7.5 | 0 | 0 | 0 | 0 | 0 | 0 | 0 | 0 |
| 5 [c] | 3.75 | 0 | 0 | 0 | 0 | 0 | 0 | 0 | 0 |
| 6 [d] | 15 | 33% | 11.7 | 100% | 29.4 | 30% | 7.6 | 44% | 10 |
| 7 [d] | 7.5 | 10% | 6.8 | 100% | 25.2 | 30% | 7.6 | 67% | 12.6 |
| 8 [d] | 3.75 | 0% | 5 | 44% | 10 | 22% | 7.9 | 67% | 10.3 |

[a] A/Michigan/45/2015 (H1N1)
[b] A/Singapore/INFIMH-16-0019/2016 (H3N2)
[c] Quadrivalent vaccine antigens (A/Michigan/45/2015 (H1N1pdm09); A/Singapore/INFIMH-16-0019/2016 (H3N2); B/Colorado/06/2017 (Vict); B/Phuket/3073/2013 (Yam) alone, not conjugated to TMV NtK Carrier
[d] QIV Vaccine (A/Michigan/45/2015 (H1N1pdm09); A/Singapore/INFIMH-16-0019/2016 (H3N2); B/Colorado/06/2017 (Vict); B/Phuket/3073/2013 (Yam) conjugated 1:1 TMV NtK:HA Antigen

TABLE 40

Percentage of Animals and HAI Geometric Mean Titers Generated Against Influenza A Antigens - Days 42 and 90

| | | Day 42 | | | | Day 90 | | | |
|---|---|---|---|---|---|---|---|---|---|
| | Antigen | H1N1 | | H3N2 | | H1N1 | | H3N2 | |
| Group | (µg) | % | GMT | % | GMT | % | GMT | % | GMT |
| 1 | None | 0 | 0 | 0 | 0 | 0 | 0 | 0 | 0 |
| 2 | TMV NtK | 0 | 0 | 0 | 0 | 0 | 0 | 0 | 0 |
| 3 [c] | 15 | 0 | 0 | 0 | 0 | 0 | 0 | 0 | 0 |
| 4 [c] | 7.5 | 0 | 0 | 0 | 0 | 0 | 0 | 0 | 0 |
| 5 [c] | 3.75 | 0 | 0 | 0 | 0 | 0 | 0 | 0 | 0 |
| 6 [d] | 15 | 70% | 15.2 | 80% | 20 | 100% | 183.8 | 100% | 91.9 |
| 7 [d] | 7.5 | 90% | 21.4 | 70% | 21.4 | 90% | 137.2 | 60% | 26.4 |
| 8 [d] | 3.75 | 78% | 15.9 | 67% | 15.9 | 89% | 117.6 | 78% | 27.2 | a. A/Michigan/45/2015 (H1N1)
b. A/Singapore/INFIMH-16-0019/2016 (H3N2)
[c] Quadrivalent vaccine antigens (A/Michigan/45/2015 (H1N1pdm09); A/Singapore/INFIMH-16-0019/2016 (H3N2); B/Colorado/06/2017 (Vict); B/Phuket/3073/2013 (Yam) alone, not conjugated to TMV NtK Carrier
[d] QIV Vaccine (A/Michigan/45/2015 (H1N1pdm09); A/Singapore/INFIMH-16-0019/2016 (H3N2); B/Colorado/06/2017 (Vict); B/Phuket/3073/2013 (Yam) conjugated 1:1 TMV NtK:HA Antigen.

Like the HAI titers, virus neutralization (VN) titers were only observed in animals receiving the QIV vaccine. As presented in Table 41, VN titers against A/Michigan/45/2015 (H1N1) and A/Singapore/INFIMH-16-0019/2016 (H3N2) were also not observed until Day 21 VN titers remained detectable on Day 28 and Day 42 and were highest on Day 90.

TABLE 41

Neutralization Geometric Mean Antibody
Titers Induced to Influenza A Antigens

| A/Michigan/45/2015 (H1N1) | | | | A/Singapore/INFIMH-16-0019/2016 (H3N2) | | |
|---|---|---|---|---|---|---|
| Dose µg/mL | | | | Dose µg/mL | | |
| Day | 30 | 15 | 7.5 | Day | 30 | 15 | 7.5 |
| −1 | 50 | 50 | 50 | −1 | 50 | 50 | 50 |
| 14 | 50 | 50 | 50 | 14 | 50 | 50 | 50 |
| 21 | 100 | 216 | 136 | 21 | 293.95 | 158.74 | 79.37 |
| 28 | 216 | 151.6 | 114.9 | 28 | 147 | 114.87 | 141.42 |
| 42 | 216 | 186.6 | 233.3 | 42 | 370.35 | 151.57 | 186.61 |
| 90 | 635 | 857.4 | 606.3 | 90 | 864.05 | 303.14 | 263.9 |

In the study outlined in Table 38, the mice were also monitored for clinical signs and injection site reactions. At necropsy, organ weights were measured and gross necropsy and histopathology on tissues was performed. There were no test article-related gross findings for any animals necropsied on Day 21 or Day 90.

For the animals euthanized on Day 21, a test article-related microscopic finding of minimal to mild mixed cell infiltration at the injection site was noted in 3 out of 9 animals in Group 2 (TMV NtK Control), 1 out of 9 animals in Group 3 (HA Alone), and 9 out of 9 animals in Group 6 (QIV). Minimal degeneration/regeneration of the myofiber of the injection site was also noted in 1 out of 9 animals examined from Group 6. No other microscopic test article related finding was noted for the mice euthanized on Day 21 or Day 90.

In conclusion, the QIV vaccine induced a detectable humoral immune response based on HAI and virus neutralization assays. The most robust response was to A/Michigan/45/2015 (FEINT) and A/Singapore/INFIMH-16-0019/2016 (H3N2). HAI and VN Titers were first detectable on Day 21 and were highest on Day 90. These data indicate that the QIV vaccine is safe and immunogenic in mice.

Immunogenicity and Challenge Study in
Ferrets—Example 14(c)

An immunogenicity and challenge study using the QIV vaccine was also conducted in ferrets, which are accepted as the most representative animal model for influenza infection, to evaluate vaccine efficacy through reduction of viral loads post-challenge in relation to a licensed vaccine comparator. As shown in the study design illustrated in FIG. 42, blood for immunogenicity was taken on the following study days: - 3, 7, 14, 21, 28, and 42. On study day 43, the animals were challenged and nasal wash for virus titer took place on study days 45 and 47.

Briefly, ferrets N=30 (15M/15F) per group were immunized with the one of the following on Study Day 0 and 14:
 1. Placebo buffer as negative control (same quantity as Group 4)
 2. Fluzone® quadrivalent as a licensed comparator (15 µg per HA, 60 µg total HA) vaccine
 3. QIV at 15 µg per HA antigen (60 µg total HA antigen; 60 µg TMV NtK carrier)
 4. QIV at 45 µg per HA antigen (180 µg total HA)

Figure 42:
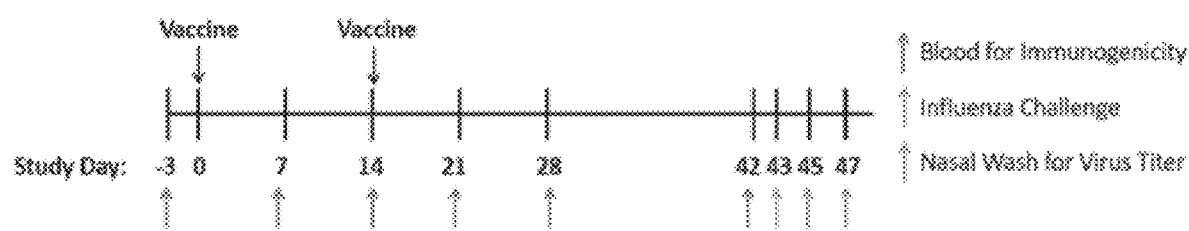
FIG. 42 is an illustration of an immunogenicity and challenge study of a quadrivalent vaccine in ferrets, according to multiple embodiments and alternatives.

Following each dose, injections sites and clinical signs were monitored daily for 7 consecutive days. As shown in FIG. 42, animals were bled at certain intervals for measurement of HAI and neutralization antibody titers. Animals from the individual dose groups were subdivided into two groups (N=12, 6M/6F) and challenged on Day 43 with $1\times10^6$ plaque forming units (PFU) of either A/Michigan/45/2015 (H1N1)pdm09 or A/Singapore/INFIMH-16-0019/2016 (H3N2) (as non-limiting examples). Animals were monitored and nasal washes taken 2- and 4-days post-challenge to quantify residual influenza virus titers and assess viral clearance.

In ferrets dosed with either the 15 or 45 µg dose levels of QIV and Fluzone®, hemagglutination inhibition (HI) antibodies were detected against all four viruses tested [A/Michigan/45/2015 (H1N1)pdm09, A/Singapore/INFIMH-16-0019/2016 (H3N2), B/Colorado/06/2017 and B/Phuket/3073/2013], The QIV vaccine elicited the strongest HI responses to B/Phuket, B/Colorado and A/Singapore/INFIMH-16-0019/2016 (H3N2). The weakest HI responses were against the A/Michigan/45/2015 (H1N1) virus. Virus Neutralization (VN) titers were detected against all viruses, with order of descending response: A/Michigan/45/2015 (H1N1)pdm09, A/Singapore/INFIMH-16-0019/2016 (H3N2), B/Phuket and B/Colorado/06/2017 showing lowest response.

Figure 43:
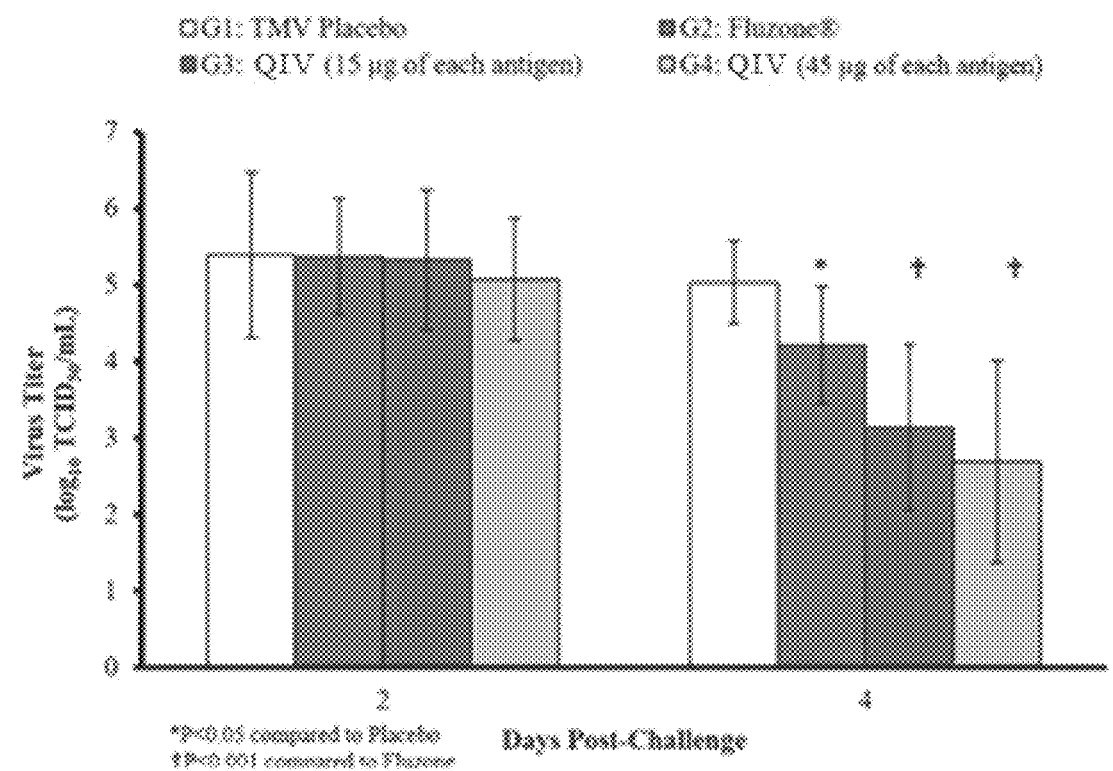
FIG. 43 is an illustration of the nasal wash virus titers following virus challenge in ferrets, according to multiple embodiments and alternatives.

Following influenza challenge with A/Michigan/45/2015 (H1N1)pdm09, as shown in FIG. 42, virus was detected in the nasal washes of all challenged ferrets on Day 2 and 4 post challenge. FIG. 43 illustrates the nasal wash titers following the H1N1 challenge (log 10 $TCID_{50}$/mL), wherein the QIV vaccine is referred to as "QIV". As shown in FIG. 43, there were no statistical differences in viral titers at Day 2 post-challenge, however, an increase in average body temperature of 1.0° C. was only observed in placebo controls. When compared to the placebo group on 4-day post-challenge, all three vaccine groups yielded statistically reduced viral titers with the QIV vaccine showing dose-dependent log reductions (2.3 and 1.9 log 10 TCID50/mL) that were statistically greater than Fluzone® (0.83 log 10 TCID50/mL). In FIG. 43, the p value is less than 0.05 for the Fluzone® value compared to the placebo, and the p value is less than 0.001 for the QIV value compared to Fluzone®. Also, the weight loss observed in Fluzone® and QIV vaccinated ferrets s comparable to placebo controls.

Figure 44:
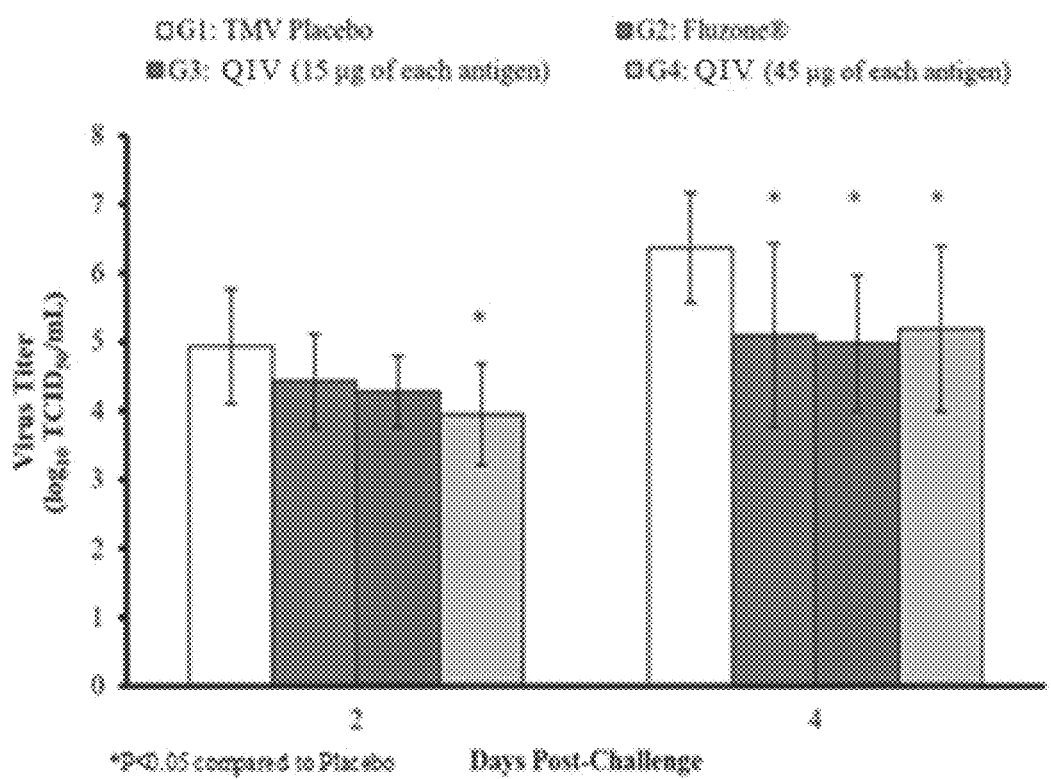
FIG. 44 is an illustration of the nasal wash virus titers following virus challenge in ferrets, according to multiple embodiments and alternatives.

FIG. 44 illustrates the nasal wash titers following the H3N2 challenge (log 10 $TCID_{50}$/mL), wherein the QIV vaccine is referred to as "QIV". As shown in FIG. 44, following challenge with A/Singapore/INFIMH-16-0019 (H3N2), virus was detected in the nasal washes of all challenged ferrets on Days 2 and 4 post-challenge. When compared to the placebo group, a maximal log reduction in viral titers was observed on Day 2 in the QIV vaccine 45 µg dose group (1.0 log 10 $TCID_{50}$/mL) which was statistically lower than placebo. QIV vaccine and Fluzone® yielded log reductions of 0.7 log 10 TCID50/mL and 0.5 log 10 TCID50/mL, respectively which were not statistically reduced compared to the placebo group (the p value is less than 0.05). As shown in FIG. 44, on Day 4 a comparable level of significant log reduction in viral titers was observed for all vaccinated groups, Fluzone® (1 log 10 $TCID_{50}$/mL), QIV vaccine (15 µg dose, 1.4 log 10 $TCID_{50}$/mL), and QIV vaccine (45 µg, 1.2 log 10 TCID50/mL). In addition, maximal average weight loss in the placebo and Fluzone® vaccinated groups was comparable at 3.1% and 2.6%, respectively. QIV immunized animals had less infection-induced maximal average weight loss of 2.1% (15 µg QIV) and 1.2% (45 µg QIV).

In regards to studies of immunogenic response, the QIV vaccine of the present example induced a detectable humoral immune response against the four antigens tested in HI and VN assays. A strong VN response corresponded with a reduction in nasal wash viral titers observed on Day 4 post challenge in vaccinated ferrets challenged with A/Michigan/45/2015 (H1N1)pdm09. The log reduction in viral titers observed on Day 4 in the QIV vaccinated ferrets was 1.1 to 1.5 log greater when compared to Fluzone®. Against A/Singapore/INFIMH-16-0019/2016 (H3N2), a strong HI response was observed in all three groups of vaccinated ferrets. In ferrets challenged with A/Singapore/INFIMH-16-0019/2016 (H3N2), improved protection was observed for high dose group day 2 post infection and at day 4, with a similar log reduction in viral titers being observed in the QIV vaccinated ferrets and Fluzone® both resulting in statistically lower viral titers than Placebo. These data indicate that the QIV vaccine is immunogenic and provides a level of protection to ferrets against challenge with H1N1 and H3N2 homologous virus.

Matrix Immunogenicity Study in Mice—Example 14(d)

The goal of this study was to evaluate the immunogenicity of the QIV vaccine at different conjugation ratios of TMV NtK to HA antigen. For this study, a monovalent vaccine was formulated using A/Singapore/INFIMH-16-0019/2016 (H3N2). As shown in Table 42, a fixed dose of HA with increasing TMV was compared to a fixed dose of TMV with decreasing doses of HA (data not shown).

TABLE 42

Overview of Matrix Study

| Group | Treatment Group | N | Vaccine Antigen Dose (µg) | TMV NtK Content | Vaccination (days) | Blood Collections (Days) |
|---|---|---|---|---|---|---|
| 1 | Vehicle Control | 5 | 0 | 0 | 0, 14 | 12, 28, 42 and 60 |
| 2 | Monovalent 1:1 | 5 | 15 | 15 | 0, 14 | 12, 28, 42 and 60 |
| 3 | Monovalent 4:1 | 5 | 15 | 60 | 0, 14 | 12, 28, 42 and 60 |
| 4 | Monovalent 8:1 | 5 | 15 | 120 | 0, 14 | 12, 28, 42 and 60 |
| 5 | Monovalent 16:1 | 5 | 15 | 240 | 0, 14 | 12, 28, 42 and 60 |
| 6 | Monovalent 24:1 | 5 | 15 | 360 | 0, 14 | 12, 28, 42 and 60 |

Eight week old female BALB/c mice, five per group, were immunized with A/Singapore/INFIMH-16-0019/2016 (H3N2) monovalent influenza vaccine by subcutaneous route of administration with the indicated vaccine composition on Days 1 and 14. Mice were bled and serum was collected on Days 12, 28, 42 and terminal serum was collected on Day 60.

Figure 45:
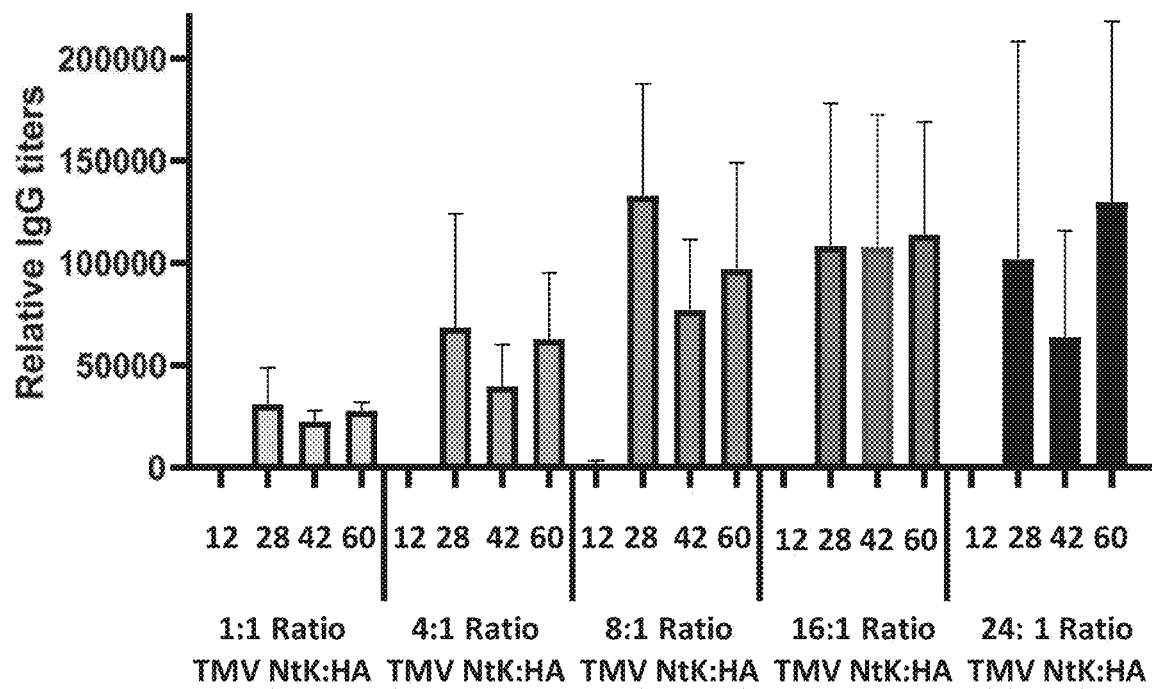
FIG. 45 is an illustration of the immunogenicity of a monovalent vaccine produced in mice at various virus to recombinant antigen ratios, according to multiple embodiments and alternatives.

FIG. 45 illustrates the immunogenicity of the monovalent vaccine produced at varying ratios of TMV NtK: HA antigen. The relative IgG titers are expressed as ng IgG per mL of serum. As shown in FIG. 45, at day 60 (the end of the study), IgG titers induced by the monovalent vaccines prepared with increasing TMV-NtK: HA antigen conjugation ratios continued to show a significant improvement compared to the benchmark 1:1 ratio group.

Furthermore, in the HA antigen study wherein the dose of HA was fixed at 15 µg with increasing TMV NtK concentrations, the 8:1 and 16:1 vaccine formulations induced the highest mean response that was stable over time. This data support the use of the vaccines produced according to multiple embodiments and alternatives as an effective strategy to generate humoral immunity.

Accordingly, the immunogenicity studies in mice and the efficacy study in ferrets clearly demonstrate a significant increase in the generation of humoral immunity by the QIV vaccine of the present example. Additionally, immunogenicity was shown to be related to the conjugation of the HA antigen to the inactivated TMV NtK carrier. In mice, the humoral response continued to increase over 90 days. Moreover, immunization of the QIV vaccine was able to significantly reduce H1N1 and H3N2 viral loads following virus challenge that was greater than or equivalent to the conventional vaccine comparator, Fluzone®. In other words, vaccination with the QIV vaccine was able to reduce morbidity and virus levels caused by infection with homologous H1N1 and H3N2 influenza strains to the vaccine strain which were greater than or equal to the conventional vaccine comparator, Fluzone®. It is expected that vaccines manufactured in accordance with the present embodiments will show similar improved efficacy as the QIV vaccines of Example 14, across a wide range of antigens conjugated to a virus such as TMV to be used against many kinds of viruses.

Pharmacokinetic Studies—Examples 14(e) and 14(f)

Pharmacokinetic studies were performed to evaluate the biodistribution of the QIV vaccine following a single intramuscular injection in male New Zealand White rabbits over an eight day period. The study used a RT-qPCR methodology that was developed and qualified to measure the TMV NtK viral RNA extracted from tissue or blood, and the study compared two different QIV vaccine formulations prepared with differing amounts of the TMV NtK carrier. The analyzed tissues included blood, skeletal muscle (injection site), lymph nodes, spleen, thymus, heart, liver, lung, kidney and tested.

Figure 46:
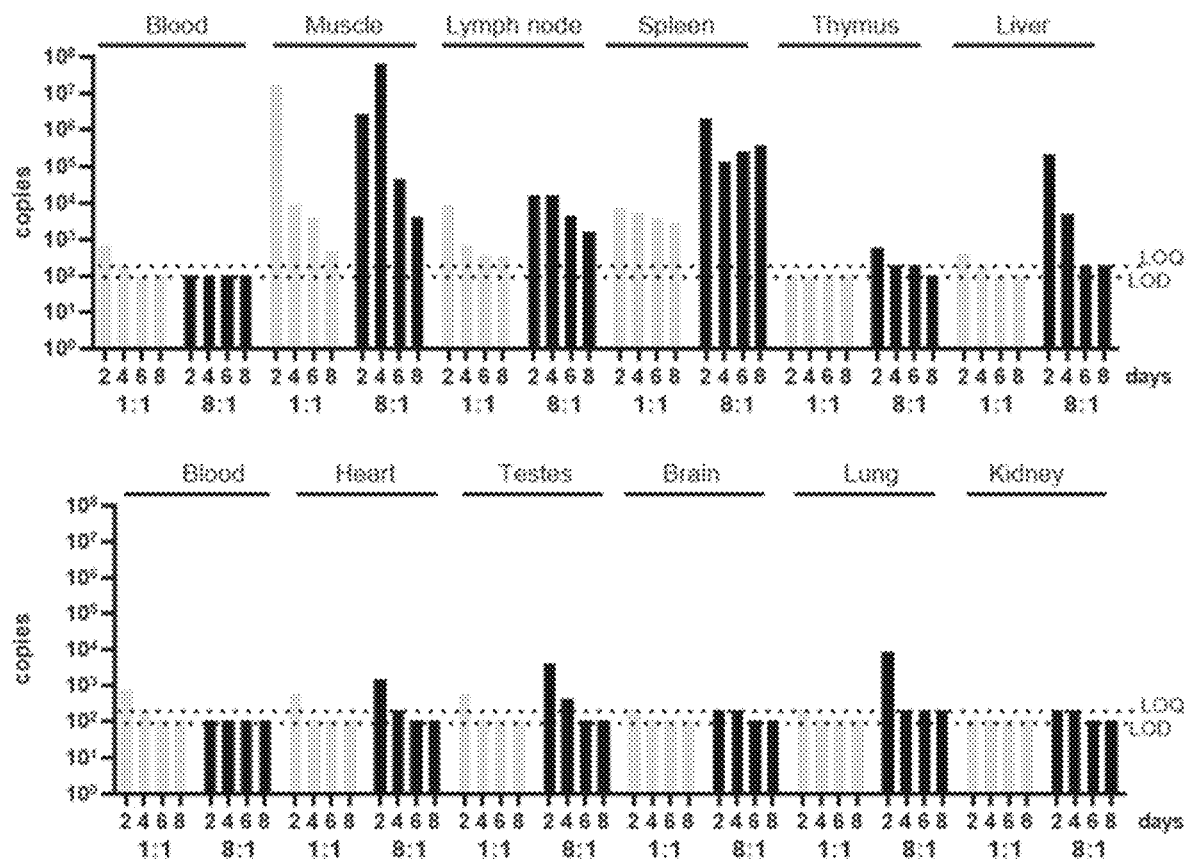
FIG. 46 is an illustration of TMV vRNA in tissues over time following an injection of a quadrivalent vaccine, according to multiple embodiments and alternatives.
Figure 47:
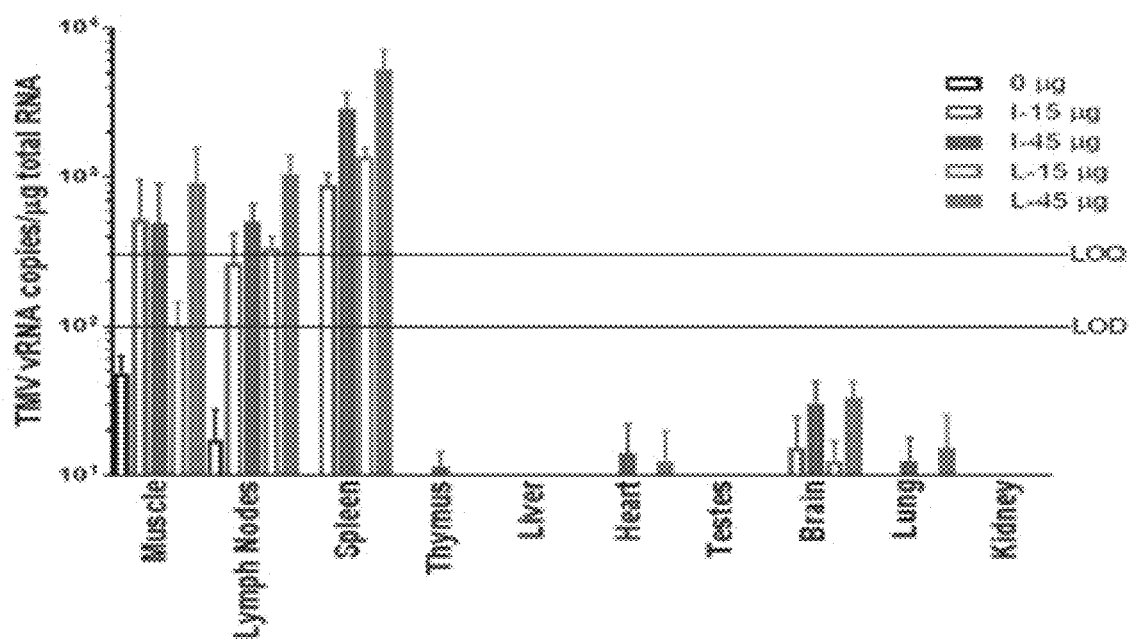
FIG. 47 is an illustration of TMV vRNA in tissues eight days following an injection of a quadrivalent vaccine, according to multiple embodiments and alternatives.

FIG. 46 shows the comparative distribution of the TMV vRNA in tissues over time as measured by RT-PCR following a single injection of two different QIV formulations, incorporating either 45 µg (1:1 formulation monovalent vaccine) or 1440 µg (8:1 formulation quadrivalent vaccine) of the TMV NtK carrier in a 0.5 mL dose (as non-limiting examples). FIG. 47 shows the biodistribution of the TMV vRNA in tissues by organ and dose group eight days after a single injection. In FIGS. 46 and 47, "LOQ" refers to the limit of quantitation and "LOD" refers to the limit of detection.

As expected, the two formulations showed a consistent distribution pattern. In FIGS. 46 and 47, the highest levels of the QIV were quantifiable from injection site skeletal muscle tissue through the study duration with amounts decreasing over time with both formulations. After skeletal muscle, the QIV was most abundant and detected throughout the study in spleen and draining lymph nodes, indicating that QIV traffics to these tissues post-immunization. Transient levels were detected in liver, heart, and testes at the 24 hour-post dosing time point and then below the LOQ with both formulations thereafter. The 8:1 formulation had low, transient signal detected in blood, lung, and thymus tissues 24 hours post-immunization that were below the limit of quantitation (LOQ) by Day 3 post-immunization, which is likely due to the 32-fold higher amounts of TMV NtK included in that formulation. No quantifiable QIV residuals were detected in brain or kidney tissue with either QIV formulation.

Accordingly, in all formulations the vaccine was observed to traffic from the injection site to immune organs and no accumulation was observed in non-target organs. Likewise, the TMV-specific Q-RT-PCR signal was observed to be dose dependent when measured at site of injection with rapid clearance from all non-target organs. Therefore, the detection in the immune system organs suggests a "depot" effect (i.e. sustained release of antigen at the site of injection) and prolonged stimulation of the immune system.

Toxicology Studies—Examples 14(g) and 14(h)

As previously noted in Table 35 and as described in Table 43 below, several toxicological studies were conducted according to GLP requirements to evaluate the potential toxicity of the QIV vaccine and to support the clinical use of the QIV vaccine for the prevention of disease caused by infection with influenza virus (as a non-limiting example). Two repeat dose toxicology studies in New Zealand White rabbits were performed using two formulations of QIV that differed in the content of the TMV NtK carrier conjugated with the purified recombinant HA antigens, according to multiple embodiments and alternatives. As described in more detail below, the studies revealed no treatment-related or toxicologically significant clinical findings which support the safe use of the TMV NtK:HA conjugate in human studies.

larly twice (once daily) on study days 1 and 29 to male and female New Zealand White rabbits, and the reversibility of effects after a 28-day recovery period was evaluated. As shown in Table 44, each group consisted of 10 rabbits/sex/group. On study day 30 (1 day after the last dose) five rabbits/sex/group were sacrificed and on study day 57 (28 days after the last dose) five rabbits/sex/group were sacrificed.

TABLE 44

Repeat Dose Toxicity Study Design, Example 14(g)-1:1 QIV formulation

| Group | Treatment | Vaccine Dose per Antigen (μg) | Vaccine Dose TMV NtK carrier (μg) | No. of Rabbits (M + F) Necropsied on Day 31 | Day 57 |
|---|---|---|---|---|---|
| 1 | Control (vehicle) | 0 | 0 | 5 + 5 | 5 + 5 |
| 2 | QIV Vaccine | 15 | 60 | 5 + 5 | 5 + 5 |
| 3 | QIV Vaccine | 45 | 180 | 5 + 5 | 5 + 5 |

The test articles were administered by intramuscular (IM) injection on study Days 1 and 29. At each injection, animals in each group received 0.5 mL of the control article (Group 1), low dose vaccine (Group 2), or high dose vaccine (Group 3) using a 25-gauge needle attached to a plastic, 1-mL syringe (as non-limiting examples). The administration site was the relatively large muscle mass on the posterior aspect of the hind limb and was shaved or re-shaved (as appropriate). On each day of injection, the administration site was wiped with alcohol and allowed to dry thoroughly for a minimum of 10 minutes prior to dosing. The IM administration site alternated between hind limbs with the right hind limb receiving the first dose.

Five rabbits/sex/group were euthanized on Study Day 31 (two days after the last dose), while the remaining study animals (4/sex/group) continued to be observed and were euthanized on study day 57 (28 days after the last dose). Experimental endpoints included morbidity/mortality; physical examinations, clinical signs of toxicity, and inoculation site (Draize) reactogenicity scoring; body weights; body weight changes; food consumption; body temperatures; ophthalmology; clinical pathology (clinical chemistry, hematology, coagulation); organ weights; immunogenicity analysis; gross pathology at necropsy; and microscopic pathology.

TABLE 43

Overview of Toxicology Study

| Study | Treatment | Active Components | Route of Administration | Species |
|---|---|---|---|---|
| Example 14(g) 1:1 QIV formulation | Vehicle Control | — | Intramuscular | New Zealand White Rabbis |
| | QIV Low dose 15 μg/HA | 60 μg HA 60 μg TMV NtK | Intramuscular | New Zealand White Rabbis |
| | QIV High Dose 45 μg/HA | 180 μg HA 180 μg TMV NtK | Intramuscular | New Zealand White Rabbis |
| Example 14(h) 8:1 QIV formulation | Vehicle Control | — | Intramuscular | New Zealand White Rabbis |
| | TMV NtK Control | 1.44 mg TMV NtK | Intramuscular | New Zealand White Rabbis |
| | QIV High Dose 45 μg/HA | 180 μg /HA 1.44 mg TMV NtK | Intramuscular | New Zealand White Rabbis |

As shown in Table 43, two repeat dose GLP toxicity studies were performed in rabbits using different virus to antigen ratios. In some embodiments, the QIV vaccine was administered as a single intramuscular injection on an annual basis. To investigate the efficacy of this approach, a strategy of the number of human doses plus 1 (N+1) was used with the second dose administered 28 days following the first dose. Test articles included the intended human high dose of the QIV vaccine at each conjugation level of the TMV NtK carrier molecule (1:1 and 8:1 formulations) and the high dose of the TMV NtK carrier alone.

In the repeat dose toxicity study of the QIV vaccine at a 1:1 Ratio of TMV NtK carrier, HA Antigen, a seasonal influenza vaccine candidate was administered intramuscu- All study rabbits survived to the scheduled necropsies. No treatment-related or toxicologically significant clinical findings or inoculation site reactogenicity were observed. No treatment-related or toxicologically significant effects were observed for body weights, body weight changes, food consumption, body temperatures, ophthalmology, clinical chemistry, hematology, and organ weights.

Fibrinogen levels were increased (p<0.05 or <0.01) in the vaccine treatment groups usually at two days post dose. The increase in fibrinogen in these groups was considered to be related to vaccine treatment, but was considered an expected (inflammatory) response following treatment with an immunogenic substance. Fibrinogen was no longer increased (p>0.05) at the end of the 28-day recovery period (reversible effect).

Mixed cell infiltration in the left sciatic nerve and injection site (side of last IM administration on Study Day 29) was a common microscopic finding seen in the intramuscularly dosed vaccine toxicology studies. This lesion was recoverable in the sciatic nerve, but not fully recovered in the injection site at the end of the 28-day recovery period. This lesion was not considered adverse, but was an anticipated finding consistent with the administration of an immunogenic material.

In conclusion, intramuscular administration of the QIV vaccine at doses of 15 or 45 µg once every four weeks for two injections (study days 1 and 29) was well tolerated. Any findings noted did not result in any adverse or limiting toxicity, were considered to be of minimal toxicological significance noted in only one sex, reversible, transient, no alteration in organ function, etc.), and/or were anticipated findings (such as fibrinogen increases and mixed cell infiltration in the injection site or sciatic nerve) following administration of an immunogenic substance.

Repeat Dose Toxicity Study—Example 14(h)

In the repeat dose toxicity study of the QIV vaccine at a 8:1 Ratio of TMV NtK carrier, HA Antigen, a seasonable influenza vaccine candidate was also administered intramuscularly twice (once daily) on study days 1 and 29 to male and female New Zealand White rabbits, and the reversibility of effects after a 28-day recovery period was evaluated. As shown in Table 45, each group consisted of 8 rabbits/sex/group. On study day 30 (1 day after the last dose) five rabbits/sex/group were sacrificed and on study day 57 (28 days after the last dose) five rabbits/sex/group were sacrificed.

TABLE 45

Repeat Dose Toxicity Study Design,
Example 14(h)-1:1 QIV formulation

| Group | Treatment | Vaccine Dose per Antigen (µg) | Vaccine Dose TMV NtK carrier (µg) | No. of Rabbits (M + F) Necropsied on | |
|---|---|---|---|---|---|
| | | | | Day 31 | Day 57 |
| 1 | Control (vehicle) | 0 | 0 | 4 + 4 | 4 + 4 |
| 2 | TMV NtK Control | 0 | 1440 | 4 + 4 | 4 + 4 |
| 3 | QIV Vaccine | 45 | 1440 | 4 + 4 | 4 + 4 |

The test articles were administered by IM injection on Study Days 1 and 29. At each injection, animals in each group received 0.5 mL of the control article (Group 1), low dose vaccine (Group 2), or high dose vaccine (Group 3) using a 25-gauge needle attached to a plastic, 1-mL syringe (as non-limiting examples). The administration site was the relatively large muscle mass on the posterior aspect of the hind limb and was shaved or re-shaved (as appropriate). On each day of injection, the administration site was wiped with alcohol and allowed to dry thoroughly for a minimum of 10 minutes prior to dosing. The administration site alternated between hind limbs with the right hind limb receiving the first dose.

Four rabbits/sex/group were euthanized on study day 31 (two days after the last dose), while the remaining study animals (4/sex/group) continued to be observed and were euthanized on study day 57 (28 days after the last dose). Experimental endpoints included morbidity/mortality; physical examinations, clinical signs of toxicity, and inoculation site (Draize) reactogenicity scoring; body weights; body weight changes; food consumption; body temperatures; ophthalmology; clinical pathology (clinical chemistry, hematology, coagulation); organ weights; immunogenicity analysis; gross pathology at necropsy; and microscopic pathology.

All study rabbits survived to the scheduled necropsies. No treatment-related or toxicologically significant clinical findings or inoculation site reactogenicity were observed. No treatment-related or toxicologically significant effects were observed for body weights, body weight changes, food consumption, body temperatures, ophthalmology, clinical chemistry, hematology, organ weights, and gross and microscopic pathology.

Fibrinogen levels were increased (p<0.01) in the treated groups usually at two days post dose. The increase in fibrinogen in these groups was considered to be related to treatment, but was considered an expected (inflammatory) response following treatment with immunogenic substances. Fibrinogen was no longer increased (p>0.05) during the recovery period (reversible effect).

Accordingly, IM administration of the QIV vaccine candidate, or inactivated TMV NtK at doses of either 45 µg of each HA antigen (180 µg total HA±180 µg TMV NtK) or 1440 µg of each HA antigen, respectively, once every four weeks for two injections (Study Days 1 and 29) was well tolerated. The findings in these GLP toxicological studies did not result in any adverse or limiting toxicity, were considered to be of minimal toxicological significance (e.g., noted in only one sex, reversible, transient, no alteration in organ function, etc.), and/or were anticipated findings (such as fibrinogen increases) following administration of immunogenic substances. No significant toxicological issues were noted with either 1:1 or 8:1 (TMV NtK:HA antigen) formulations of the QIV vaccines in these studies.

Figure 48:
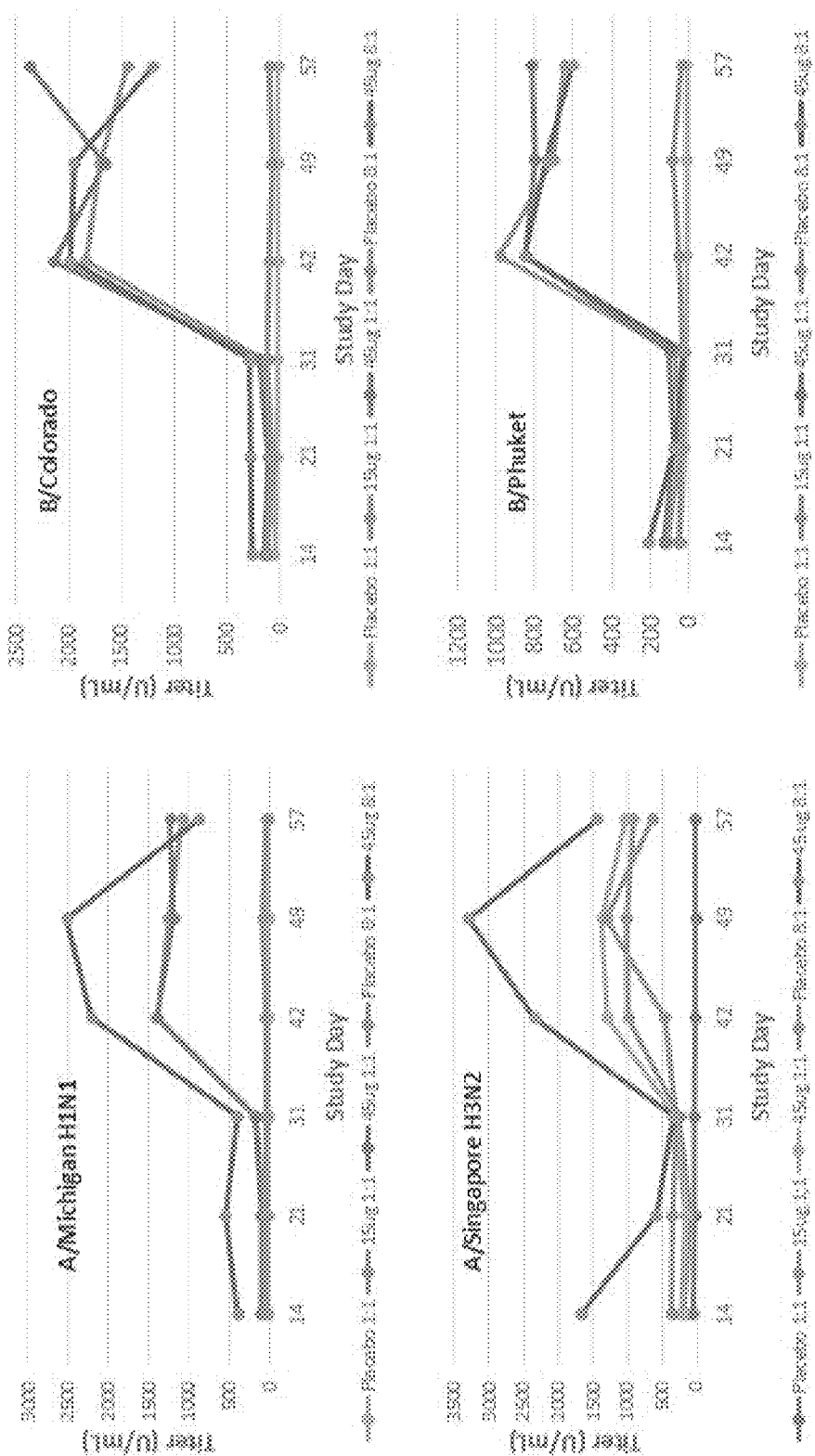
FIG. 48 is an illustration of total anti-influenza titers based on an ELISA analysis from rabbit serum samples following injections of a quadrivalent vaccine, according to multiple embodiments and alternatives.

Furthermore, during the two GLP toxicological studies (Examples 14(g) and 14(h)), a robust antigen-specific immunogenic response was also measured based on ELISA, HAI, and neutralization antibody titers in rabbits receiving the low and high dose of the QIV vaccine test articles. FIG. 48 illustrates the total anti-HA IgG ELISA analysis from rabbit serum samples following QIV vaccine immunizations on Day 1 and Day 29. As shown in FIG. 48, the immunologic response peaked after the second administration of the QIV vaccine, as expected from the immunization of naïve animals. Anti-influenza titers to all four influenza antigens (Michigan H1N1, Singapore H3N2, B/Colorado, and B/Phuket as non-limiting examples) were measured in serum samples after the day 29 injection. Moreover, the mean anti-influenza titers up to 90-fold higher (than the controls) were detected on study days 42, 49, and 57.

As shown in Table 46 below, HAI titers were detected in most animals on study days 42, 49, and 57 against A/Michigan/45/2015(H1N1), A/Singapore/MIN/H-16-0019/2019 (H3N2) and B/Colorado/06/2017 viruses (as non-limiting examples). In contrast, HAI titers against the B/Phuket/3073/2013 virus (as a non-limiting example) were generally seen in 4 or fewer animals on Study Days 42, 49, and 57 across three species (mice, ferrets and rabbits). The primary measure of immunity was the generation of HAI antibody titers, the recognized serum biomarker of protection for influenza infection. In immunologically naïve animals, the humoral immune response was predominantly detected following a second (booster) immunization. Immunogenicity to the vaccine hemagglutinin antigens was dependent upon

TABLE 46

Percentage of Animals with Detectable HAI Titers on Study Day 49 of the GLP Toxicology Studies

| | Dose | Percentage of animals with detectable HI titer at Study Day 49 (HI Titer Response Range) | | | |
|---|---|---|---|---|---|
| | | A/Michigan (H1N1) | H3/Singapore (H3N2) | B/Colorado (B/Victoria) | B/Phuket (B/Yamagata) |
| Placebo [from the 1:1 ratio study] | 0 | 0% | 0% | 0% | 0% |
| Placebo [from the 8:1 ratio study] | 0 | 0% | 0% | 0% | 0% |
| TMV NtK [from the 8:1 ratio study] | 1440 μg | 0% | 0% | 0% | 0% |
| QIV [1:1 TMV to HA Ratio] | 15 μg/HA | 100% (80-640) | 80% (20-160) | 50% (20-80) | 30% (10-20) |
| | 45 μg/HA | 100% (80-640) | 100% (20-160) | 70% (20-80) | 30% (20-40) |
| QIV [8:1 TMV to HA Ratio] | 45 μg/HA | 100% (40-320) | 100% (10-800) | 38% (10) | 100% (10-160) |

Figure 49:
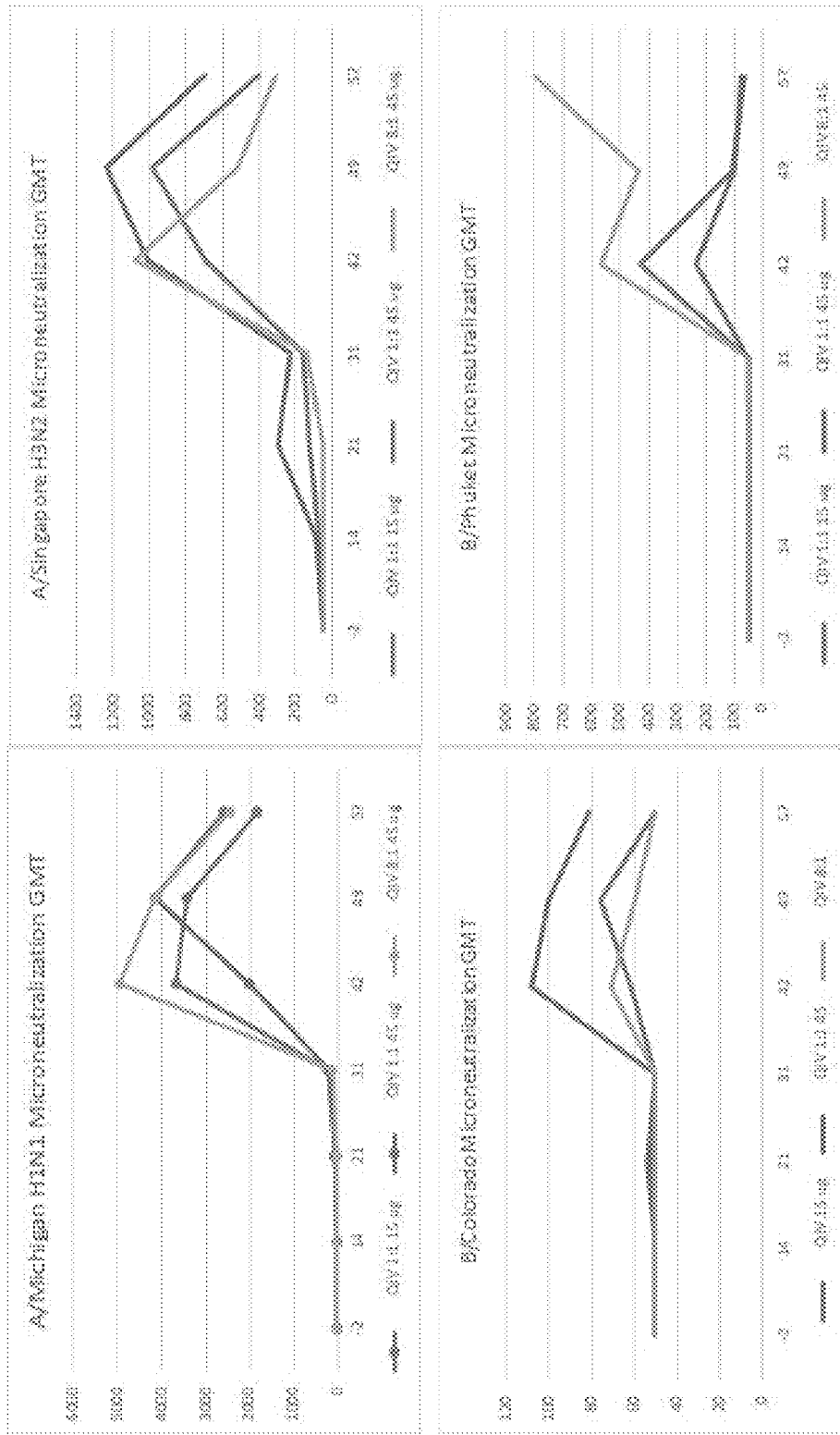
FIG. 49 is an illustration of neutralization titers measured in rabbits following injections of a quadrivalent vaccine, according to multiple embodiments and alternatives.

FIG. 49 illustrates the measurement of microneutralization GMT titers throughout the GLP Toxicology Study using the 8:1 QIV Formulation for each virus in the QIV vaccine. Also, Table 47 below, provides the percentage of animals with detectable microneutralization titers on study day 49 of both GLP Toxicology Studies (i.e. both the 1:1 and 8:1 QIV formulations). As shown in FIG. 49 and Table 47, neutralization titers against these same four viruses (as non-limning examples) were also consistently measured in rabbits receiving the low and high dose of the vaccine on Study Days 42, 49, and 57, with the highest titers seen against the A/Michigan/45/2015 (H1N1)pdm09 and A/Singapore/INFIMH-16-0019/2019 (H3N2) viruses conjugation to the TMV NtK carrier. The QIV vaccine prepared at a ratio of 8:1 TMV NtK carrier-to-recombinant HA antigen was shown to be desirable. In a disease challenge model, immunization of ferrets with QIV significantly reduced viral loads in animals subsequently challenged with homologous H1N1 and H3N2 strains as assessed from nasal wash samples. This reduction in viral load was greater than or equal to that of a licensed comparator. Immunization also ameliorated clinical signs of morbidity associated with the challenge viruses.

The studies also investigated the distribution and safety of the QIV vaccine. There has been no detection of edema or injection site reactions in any of the studies. Biodistribution

TABLE 47

Percentage of Animals with Detectable Microneutralization Titers on Study Day 49 of the GLP Toxicology Studies Percentage of Animals with Measurable Titer

| | A/Michigan H1N1 | | | A/Singapore H3N2 | | | B/Colorado | | | B/Phuket | | |
|---|---|---|---|---|---|---|---|---|---|---|---|---|
| Study Time Point | QIV 1:1 15 μg | QIV 1:1 45 μg | QIV 8:1 45 μg | QIV 1:1 15 μg | QIV 1:1 45 μg | QIV 8:1 45 μg | QIV 1:1 15 μg | QIV 1:1 45 μg | QIV 8:1 45 μg | QIV 1:1 15 μg | QIV 1:1 45 μg | QIV 8:1 45 μg |
| −2 | 0% | 0% | 0% | 0% | 0% | 0% | 0% | 0% | 0% | 0% | 0% | 0% |
| 14 | 0% | 0% | 0% | 20% | 40% | 0% | 0% | 0% | 0% | 0% | 0% | 0% |
| 21 | 35% | 30% | 12.5% | 60% | 90% | 12.5% | 5% | 5% | 0% | 0% | 0% | 0% |
| 31 | 90% | 75% | 75% | 55% | 85% | 12.5% | 0% | 0% | 0% | 0% | 0% | 0% |
| 42 | 100% | 100% | 100% | 100% | 100% | 88% | 20% | 56% | 12.5% | 100% | 78% | 100% |
| 49 | 100% | 100% | 100% | 100% | 100% | 100% | 50% | 75% | 12.5% | 80% | 63% | 100% |
| 57 | 100% | 100% | 100% | 80% | 100% | 100% | 0% | 30% | 0% | 40% | 50% | 100% |

Accordingly, the studies discussed in this Example demonstrate that the QIV vaccine consistently produces a robust immune response following intramuscular administration studies (measuring RNA from the TMV NtK carrier) with QIV found that, outside of the injection site muscle, QIV was measured in the spleen and lymph nodes at all time points tested indicating that TMV viral RNA was relatively stable or decreased slowly in these organs which provides a potential mechanism of action and presentation of the antigens to the immune system. In repeat dose toxicity studies, the only finding was a reversible elevation in fibrinogen levels from the clinical chemistry profile in the treated groups usually at two days post-dosing, an expected finding for an immunological substance. No other treatment-related or toxicologically significant effects were observed for body weights, body weight changes, food consumption, body temperatures, ophthalmology, clinical chemistry, hematology, organ weights, and gross and microscopic pathology.

In conclusion, the data support the advancement of the TMV NtK conjugate to human clinical studies and offers clear advantages over currently licensed influenza vaccines. Since no toxicologically significant findings have been observed with the QIV vaccine, the probability is increased that no such events will be observed for any other antigen(s), purified in accordance with the antigen platform, that is conjugated to the TMV NtK carrier described herein. Accordingly, it is expected that other antigens conjugated to the inactive TMV NtK will have similar biodistribution and toxicology profiles, and thus are suitable for use in humans.

Example 15(a) to (c)—Coronavirus Vaccine Candidate: RBD-Fc (SARS-2) Conjugated to TMV A Covid-19 vaccine was produced by forming an antigen through the expression of a recombinant version of the RBD SARS-2 spike protein fused to the Fc domain of a human IgG1 in *Nicotiana benthamiana* (Nb) plants (as a non-limiting example). Before conjugation, the formed antigen was then purified according to an antigen purification platform as described herein, in accordance with multiple embodiments and alternatives, and the TMV virus particles were purified and inactivated according to a virus purification platform described herein, in accordance with multiple embodiments and alternatives. The purified recombinant RBD-Fc antigen was then conjugated to the purified and inactivated TMV virus particle in accordance with the teachings of multiple embodiments and alternatives herein. Upon delivery to a mammalian subject (e.g., human or animal), the RBD-Fc to TMV conjugate presents the SARS-2 spike glycoprotein RBD fused to the human IgG1 Fc domain via the chemical conjugation to the TMV virus particles. As discussed in more detail below, the presentation of the RBD-Fc fusion in this embodiment has been demonstrated to enhance Th1 and Th2 responses in all mammalian disease models tested to date.

Figure 50A:
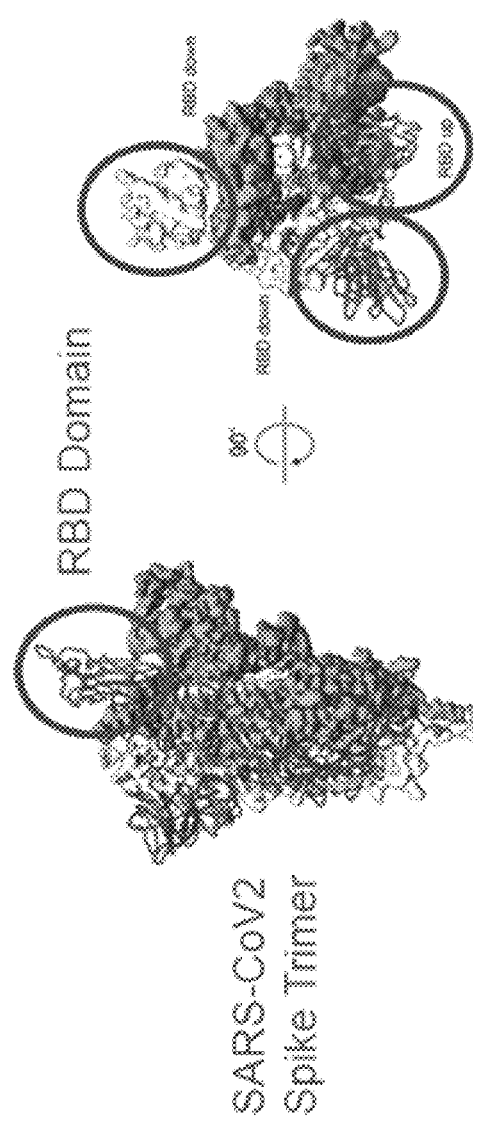
FIG. 50 (A) is an illustration of the protein structure of the Covid-19 Spike timer in space-filling model with the receptor binding domain circled in lateral and vertical views.
FIG. 50(B) is an illustration of the fusion of the Covid-19 receptor binding domain to a human Fc domain, according to multiple embodiments and alternatives.
Figure 50B:
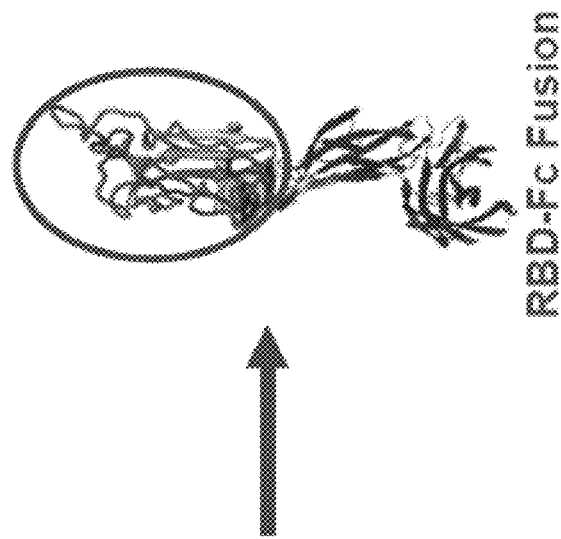

For this example, the antigen for the Covid-19 vaccine was selected by targeting the RBD domain of the SARS-2 spike glycoprotein because it serves as the binding site for the human ACE-2 receptor and the binding site overlaps with characterized neutralizing antibodies. The SARS-2 spike glycoprotein is found in the S1 subunit at the amino acids numbered approximately 320 to 520, In FIG. 50(A), the SARS-2 spike trimer is shown in space-filling model with RBD circled in lateral and vertical views, FIG. 50(B) shows the RBD domain fused to a human 171 allotype IgG1 Fc domain, expressed and purified from plants according to multiple embodiments and alternatives.

Several considerations went into selecting SARS-2 RBD as a fusion partner for developing the RBD-Fc antigen described in the present example and the next example. SARS-2 RBD is a binding site for neutralizing antibodies. Also, as discussed below, CR 3022 is a human mAb isolated from a SARS patient that binds a domain in the SARS-2 RBD domain. CR 3022 binding can neutralize both SARS-1 and SARS-2 CoV. The SARS-2 RBD also presents the ACE-2 (angiotensin II) binding domain.

In accordance with the method for the present example, multigenic constructs were designed and built to contain genes encoding the proteins necessary to synthesize a Covid-19 antigen targeting the RBD domain of SARS-2. In the present example, the following antigen sequence (collectively referred to herein as the "RBD-Fc 121 Construct") was used for the synthesis of a Covid-19 antigen:

```
1. "(SEQ ID NO: 1)" Signal Peptide:
MGKMASLFATFLVVLVSLSLASESSA

2. "(SEQ ID NO: 2)" SARS-2 virus Spike amino
acids numbered 331-632:
NITNLCPFGEVFNATRFASVYAWNRKRISNCVADYSVLYNSASFS

TFKCYGVSPTKLNDLCFTNVYADSFVIRGDEVRQIAPGQTGKIAD

YNYKLPDDFTGCVIAWNSNNLDSKVGGNYNYLYRLFRKSNLKPFE

RDISTEIYQAGSTPCNGVEGFNCYFPLQSYGFQPTNGVGYQPYRV

VVLSFELLHAPATVCGPKKSTNLVKNKCVNFNFNGLTGTGVLTES

NKKFLPFQQFGRDIADTTDAVRDPQTLEILDITPCSFGGVSVITP

GTNTSNQVAVLYQDVNCTEVPVAIHADQLTPT

3. "(SEQ ID NO: 3")" Fc Hinge:
VEPKSCDKTHTCPPCP

4. "(SEQ ID NO: 4")" IgG1 171 allotype Fc:
APELLGGPSVFLFPPKPKDTLMISRTPEVTCVVVDVSHEDPEVKF

NWYVDGVEVHNAKTKPREEQYNSTYRVVSVLTVLHQDWLNGKEYK

CKVSNKALPAPIEKTISKAKGQPREPQVYTLPPSRDELTKNQVSL

TCLVKGFYPSDIAVEWESNGQPENNYKTTPPVLDSDGSFFLYSKL

TVDKSRWQQGNVFSCSVMHEALHNHYTQKSLSLSPG
```

Figure 51:
FIG. 51 is an illustration of an expression plasmid containing the construct of a recombinant Covid-19 antigen, according to multiple embodiments and alternatives.

Illustratively, and without limitation, FIG. 51 shows an assembled TRBO expression plasmid for a SARS-CoV2 RBD-Fc fusion peptide (i.e., antigen) for production in Nb plants. Successful infiltration and plant incubation were followed by extraction and purification of the antigen as described herein. As illustrated and discussed further herein, a fusion peptide was formed having a first peptide which comprises a receptor binding domain (RBD) of a pathogen (specifically, a coronavirus and namely the SARS-CoV-2 spike (S) glycoprotein RBD), fused to a second peptide which comprises a fragment crystallizable (Fe) region of an antibody (containing a sequence of amino acids as set forth in SEQ ID NO: 4, human IgG1 Fe domain), and a hinge portion linking the first peptide and second peptide (containing a sequence of amino acids as set forth in SEQ ID NO: 3). In Example 15, the RBD contained a sequence of amino acids as set forth in SEQ ID NO: 2, and in Example 16, the RBD contained a sequence of amino acids as set forth in SEQ ID NO: 8. It will be noted that the reference to codons in the plasmid of FIG. 51 includes both the RBD and Fe region as well as the hinge portion. The sequences encoding the RBD-Fc antigen were optimized for efficient plant expression. In accordance with the plasmid design, donor plasmids containing the referenced nucleic acid sequences for the fusion peptide were synthesized. The antigen donor plasmid and TRBO expression plasmid were digested using suitable restriction enzymes. The antigen was ligated into the TRBO expression plasmid and subsequent colonies were screened to confirm clones. Assembled expression plasmids (FIG. 51) from successful ligations were amplified in *E. coli* and DNA purified. The vector DNA-confirmed clones of the antigen in the TRBO expression plasmid were used to transform *Agrobacterium tumefaciens* in preparation for infiltration into Nb plants. Individual colonies were transferred in a sterile manner, incubated, and 20% glycerol stocks from culture were produced and retained as antigen Master Cell Banks. As further illustrated in FIG. 51, the exemplary construct included a cauliflower mosaic virus (CaMV) 35S promoter, which is a DNA dependent RNA promoter set to transcribe the TMV expression vector with an accurate 5' end. In addition, the TMV replicase is composed of the 126 kDa and 183 kDa replication associated proteins. In FIG. 51, the "30 k" refers to a movement protein produced from a sub-genomic promoter in the 3' end of the 183 kDa protein coding region. In the exemplary construct, the antigen gene is transcribed from a sub-genomic promoter in the 3' end of the 30 kDa protein coding region and the 3' untranslated region has a ribozyme to insure termination of the transcript near the authentic 3' end. Furthermore, there is an *E. coli* origin for replication and border regions for the TI plasmid and other elements for efficient replication in *Agrobacterium* and insertion into plant cells.

Accordingly, a plasmid providing a construct for an antigen which is conjugable with a virus can be manufactured in accordance with multiple embodiments and alternatives herein. Such a construct may comprise first and second coding regions that encode a fusion peptide. In non-limiting fashion, the first coding region contains a nucleic acid sequence encoding an amino acid sequence as set forth in SEQ ID NO: 2 above, or by way of further example SEQ ID NO: 8 below. The first peptide may comprise or substantially comprise a receptor binding domain of a pathogen, such as a virus, non-limiting examples of which include coronaviruses and influenza viruses as discussed further herein. Additionally, and again in similar non-limiting fashion, the second coding region contains a nucleic acid sequence encoding an amino acid sequence as set forth in SEQ ID NO: 4 above. The second peptide may be a fragment crystallizable (Fe) region of an antibody capable of binding to a Fc receptor. In some embodiments, the first peptide and the second peptide are linked by a hinge portion coded by a third coding region. The third coding region may contain a nucleic acid sequence encoding an amino acid sequence as set forth in SEQ ID NO: 3 above. In some embodiments, the hinge portion is a portion of the Fe region. In some embodiments, one or more nucleic acid sequences identified herein will be part of a heterologous expression system.

Plant Expression, Purification, and Characterization—Example 15(a)

in the present example, an RBD-FC 121 fusion peptide (hereafter, referred to in this example as "RBD-Fc 121 antigen") was expressed in tobacco plants, harvested then purified. Expression occurred in naïve wild-type Nb plants, which were infected with an expression vector (such as the vector shown in FIG. 51 as a non-limiting example) for protein replication of the RBD-Fe 121 antigen, in accordance with multiple embodiments and alternatives herein, with growth and incubation of the plants occurring in a contained and controlled indoor environment. Purification of the RBD Fc-121 antigen was performed according to an antigen purification platform described herein (for example, as illustrated at Table 2 and FIG. 8), with the multi-modal ceramic hydroxyapatite (CHT) chromatography column step omitted for this particular example. Accordingly, for the present example, FIG. 50(B) shows the RBD domain fused to the human 171 allotype IgG1 Fe domain, expressed and purified from plants according to multiple embodiments and alternatives.

Figure 52:
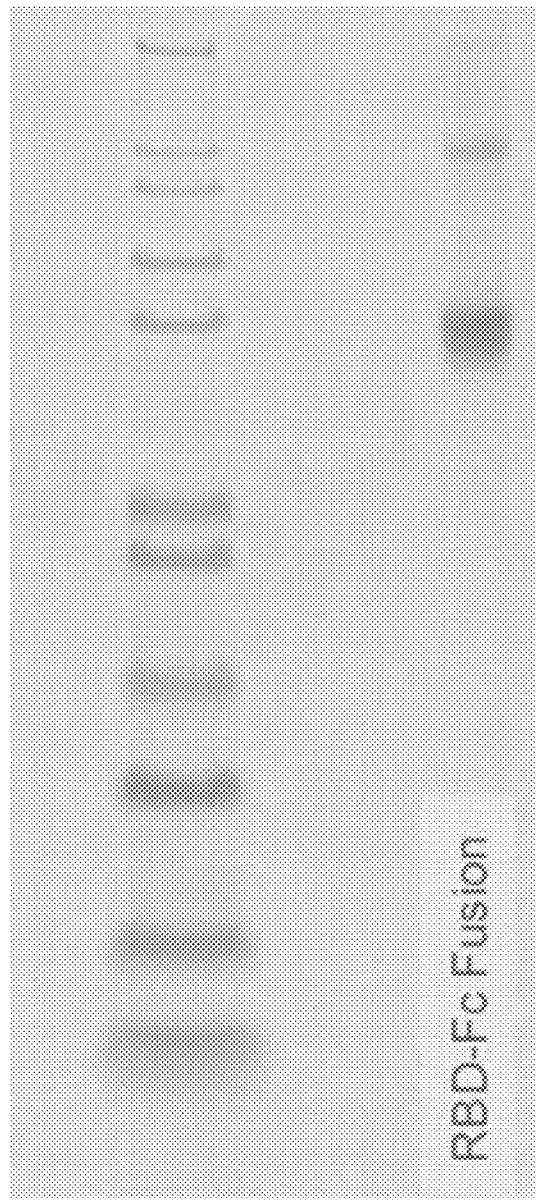
FIG. 52 is a SDS-PAGE analysis of a purified recombinant Covid-19 antigen, according to multiple embodiments and alternatives.
Figure 53:
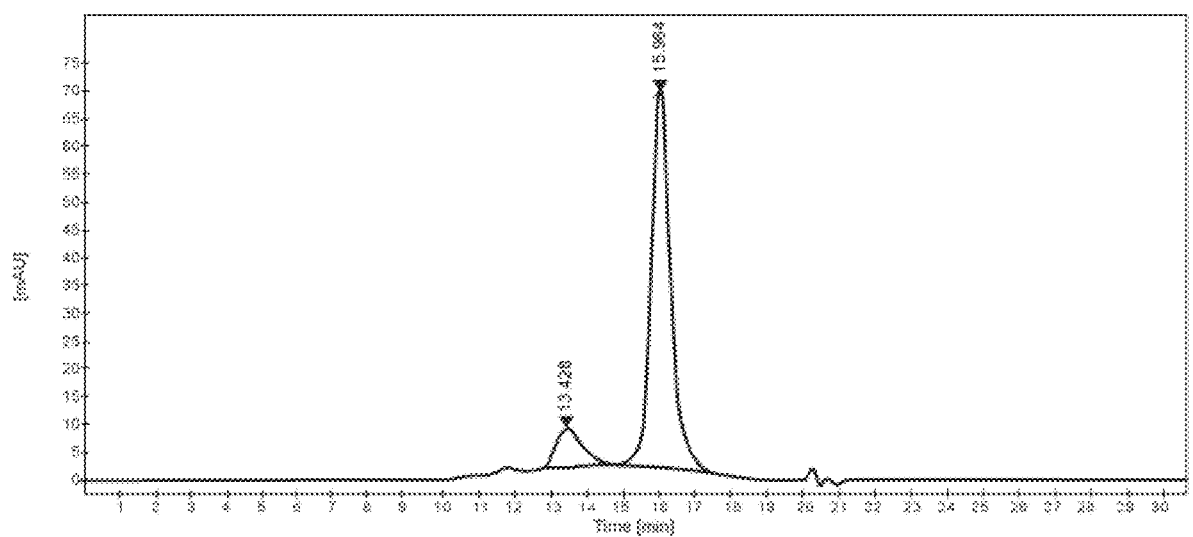
FIG. 53 is a report of SEC-HPLC of a purified recombinant Covid-19 antigen, according to multiple embodiments and alternatives.

As shown in FIGS. 52-53, an antigen purification platform according to multiple embodiments and alternatives successfully purified the RBD-Fc 121 antigen resulting in high yields (>400 mg of RBD-Fc protein) with pure, stable antigen as RBD-Fc monomer in a manner that is compliant with GLP regulations. FIG. 52, taken from the conclusion of the purification platform applied to this antigen, contains a SUS page gel indicating purity for the RBD-Fc 121 antigen, wherein lane 1 shows the marker and lane 2 shows the purified RBD-Fc 121 protein. As shown by the clear and visible bands in lane 2 of FIG. 52, the RBD-Fc 121 antigen product is pure. In addition, the protein migration shown in FIG. 52 is consistent with the SEC-HPLC report of the free, purified RBD-Fc 121 shown in FIG. 53. In FIG. 53, the SEC-HPLC report of the free RBD-Fc 121 antigen produced the signal data detailed in Table 48 below.

TABLE 48

SEC-HPLC Data of free, purified RBD-Fc 121 Antigen

| RT [min] | Width [min] | Area | Height | Area % | Peak Symmetry |
|---|---|---|---|---|---|
| 13.428 | 0.64 | 327.78 | 7.19 | 11.18 | 0.71 |
| 15.964 | 0.57 | 2605.08 | 68.46 | 88.82 | 0.68 |

Table 48 and FIG. 53 illustrate that >90'%© of the purified RBD-Fc 121 antigen is in monomeric form. Likewise, low impurities were present in the batches at less than 0.442 EU/mg. Therefore, the RBD-Fc 121 antigen was successfully and sufficiently purified consistent with GLP.

Figure 54:
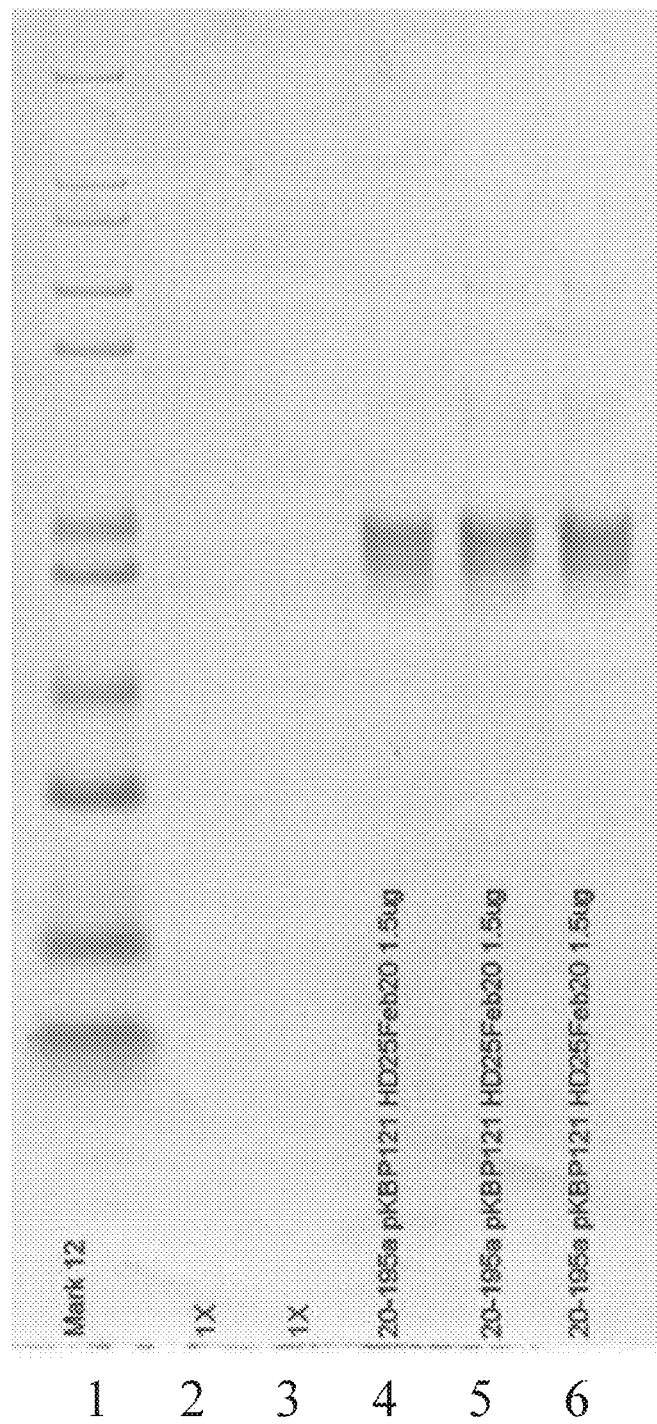
FIG. 54 is a SUS-PAGE analysis of a purified recombinant Covid-19 antigen, according to multiple embodiments and alternatives.

The stability of the RBD-Fc 121 antigen is reflected in FIG. 54 and Table 49 (below). FIG. 54 contains a SDS Page gel of the purified RBD-Fc 121 antigen 5 weeks after purification. In FIG. 54, the lanes include: lane 1—marker, lane 2—blank, lane 3—blank, and lanes 4-6—RED-Fc 121 antigen 5 weeks after purification. The clear and visible bands in FIG. 54 indicate the purified RBD-Fc 121 antigen is highly stable. In addition, as shown in Table 49 below, the purified RBD-Fc 121 antigen maintained its potency for at least 5 weeks following purification based on ELISA results.

TABLE 49

Potency of Purified RBD-Fc 121 Antigen as Measured by ELISA

| Test Parameter | Test Method | units | 2 week | 3 week | 4 week | 5 week |
|---|---|---|---|---|---|---|
| Potency | ELISA | ug/mL | 7010 | 8188 | 7096 | 5178 |

Conjugation and Preparation—Example 15(a)

The purified RBD-Fc 121 antigen was then conjugated with a TMV NtK carrier. The TMV NtK virions with surface lysine residues for efficient conjugation were manufactured in Nb plants (again, as a non-limiting example). The TMV NtK carrier was purified according to a virus purification platform described herein (for example, as illustrated at Table 1 and FIG. 1). In accordance with multiple embodiments and alternatives herein, following purification the TMV NtK was subject to micron filtration (e.g. 0.45) and treated with UV inactivation (as discussed in Example 8 herein).

Figure 55:
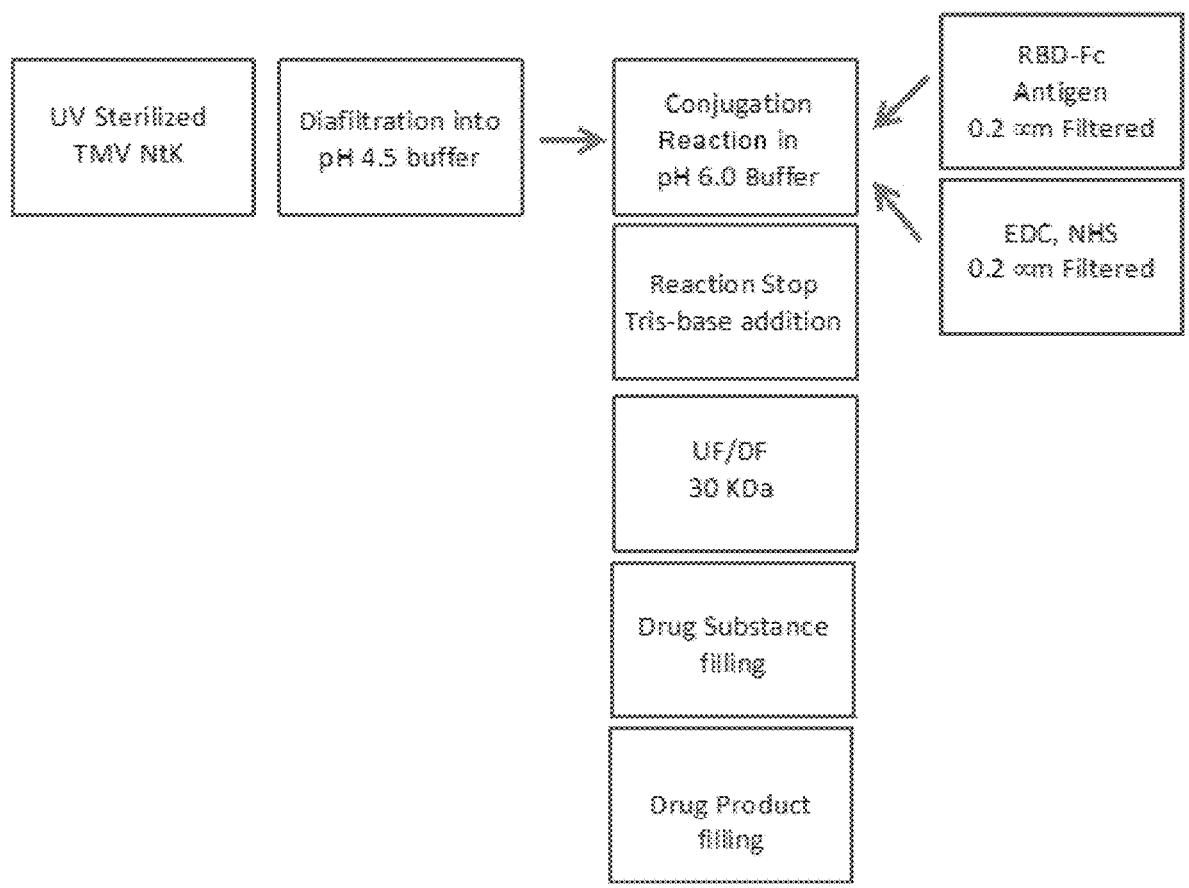
FIG. 55 is an illustration of some of the steps of the conjugation platform of recombinant Covid-19 antigen to a virus and drug substance filling, according to multiple embodiments and alternatives.

The purified and inactive TMV NtK was then chemically conjugated to the RBD-Fc 121 antigen to produce a Covid-19 vaccine, in accordance with multiple embodiments and alternatives herein (for example, as illustrated at Table 3), As shown in FIG. 55, an exemplary conjugation procedure may include at least the following steps:

Purified RBD-Fc 121 antigen was diafiltered into a 50 mM MES buffered salt (50 mM NaCl) solution, concentrated to a target concentration appropriate for conjugation, and subjected to 0.2 micron filtration.

Purified RBD-Fc 121 antigen was conjugated to the purified TMV NtK particles using EDC and Sulfo-NHS chemistries within a 1-hour mixing reaction.

As previously indicated, conjugation may occur at a range of TMV NtK:antigen (mg:mg) ratios, including without limitation 8:1, 4:1, and 1:1.

Now returning to the present example, the RBD-Fc 121 antigen and TMV NtK underwent a conjugation reaction performed at a pH of about 6.0, in EDC (4 mM) and Sulfo NHS (5 mM). In this regard, the of the conjugation reaction and the pH of the purification step need not be the same. The conjugation reaction was quenched with free amine (Tris Base), optionally using a 30 kDa UF membrane to remove residual EDC, Sulfo NHS, and Tris Base.

Accordingly, the conjugated drug substance was diafiltered and formulated. As the conjugate exceeded 0.2 microns, all steps downstream of the TMV NtK UV treatment and antigen 0.2-micron filtration were maintained in a state of asepsis.

At this point, the TMV NtK:RBD-Fc conjugate will be (and in the case of Example 15, was) ready for drug substance filling and drug product filling. A suitable delivery mechanism of the vaccine would include a liquid vial or lyophilized material to be reconstituted with physiologic buffering for project injection, with administration of the vaccine according to optional methods described herein.

To determine the percent conjugation between the TMV NtK and the RBD-Fc 121 antigen, the SV was measured using an AUC. As previously noted, the fraction between 1-40 S indicates the percent RBD-Fc monomer/trimer, and the fraction between 40-2000 S indicates the percent TMV NtK:RBD-Fc conjugate, according to multiple embodiments and alternatives.

Figure 56:
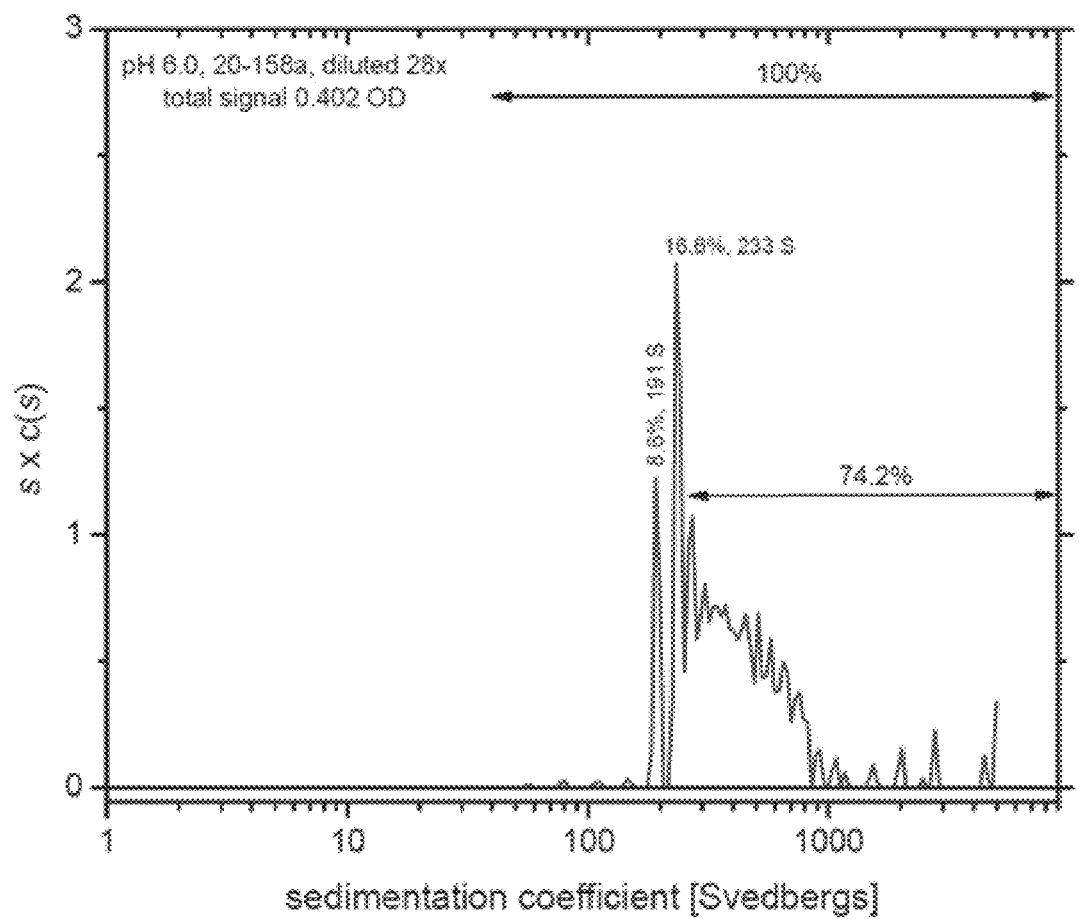
FIG. 56 is a normalized sedimentation coefficient distribution of a recombinant Covid-19 antigen conjugated to a virus, according to multiple embodiments and alternatives.
Figure 57:
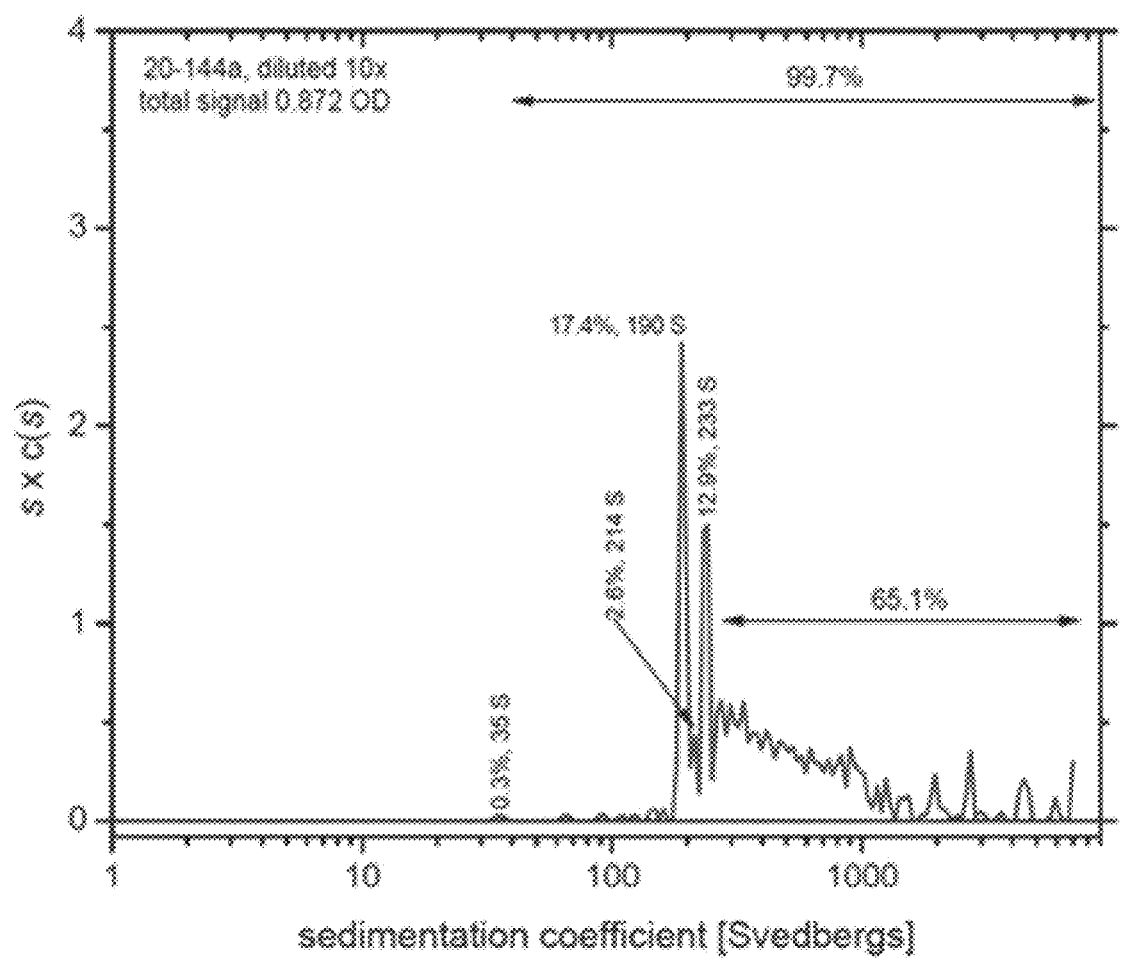
FIG. 57 is a normalized sedimentation coefficient distribution of a recombinant Covid-19 antigen conjugated to a virus, according to multiple embodiments and alternatives.

In the present example, FIG. 56 shows the normalized sedimentation coefficient for sample 4 (in which the TMV: RBD-Fc conjugate was diluted by a factor of 28), and FIG. 57 shows the normalized sedimentation coefficient for another sample (where the TMV:RBD-Fc conjugate was diluted by a factor of 10). FIG. 56 shows 100% total virus associated material (i.e. virus-antigen conjugates) and FIG. 57 shows 99.7% total virus associated material (i.e. virus-antigen conjugates). The results in FIGS. 56 and 57 indicate virtually complete engagement of the RBD-Fc products in TMV-conjugation events.

Figure 58:
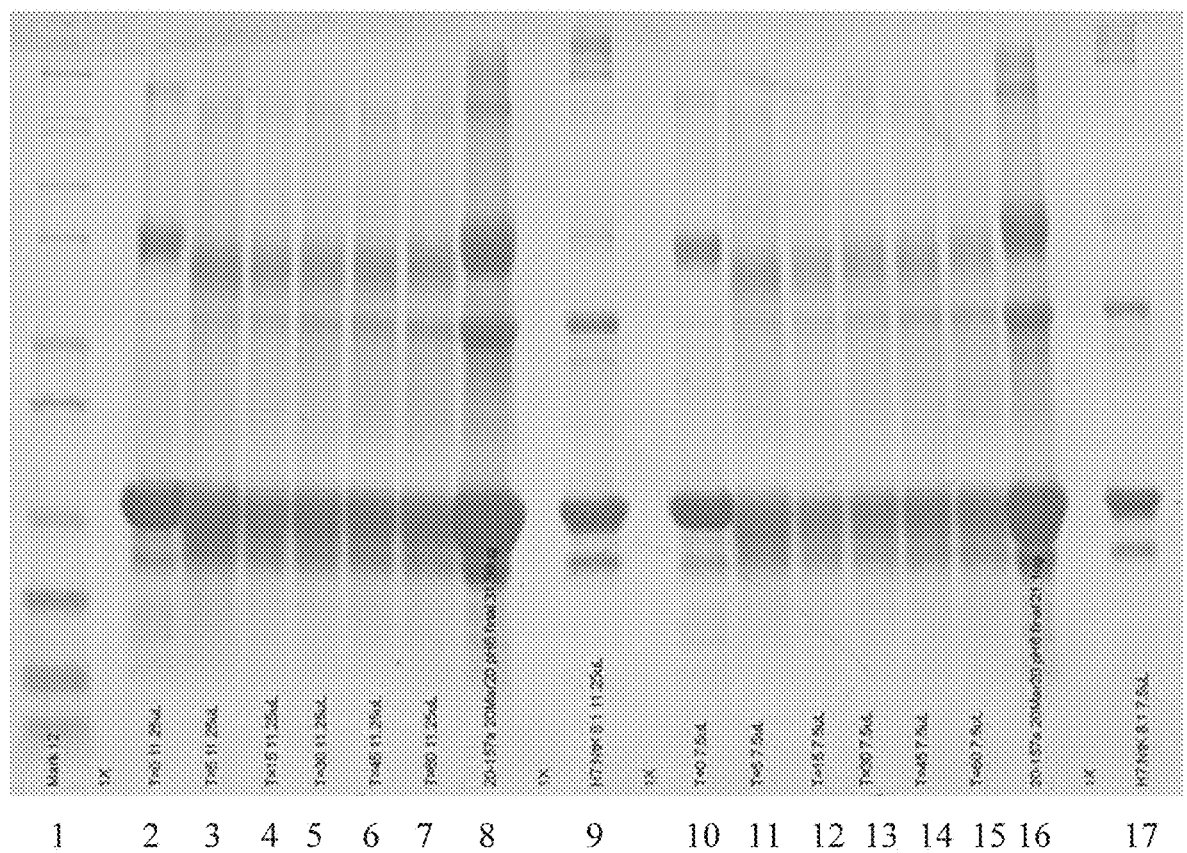
FIG. 58 is a SDS-PAGE analysis of a recombinant Covid-19 antigen conjugated to a virus, according to multiple embodiments and alternatives.

The successful conjugation between the TMV NtK and the RBD-Fc 121 antigen was confirmed by SDS-Page analysis. FIG. 58 contains a SDS Page gel of the TMV NtK: RBD-Fc conjugate at different time periods post-conjugation. In FIG. 58, the lanes include: lane 1—marker, lane 2—the conjugate mixture at 0 min, lane 3—the conjugate mixture at 5 min post-conjugation, lane 4—the conjugate mixture at 15 min post-conjugation, lane 5—the conjugate mixture at 30 min post-conjugation, lane 6—the conjugate mixture at 45 min post-conjugation, lane 7—the conjugate mixture at 60 min post-conjugation, lane 8 the final conjugate mixture after mixing, lane 9—a TMV:HA conjugate as a control, lane 10—the conjugate mixture 0 min, lane 11—the conjugate mixture at 5 min post-conjugation, lane 12—the conjugate mixture at 15 min post-conjugation, lane 13—the conjugate mixture at 30 min post-conjugation, lane 14—the conjugate mixture at 45 rain post-conjugation, lane 15—the conjugate mixture at 60 min post-conjugation, lane 16—the final conjugate mixture after mixing, and lane 17—a TMV:HA conjugate as a control. The clear and visible bands in lanes 8 and 16, which are similar to the bands in lanes 9 and 17, indicate successful conjugation of TMV NtK to the RBD-Fc 121 antigen.

Accordingly, almost 100% conjugation of the RBD-Fc 121 antigen to the TM NtK was confirmed by AUC and SDS Page.

In Vitro Testing—Example 15(b)

To determine the efficacy of the TMV NtK to RBD-Fc 121 conjugate as a Covid-19 vaccine candidate, the binding of the antigen to CR 3022 and the ACE-2 receptor were analyzed, as well as the immune response in mice. As discussed in more detail below, the data indicates the RBD-Fc antigen that was conjugated to TMV NtK, bound successfully to the human ACE-2 receptor. As further shown in Table 51, the initial immune responses stimulated after one vaccine dose with the TMV NtK:RBD-Fc conjugate supported this observation. Likewise, the RBD-Fc 121 antigen which was conjugated to TMV NtK SARS-RBD-specific, human neutralizing monoclonal antibody (mAb), CR 3022.

Figure 59A:
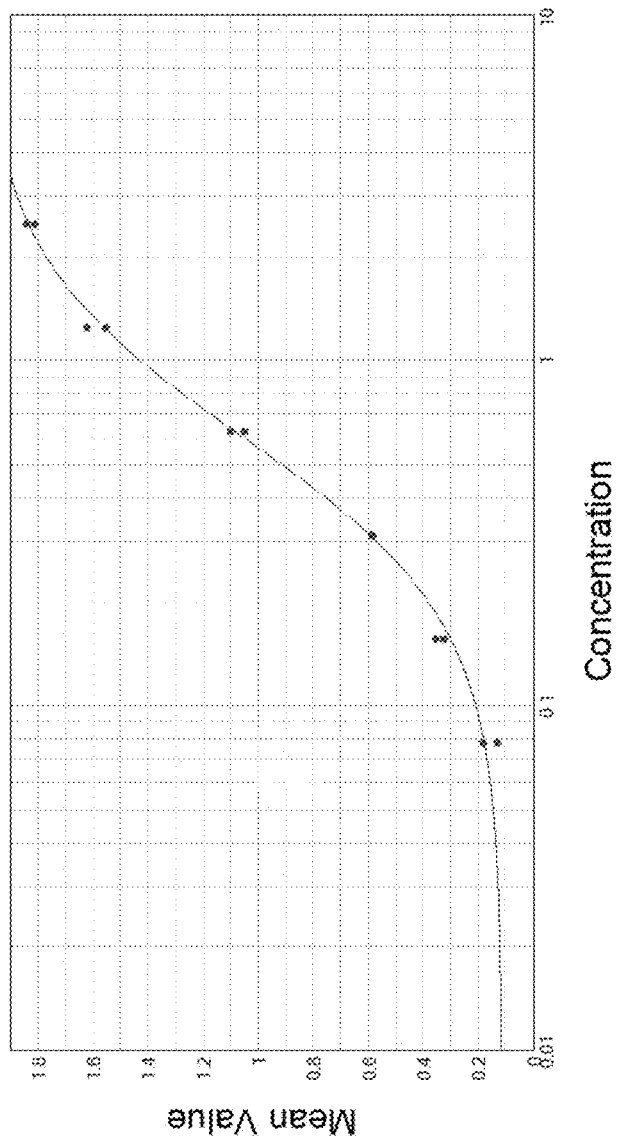
FIG. 59(A) is an ELISA standard curve illustrating the binding of the recombinant Covid-19 antigen to a Covid-19 human neutralizing monoclonal antibody.
Figure 59B:
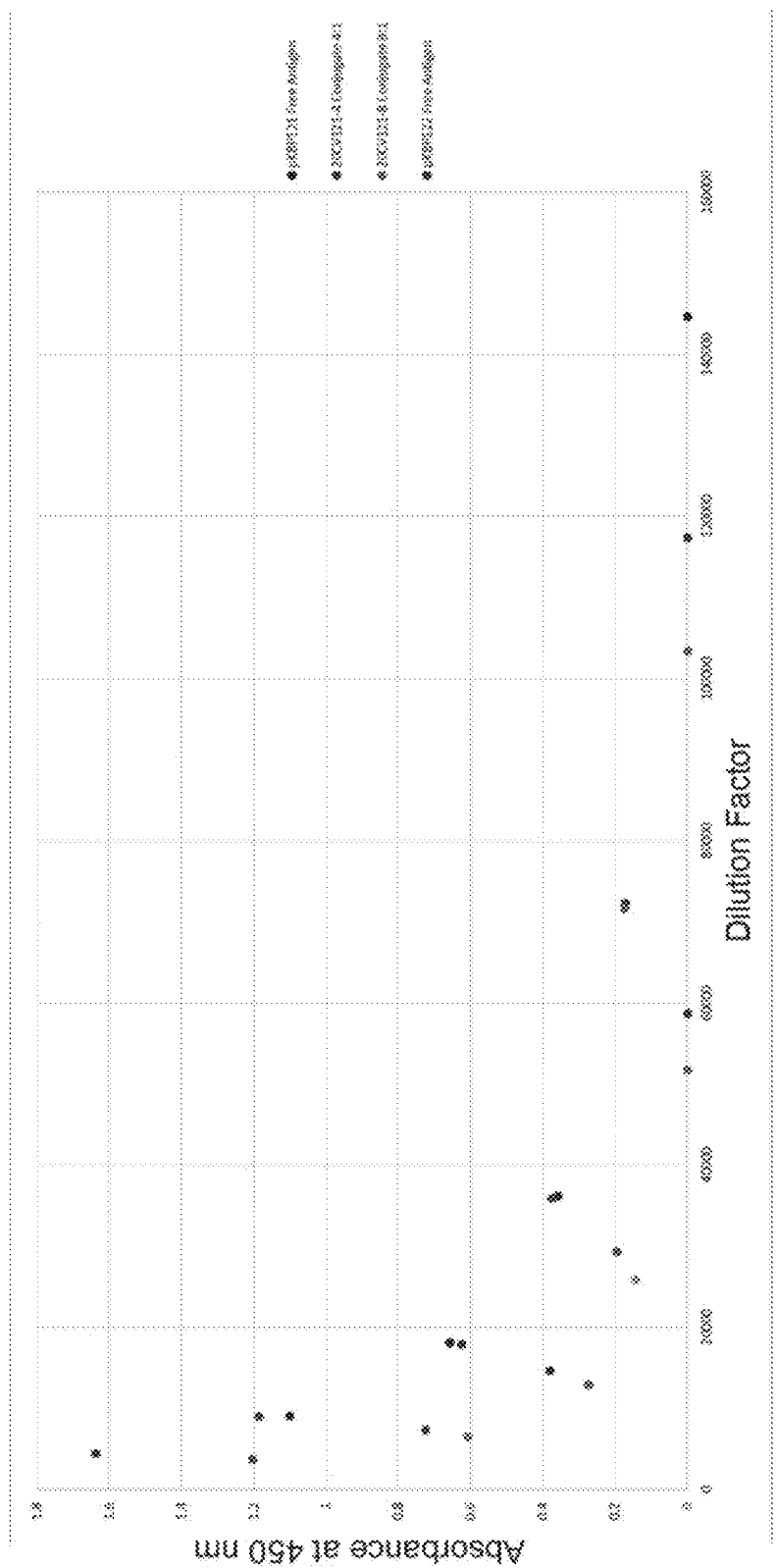
FIG. 59(B) is a graph illustrating the binding of various vaccine alternatives in accordance with multiple embodiments and alternatives described herein (sometimes referred to herein as vaccine candidates), and the binding to a Covid-19 human neutralizing monoclonal antibody, according to multiple embodiments and alternatives.

To determine the binding efficacy of the conjugate, an ELISA test was developed to measure the RBD potency for both free antigen (i.e. RBD-FC 121 alone) and conjugated forms (TMV to RBD-Fc) using CR3022 mAb for capture. The ELISA test was conducted to find sera that did not bind to the Fe portion of the antigen in order to eliminate background binding. This test was conducted through various methods including pre-absorption and/or binding to the kappa region of the CR3022 light chain. FIG. 59 illustrates the CR 3022 ELISA data by showing the conservation of RBD conformation among the free antigen and the TMV: RBD-Fc conjugate formulated at a 8:1 and 4:1 (TMV NtK:antigen) ratio, respectively. In FIG. 59(A), the ELISA standard curve illustrates the sensitivity and linearity for binding of SARS-2 Spike antigen to the CR 3022 antibody. In FIG. 59(B), the TMV:RBD-Fc conjugate is referred to as "TMV:RBD-Fc." FIG. 59(B) shows strong, dose-dependent binding of CR 3022 to both the RBD-Fc 121 antigen and formulated TMV to RBD-Fc 121 conjugate. Accordingly, FIG. 59 indicates the RBD-Fc 121 antigen shows greater than five times the reactivity to CR 3022 as compared to commercially sourced control SARS Spike and RBD reagents. This data also suggests that the purified RBD-Fc 121 antigen maintains essential conformational epitopes in a more favorable manner compared to conventional purchased reagents.

Figure 60:
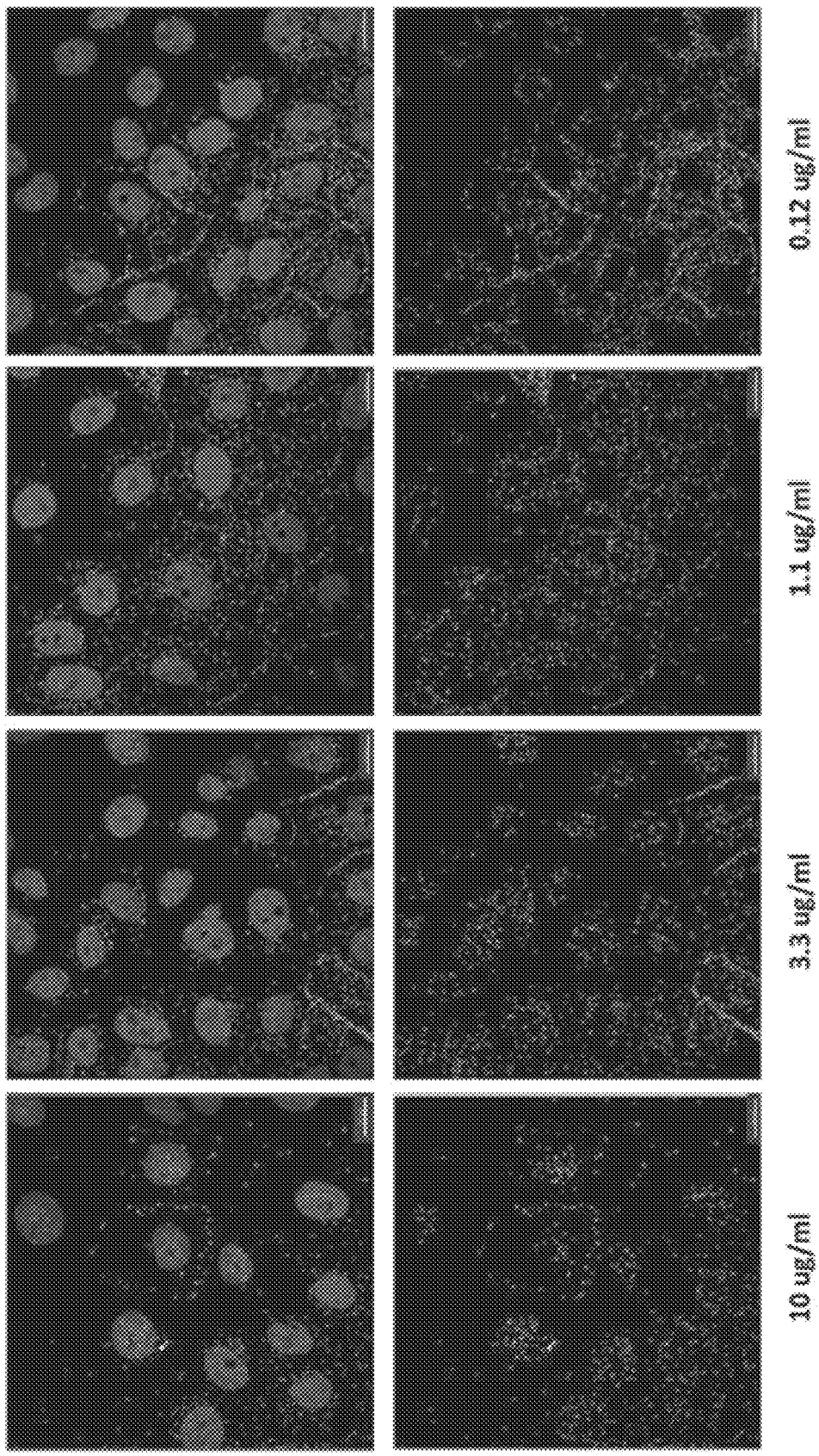
FIG. 60 consists of confocal microscopy images illustrating the co-localization of the recombinant Covid-19 antigen to ACE-2 specific antibodies, according to multiple embodiments and alternatives.

To analyze the ability of the RBD-Fc 121 antigen to bind to the ACE-2 receptor, quantitative and functional ACE-2 binding was performed using two-color confocal microscopy and analysis by co-localization and competitive binding methods on Vero e6 cells. Vero cells are derived from the kidney of an African green monkey and are commonly used in cellular research. The Vero e6 cells are a subclone of Vero76, exhibiting a range of virus susceptibility. Herein, the binding ability of the native agonist, angiotensin II, was compared with the RBD-Fc fusion by analyzing the concentration dependent ability to block binding of an ACE-2 specific antibody to the receptor on living Vero e6 cells. Influenza H7 HA was used as a control. FAM-angiotensin II bound to Vero e6 cells as expected, with an average of a 2.79-fold increase over the non-specific H7 control. FIG. 60 illustrates the ligand co-localization between the angiotensin II and the RBD-Fc 121 antigen to Vero e6 cells via confocal microscopy at the following ACE-2 specific antibody concentrations: 10 ug/ml, 3.3 ug/ml, 1.1 ug/ml, and 0.12 ug/ml, wherein the scale bars are equal to 15 In FIG. 60, the general trend shows that the binding of the RBD-Fc 121 antigen to Vero e6 cells occurred in a concentration-dependent manner with an increase of 2.58-fold increase over the H7 HA control. In other words, increased binding of the RBD-Fc 121 antigen (at the higher concentrations) was observed to correlate with decreased detection of ACE-2 antibody (at the lower concentrations).

Figure 61A:
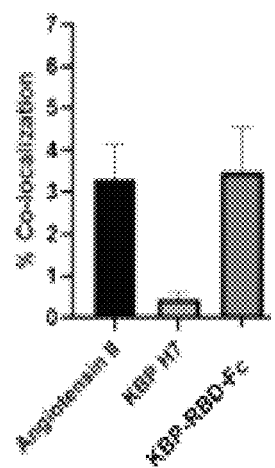
FIG. 61(A) is a graph illustrating the co-localization of a native agonist and a recombinant Covid-19 antigen to ACE-2 specific antibodies, according to multiple embodiments and alternatives.
Figure 61B:
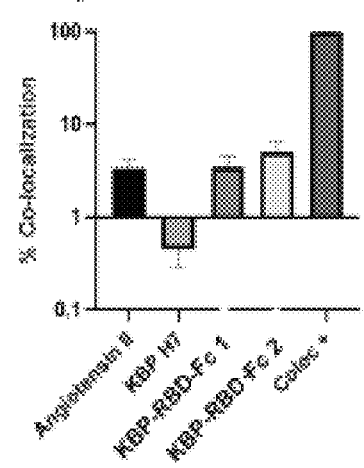
FIG. 61(B) is a graph illustrating the co-localization of a native agonist and a recombinant Covid-19 antigen to ACE-2 specific antibodies in the presence of a co-localization control, according to multiple embodiments and alternatives.

FIG. 61(*a*) also illustrates the ligand co-localization events shown in FIG. 60. FIG. 61(*b*) illustrates that adding a co-localization control reduces all specific binding, demonstrating a reduction in ACE-2 antibody binding in the presence of both angiotensin II and the RBD-Fc 121 antigen. As shown in FIGS. 60 and 61, the binding of H7 HA did not impact the detection of ACE-2 by monoclonal antibody at any concentration. These figures also illustrate that the RBD-Fc 121 antigen effectively competes for ACE-2 antibody binding on Vero e6 cells and co-localizes with ACE-2 cells with similar affinity and specificity as angiotensin II.

Accordingly, FIGS. 59-61 illustrate that the RBD-Fc 121 antigen maintains functional conformation and activity through the binding of CR 3022 and ACE-2. The binding to ACE-2 shows similar affinity and specificity as the native agonist, angiotensin II, suggesting that the conformation of the spike protein RBD in the recombinant RBD-Fc 121 fusion peptide complex is comparable to that observed with native SARS-2 Spike protein. This data indicates that the RBD-Fc 121 antigen displays the correct structure necessary to elicit the production of neutralizing antibodies against the RBD of the Covid-19 spike protein.

In Vivo Testing—Example 15(c)

The TMV NtK:RBD-fc 121 Covid-19 vaccine described above was evaluated for immunogenicity in two parallel evaluations using female C57BL/6 mice. As shown in FIGS. 62(A)-(D), the collected serum was tested for total IgG anti-RBD reactivity by ELISA, using recombinant COV2 RBD-His as capture antigen to compare immune response between groups.

In the first evaluation, 10 animals were used per group wherein 5 animals per group were sacrificed at day 14 to have sufficient sera for broad testing. The 5 remaining animals per group were boosted on day 14 and sacrificed on day 28. In the second evaluation, 5 animals were used per group, each receiving prime and boost vaccinations on days 0 and 14 respectively, with blood draws at days 0, 12, 14, 28, and terminal from all animals. In both evaluations, the trial endpoints include measurement of antigen-specific geometric mean antibody titers induced in mice, SARS-2 neutralizing titers, and antibody isotype analysis. The trials are outlined in Table 50 below which included various dosages, different vaccines (including purified TMV NtK only, RBD-Fc only, and the TMV:RBD-Fc conjugate), and compared identical doses both with and without the use of CpG oligodeoxynucleotides (CpG) as an adjuvant. The CpG was added to the vaccine formulation such that the concentration of the antigen remains the same in a consistent 100 mcL injection as the neat (non-adjuvanted) vaccine formulation. In some embodiments, monophosphoryl lipid A (MPLA) and/or SE-M were utilized as adjuvants for enhancing the immune response of the subject to the vaccine. "SE-M" is a type of stable emulsion, which typically uses a MIA Toll-Like Receptor agonist as the adjuvant.

TABLE 50

TMV NtK:RBD-Fc Vaccine Immunogenicity Testing in Mice

| Group | Vaccine | Antigen Dose (μg) | Adjuvant | Immunization Days | Bleed Dates |
|---|---|---|---|---|---|
| 1A | Purified TMV only | n/a | none | 0 | 0, 14 |
| 1B | Purified TMV only | n/a | none | 0, 14 | 0, 14, 28 |
| 2A | RBD-Fc antigen only | 45 | none | 0 | 0, 14 |
| 2B | RBD-Fc antigen only | 45 | none | 0, 14 | 0, 14, 28 |
| 3A | TWA:BD-Fe Conjugate | 15 | none | 0 | 0, 14 |
| 3B | TMV:RBD-Fc Conjugate | 15 | none | 0, 14 | 0, 14,28 |
| 4A | TMV:RBD-Fe Conjugate | 45 | none | 0 | 0, 12, 14, |
| 4B | TMV:RBD-Fe Conjugate | 45 | none | 0, 14 | 0, 14, 28 |
| 5A | TMV:RBD-Fc Conjugate | 15 | CpG (50 μg) | 0 | 0, 14 |
| 5B | TMV:RBD-Fe Conjugate | 15 | CpG (50 μg) | 0, 14 | 0, 14, 28 |
| 6A | TMV:RBD-Fe Conjugate | 45 | CpG (50 μg) | 0 | 0, 14 |
| 6B | TMV:RBD-Fc Conjugate | 45 | CpG (50 μg) | 0, 14 | 0, 14, 28 |

Figure 62A:
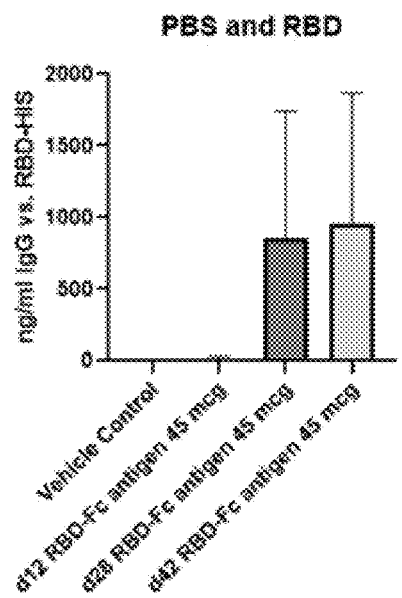
FIG. 62(A) is a graph illustrating the immune response in animals immunized with a recombinant Covid-19 antigen and a control.
Figure 62B:
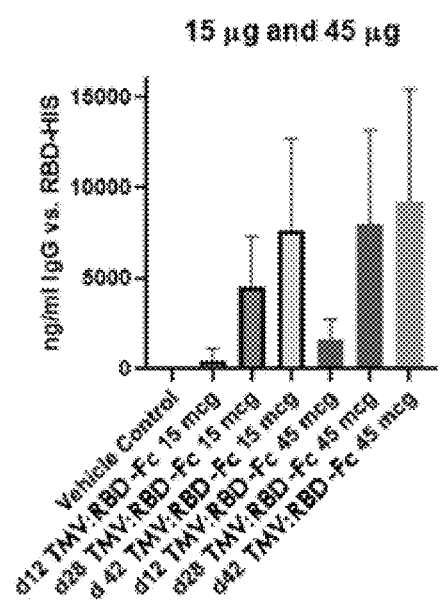
FIG. 62(B) is a graph illustrating the immune response in animals immunized with a recombinant Covid-19 antigen conjugated to a virus (unadjuvanted).
Figure 62C:
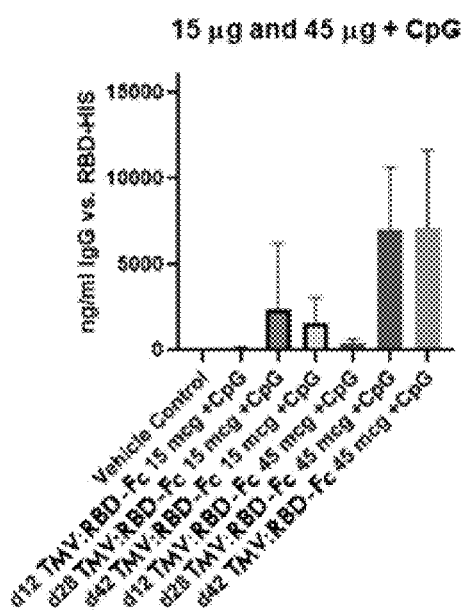
FIG. 62(C) illustrates the immune response in animals immunized with an adjuvanted Covid-19 antigen conjugated to a virus.
Figure 62D:
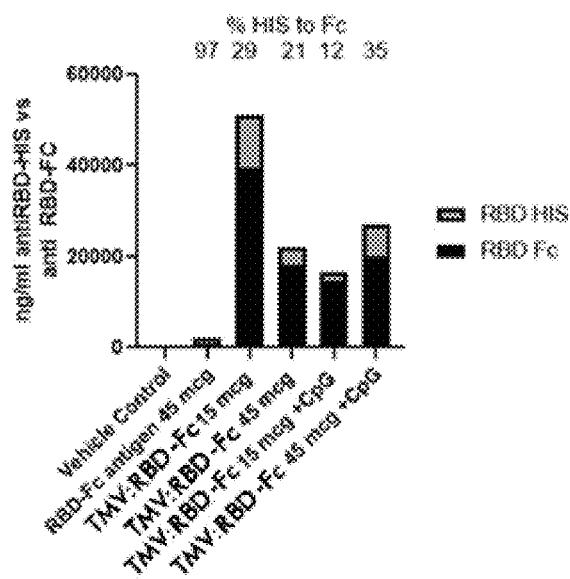
FIG. 62(D) compares the IgG titers recognizing the Covid-19 antigen (in black) and RBD-His (in gray).

FIG. 62(A) illustrates the immune response (ng/mL) stimulated by RBD-Fc antigen only at 12, 28, and 42 days post first vaccination. FIG. 62(B) illustrates the immune response (ng/mL) stimulated by TMV:RBD-Fc conjugate at dosages of 15 mcg and 45 neat (unadjuvanted) at 12, 28 and 42 days post-first vaccination. FIG. 62(C) illustrates the immune response (ng/mL) stimulated by adjuvanted TMV:RBD-Fc conjugate (15 mcg) and TMV:RBD-Fc conjugate (45 mcg+CpG) vaccines at 12, 28 and 42 days post-first vaccination. In FIG. 62(D), comparative IgG titers recognizing the RBD-Fc antigen (in black) and RBD-His (in gray) are shown from sera taken at day 42. The relative ratio of reaction to RBD-His is shown as a percentage of total, RBD-Fc response, above each stacked plot member.

Baseline serum antibody levels were very low for RBD-His and RBD-121-Fc antigen, being <100 ng/mL. Further, no significant response was measured for PBS vehicle control animals, and the unconjugated RBD-Fc antigen produced a limited antibody response demonstrating that conjugated to the TMV NtK carrier is needed to produce a robust immune response.

As shown in FIGS. 62(B) and 62(C), all TMV:RBD-Fc vaccine groups showed measurable antibody responses by day 12. As shown in FIGS. 62(A), 62(B) and 62(C), a dose response was observed when comparing the RBD-Fc antigen alone and the TMV:RBD-Fc Conjugate. Further, strong boosting was observed from day 12 to day 28 following the second vaccination. The TMV:RBD-Fc conjugate groups showed expansion of antibody titers from day 28 to day 42, whereas CpG adjuvanted vaccines showed consistent (45 µg+CpG) or declining titers (15 µg+CpG). The non-adjuvanted TMV:RBD-Fc conjugate groups showed similar quantitative titers than CpG adjuvanted vaccines with all sera analyzed simultaneously against a single capture protein.

As shown in FIG. 62(D), the relative immune response to the SARS-2 RBD was tested, as well as the human Fc portion of the antigen to the immune response. Day 42 sera were analyzed by ELISA using either the SARS-2 RBD-His or the RBD-121-Fc proteins as capture agents. ELISA data was measured after 1:100 dilutions of PBS/RBD-121-Fc antigen immune groups, and 1:1000 for TMV:RBD-Fc conjugate groups. Titers recognizing the RBD were significantly lower than for RBD-Fc antigen, with the percentage of anti-RBD varying by the TMV:RBD-Fc group from 12-35% (FIG. 62(D)), The immune response titers were not significantly different across the TMV:RBD-Fc conjugate groups, regardless of the capture antigen.

Figure 63A:
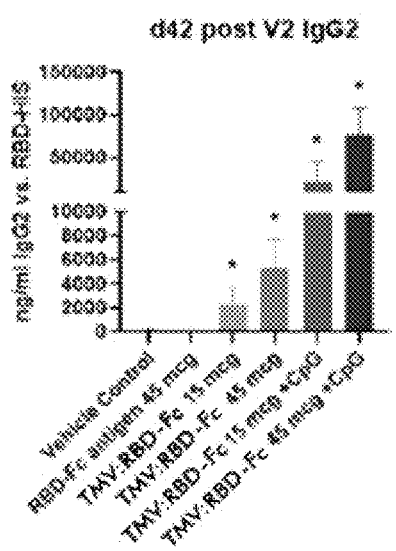
FIGS. 63(A)-63(C) are graphs illustrating an IgG isotype analysis for individual sera taken from animals immunized with a recombinant Covid-19 antigen conjugated to a virus, controls, and adjuvant, according to multiple embodiments and alternatives.
Figure 63B:
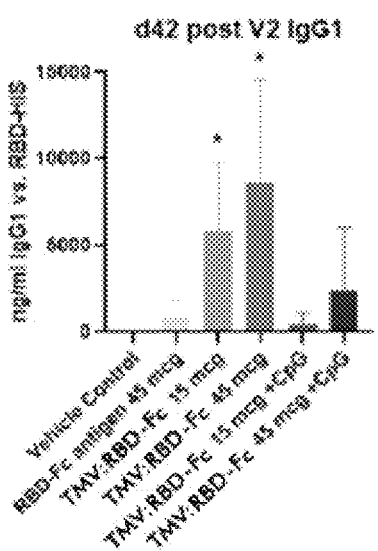
Figure 63C:
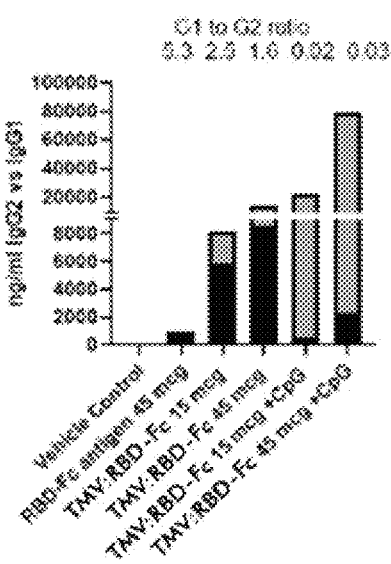

A favorable balance of Th1/Th2 cytokines produced facilitates a safe and effective immune response, by balancing proinflammatory and anti-inflammatory responses Given the importance of Th1/Th2 balance, IgG isotype analysis was also conducted by measuring IgG1 (Th2) and IgG2 (IgG2a+IgG2c; Th1)) isotype for individual sera taken at day 42 and the results are shown in FIG. 63. FIG. 63(A) illustrates the Th1 response (IgG2a and IgG2c), FIG. 63(B) illustrates the Th2 response (IgG1), and FIG. 63(C) is a stack plot comparison of relative IgG2 versus IgG1 antibody by ELISA. In FIG. 63, the "*" indicates a p<0.05 compared to other groups.

As expected, the PBS and RBD-Fc antigen groups showed low overall IgG2 antibody responses, compared with all TMV:RBD-Fc conjugate groups. All TMV:RBD-Fc conjugate groups were different from each other, with significantly improved IgG2 titers by dose and by addition of adjuvant. The IgG1 titers were significantly higher in non-adjuvanted TMV:RBD-Fc conjugate groups, compared with all other groups, with the CpG adjuvanted group significantly lower and equivalent to RBD-Fc alone group. The ratio of IgG1 to G2 isotype varied across groups, with primarily IgG1 isotype titer in the RBD-121-Fc group, an IgG1 to G2 ratio greater than 1 for non-adjuvanted TMV:RBD-fc conjugate groups, and a IgG1 to G2 ratio less than 0.1 for TMV:RBD-Fc conjugate+CpG adjuvant groups. In summary, the CpG adjuvant strongly skewed the isotype response to TMV:RBD-Fc conjugate vaccine to the Th1 type, with non-adjuvanted TMV:RBD-Fc conjugate showing a more balanced mix of Th1/Th2 response. The unconjugated protein stimulated almost entirely a Th2 response.

Figure 64:
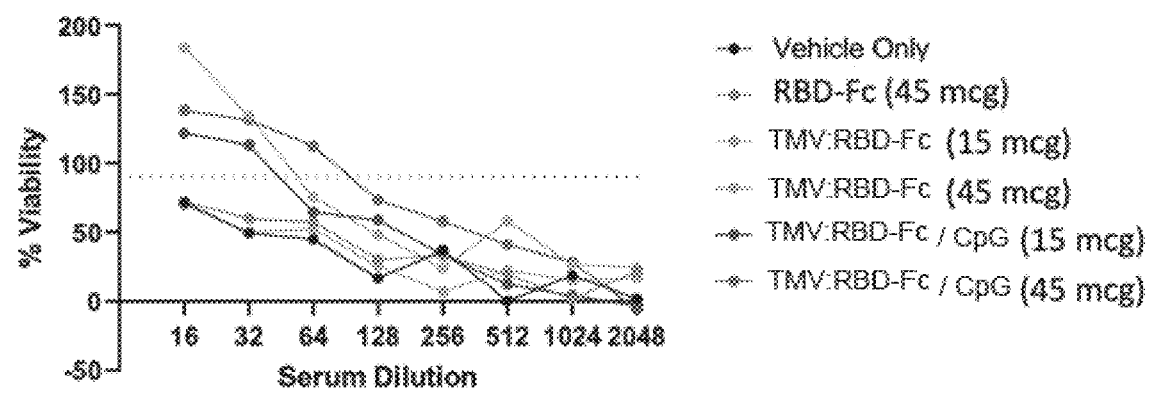

In the first evaluation mentioned above, SARS-2 neutralizing titers were measured using Vero E6 cell viability tests from day 14 samples. FIG. 64 shows the mean cell viability after co-incubation of SARS-2 virus with murine sera, wherein the average cell viability as percentage of total cells is plotted against the serum dilution. The data shown in FIG. 64 illustrate significantly increased viability observed in TMV:RBD-Fc 121 vaccine groups (45 mcg alone, 15 and 45 mcg CpG) compared with the control groups—vehicle alone and antigen alone. The geometric mean neutralization titers were calculated for each group and are shown in Table 51.

TABLE 51

| Geometric Mean Neutralization Titers Induced by TMV:RBD-Fc 121 Vaccine in Mice | |
|---|---|
| Group | GMT Neutralization Titer |
| Vehicle alone | <16 |
| Antigen alone (RBD-Fc) | <16 |
| TMV:RBD-Fc 121 vaccine 15 mcg | <16 |
| TMV:RBD-Fc 121 vaccine 45 mcg | 32 |
| TMV:RBD-Fc 121 vaccine 15 mcg + CpG | 35.8 |
| TMV:RBD-Fc 121 vaccine 45 mcg + CpG | 64 |

The data in Table 51 show measurable neutralization titers induced in mice following prime vaccine for adjuvanted and neat (non-adjuvanted) TMV:RBD-Fc 121 vaccines.

Figure 65:
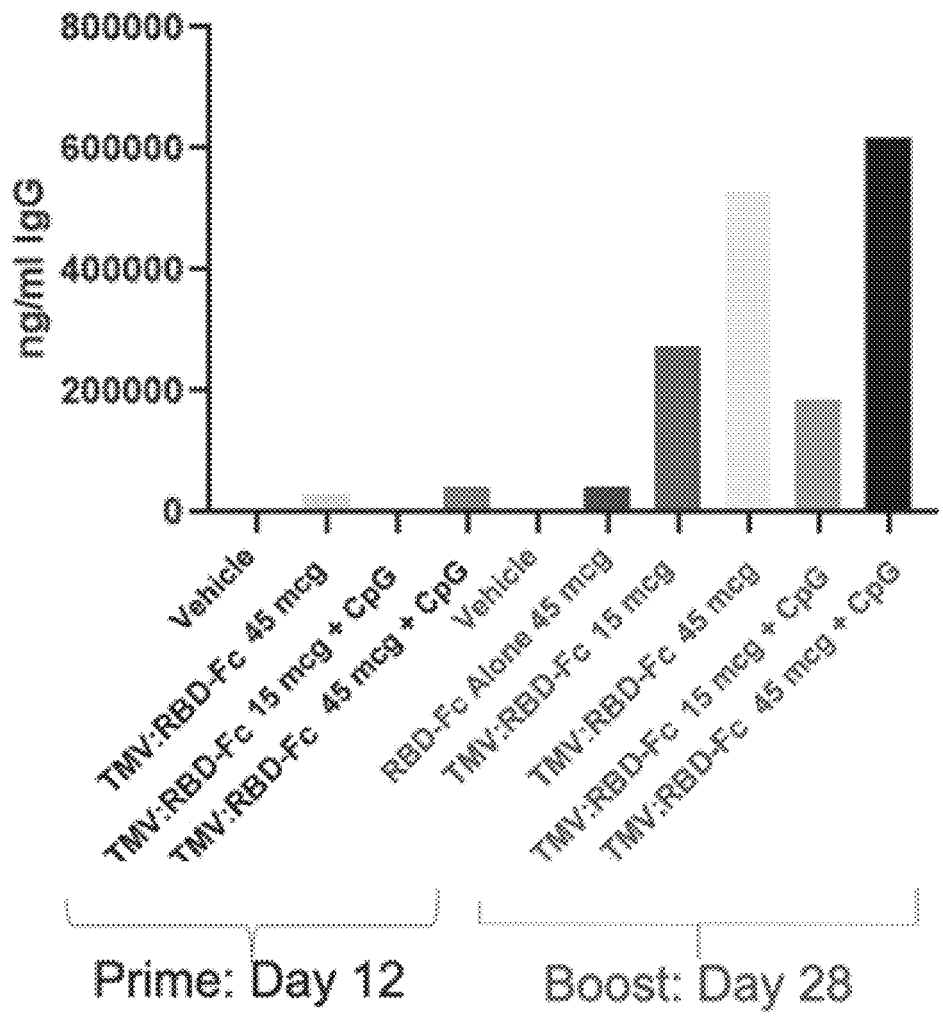
FIG. 65 is a graph illustrating the immune response titers in animals immunized with a recombinant Covid-19 antigen conjugated to a virus, controls, and historical comparisons, according to multiple embodiments and alternatives.

In the second evaluation, a recombinant RBD protein (6-His fusion) was used as the capture protein and antigen specific antibodies were measured and expressed as ng IgG bound/mL of pooled group sera. FIG. 65 illustrates the measured response titers following vaccine 1 (prime; day 12) and vaccine 2 (boost, day 28) induced in mice by TMV:RBD-Fc 121 vaccines. The samples represent analysis of pooled sera from 5 animals in each group and the capture antigen is a recombinant RBD-6-His protein. As shown in FIG. 65, measurable responses were observed at day 12 (following vaccine 1—prime vaccination) for the TMV:RBD-Fc 121 vaccine at 45 mcg neat or mixed with CpG adjuvant. Following vaccination 2 (indicated by "boost" in FIG. 64) at day 28, similar titers were present for TMV:RBD-Fc 121 vaccine at 45 mcg neat or mixed with CpG antigen group sear. Moreover, these titers appear significantly greater than that induced by TMV:RBD-Fc 121 vaccine at 15 mcg neat or mixed with CpG antigen. In FIG. 65, all TMV:RBD-Fc 121 groups are significantly higher than the immune response induced by RBD-Fc antigen alone. These trials show dose dependency of the TMV:RBD-Fc 121 vaccine and reveal that adjuvant does not make a significant contribution to enhanced immune responses to the RBD-Fc 121 antigen when conjugated to inactivated TMV particles. Moreover, as shown in FIG. 65, the TMV:RBD-Fc 121 vaccine induced a level of response greater than 600 mcg/mL when provided at the 45 mcg dose.

Using a SARS-2 plaque assay, the sera was tested for the generation of virus neutralizing antibody (Nab) titers in immunologically naïve animals. Nab titer was detectable following a single immunization but was greatly increased to <4000 GMT following a second (booster immunization). As shown in Table 52 below, two different neutralization assay methods were used showing comparable titers and providing a high degree of validity to the results. It should be noted that adjuvant did not increase the Nab titer in either experiment. Data support the effectiveness of as little as 15 mcg of TMV:RBD-Fc 121 vaccine—as it shows Nab titer of ~200 post first dosing and >4,000 after second dose in one trial and >600 titer in second trial.

TABLE 52

Neutralizing Antibody Titers Induced by TMV:RBD-Fc 121 vaccines in Two Murine Pre-Clinical Trials as Measured by Geometric Mean Titer (GMT) Using CPE Neutralizing Assay and PRNT50 Methods

| Vaccination Group | Murine Trial 1 | | Murine Trial 2 | | | |
|---|---|---|---|---|---|---|
| | Post-Vaccine 1: Day 14* GMT | Post-Vaccine 2: Day 28* GMT | Post-Vaccine 1: Day 12** Pooled PRNT50 | Post-Vaccine 2: Day 28** Pooled PRNT50 | Post-Vaccine 2: Day 42** Pooled PRNT50 | Post-Vaccine 2: Day 42* GMT |
| Vehicle Only | <32 | <64 | <20 | <20 | <20 | <64 |
| TMV + RBD-121-Fc (45 mcg) | 56 | 1176 | <20 | NA | NA | NA |
| RBD-121-Fc (45 mcg) | NA | NA | <20 | <20 | 80 | 294 |
| TMV:RBD-Fc 121 Conjugate (15 mcg) | 194 | 4096 | <20 | 20 | 640 | 676 |
| TMV:RBD-Fc 121 (45 mcg) | 128 | 1783 | <20 | 320 | 5120 | 2702 |
| TMV:RBD-Fc 121 (15 mcg) + CpG (50 mcg) | 169 | 1176 | <20 | 20 | 320 | 338 |
| TMV:RBD-Fc 121 (45 mcg) + CpG (50 mcg) | 388 | 1552 | <20 | 320 | 1280 | 1552 |

*TCID50 value: CPE neutralization assay
**PRNT50: p < 0.05 compared with virus control Further analysis of murine sera showed a balanced Th1/Th2 immune response elicited by TMV:RBD-Fc 121 vaccines and, immunogenicity to the vaccine was heavily reliant upon conjugation to the TMV NtK carrier. In one in vitro model to assess the potential of the TMV:RBD-Fc vaccine to induce antibody-enhanced disease (ADE), sera containing neutralizing antibody titers of ≥2700 displayed no evidence of enhanced SARS-CoV-2 entry into macrophages. This indicates the vaccine strategy stimulates Nab titers without promoting ADE.

In addition, Th1 immune responses were explored through cellular stimulation analysis. In this study, groups of 5 mice were immunized by subcutaneous dosing once at day 1 and day 14, with either 15 µg or 45 µg antigen dose, with or without CpG, in 50 mcL, total volume (PBS comprising buffer). On days 0, 12, 18 and 42 sera were collected, and the magnitude of the antibody response to the vaccine antigen was assessed as total titers against the target antigen and compared with PBS immune sera or pre-immune sera. Unconjugated protein RBD-Fc was used as the target for IgG assessment as well as RBD-HIS to assess response to total antigen and RBD (spike S1 domain) component of antigen. Approximately 6 weeks after the first immunization, vaccinated mice were euthanized and terminal sera collected, and spleens harvested for IFNγ ELISpot analysis. An overview of the study is shown in Table 53,

TABLE 53

Overview of Matrix Study

| Group | Vaccine | Antigen Dose (µg) | Adjuvant | Immunization Days | Bleed Dates |
|---|---|---|---|---|---|
| 1 | Vehicle Only | n/a | none | 0, 14 | 0, 12, 28, 42 |
| 2 | RBD-Fc | 45 | none | 0, 14 | 0, 12, 28, 42 |
| 3 | TMV:RBD-Fc | 15 | none | 0, 14 | 0, 12, 28, 42 |
| 4 | TMV:RBD-Fc | 45 | none | 0, 14 | 0, 12, 28, 42 |
| 5 | TMV:RBD-Fc | 15 | CpG (50 µg) | 0, 14 | 0, 12, 28, 42 |
| 6 | TMV:RBD-Fc | 45 | CpG (50 µg) | 0, 14 | 0, 12, 28, 42 |

Figure 66A:
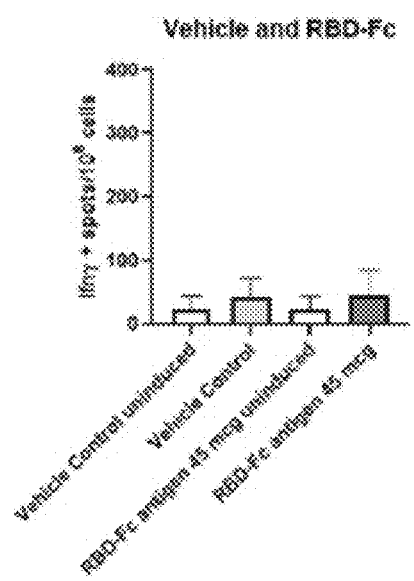
FIG. 66(A) is a graph illustrating an IFNγ ELISpot analysis for animals immunized with a virus and a recombinant Covid-19 antigen.
Figure 66B:
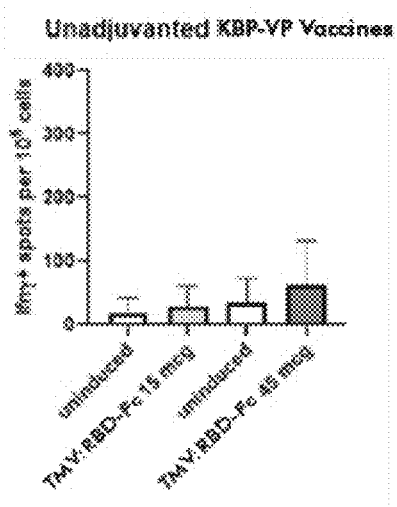
FIG. 66(B) is a graph illustrating an IFNγ ELISpot analysis for animals immunized with an unadjuvanted TMV:RBD-Fc vaccine.

Spleens from two animals of each group were harvested at day 42, single cell suspensions were generated, cells were stimulated for 36 hours with the SARS-CoV-2 RBD-HIS protein and the number of IFNγ secreting cells were measured. The results are shown in FIG. 66, wherein FIG. 66(A) illustrates the IFNγ ELISpot analysis for vehicle and RBD-Fc only, FIG. 66(B) illustrates the IFNγ ELISpot analysis for unadjuvanted TMV:RBD-Fc vaccine, and FIG. 66(C) illustrates the IFNγ ELISpot analysis for TMV:RBD-Fc vaccine with the CpG adjuvant.

Figure 66C:
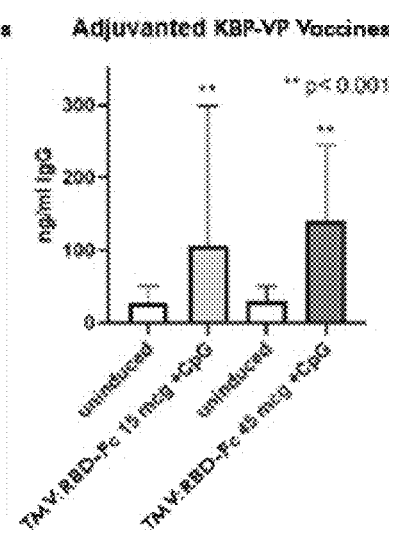
FIG. 66(C) is a graph illustrating an IFNγ ELISpot analysis for animals immunized with a TMV:RBD-Fc vaccine and an adjuvant.

As shown in FIG. 66, only cells recovered from mice vaccinated with TMV:RBD-Fc vaccines containing the CpG adjuvant induced statistically significant numbers of IFNγ secreting cells at day 42 (four weeks post-2nd immunization), with equivalent numbers in both 15 and 45 lag dose groups (FIG. 66(C)). This data is supportive of the IgG isotype analysis which indicates that TMV:RBD-Fc vaccine with CpG adjuvant co-delivery stimulates Th1 responses in mice.

Figure 67:
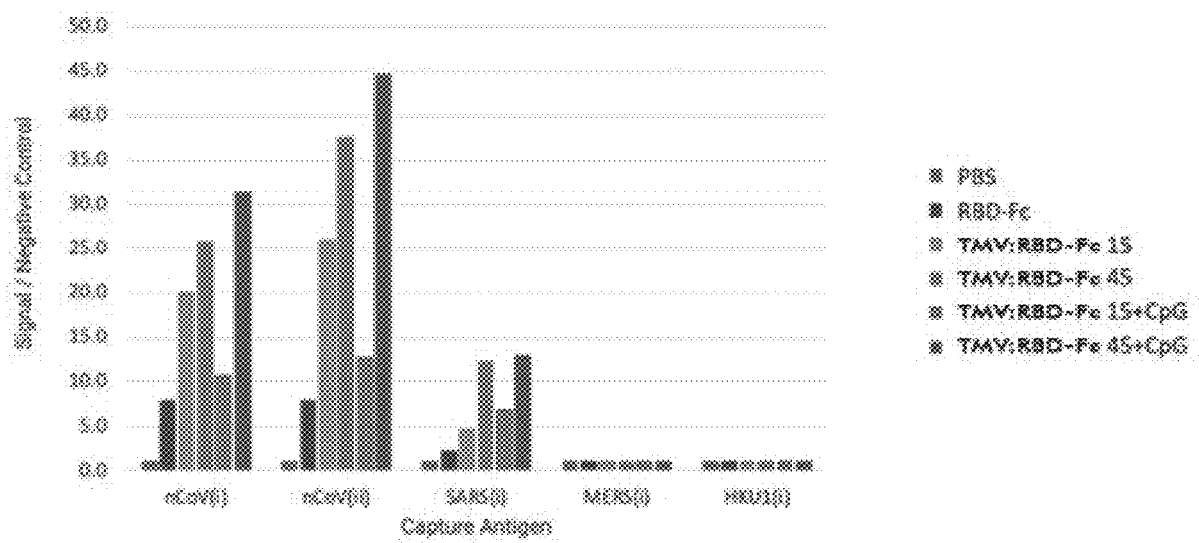
FIG. 67 is a graph illustrating a VaxArray® analysis of murine sera from mice immunized with various TMV:RBD-Fc vaccine dosages, and both with and without adjuvant, according to multiple embodiments and alternatives.

In addition, a VaxArray® SeroAssay analysis of murine sera was conducted from mice immunized with various TMV:RBD-Fc vaccine dosages, and both with and without adjuvant, to evaluate the relevance of binding to heterologous coronavirus antigens. In FIG. 67, nCoV antigen (i) is full SARS-CoV2 spike protein, (ii) is the S1 (RBD) domain, SARS(i) is full SARS-1 spike as is MFRS(i) and HKU1(i), each produced in mammalian systems. The relative titer is represented as fold enhancement of signal over controls reported. Strong reactivity was noted to both SARS-2 antigens and apparent cross reactivity to SARS-1 antigen. As shown in FIG. 67, no binding was observed to divergent MERS or HKU1 spike proteins. Accordingly, the results in FIG. 67 indicate that anti-sera from mice with neutralization titers recognized heterologously produced (mammalian cell) SARS-2 Spike proteins, RBD, and SARS-1 Spike Proteins (i.e. exhibit cross reactivity).

The murine testing also studied a murine macrophage line (Raw 264.7) lacking ACE-2 binding domains, which found that anti-spike RBD neutralizes viral killing and does not promote antibody-dependent enhancement of infection in murine macrophages. In humans, ACE-2 functions as a cell surface receptor for the spike protein of SARS-CoV2 during the invasion of respiratory epithelial cells. Concomitantly, in humans, mice and other organisms, neutralizing antibodies against the receptor binding domain of this spike protein have been found in patients that have recovered from SARS-CoV and are believed to be protective against infection with SARS-CoV2. However, it has also been shown that non-neutralizing antibodies are able to enhance the severity of SARS-CoV infections, and have impeded successful vaccine development for coronaviruses, including SARS-CoV1 and SARS-CoV2.

In the murine testing study, the abilities of certain antibodies including ones generated by the subject TMV:RBD-Fc vaccines were compared in regards to antibody-dependent enhancement of SARS-CoV2 infection. Raw 264.7 cells were grown into a 96 well plate in VGCM and allowed to adhere overnight. Cells were washed extensively prior to the addition of sera or antibodies. The antibodies of the study (or pooled sera) were simultaneously incubated for 1 hour to facilitate viral inactivation by neutralizing antibodies prior to incubation with macrophages. Following this incubation, media containing both antibodies and SARS-CoV2 was added to the macrophages and incubated for 48 hours, at which time viability was assessed thru the addition of Cell Titer Glo (Promega) and evaluated on the basis of luminescence output.

As further shown in FIGS. 68(A-B), non-neutralizing antibodies against the nucleocapsid and spike proteins of SARS-CoV2 enhanced viral entry into murine macrophages, a cell type that does not express ACE2 on the cell surface and is normally resistant to infection. Viability of macrophages exposed to the virus in the absence of antibody averaged 91.5% of the cell viability control at 48 hours post-infection (n=10). FIG. 68(A); FIG. 68(B), first and fifth bars. In the presence of anti-nucleocapsid antibodies raised against the whole spike protein at 6.25 ug/ml, viability fell to an average of 55.69% with the greatest concentration-dependent drop above 1 ug/ml. FIG. 68(A). In the presence of polyclonal antibodies raised against the whole spike protein at 6.25 ug/ml, viability fell to an average of 59.78%. FIG. 68(A). In contrast, pooled murine sera from the study in Example 15(b) against TAP COVID-19 vaccine at 6.25 ug/ml showed high neutralization titers without observable antibody-dependent enhancement, as indicated by an average viability of 125.56% compared to the cell viability control. Statistical differences were measured using one-way ANOVA with Tukey's P values, with the results provided in FIG. 68B. Accordingly, non-neutralizing antibodies (against the nucleocapsid or spike protein) promoted viral entry into the macrophages, while antibodies generated from the TMV:RBD-fc vaccines did not demonstrate this effect.

Accordingly, the in vivo testing shows that TMV:RBD-Fc 121 vaccines induce measurable and statistically significant SARS-2 neutralizing antibody titers over controls. The TMV:RBD-Fc 121 vaccine of the present example shows a strong, vigorous, and promising immune response. It should also be noted that the entire vaccine manufacturing process, from the initial sequencing of the Covid-19 antigen to the final production of the cGMP vaccine for drug product sterility and release, can be accomplished in 8 weeks of time, which is a significant advantage over conventional vaccine production methods which typically take more than 6 months.

Furthermore, as described in Example 14, the studies with the QIV vaccine show very high promise in experimental animals for H1, H3, H5, and H7 influenza models, and no toxicologically significant findings were observed. This data, as well as the role of inactivated TMV as a carrier, suggests similar potential for the Covid-19 vaccines disclosed herein due to the similar structural components and development platforms. Based on the stability of the QIV vaccine discussed in Example 13, it is likewise expected that the Covid-19 vaccines disclosed herein will exhibit high stability at room temperature for at least a six month period.

Accordingly, through the practice of certain embodiments herein, a conjugable antigen can be manufactured, suitable for conjugation a carrier. The teachings herein contemplate and are otherwise directed to antigens which can be conjugated to virus particles, virus particles, vaccines, constructs, and other compositions of matter as well as all methods employed in the making of these. Such an antigen may be a recombinant antigen, and generally comprises a fusion peptide having a first peptide which comprises a receptor binding domain of a pathogen, a non-limiting example being a coronavirus, and a second peptide which comprises a fragment crystallizable (Fe) region of an antibody capable of binding to a Fe receptor. In some embodiments, the first peptide and the second peptide are linked by a hinge portion. Optionally, this hinge portion may be a portion of the Fe region. In some embodiments, the hinge portion contains an amino acid sequence as set forth in SEQ ID NO: 3. Exemplary coronaviruses from which a receptor binding domain may be obtained include without limitation SARS-CoV-1, SARS-CoV-2, and MERS.

Now with reference to FIG. 50, an exemplary receptor binding domain of a SARS-CoV-2, the receptor binding domain is contained in a S-1 subunit of a spike protein of the coronavirus, and it comprises contact residues which are located in a range from about position 289 to about position 662. In some embodiments, the second peptide may comprise an Fe domain of an IgG1 antibody, with such domain containing as noted herein an amino acid sequence as set forth in SEQ ID NO: 4.

Consistent with the teachings herein, in some embodiments a vaccine is manufactured, comprising at least one conjugable antigen, as described according to the multiple embodiments and alternatives of this disclosure, and a carrier comprising a virus particle. In some embodiments, such a virus particle is a virus, for example TMV. The first peptide of the conjugable antigen may contain an amino acid sequence as set forth in SEQ ID NO: 2, alternatively the amino acid sequence may be as set forth in SEQ ID NO: 8. The first peptide may contain contact residues located in a range from about position 289 to about position 662 of a S-1 subunit of a spike protein of the coronavirus, which will contact an ACE-2 receptor on a cell of a mammalian subject to whom such a vaccine is administered, after the antigen is released from the virus particle carrier following administration. For the RBD-FC 121 antigen, the contact residues may be located in a range from about position 301 to about position 662 of the S-1 subunit. It has been found that with regard to the conjugable antigen referred to herein as the RBD-FC 121 antigen, the first peptide lacks an amino acid sequence as set forth in SEQ ID NO: 5, while the first peptide of RBD-Fc 139 antigen does contain this sequence. In both cases, when the conjugable antigen of the vaccine is released in a mammalian subject, having cells that include one or more ACE-2 receptors, the at least one conjugable antigen binds to the one or more ACE-2 receptors. In some embodiments, a virus particle used in the manufacture of such a vaccine has surface lysine residues, which chemically associate with the fusion peptide, more specifically the first peptide, resulting from the conjugation reaction.

Consistent with the breadth of teachings herein, in some embodiments a vaccine in accordance with teachings herein is multivalent and comprises at least one conjugable antigen having a receptor binding domain of a type A influenza virus and at least one conjugable antigen having a receptor binding domain of a coronavirus. Other possible combinations are within the scope of present embodiments, and the combinations provided herein are illustrative and non-limiting. In some embodiments, a vaccine in accordance with teachings herein is multivalent and comprises at least one conjugable antigen having a receptor binding domain of a type B influenza virus and at least one conjugable antigen having a receptor binding domain of a coronavirus. Alternatively, a vaccine in accordance with teachings herein is multivalent and comprises at least one conjugable antigen having a receptor binding domain of a type A influenza virus, at least one conjugable antigen having a receptor binding domain of a type B influenza virus, and at least one conjugable antigen having a receptor binding domain of a coronavirus. Various ratios may be selected and expressed as follows, virus particle:antigen by wt (i.e., ratio of the virus particle and the at least one conjugable antigen by weight). As desired, this ratio may be in a range between about 1:1 and about 8:1, more specifically 8:1. Optionally, CpG may be included with a vaccine in accordance with the teachings herein as an adjuvant for enhancing the immune response of the mammalian subject to the vaccine.

Example 16—Coronavirus Vaccine Candidate: Plant Expression, Purification, Characterization, and Conjugation of RBD-Fc 139 (SARS-2) to TMV In addition to the RBD-Fc 121 antigen, it is expected that any type of virus antigen, including other Covid-19 antigens, may be purified and conjugated to inactivated TMV for use as an effective vaccine candidate according to multiple embodiments and alternatives. In some embodiments, the following antigen sequence (referred to herein as "RED-Fc 139 Construct") is used for the synthesis of a Covid-19 antigen:

1. "(SEQ ID NO: 1") Signal Peptide:
MGKMASLFATFLVVLVSLSLASESSA

2. "(SEQ ID NO: 5") SARS-2 virus Spike amino acids numbered 319-330:
RVQPTESIVRFP 3. (SEQ ID NO: 6") SARS-2 virus Spike amino acids numbered 331-591:
NITNLCPFGEVFNATRFASVYAWNRKRISNCVADYSVLYNSASFS

TFKCYGVSPTKLNDLCFTNVYADSFVIRGDEVRQIAPGQTGKIAD

YNYKLPDDFTGCVIAWNSNNLDSKVGGNYNYLYRLFRKSNLKPFE

RDISTEIYQAGSTPCNGVEGFNCYFPLQSYGFQPTNGVGYQPYRV

VVLSFELLHAPATVCGPKKSTNLVKNKCVNFNFNGLTGTGVLTES

NKKFLPFQQFGRDIADTTDAVRDPQTLEILDITPCS

4. "(SEQ ID NO: 7") Tobacco etch virus NIA cleavage sequence:
enlyfqg

5. "(SEQ ID NO: 3") Fc Hinge:
VEPKSCDKTHTCPPCP

6 "(SEQ ID NO: 4") IgG1 171 allotype Fc:
APELLGGPSVFLFPPKPKDTLMISRTPEVTCVVVDVSHEDPEVKF

NWYVDGVEVHNAKTKPREEQYNSTYRVVSVLTVLHQDWLNGKEYK

CKVSNKALPAPIEKTISKAKGQPREPQVYTLPPSRDELTKNQVSL

TCLVKGFYPSDIAVEWESNGQPENNYKTTPPVLDSDGSFFLYSKL

TVDKSRWQQGNVFSCSVMHEALHNHYTQKSLSLSPG

In an embodiment of the RBD-FC 139 Construct, the following antigen sequence is used for the synthesis of a Covid-19 antigen:

"(SEQ ID NO: 8") SARS-2 virus Spike amino acids numbered 319-591:
RVQPTESIVRFPNITNLCPFGEVFNATRFASVYAWNRKRISNCVA

DYSVLYNSASFSTFKCYGVSPTKLNDLCFTNVYADSFVIRGDEVR

QIAPGQTGKIADYNYKLPDDFTGCVIAWNSNNLDSKVGGNYNYLY

RLFRKSNLKPFERDISTEIYQAGSTPCNGVEGFNCYFPLQSYGFQ

PTNGVGYQPYRVVVLSFELLHAPATVCGPKKSTNLVKNKCVNFNF

NGLTGTGVLTESNKKFLPFQQFGRDIADTTDAVRDPQTLEILDIT

PCS

Multigenic constructs were designed and built to contain genes encoding the proteins necessary to synthesize the RBD-Fc 139 antigen, which also targets the RBD domain of SARS-2 in a similar manner to RBD-Fc 121. According to multiple embodiments and alternatives, the RBD-Fc 139 construct was ligated into the TRBO vector (as a non-limiting example) and subsequent colonies were screened to confirm clones. The assembled expression plasmids containing the RBD-Fc 139 Construct, similar to the plasmid shown in FIG. 51, were amplified, and then purified for use in the production of a Master Cell Bank.

Figure 69:
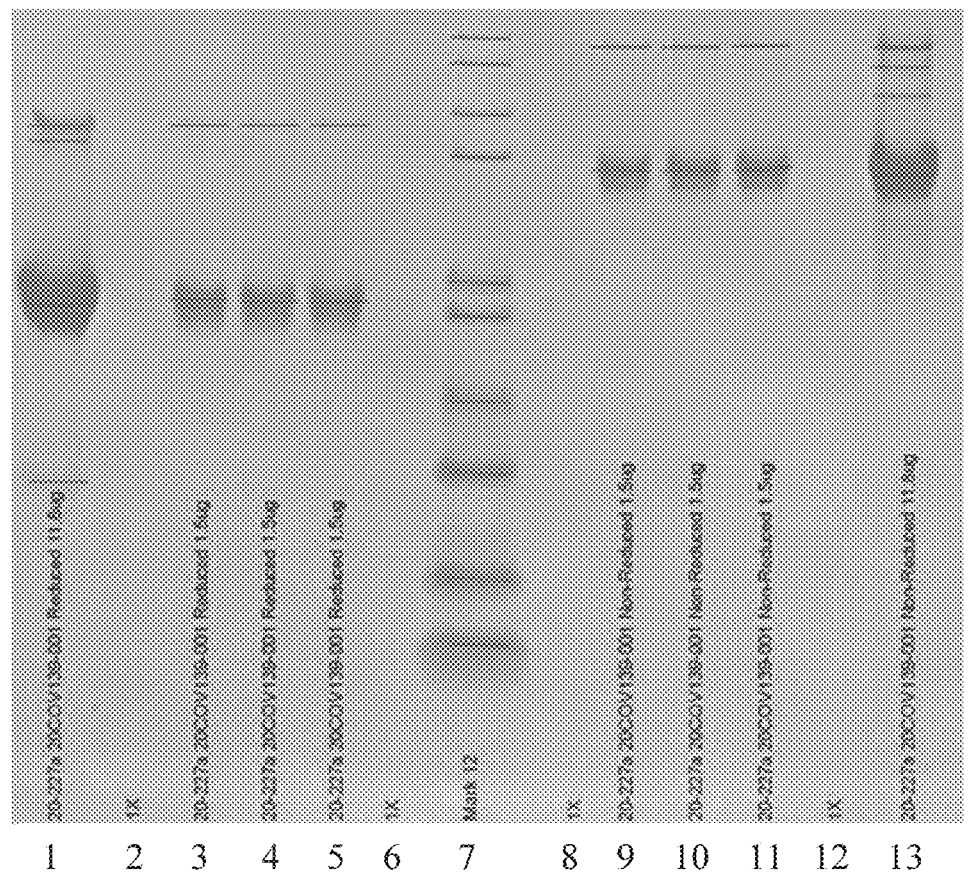
FIG. 69 is a SUS-PAGE analysis of a purified recombinant Covid-19 antigen, according to multiple embodiments and alternatives.
Figure 70:
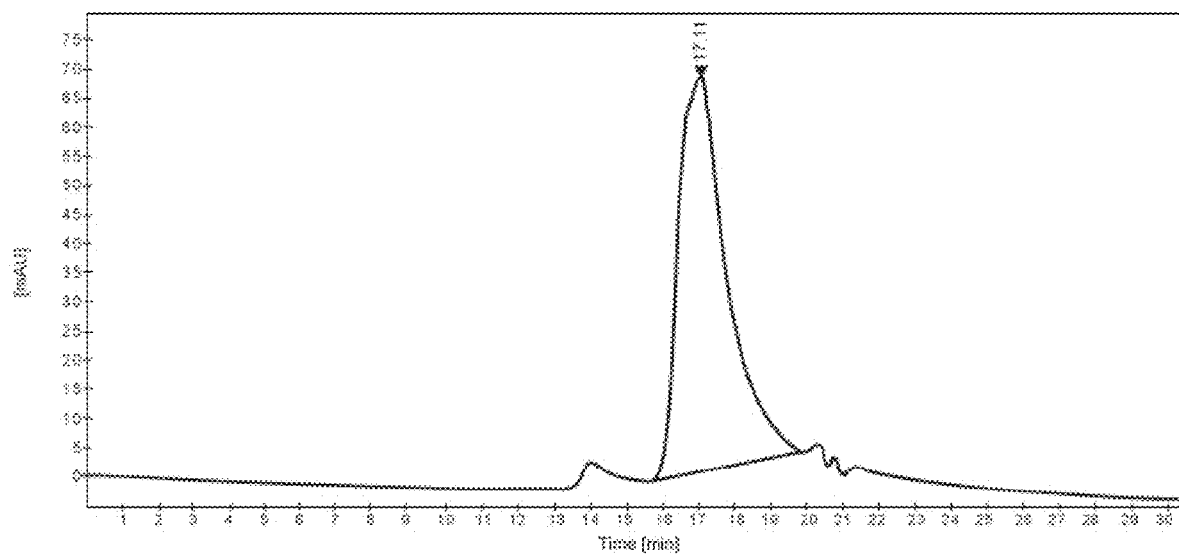
FIG. 70 is a report of SEC-HPLC of a purified recombinant Covid-19 antigen, according to multiple embodiments and alternatives.

According to multiple embodiments and alternatives, the RBD-Fc 139 antigen is expressed in plants and purified using an antigen purification platform described herein. As shown in FIGS. 69-70, the antigen purification platform, according to multiple embodiments and alternatives, successfully purified RBD-Fc 139 resulting in high yields with pure, stable antigen as RBD-Fc monomer in a manner that is compliant with GLP regulations. FIG. 69, taken from the conclusion of the antigen purification platform, contains a SDS page gel indicating purity and successful purification for the RBD-Fc 139 antigen in both reducing and non-reducing conditions. In FIG. 69, the lanes include: lane 1—11.8 ug of purified antigen in reducing conditions, lane 2—blank, lanes 3-5:1.5 ug of purified antigen in reducing conditions, lane 6—blank, lane 7—marker, lane 8—blank, lanes 9-11—1.5 ug of purified antigen in non-reducing conditions, lane 12—blank, and lane 13, 11.8 ug of purified antigen in non-reducing conditions. The clear and visible bands indicate the RBD-Fc 139 antigen product is highly pure.

FIG. 70 is the SEC-HPLC report of the free RBD-Fc 139 antigen, which produced the signal detailed in Table 54 below. The 100% area under the peak indicates that 100% of the RBD-Fe 139 antigen is in monomeric form.

TABLE 54

SEC-HPLC Data of free, purified RBD-Fc 139 Antigen

| RT [min] | Width [min] | Area | Height | Area % | Peak Symmetry |
|---|---|---|---|---|---|
| 17.110 | 1.18 | 2220.84 | 23.81 | 100 | 0.78 |

Therefore, the SDS page gel and the SEC-HPLC report of the free RBD-fc 139 antigen confirm the antigen purification platform which was used, according to multiple embodiments and alternatives, successfully purified the RBD-Fc 139 antigen.

In parallel to the Covid-19 antigen production, the TMV NtK virions with surface lysine residues for efficient conjugation are manufactured in plants and purified according to the virus purification platform described herein. Following purification, the TMV Ntk is subject to micron filtration and immediately treated with UV inactivation. The RBD-Fc 139 antigen is then conjugated to the inactivated TMV via the surface exposed lysine residues utilizing the conjugation of recombinant antigen embodiments described herein.

Also in accordance with the present embodiments herein, a TMV:RBD-Fc 139 conjugate is currently being studied as a vaccine candidate for Covid-19 Disease. However, based on the success of the quadrivalent vaccine and the strong immune responses by the initial TMV:RBF-Fc 121 conjugate, the TMV:RBD-Fc 139 conjugate is also expected to be a viable Covid-19 vaccine.

It will be readily appreciated that the breadth of teachings herein accords with multiple embodiments with a broad array of options in alternative manners for practicing the embodiments. Accordingly, and without limitation, in an embodiment, referred to herein as embodiment A, directed to an antigen, a fusion peptide is formed of a first peptide which comprises a receptor binding domain of a pathogen, and a second peptide which comprises a fragment crystallizable (Fe) region of an antibody capable of binding to a Fe receptor. In an embodiment within the scope of embodiment A, and referred to herein as embodiment B, the antigen further comprises a hinge portion linking the first peptide and the second peptide. Being a portion of the Fc region and more specifically as referred to herein as embodiment C, the hinge portion may contain an amino acid sequence as set forth in SEQ ID NO: 3. In an embodiment within the scope of embodiment A and referred to herein as embodiment D, the pathogen is a coronavirus having a receptor binding domain, and more specifically as referred to herein as embodiment E, the coronavirus is chosen from the group consisting of SARS-CoV-1 and SARS-CoV-2. In an embodiment within the scope of embodiment E, and referred to herein as embodiment F, the receptor binding domain of the coronavirus comprises contact residues are located in a range from about position 289 to about position 662 of a S-1 subunit of a spike protein of the coronavirus, wherein the contact residues contact an ACE-2 receptor on a cell of a mammalian subject, or alternatively, in an embodiment referred to herein as embodiment G, the contact residues are located in a range from about position 301 to about position 662 of the S-1 subunit. In an embodiment within the scope of embodiment F, and referred to herein as embodiment H, the receptor binding domain of the coronavirus lacks an amino acid sequence as set forth in SEQ ID NO: 5.

In an embodiment within the scope of embodiment D, and referred to herein as embodiment I, the coronavirus is a Middle East respiratory syndrome coronavirus. In an embodiment within the scope of embodiment A, and referred to herein as embodiment J, the second peptide is an Fc domain of an IgG1 antibody and more specifically as referred to herein as embodiment K, the Fc domain contains an amino acid sequence as set forth in SEQ ID NO: 4 and the first peptide contains an amino acid sequence as set forth in either SEQ ID NO: 2 or SEQ ID NO: 8. Accordingly, an antigen may be practiced (i.e., made, formed, designed, used, and so forth) in accordance with embodiment A as more fully described herein. Optionally and as desired by those practicing the embodiments herein, an antigen as described herein may be practiced by incorporating with embodiment A any one or more of embodiments B, C, E, F, G, H, I, or J, and embodiments may be directed to compounds, methods, and genetic constructs in the practice of any one or more of these alternative embodiments. Likewise, embodiments may be directed to a vaccine comprising an antigen, a method of forming an antigen, or a genetic construct useful in forming an antigen, as recited in embodiment A, B, C, D, E, F, G, H, I, or J, and further comprising in combination with any aforementioned embodiment, a carrier comprising a virus particle, wherein the virus in some embodiments is a virus, and more particularly a tobacco mosaic virus, and wherein the fusion peptide chemically associates with lysine residues on a surface of the earlier.

Still further, and without limitation, in an embodiment referred to herein as embodiment K, a vaccine comprises an influenza hemagglutinin antigen (HA) and a carrier comprising a virus particle having surface lysine residues, wherein the HA chemically associates with the surface lysine residues. In an embodiment within the scope of embodiment K, and referred to herein as embodiment L, the virus particle releases the at least one antigen in a mammalian subject having cells that include one or more ACE-2 receptors, the at least one antigen binds to the one or more ACE-2 receptor. In an embodiment within the scope of embodiment K, and referred to herein as embodiment M, the virus particle is a virus, or more specifically as referred to herein as embodiment N, the virus is a tobacco mosaic virus. In an embodiment within the scope of any of embodiment K, L, M, or N, and referred to herein as embodiment O, the vaccine is multivalent, and the HA is chosen from the group consisting of type A HA and type B HA, and the vaccine further comprises at least one antigen having a receptor binding domain of a coronavirus, wherein the at least one antigen having a receptor binding domain of a coronavirus chemically associates with the surface lysine residues. In an embodiment within the scope of embodiment O, and referred to herein as embodiment P, the HA comprises two or more type A hemagglutinin antigens (HAs) and two or more type B HAs. Also, in an embodiment within the scope of embodiment O, and referred to herein as embodiment Q, additional features found in any one or more of embodiments A, B, C, D, E, F, G, H, or J are incorporated with the coronavirus element of the vaccine. Further, in an embodiment referred to herein as embodiment R, in a vaccine within the scope of embodiment Q, a ratio of virus particle and at least one antigen (by weight) is in a range between 1:1 and 8:1 and, more particularly in an embodiment referred to as embodiment S that range is 8:1.

Additional Embodiments and Uses of Novel Subject Matter Herein

Figure 71:
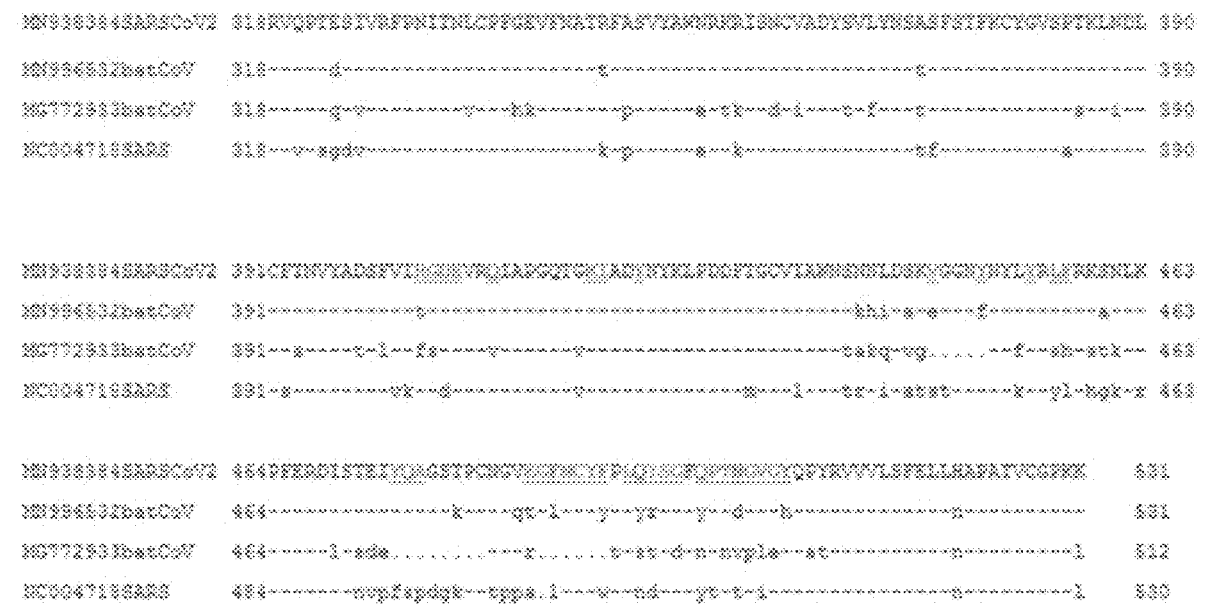

In addition to antigens described above, including the RBD-Fc antigens for treatment against SARS-CoV2, myriad other antigens can be formed according to the multiple embodiments and alternatives described herein. The scope of the descriptions and teachings herein are intended to be limited only in accordance with the claims. For example, a strategy similar to Examples 14, 15, and 16 can be employed to derive candidate vaccines from other human-infecting coronaviruses, including acute respiratory syndrome coronavirus (SARS-1) and Middle East respiratory syndrome coronavirus (MERS). As illustrated in FIG. 71, domains of homology can be identified into functional regions in the Spike S1 domain which correlated with receptor binding and other essential activities.

In this regard, FIG. 71 shows the Receptor Binding Domain of the spike protein sequence alignment of SARS-CoV-2 and other related Coronaviruses. Shown here is a sequence alignment for the interacting (i.e. binding) domain of SARS-CoV-2 (MN938384), Bat-CoV (MN996532 and MG772933) and SARS-CoV (NC004718). The key amino acids described for the interaction with ACE2 and SARS-CoV2 are underlined. (Lines (-)=same amino acid, dots (.)=deletion). FIG. 71 is from Ortega J T, Serrano M L, Pujol F H, Rangel H R. Role of changes in SARS-CoV-2 spike protein in the interaction with the human ACE-2 receptor: An in silico analysis. EXCLI J. 2020; 19:410-417. Published 2020 Mar. 18. Doi:10.17179/excli2020-1167.

As seen in the constructs for the RBD-Fc 121 antigen and RBD-Fc 139 antigen, and reading the N-terminus, the core elements of functionality extend from the "RVQPT" motif for the RBD-Fc 139 Construct to the "CGPKK" domain for both the RBD-Fc 121 and RBD-Fc 139 Constructs. Looking more closely at the RBD-Fc 121 Constructs, there extends beyond the core domain a more extended protein domain which facilitates appropriate folding. Indeed, this strategy is expected to extend to any type of coronavirus antigen, through the processes of:

1. Protein homology analysis—shown in FIG. 71,
2. In silico protein folding using extant coronavirus Spike models,
3. Creation of extensin signal peptide—RBD genetic fusion that promotes efficient cleavage as judged by SignalIP or Phobius;
4. Genetic fusion with Fc reading frame—as illustrated by the RBD-Fc 121 and 139 Constructs;
5. Expression in plants,
6. Purification by Protein A and other methods illustrated in this patent application,
7. Conjugation to TMV in accordance with multiple embodiments and alternatives described herein Such a vaccine can be formed to contain a number of different and diverse antigens, and used to prevent an identified coronavirus pathogen such as SARS-1 or MFRS, or formulated with either the RBD-Fc 121 or 139 antigen into a multivalent vaccine to prevent SARS-1, SARS-2, and HERS, as non-limiting examples. In accordance with multiple embodiments and alternatives described herein, for example with influenza A and B antigens, multivalent TMV conjugate vaccines can be mixed as equal or proportional quantities of each TMV-antigen conjugate and applied in a single immunization. As described herein, multivalent TMV-conjugate vaccines do not show immune dominance of one antigen preventing response to a second or third or fourth. Indeed, both HAI and neutralizing antibodies were generated against all strains in animals immunized with a quadrivalent TMV influenza vaccine, as seen with Example 14. Using this quadrivalent vaccine, protection can be measured against more than one individual influenza vaccine.

Thus, it is anticipated that the approaches described herein, in accordance with multiple embodiments and alternatives, are likely to provide a wide and varied range of antigens upon a single virus particle carrier. To illustrate in a non-limiting way, in an embodiment a multivalent vaccine is provided in accordance with the teachings herein, comprising two, three, four, five, or more different antigens against various viruses and other pathogens. At least one antigen may neutralize or stimulate an immune response against one type of virus (e.g., influenza), while at least one other antigen may do the same against another type of virus (e.g., a pandemic virus like coronavirus). An antigen occupying a position on the carrier could be comprised of a fusion protein modeled after the receptor binding domain of a virus, combined with a fusion partner, such as the Fc domain of an antibody from the tail region of an IgG1 molecule. The influenza portion of the at least one antigen on a single vaccine may comprise both type A and type B influenza. Likewise, an approach may provide at least one antigen directed against one or more coronaviruses. The flexibility of the approaches herein and wide scope of combinable antigen-virus conjugates contemplated herein promote the ability to manufacture broad spectrum vaccines at a large scale in a compressed time period, often measuring weeks as opposed to many months.

It will be understood that the embodiments described herein are not limited in their application to the details of the teachings and descriptions set forth, or as illustrated in the accompanying figures. Rather, it will be understood that the present embodiments and alternatives, as described and claimed herein, are capable of being practiced or carried out in various ways. Also, it is to be understood that words and phrases used herein are for the purpose of description and should not be regarded as limiting. The use herein of "including," "comprising," "e.g.," "containing" or "having" and variations of those words is meant to encompass the items listed thereafter, and equivalents of those, as well as additional items.

Accordingly, the foregoing descriptions of several embodiments and alternatives are meant to illustrate, rather than to serve as limits on the scope of what has been disclosed herein. The descriptions herein are not intended to be exhaustive, nor are they meant to limit the understanding of the embodiments to the precise forms disclosed. It will be understood by those having ordinary skill in the art that modifications and variations of these embodiments are reasonably possible in light of the above teachings and descriptions.

What is claimed is:

1. An antigen, comprising: a fusion peptide having a first peptide which comprises a receptor binding domain of a pathogen, and a second peptide wherein the fusion peptide is capable of being chemically linked with a virus particle, and wherein the second peptide is a fragment crystallizable (Fc) region of an antibody capable of binding to a Fc receptor.

2. The antigen of claim 1, wherein the Fc region is an Fc domain of an IgG1 antibody.

3. The antigen of claim 2, wherein the Fc domain contains an amino acid sequence as set forth in SEQ ID NO: 4.

4. The antigen of claim 1, further comprising a hinge portion linking the first peptide and the second peptide.

5. The antigen of claim 4, wherein the hinge portion is a portion of the Fc region of said antibody.

6. The antigen of claim 5, wherein the hinge portion contains an amino acid sequence as set forth in SEQ ID NO: 3.

7. The antigen of claim 1, wherein the pathogen is a coronavirus having said receptor binding domain.

8. The antigen of claim 7, wherein the coronavirus is chosen from the group consisting of SARS-CoV-1 and SARS-CoV-2.

9. The antigen of claim 8, wherein the receptor binding domain of the coronavirus is located on a S-1 subunit of a spike protein of the coronavirus and comprises contact residues located in a range from about position 289 to about position 662, wherein the contact residues contact an ACE-2 receptor on a cell of a mammalian subject.

10. The antigen of claim 9, wherein the contact residues are located in a range from about position 301 to about position 662 of the S-1 subunit.

11. The antigen of claim 9, wherein the receptor binding domain of the coronavirus lacks an amino acid sequence as set forth in SEQ ID NO: 5.

12. The antigen of claim 7, wherein the coronavirus is a Middle East respiratory syndrome coronavirus.

13. The antigen of claim 1, wherein the fusion peptide chemically associates with surface lysine residues of a carrier, the carrier comprising a virus particle having the surface lysine residues.

14. The antigen of claim 1, wherein the first peptide contains an amino acid sequence as set forth in SEQ ID NO: 2.

15. The antigen of claim 1, wherein the first peptide contains an amino acid sequence as set forth in SEQ ID NO: 8.

16. The antigen of claim 1, wherein the antigen is a recombinant antigen.

17. The antigen of claim 1, wherein the virus particle is a virus.

18. The antigen of claim 17, wherein the virus is a tobacco mosaic virus.

19. A vaccine, comprising at least one antigen as recited in claim 1 and a carrier comprising a virus particle, wherein the at least one antigen is chemically linked to said virus particle.

20. The vaccine of claim 19, wherein the pathogen of the at least one antigen is a coronavirus having said receptor binding domain.

21. The vaccine of claim 19, wherein when the virus particle releases the at least one antigen in a mammalian subject having cells that include one or more ACE-2 receptors, the at least one antigen binds to the one or more ACE-2 receptors.

22. The vaccine of claim 21, wherein the pathogen of the antigen is a coronavirus chosen from the group consisting of SARS-CoV-1 and SARS-CoV-2.

23. The vaccine of claim 22, wherein the receptor binding domain of the coronavirus is located on a S-1 subunit of a spike protein of the coronavirus and comprises contact residues located in a range from about position 289 to about position 662, wherein the contact residues contact an ACE-2 receptor on a cell of a mammalian subject.

24. The vaccine of claim 23, wherein the contact residues are located in a range from about position 301 to about position 662 of the S-1 subunit.

25. The vaccine of claim 23, wherein the receptor binding domain of the coronavirus lacks an amino acid sequence as set forth in SEQ ID NO: 5.

26. The vaccine of claim 19, wherein the Fc region is an Fc domain of an IgG1 antibody.

27. The vaccine of claim 19, wherein the antigen further comprises a hinge portion linking the first peptide and the second peptide.

28. The vaccine of claim 27, wherein the hinge portion is a portion of the Fc region of said antibody.

29. The vaccine of claim 19, wherein the virus particle is a virus.

30. The vaccine of claim 29, wherein the virus is a tobacco mosaic virus.

31. The vaccine of claim 19, wherein a ratio of the virus particle and the at least one antigen is expressed as virus particle:antigen by wt, and said ratio is in a range between 1:1 and 8:1.

32. The vaccine of claim 19, further comprising an adjuvant for enhancing an immune response of a mammalian subject to the vaccine, wherein the adjuvant is chosen from the group consisting of CpG, MPLA, and SE-M.

33. The vaccine of claim 31, wherein the ratio of the virus particle and the at least one antigen is about 8:1.

34. The antigen of claim 1, wherein the pathogen is a coronavirus having said receptor binding domain, wherein said receptor binding domain of the coronavirus lacks an amino acid sequence as set forth in SEQ ID NO: 5.

35. The vaccine of claim 19, wherein the pathogen of the at least one antigen is a coronavirus having said receptor binding domain, wherein said receptor binding domain of the coronavirus lacks an amino acid sequence as set forth in SEQ ID NO: 5.

* * * * *